US005922585A

United States Patent [19]
Young et al.

[11] Patent Number: 5,922,585
[45] Date of Patent: Jul. 13, 1999

[54] **RNA POLYMERASE II HOLOENZYME FROM *SACCHAROMYCES CEREVISIAE***

[75] Inventors: Richard A. Young, Weston; Anthony J. Koleske, Braintree; Craig M. Thompson, Summerville, all of Mass.

[73] Assignee: Whitehead Institute for Biomedical Research, Cambridge, Mass.

[21] Appl. No.: 08/218,265

[22] Filed: Mar. 25, 1994

[51] Int. Cl.⁶ .............................. C12N 9/12; C12N 15/54; C12N 15/31
[52] U.S. Cl. .......................... 435/194; 530/350; 530/371; 536/23.74; 536/23.2; 536/24.1
[58] Field of Search ..................................... 530/350, 371; 435/194; 935/9, 14, 36, 37; 536/23.74, 24.1, 23.2

[56] References Cited

PUBLICATIONS

Lars, J., and Corden, J.L., "Phosphorylation of RNA polymerase by the Murine Homologue of the Cell–Cycle Control Protein cdc2," *Nature*, 339:679–684 (1989).
Koleske, A.J. and Young, R.A., "An RNA Polymerase II Holoenzyme Responsive to Activators," *Nature*, 368:466–469 (1994).
Koleske, A.J., et al., "A Novel Transcription Factor Reveals a Functional Link Between the RNA Polymerase II CTD and TFIID," *Cell*, 69:883–894 (1992).
Oliver, S.G., et al., "The Complete DNA Sequence of Yeast Chromosome III," *Nature*, 357:38–46 (1992).
Thompson, C.M., et al., "A Multisubunit Complex Associated with the RNA Polymerase II CTD and TATA–Binding Protein in Yeast," *Cell*, 73:1361–1375 (1993).
Nonet, M.L. and Young, R.A., "Intragenic and Extragenic Suppressors of Mutations in the Heptapeptide Repeat Domain of *Saccharomyces cerevisia* RNA Polymerase II," *Genetics*, 123:715–724 (1989).
Conaway, R.C. and Conaway, J.W., "General Initiation Factors for RNA Polymerase II," *Annu. Rev. Biochem.*, 62:161–190 (1993).
Dynlacht, B.D., et al., "Isolation of Coactivators Associated with the TATA–Binding Protein That Mediate Transcriptional Activation," *Cell*, 563–576 (1991).
Taggart, A.K.P., et al., "The TATA–Binding Protein and Associated Factors are Components of Pol III Transcription Factor TFIIIB,"*Cell*, 71:1015–1028 (1992).
Cormack, B.P. and Struhl, K., "The TATA–Binding Protein is Required for Transcription by all Three Nuclear RNA Polymerases in Yeast Cells," *Cell*, 69:685–696 (1992).
Usheva, A., et al., "Specific Interaction Between the Non-phosphorylated Form of RNA Polymerase II and the TATA–Binding Protein," *Cell*, 69:871–881 (1992).
Comai, L., et al., "The TATA–Binding Protein and Associated Factors Are Integral Components of the RNA Polymerase I Transcription Factor, SL1," *Cell*, 68:965–976 (1992).
Sharp, P.A., "TATA–Binding Protein is a Classless Factor," *Cell*, 68:819–821 (1992).

Blum, H., et al., "Improved Silver Staining of Plant Proteins, RNA and DNA in Polyacrylamide Gels," *Electrophoresis*, 8:93–99 (1987).
Leung, D.W., et al., "A Method for Random Mutagenesis of a Defined DNA Segment Using a Modified Polymerase Chain Reaction," *Technique*, 1(1):11–15 (1989).
Rothstein, R., "Targeting, Disruption, Replacement, and Allele Rescue: Integrative DNA Transformation in Yeast," *Methods in Enzymology*, 194:281–301 (1991).
Smith, D.B. and Johnson, K.S., "Single–Step Purifications of Polypeptides Expressed in *Escherichia coli* as Fusions with Glutathione S–Transferase," *Gene*, 67:31–40 (1988).
Nicolet, C.M. and Craig, E.A., "Inducing and Assaying Heat–Shock Response in *Saccharomyces cerevisiae*," *Methods in Enzymology*, 194:710–717 (1991).
Nonet, M., et al., "Eucaryotic RNA Polymerase Conditional Mutant That Rapidly Ceases mRNA Synthesis," *Mol. and Cell. Biol.*, 7(5):1602–1611 (1987).
Elder, R.T., et al., "RNA from the Yeast Transposable Element Ty1 has Both Ends in the Direct Repeats, a Structure Similar to Retrovirus RNA," *Proc. Natl. Acad. Sci. USA*, 80:2432–2436 (1983).
Kolodziej, P.A., et al., "RNA Polymerase II Subunit Composition, Stoichiometry, and Phosphorylation," *Mol. and Cell. Biol*, 10(5):1915–1920 (1990).
Studier, F.W. and Moffatt, B.A., "Use of Bacteriophage T7 RNA Polymerase to Direct Selective High–Level Expression of Cloned Genes," *J. Mol. Biol.*, 189:113–130 (1986).
Woontner, M., et al., "Transcriptional Activation in an Improved Whole–Cell Extract from *Saccharomyces cerevisiae*," *Mol. and Cell. Biol.*, 11(9):4555–4560 (1991).
Schiestl, R.H. and Gietz, R.D., "High Efficiency Transformation of Intact Yeast Cells using Single Stranded Nucleic Acids as a Carrier," *Curr. Genet.*, 16:339–346 (1989).
Hoffman, C.S. and Winston, F., "A Ten–Minute DNA Preparation from Yeast Efficiently Releases Autonomous Plasmids for Transformation of *Escherichia coli*," *Gene*, 57:267–272 (1987).
Buchman, A.R., et al., "Connections Between Transcriptional Activators, Silencers, and Telomeres as Revealed by Functional Analysis of a Yeast DNA–Binding Protein," *Mol. and Cell. Biol.*, 8(1):5086–5099 (1988).
Thompson, N.E., et al., "Inhibition of in Vivo and in Vitro Transcription by Monoclonal Antibodies Prepared against Wheat Germ RNA Polymerase II That React with the Hepatapeptide Repeat of Eukaryotic RNA Polymerase II,"*J. Biol. Chem.*, 264(19):11511–11520 (1989).

(List continued on next page.)

*Primary Examiner*—Keith D. Hendricks
*Attorney, Agent, or Firm*—Darby & Darby

[57] ABSTRACT

An RNA polymerase II holoenzyme that contains, in addition to RNA polymerase, a subset of the general transcription factors together with nine SRB proteins is described. This holoenzyme will selectively initiate transcription in vitro when supplemented with TATA-binding protein (TBP) and factor a (TFIIE). The SRB proteins act positively and negatively to regulate transcription initiation, at least in part, via functional interactions with RNA polymerase II.

22 Claims, 60 Drawing Sheets

OTHER PUBLICATIONS

Alani, E., et al., "A Method for Gene Disruption That Allows Repeated Use of URA3 Selection in the Construction of Multiply Disrupted Yeast Strains," *Genetics*, 116:541–545 (1987).

Sawadogo, M. and Sentenac, A., "RNA Polymerase B (II) and General Transcription Factors," *Annu. Rev. Biochem.*, 59:711–754 (1990).

Pugh, B.F. and Tjian, R., "Transcription from a TATA–Less Promoter Requires a Multisubunit TFIID Complex," *Genes & Dev.*, 5:1935–1945 (1991).

Young, R.A., "RNA Polymerase II," *Annu. Rev. Biochem.*, 60:689–715 (1991).

Nonet, M., et al., "Functional Redundancy and Structural Polymorphism in the Large Subunit of RNA Polymeraser II," *Cell*, 50:909–915 (1987).

Liao, S–M., et al., "RNA Polymerase II Carboxy–Terminal Domain Contributes to the Response to Multiple Acidic Activators In Vitro," *Genes & Dev.*, 5:2431–2440 (1991).

Sayre, M.H., et al., "Purification and Properties of *Saccharomyces cerevisiae* RNA Polymerase II General Initiation Factor a," *J. Biol. Chem.*, 267(32):23383–23387 (1992).

Flores, O., et al., "Factors Involved in Specific Transcription by Mammalian RNA Polymerase II," *J. Biol. Chem.*, 263(22):10812–10816 (1988).

Knapp, G., et al., "Transcription and Processing in Intervening Sequences in Yeast tRNA Genes," *Cell*, 14:221–236 (1978).

Kunkel, T.A., et al., "Rapid and Efficient Site–Specific Mutagenesis Without Phenotypic Selection," *Methods in Enzymology*, 154:367–382 (1987).

Boeke, J.D., et al., "5–Fluoroorotic Acid as a Selective Agent in Yeast Molecular Genetics," *Methods in Enzymology*, 154:164–175 (1987).

Gill, G. and Tjian, R., "Eukaryotic Coactivators Associated with the TATA Box Binding Protein," *Current Opinion in Genetics & Dev.*, 2:236–242 (1992).

Hanahan, D., et al., "Plasmid Transformation of *Escherichia coli* and Other Bacteria," *Methods in Enzymology*, 204:63–113 (1991).

Doignon et al. *Yeast*, 9(2):189–199, 1993.

Sayre et al., *J. Biol. Chem*, 267(32), Nov. 15, 1992.

FIG. 2A

```
GGTGACCACTACAGGAACGCAAACTTAAGCTACATTGTTCACCATATTATACTATATATATAACCTCCGGCTGAGCTTTACAGGTGCGTTTGTCCTCGAA 100
GAACGAAAGCAGCCCGAAAAAAAAGCTGGCTGGAGAACAATAGCGGGTTGACCGCTAAACGAGCACACACGTGATGTGTCGTG 200
AACTGTATCGTGGTAGTATGATGCTAGTATGTACCAGCGGTCGTTCGGTAGACTCTACTCTCCTTGTTCCCCGGTG 300
CCATCTTTGAGTTTGCGTGCCGTTATCTCCGGAGCAAGGGTCTGGCTTCGTACGCATAGAGGCTGAGGACGAACAGTGTCGCGTTTCAGGCGTGGATA 400
TAGAATACATAGCTATATAGATGGGTAGTGCGCATGGGAAAGTGCAATTGAGCGAAGGAAGGGGCAGGTGGACTGTAGATGTCGCCGGTGATTTATCG 500
TTGTTCTCTTCCTTGTGTTTCTTATGCCGTTAGTATGCCAGTTTCGCGGTGTGATTCCCAAAGTGAAATTTTACTGGAAGAGCAAATCTTGTAAGTCGGC 600
GCTCGAAAGCACAGTAGCAATCCATCATGGGAAAATCAGCGTATGTAAAAGCTGGAGCGTCCTTCGTGGCCATCGGAATTTCTTCAATTGAACTACCTGT 700
                                                 M  G  K  S  A                 V  I  F  V  E  R  A  T
                                                                            ↑ (SRB2-1)
TGCTAACAACAGTTTTTTTTCTCTCTTTATGTATATACGCTTATATTCGTGAAAGAGCCACTCCCGCTACACTAACGGAACTGAAGGATGCTCTCT 800
 P  A  T  L  T  E  L  K  D  A  L
CGAATAGTATCCTGTCCGGTGCCGAGACCCTTGGTGTCGATAGACTTTCGGACGTACCGGTGCTCTATCAAGAACTACCCGGATGTCTCCAAGCTCATGTA 900
 S  N  S  I  L  S  V  R  D  P  W  S  I  D  F  R  T  Y  R  C  S  I  K  N  L  P  A  D  Y  S  K  L  M  Y
CTCGATAACGTTCCACCACCATGGCCGGCAGACCGTGCTAATCAAGGACGACACAACTCAGGCGATGTGGTACCTCCGCCAGCGGCGGATATCCCTCGGCGCTG 1000
 S  I  T  F  H  H  H  G  R  Q  T  V  L  I  K  D  N  S  A  M  V  T  T  A  A  A  A  D  I  P  P  A  L
```

```
GTGTTCAATGGCTCATCTACGGGCCGTTCCTGAGTCCATAGACACTATTTGTCTCCAAGCTGTCCAACATCTGGATGCAGAGGCAGCTCATCAAGGGTG 1100
 V  F  N  G  S  S  T  G  V  P  E  S  I  D  T  I  L  S  S  K  L  S  N  I  W  M  Q  R  Q  L  I  K  G

ATGCCGGTGAGACGTTGATCTTGGACGGGCTCACCGTGCCACTCGTCAACCTCTTCTCCTCCACTGGTTCAAGGGTCTCTTAAGAACTGCAGGCGGA 1200
 D  A  G  E  T  L  I  L  D  G  L  T  V  R  L  V  N  L  F  S  S  T  G  F  K  G  L  L  I  E  L  Q  A  D

CGAAGCGGGCGAGTTTGAGACCAAGATTGCAGGCATCGAAGGACACCTAGTGAAATCCGGGCCAAGGAGTACAAAACCTCATCGACTCGTTGGGGCCG 1300
 E  A  G  E  F  E  T  K  I  A  G  I  E  G  H  L  A  E  I  R  A  K  E  Y  K  T  S  S  D  S  L  G  P

GACACCAGCAACGAAATATGTCGATTTGGCGTACCAGTATGTTCCTGCTCGTGAGTTCTTACGAATGCTTTTTCTTTTTTTTCTGTTTG 1400
 D  T  S  N  E  I  C  D  L  A  Y  Q  Y  V  R  A  L  E  L

TATATTGCGGGTGTATACGTATAGATAGTCTAAATAGTAATCTTCAACCTTATGTATCTCGGCTCATGCAGTGAGGAAATCCATGGATAAGCCCGGA 1500

TTGTAGTCATCGTCGCTGTCGCTGTCGCCTGTGTCGCTGGCCTCCTGTGTTTCCTTCTGTCGGTTGAGAGTTCTCTTCAGCGTCTTCCT 1600

CCTCCCTTGCATTGTCAATAAACTTGTTCAGTGTACTCGTATGCTCAAGTGGGCGGGTTCCTGGTGTAGCACCTCGTAGCCCTCGTAGGTCGGCCTC 1700

TGTCATGGCAACGAATATCGTGGTGTTCGTTTCTCGATCACTCTGGTGTTCTTCAACATTCTCCGATGCATTTCTCATGTATAGCCAACTCCACCAAGTTTTT 1800

GAATCCATTATATGCGTGGTGTTCGTGTAAGGAACGTTTTCGTGTAGAATTTGAGCCCACTCTTCTTCGTAGGATCGTGTCTTTCCTCTTTGGTCTCCGAAC 1900

CGTCTTCGCCCTCTATGCAAGAGCTTGTTCCAGCCAAGGCGATAGAATTC 1949
```

FIG. 5A

```
-319  GATCTCGACGATTTGGGATTCTTATAAGGGCGCATAAAAATAAATAACTACCATTCATAACAGAAATTCATTCGT
-243  ATATACATAAAGTTCTCATAAACGTATATATATATATATATATATTGATATCAAAGTGTGTTACTTTCT
-168  ACATTCATAGACGGGAAGAAAGTGAGGAAAAGTTGTTTCTCTTGTCACTGCAGCCCTTTGAAAAAGTAGAA
-93   CTGCAGAAAAATAACTGAACGTAAAGCATTATTACTTTTCAAAGGCAAAAGAGATAGAGCCAAAAAAATTGTA
-18   AGCAGCTTAAAGCCATAATGACAACGGAAGATCCAGATTCAAATCACTTAAGTTCCGAAACTGGCATTAAATTG
  1                   M  T  T  E  D  P  D  S  N  H  L  S  S  E  T  G  I  K  L

58   GCATTGGACCCGAACTTAATTACATTGGCACTAAGTTCTAATCCAAACTCTAGCCTTCATTCACCAACGTCTGAT
 20    A  L  D  P  N  L  I  T  L  A  L  S  S  N  P  N  S  S  L  H  S  P  T  S  D

133   GAACCCGTACCTGAATCTGCAGGAAAAGCAGATACTAGTATTCGACTAGAAGGTGATGAGTTAGAGAATAAAACT
 45    E  P  V  P  E  S  A  G  K  A  D  T  S  I  R  L  E  G  D  E  L  E  N  K  T

208   AAGAAAGACAATGATAAGAACTTAAAATTTTGAAGAATAAAGATTCTCTAGTCAGTAATCCACACGAAATTTAT
 70    K  K  D  N  D  K  N  L  K  F  L  K  N  K  D  S  L  V  S  N  P  H  E  I  Y

283   GGCTCCATGCCGTTGGAGCAATTGATCCCAATCATCTTAAGACAGCGTGGTCCAGGCTTTAAATTCGTTGATTTA
 95    G  S  M  P  L  E  Q  L  I  P  I  I  L  R  Q  R  G  P  G  F  K  F  V  D  L

358   AATGAAAAAGAATTGCAAAATGAGATTAAGCAGTTGGTAGTGATAGTGACGGTCATAACAGGCGAGAAGAAG
120    N  E  K  E  L  Q  N  E  I  K  Q  L  G  S  D  S  S  D  G  H  N  S  E  K  K
```

FIG. 5B

```
433  GACACTGATGGCGCTGATGAGAATGTACAAATTGGAGAAGATTTCATGGAAGTGGATTATGAAGATAAGATAAT
145   D  T  D  G  A  D  E  N  V  Q  I  G  E  D  F  M  E  V  D  Y  E  D  K  D  N

508  CCAGTGGATTCACGAAATGAAACAGACCACAAAACGAATGAAAATGGCGAGACCGATGATATTGAAACGGTA
170   P  V  D  S  R  N  E  T  D  H  K  T  N  E  N  G  E  T  D  D  N  I  E  T  V

583  ATGACACAGGAACAGTTTGTTAAAAGAAGGAGGGATATGCTAGAGCATATAAATCTGGCCATGAACGAATCGTCT
195   M  T  Q  E  Q  F  V  K  R  R  R  D  M  L  E  H  I  N  L  A  M  N  E  S  S

658  TTGGCTTTGGAATTCGTTTCTTTGCTACTGTCGAGTGTTAAAGAGTCTACAGGTATGTCATCAATGTCACCATTT
220   L  A  L  E  F  V  S  L  L  L  S  S  V  K  E  S  T  G  M  S  S  M  S  P  F

733  CTTAGGAAAGTTGTTAAACCTTCTAGTTTAAACAGTGATAAATTCCATATGTTGCACCTACAAAAAAGAATAT
245   L  R  K  V  V  K  P  S  S  L  N  S  D  K  I  P  Y  V  A  P  T  K  K  E  Y

808  ATCGAGTTGGATATATTGAATAAGGATGGAAGTTAAACGAATCTAAAGATCTCCTACGCGCAAGT
270   I  E  L  D  I  L  N  K  G  W  K  L  Q  S  L  N  E  S  K  D  L  L  R  A  S

883  TTTAATAAACTGAGTTCCATATTACAGAACGAACATGACTATTGGAATAAGATAATGCAGAGTATTAGCAACAAG
295   F  N  K  L  S  S  I  L  Q  N  E  H  D  Y  W  N  K  I  M  Q  S  I  S  N  K
```

FIG. 5C

```
958   GATGTTATTTTTAAGATTAGGGACACAGGACTAGTGGTCAAAAGCTGTTGGCAATTAAGTATGGTTACGAAGACTCT
320    D  V  I  F  K  I  R  D  R  T  S  G  Q  K  L  L  A  I  K  Y  G  Y  E  D  S

1033  GGATCTACCTATAAGCATGACAGAGGTATTGCTAATATAAGGAATAATATAGAATCACAAAATTTGGATTTGATA
345    G  S  T  Y  K  H  D  R  G  I  A  N  I  R  N  N  I  E  S  Q  N  L  D  L  I

1108  CCCCACAGTAGTTCAGTGTTCAAAGGCACTGATTTCGTACATTCAGTAAAGAAATTCTTAAGGGTTCGTATCTTC
370    P  H  S  S  V  F  K  G  T  D  F  V  H  S  V  K  K  F  L  R  V  R  I  F

1183  ACAAAAATCGAATCAGAAGATGATTACATATTGAGTGGCGAAAGTGTGATGGATAGGGATAGTGAAAGTGAAGAA
395    T  K  I  E  S  E  D  D  Y  I  L  S  G  E  S  V  M  D  R  D  S  E  S  E  E

1258  GCTGAAACGAAAGATATCAGAAAGCAAATCCAACTTTTGAAAAAGATCATTTTTGAAAAGAACTGATGTACCAA
420    A  E  T  K  D  I  R  K  Q  I  Q  L  L  K  K  I  I  F  E  K  E  L  M  Y  Q

1333  ATAAGAAAGAATGCGCTTTGTTGATTCCTATGGTGTCAGTATTGAAACGAAACAAGTAATAATTGAACTA
445    I  K  K  E  C  A  L  L  I  S  Y  G  V  S  I  E  N  E  N  K  V  I  E  L

1408  CCTAACGAAAAATTTGAAATCGAGTTGTTGTCCCTTGACGATGACTCCATTGTCAATCATGAACAAGACTTACCA
470    P  N  E  K  F  E  I  E  L  L  S  L  D  D  D  S  I  V  N  H  E  Q  D  L  P
```

FIG. 5D

```
1483  AAATCAACGACAAGAGAGCAAATTTAATGCTTGTTGTTATGTTGAGACTATTATTAGTCGTTATATTCAAGAAAACA
495      K  I  N  D  K  R  A  N  L  M  L  V  M  L  R  L  L  L  V  V  I  F  K  K  T

1558  TTACGATCGAGAATAAGCTCACCCCACGGACTGATCAATTTGAATGTTGACGATGATATCTTAATAATACGTCCC
520      L  R  S  R  I  S  S  P  H  G  L  I  N  L  N  V  D  D  D  I  L  I  I  R  P

1633  ATTCTTGGTAAAGTTCGGTTTGCTAATTACAAACTGTTACTAAAAAAAATCATAAAGGATTACGTGCTCGATATA
545      I  L  G  K  V  R  F  A  N  Y  K  L  L  K  K  I  I  K  D  Y  V  L  D  I

1708  GTTCCTGGCTCAAGTATAACAGAAACGGAAGTTGAGAGAGAACAACCTCAAGAAAATAAAACATTGATGATGAA
570      V  P  G  S  S  I  T  E  T  E  V  E  R  E  Q  P  Q  E  N  K  N  I  D  D  E

1783  AATATAACTAAATTAAATAAAGAGATCCGTGCCTTCGATAAACTATTGAATATACCTAGACGTGAACTCAAAATA
595      N  I  T  K  L  N  K  E  I  R  A  F  D  K  L  L  N  I  P  R  R  E  L  K  I

1858  AATCTACCATTAACTGAGCACAAAAGCCCTAATCTAAGTTTAATGCTCGAAAGTCCTAACTATTGTAACGCACTC
620      N  L  P  L  T  E  H  K  S  P  N  L  S  L  M  L  E  S  P  N  Y  C  N  A  L
```

FIG. 5E

```
1933  ATTCACATCAAGTTTTCAGCTGGTACGGAAGCCAACGCAGTGTCCTTTGACACAACATTTTCTGATTTTAAAGAA
 645   I  H  I  K  F  S  A  G  T  E  A  N  A  V  S  F  D  T  T  F  S  D  F  K  E

2008  GTAGAGGACTTCCTACATTTTATTGTCGCTGAGTACATCCAGCAAAAGAAGGTGTAATATCCTGAGTCACTCCTT
 670   V  E  D  F  L  H  F  I  V  A  E  Y  I  Q  Q  K  K  V  *
```

FIG. 6A

```
-432  GATCTTCAGTATCTCCGCGAACGCTACAACAATGGCCATTGCAGCAGCTAAAC
-357  CTCCACTAATTAAGGTATTTGGCGTAAATTGCTGAATAATGAAAAAAGTGAGTACGGCAGTACCACCATCGCTG
-282  CAGTAAACAGCATAAGTTTATTAATCACCGCACGAGGAACATCTACAGGCCATTATTGATTCTTTGAAGTCTTG
-207  GTTAGTTTCTACTATGCTTTCCAGTATTGCGTTCATTTTAGCTTGCCAGGTTAGTAATATATAGTGAGAGCTCTT
-132  TTGCCTTTCTTTTATTGAAAAAAATAAACCTAGAAATATCAAGACAAACAACCAAAATAA
 -57  AAAAAAGGTAGAAAATTGAATTTTCCAGCCAAGGTATTCCATATTAAGAGAAAAAGATGGTTCAGCAACTAAGC
   1                                                             M  V  Q  Q  L  S

19  CTTTTTGGATCTATTGGTGATGACGGCTACGATTACTAATTTCAACTTTGACCACATATCAGGTAATCCTCCG
   7   L  F  G  S  I  G  D  D  G  Y  D  Y  *  F  Q  L  *  P  H  I  S  G  N  P  P

94  CTACTGTATAACAGTTTATGCACTGTCTGGAAACCAAATCCATCTTACGACGTCGAGAACGTGAACTCTAGAAAC
  32   L  L  Y  N  S  L  C  T  V  W  K  P  N  P  S  Y  D  V  E  N  V  N  S  R  N

169  CAATTGGTTGAACCAAATAGAATAAAACTTTCCAAAGAGGTGCCATTTTCTTACCTGATCGATGAAACAATGATG
  57   Q  L  V  E  P  N  R  I  K  L  S  K  E  V  P  F  S  Y  L  I  D  E  T  M  M

244  GATAAGCCATTAAACTTTAGAATCTTTAAAGTCTTTTACAAACGATAAAATCCCGCTTAACTATGCTATGACACGG
  82   D  K  P  L  N  F  R  I  L  K  S  F  T  N  D  K  I  P  L  N  Y  A  M  T  R
```

```
319  AATATCTTGCACAACACAGTTCCGCAAGTCACCAACTTCAACAGCACAAACGAAGATCAAAACAACAGTAAGCAT
107   N  I  L  H  N  T  V  P  Q  V  T  N  F  N  S  T  N  E  D  Q  N  N  S  K  H

394  ACAGAAGATACTGTAAATGAAAGTCGAAACAGCGATGACATCATAGATGTCGACATGGATGCAAGTCCCGCCCCT
132   T  E  D  T  V  N  E  S  R  N  S  D  D  I  I  D  V  D  M  D  A  S  P  A  P

469  TCAAAACGAGTCATGTTCCCCTTGGTCATTGCAAATTTCAGATATCCTGCTGCAGGAAACAATAGAAGTGTTTCA
157   S  N  E  S  C  S  P  W  S  L  Q  I  S  D  I  P  A  A  G  N  N  R  S  V  S

544  ATGCAAACGATAGCTGAGACTATCATATTATCTTCAGCTGGCAAAAACTCTTCAGTATCCTCGCTCATGAACGGA
182   M  Q  T  I  A  E  T  I  I  L  S  S  A  G  K  N  S  S  V  S  S  L  M  N  G

619  TTGGGTTATGTATTCGAATTTCAGTATCTTACAATTGGTGTGAAATTTTTTATGAAGCATGGTTAATACTTGAG
207   L  G  Y  V  F  F  Q  F  Q  Y  L  T  I  G  V  K  F  F  M  K  H  G  L  I  L  E

694  TTACAAAAAATTTGGCAAATAGAAGAAGCAGGCAATTCACAAATAACAAGCGGAGGGTTCCTTTTAAAAGCATAC
232   L  Q  K  I  W  Q  I  E  E  A  G  N  S  Q  I  T  S  G  G  F  L  L  K  A  Y

769  ATCAATGTTAGTAGGGGACCGATATCGATCGTATAAACTATACAGAGACTGCCTTGATGAACTTAAAAAGGAA
257   I  N  V  S  R  G  T  D  I  D  R  I  N  Y  T  E  T  A  L  M  N  L  K  K  E
```

FIG. 6C

```
 844  CTACAAGGCTATATAGAGTTAAGTGTACCCGATAGACAGTCAATGGACTCGAGGGTAGCACATGGAAATATTCTA
 282   L  Q  G  Y  I  E  L  S  V  P  D  R  Q  S  M  D  S  R  V  A  H  G  N  I  L

919  ATATAATCATTGGCACCTGGGCATATTTTACAAATTCACTCATATAGTTATACAGAACAACAGTAACCACTTT
 307   I  *

994  TAATGTACAGGTATTTCTATATCTACAAACAAAATGTGTAGTTATATATCTAATGTTGCTATACCGAGGAATTA
1069  TAAAGTAATAAAGATGTTAAATTAAAAGACAAAAATTTTGAGAGGCTATTGGAAAAGAGAAAACTATTTCTT
1144  GGAATCTAGTTTATTCAGTTTGCTTCTCTTTTTGTTTGGCAATTGCTTCTCTTTTTAAGTTCTCAGCTTGTTC
1219  CTCCTTTTTAGCATTAGAATACTTCATTTTTGTAAAGTTCTTTGTTGTTACTCATCATTATCATTTTCAA
1294  TTTCTTTCTTTCTCTTCTTCATCCACCTTTCTCTTTTTGTCTTTGACTTATTGACATCCTTATCAGCTTCTGA
1369  AGTTTCAGAATATTGATACCTTGTGCTTCCAATTCAAGCTCTTTTTGAGCTTGTAGCTTCTTCGTCATCGTCATC
1444  ATCTTCTTCTCCAGCAACAACTTCTTGATC  1473
```

FIG. 7A

```
-285  GATCGTTGTTGTAGACTCTCTGGAAGAAAGTGCAAGAGGGCCGGTGGCTTTGGTAGCACTGGTAACTAACTTAG
-210  TGTATATACTTTGGCACACTTGTATATAATGTATAAATCCAGATAAATCCAGTGTGACCCGGACTGAATTACT
-135  GAAACTTTGAAGTGTTAAGGAAATTGTACTGCCATTAACGCATTACCTATCACTTAGTAGCATGCATAAGCCA
 -60  TGGGCTAATCATAACAGATTGTGATATAGGCATCCTGTACTCCCTTTTTTTACAAGAAAATGAGCAACCAGCA
   1                                                           M  S  N  Q  A

16  CTATATGAGAAACTCGAACAAACCAGACGATTCTGTCCGTGAAGCTGGCGAATTGATAAATATGACTACGATA
   6   L  Y  E  K  L  E  Q  T  R  T  I  L  S  V  K  L  A  E  L  I  N  M  T  T  I

91  GCCGATAGAAATGATGATGACGAGGGTTCATTCGCACAAGAAATTCTGAGCTCGCTGTGGCCACGACCAGTGTG
  31   A  D  R  N  D  D  E  G  S  F  A  Q  E  N  S  E  L  A  V  A  T  T  S  V

166  ATGATGGTGAATAACCAGACCATGCAATTGATTAAAAATGTTCAAGACTTGTTGATCCTGACCAGATCGATAAAAA
  56   M  M  V  N  N  Q  T  M  Q  L  I  K  N  V  Q  D  L  L  I  L  T  R  S  I  K
```

```
241  GAGAAATGGCTACTGAACCAAATTCCTGTAACGGAACACTCAAAAGTGACTCGTTTTGACGAGAAGCAGATAGAG
 81    E  K  W  L  L  N  Q  I  P  V  T  E  H  S  K  V  T  R  F  D  E  K  Q  I  E

316  GAATTACTGGATAACTGTATAGAAACTTTCGTTGGCGGAAAAACTACGTAAAAAGGCGGTATTTATCTATTATTT
106    E  L  L  D  N  C  I  E  T  F  V  A  E  K  T  T  *

391  GGCCAAAAAAAAAAAAAAATACATACTACATATACGCCATAAAAATCTCTGCATCTATCTTATTTCC
466  CATTATTTGGACAAATGCTTACGTCCTAATGTCCCTCGAGTCGAATGCCGGGCTCCTAATAGGGTCTGTA
541  ATCTTATAAACGGGTTCATTAGTGTCTTTACGTATAGTTCGTGTACCCTCTTGGTAGAATGACCTCATATTATTG
616  TCGTCAATAACTACGCTACTGTTGGCTGAGTCCCATGGATCATCACGAACTTCATCCCACTATAGCTAAATATAA
691  GCCGTTATTGCTAGTCCATAAAAATGATC  719
```

FIG. 8A

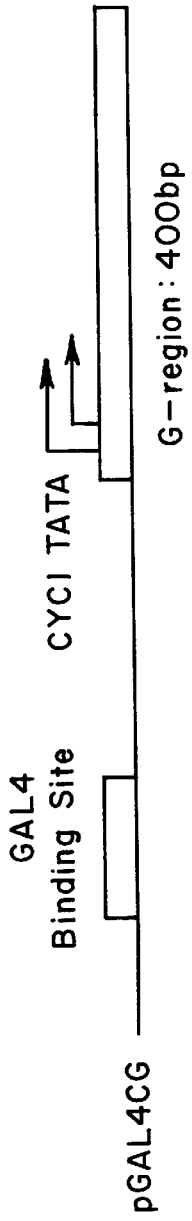

pGAL4CG

GAL4 Binding Site

CYCl TATA

G-region: 400bp

− Activator

| Extract: | WT | | | | srb5Δ | | | |
|---|---|---|---|---|---|---|---|---|
| SRB2: | − | + | − | + | − | + | − | + |
| SRB5: | − | − | + | + | − | − | + | + |

FIG. 8B

+ Activator

| Extract: | WT | | | | srb5Δ | | | |
|---|---|---|---|---|---|---|---|---|
| SRB2: | − | + | − | + | − | + | − | + |
| SRB5: | − | − | + | + | − | − | + | + |

FIG. 8C

− Activator

| Extract: | WT | | | | srb2Δ, srb5Δ | | | |
|---|---|---|---|---|---|---|---|---|
| SRB2: | − | + | − | + | − | + | − | + |
| SRB5: | − | − | + | + | − | − | + | + |

FIG. 8D

+ Activator

| Extract: | WT | | | | srb2Δ, srb5Δ | | | |
|---|---|---|---|---|---|---|---|---|
| SRB2: | − | + | − | + | − | + | − | + |
| SRB5: | − | − | + | + | − | − | + | + |

FIG. 8E

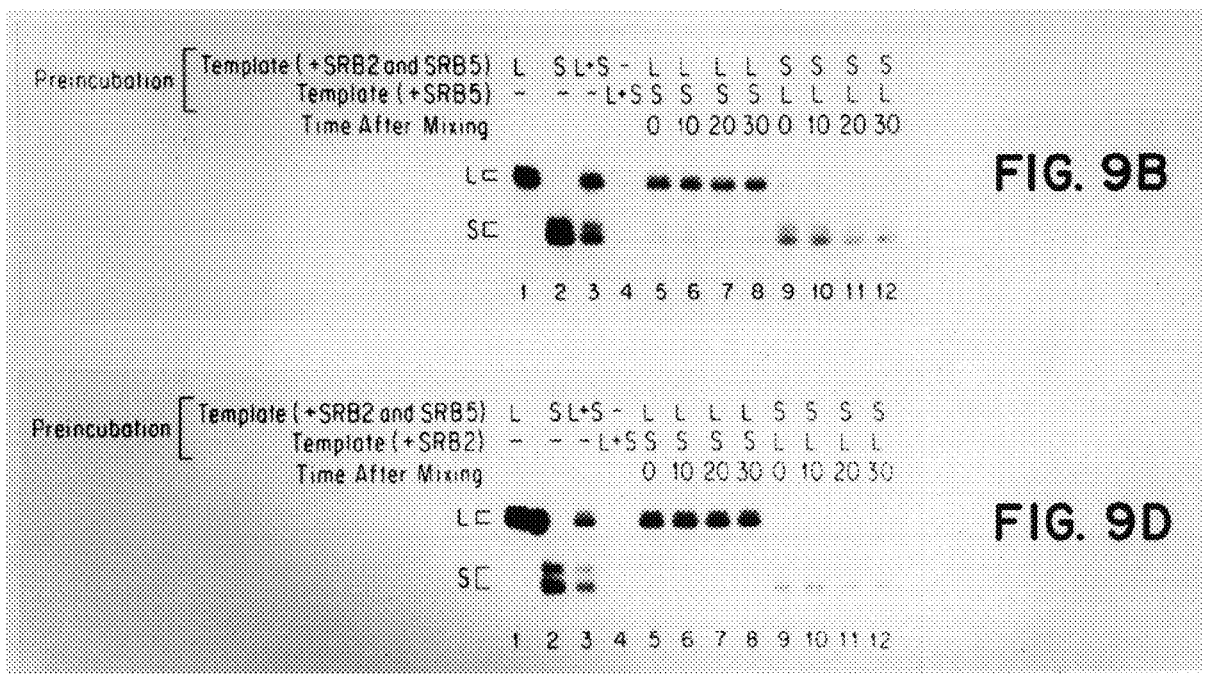

C

| holoenzyme | − | + | + | + |
|---|---|---|---|---|
| factor a | + | − | + | + |
| TBP | + | + | − | + |

FIG. 14

| Yeast | Rat | Human |
|---|---|---|
| d (TBP) | τ (native TATA factor) | TFIID |
| e (SUA7) | α | TFIIB |
| b | δ | TFIIH (BTF2) |
| g | βγ | TFIIF (RAP30/74) |
| a | ε | TFIIE |
| TFIIA | | TFIIA |

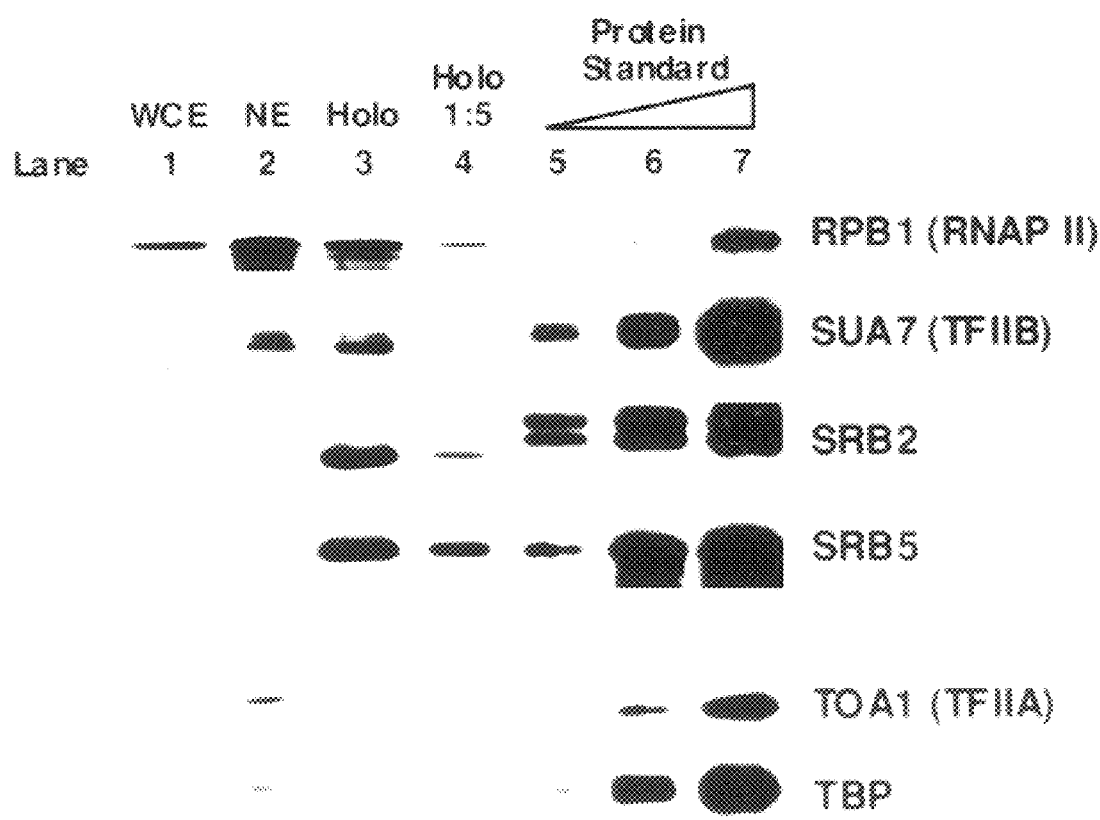

FIG. 16A

| Protein | Amount/ μg holoenzyme | MW (in kD) | Molecules/ RNA polymerase II |
|---|---|---|---|
| RNA polymerase II | 200 ng | 500 | 1.00 |
| factor e (SUA7) | 12 ng | 41 | 0.73 |
| SRB2 | 11 ng | 23 | 1.19 |
| SRB5 | 15 ng | 35 | 1.07 |
| TOA1 | — | 31 | — |
| TBP | — | 27 | — |

FIG. 16B

| Protein | Fold enrichment (holoenzyme vs. NE) | Percent in holoenzyme (approx.) |
|---|---|---|
| RNA polymerase II | 25 | 6 % |
| factor e (SUA7) | 50 | 12 % |
| SRB2 | 600-700 | 65 % |
| SRB5 | 600-700 | 65 % |
| TOA1 | -- | -- |
| TBP | -- | -- |

FIG. 19A

```
-648  TCGATGATGTCTCTTATTCTTTCAACCAGCTCGAGCCCCTGCAAACTTAAGCTAAGACAGAAAATGAAAAAAA
-573  AAAAAAAAAATCTAAATTCAAAGAATCAGCTTATAAAACATATTTTTCTTGAAGTATCATTCATTCGTTTTT
-498  ACTCGTTAATCTCATTCGTTCCTCATTCTTTGTTCTTTATTCGGCTATTTTTCACTATTAA
-423  AATAACTAGAGCTAACACAATATATTTCTCTGCTTAGTTACAAAACAAGGACATTCATTTAACTTGGCGTATC
-348  CCATACATTCGTTTATTATATATCTTTTAAACACAATTCTTTACAGTTAAACTTTCTGATTTATTATATA
-273  TTACTTAAGATTGTTCATATAACTATATGCTTATATGCGTGAAGTGCGCTTTTGTAGAACATGGCT
-198  GTTTCTGTAGAAGCCTTGTCTTTCTCTGTAATCCTTAAAGGCCAACCGTACGTGCTTAATTACAAGCTTTGTTC
-123  GCATTGCAAGAAAGTTAGAAAAAAATCAATTCGAAAGATAATTATATTCAAACGGTAAACCATTGGTTAAAA
-48   GAGGGACATAACATTCACTAGTTCAATACATTATATGCTCTTTAACATGACAGATAACACAATTGCAG
                                                        M  T  D  R  L  T  Q  L  Q
 28   ATATGTTTAGACCAAATGACGGAGCAATTCTGTGCTACTTTAAACTACATAGATAAGAACCATGGTTTTGAACGA
       I  C  L  D  Q  M  T  E  Q  F  C  A  T  L  N  Y  I  D  K  N  H  G  F  E  R
103   TTGACCGTAAATGAACCTCAGATGTCCGATAAGCATGCCACAGTAGTACCTCCTGAGGAATTTCTAACACGATA
       L  T  V  N  E  P  Q  M  S  D  K  H  A  T  V  V  P  P  E  E  F  S  N  T  I
178   GATGAGCTATCCACGGACATTATACTTAAAACAAGACAGATAAACAAGCTTATTGACTCGTTACCTGGTGTTGAC
       D  E  L  S  T  D  I  I  L  K  T  R  Q  I  N  K  L  I  D  S  L  P  G  V  D
```

```
253  GTTCAGCTGAAGAGCAATTAAGGAAGATTGATATGTTGCAGAAAAAGCTAGTTGAAGTGGAAGACGAAAAAATT
      V  S  A  E  E  Q  L  R  K  I  D  M  L  Q  K  K  L  V  E  V  E  D  E  K  I

328  GAGGCCATCAAAAAGAAGGAGAAACTTTTAAGGCACGTTGATTCTTTAATTGAAGATTTTGTAGATGGCATTGCA
      E  A  I  K  K  K  E  K  L  L  R  H  V  D  S  L  I  E  D  F  V  D  G  I  A

403  AACTCAAAAAAGAGCACATAAACTTAAGTTTTACAAAGAATTTGCGAACAGAGAGGACAGAAAATGTACTATAGTT
      N  S  K  K  S  T  *

478  ATATGGCAGAGAGTTAAGCGTTAAGCGTATGTATGTTATTCTTATAAATAATTGTGCTACTCTATTTGTACCGGAGAATTATTG
553  AAGCAATGGGAGAAAAATCATAATGGAGAAAATCTTCTACGAGTTACTTTGCAAGGCAATCTAACGATTCTAAA
628  AGACACAATACACTAAAGAAAAAACTTTGAAGTACAGTTTTTTCCCCAAGTTGAAGTGTGGACTCATTGTGAAG
703  ATGTAAAAATGTAAAAACCAACGACACTGACAATGCACTCCCAGCAAATTCATTGTAGACCTCCCATTTGATAGAAAAG
778  GAAGGTTCAGCAGTTGTCCACGGATTCCAAGATATCATTCTCTTACATTGCACGCACATGAAAATGATC  846
```

FIG. 20A

```
-240  TGATCATAGAAGGAAACGTGTTGCAATGA ATTGAGATTCGTCTCACACTTCGACTGGTC AAAAATTGGCAAGTTTATACCTCACGGCTTG
-150  AAAAGAAGGCAAGTCATCGAGCAGTGCTAT TTAAAATTTATACCATTGAAAAGGGCGATT TGGTTGATAAAGTGCTGCTATTTTATCGAA
 -60  TGGAAATCGACCAGAAAGAAGAGAGGTCA AATGCTGCTGGGCAGAGATGATGCCATTCC ATGCACCTGCTAAAGACTGACGGATACC
                                                                        M  H  L  L  K  D  W  T  D  T       10
  31  TTTGTATACATCCTGAAAAGCTCATCTTT GATATGACAAATCACTATAACGATTCTCAA CAACTGCGTACGTGAAGAGGCAGATTTCT
       F  V  Y  I  L  E  K  L  I  F  D  M  T  N  H  Y  N  D  S  Q  Q  L  R  T  W  K  R  Q  I  S       40
 121  TATTTTTAAAACTTTGGGAATTGCTAC TCACTAAGAATTGATCAATAAGGAAATCTTT CATCATTGGCTTGTAGAGTTTATAAATAAG
       Y  F  L  K  L  L  G  N  C  Y  S  L  R  L  I  N  K  E  I  F  H  H  W  L  V  E  F  I  N  K       70
 211  ATGGAAAACTTCGAATTTTGCCATTATCT TTACATATTTGATGATTTTTGGAACGAC ATCTGCCAAATTGATACAAATGCTCCTGTT
       M  E  N  F  E  F  L  P  L  S  L  H  I  L  M  I  F  W  N  D  I  C  Q  I  D  T  N  A  P  V      100
 301  GCGGCTACAATAACATCAAGTCAAAAGAG CCCTTCTTTCTGTAACAAAATCACTGAT ATGCTATTGCACAAATATATATGTTTCC
       A  A  T  I  T  S  S  Q  K  E  P  F  F  L  V  T  K  I  T  D  M  L  L  H  K  Y  Y  I  V  S      130
 391  AGCAGCAAATCAATGATAAATGACGAGAAC TACATCATCAATGATATAAGAAAACAAC AAGATAAAGTTGAATATTCTCAAAATATTA
       S  S  K  S  M  I  N  D  E  N  Y  I  H  N  D  I  K  K  N  N  K  I  K  L  N  I  L  K  I  L      160
 481  TCCAGTTTAATTTTGAAATTTTCAAGAA CAATCTTTAGAGTGTGTTTATATTTCCACA TCTAACTGGGAAATTTACAAGCCCTACTT
       S  S  L  I  L  K  I  F  Q  E  Q  S  L  E  V  F  I  F  P  T  S  N  W  E  I  Y  K  P  L  L      190
 571  TTTGAAATAGTCTCAAACGCCGACACTAAT CAAAATTCTGATATGAAGAAAAATTAGAG TTAATTAGTTACAGAAACGAGTCATTGAAG
       F  E  I  V  S  N  A  D  T  N  Q  N  S  D  M  K  K  K  L  E  L  I  S  Y  R  N  E  S  L  K      220
 661  AATAATTCTTCTATACGAAACGTAATAATG TCTGCCAGCAACGCAAATGACTTTCAATTA ACTATCGTCACCTGTAAACAATTCCAAAA
       N  N  S  S  I  R  N  V  I  M  S  A  S  N  A  N  D  F  Q  L  T  I  V  T  C  K  Q  F  P  K      250
 751  CTATCATGCAATTCATCAATTAAATTGTATAGAT ACTCAGTTCACCAAGCTACTGACGATAAC CCTACAGAATTCGATTGGCCCACTTACGTT
       L  S  C  I  Q  L  N  C  I  D  T  Q  F  T  K  L  L  D  D  N  P  T  E  F  D  W  P  T  Y  V      280
 841  GACCAAAATCCCTTACAATGCATAAAATT ATTCAATTAATTCTCTGGTCCATACATCCA TCAAGGCAATTGATCACTATGAATCTAAT
       D  Q  N  P  L  T  M  H  K  I  I  Q  L  I  L  W  S  I  H  P  S  R  Q  F  D  H  Y  E  S  N      310
 931  CAACTGGTAGCGAAATTATTACTATTGCGA ATAAATTCAACAGATGAGGATTTGCACGAA TTCCAGATAGAAGATGCCATTGTCATTG
       Q  L  V  A  K  L  L  L  R  I  N  S  T  D  E  D  L  H  E  F  Q  I  E  D  A  I  W  S  L      340
1021  GTTTTCCAATTAGCCAAAAATTTTTCGGCC CAAAAGAGGGTGTATCATATATGATGCCT TCTTTGTATGCCTGCTTAATATACTAATT
       V  F  Q  L  A  K  N  F  S  A  Q  K  R  V  V  S  Y  M  M  P  S  L  Y  R  L  L  N  I  L  I      370
```

```
1111  ACTTTATGGCATCATTAAGGTCCCTACGTAT ATCAGAAAGCTAATCAGTTCCGGCCTACTT TATCTCCAAGATTCCAATGATAAGTTGTG    400
       T  Y  G  I  I  K  V  P  T  Y    I  R  K  L  I  S  G  L  L       Y  L  Q  D  S  N  D  K  F  V
1201  CATGTCCAGCTGTTAATTAACTTGAAAATT TCACCGTTGATGAAAGTCAATACAATATG GTATTGAGGAACGTTATGAATATGACGTT    430
       H  V  Q  L  L  I  N  L  K  I    S  P  L  M  K  S  Q  Y  N  M    V  L  R  N  V  M  E  Y  D  V
1291  AAATTTATGAAATTTTTAATTTCGACCAA CTCGTGGAAATCACAGAACAAATCAAAATG CGAATACTCTCCAATGATATAACTAATTTG    460
       K  F  Y  E  I  F  N  F  D  Q    L  V  E  I  T  E  Q  I  K  M    R  I  L  S  N  D  I  T  N  L
1381  CAACTGTCGAAAACTCCTCTGAGCATTAAA ATCATGGTTGCAGAATGGTACTTATCACAT TTATGTTCCGGTATTTTATCTAGTGTTAAC    490
       Q  L  S  K  T  P  L  S  I  K    I  M  V  A  E  W  Y  L  S  H    L  C  S  G  I  L  S  S  V  N
1471  CGCACAGTGTTGCTAAAATATTCAAGATT TTTTGTATCGATCGGAGGTTTTCCACCAC TTTTTAAGTGGATCGAGTTTATGTCTAC    520
       R  T  V  L  L  K  I  F  K  I    F  C  I  D  L  E  V  F  H  H    F  F  K  W  I  E  F  I  V  Y
1561  CATCAATTGCTAAGTCATGATAGAATCTCTG GAGGCATTGATGGACATCTGCTATGCTAC CAAAAATTGTTCTCACAATTCATTAATGAC    550
       H  Q  L  L  S  D  I  E  S  L    E  A  L  M  D  I  L  L  C  Y    Q  K  L  F  S  Q  F  I  N  D
1651  CATATTCTTTTTACGAAGACGTTCATATTC ATTTACAAGAAGTTTGAAAGAAAAAGAC GTGCCTGCTTATAATGTGACTTCATTTATG    580
       H  I  L  F  T  K  T  F  I  F    I  Y  K  K  V  L  K  E  K  D    V  P  A  Y  N  V  T  S  F  M
1741  CCATTCTGAAATTTTTATGAAAAACTTC CCTTTGTTTTAAGGTGGATAACGATTTA AGGATTGAGTTACAATCTGTTTACAATGAT    610
       P  F  W  K  F  F  M  K  N  F    P  F  V  L  K  V  D  N  D  L    R  I  E  L  Q  S  V  Y  N  D
1831  GAGAAATTGAAAACTGAGAAGCTGAAGAAT GATAAATCAGAAGTCTTGAAGGTGTATTCC ATGATCAATAATTCAAACCAAGCTGTTGGA    640
       E  K  L  K  T  E  K  L  K  N    D  K  S  E  V  L  K  V  Y  S    M  I  N  N  S  N  Q  A  V  G
1921  CAGATCTTGGAATTTCCCGAGGTGTTTCAA GTAAACATCAGGTTTCTACTACACAACTCC GAGATCATTGATACAAATACAAGCAAACAG    670
       Q  I  L  E  F  P  E  V  F  Q    V  N  I  R  F  L  L  H  N  S    E  I  I  D  T  N  T  S  K  Q
2011  TTCCAGAAAGCACGAAACAATGTCATGCTT TTGATTGCCACTAACTTGAAGGAGTACAAT AAATTTATGTCCATTTCTTGAAAAGGAAA    700
       F  Q  K  A  R  N  N  V  M  L    L  I  A  T  N  L  K  E  Y  N    K  F  M  S  I  F  L  K  R  K
2101  GACTTTACTAACAAAATTTAATTCAATTG ATCTCTCTAAAACTTCTAACTTTTGAAGTG ACGCAGAATGTGTTGGGGCTGAGTATATT    730
       D  F  T  N  K  N  L  I  Q  L    I  S  L  K  L  L  T  F  E  V    T  Q  N  V  L  G  L  E  Y  I
2191  ATTCGATTATTACCAATAACTTGGAAAAT AATGACGGCTCATATGTCTGTGTTTTGAAG TATCATAAAGAACAATTCATAAAGTCAAAT    760
       I  R  L  L  P  I  N  L  E  N    N  D  G  S  Y  G  L  F  L  K    Y  H  K  E  Q  F  I  K  S  N
2281  TTTGAGAAAATTTTACTTACATGTTATGAA TTAGAAAAAAAATATCATGGCAACGAATGT GAAATAAATTATTATGAGATCCTATTGAAA    790
       F  E  K  I  L  L  T  C  Y  E    L  E  K  K  Y  H  G  N  E  C    E  I  N  Y  Y  E  I  L  L  K
```

FIG. 20C

```
      B
2371  ATTTAATAACTTATGGTCATCTCCCAAA  TTACTTGCAACATCTACAAAATCATTATG  TTGTTATTGAATGATAGCGTGAAAACTCA  820
       I  I  T  Y  G  S  S  P  K    L  L  A  T  S  T  K  I  I  M    L  L  L  N  D  S  V  E  N  S
2461  TCTAATATTTTGGAGGATATTTGTACTAC  TCAACTTGTCCGTCGGAAACCGATCTTAAC  GATATTCCATTGGTAGTGACAACCAGAC   850
       S  N  I  L  E  D  I  L  Y  Y    S  T  C  P  S  E  T  D  L  N    D  I  P  L  G  S  G  Q  P  D
2551  AATGACACTGTTGTAACCAACGATGATAAA  AGTGACGATGATGATCACACAGTCGACGAA  ATTGATCATGTAGAATATACGTTATGATG  880
       N  D  T  V  V  T  N  D  D  K    S  D  D  D  H  T  V  D  E      I  D  H  V  E  Y  Y  V  M  M
2641  GACTTTGCCAATCTTTGGGTTTTCCAAGCG  TTTACCTGTTTCTGCATCAAAAAATCATG  GAGAATAATGAGCCAGCAATGGCAATGAA   910
       D  F  A  N  L  W  V  F  Q  A    F  T  C  F  C  I  K  K  I  M    E  N  N  E  P  A  M  A  M  E
2731  GACTTGAAGAACTTCATATTCCAAATTATC  GAAATAACTAATTCTAATGATTATGTTCA  CAAATATTTGACCAACTGAAGGATATGCAG  940
       D  L  K  N  F  I  F  Q  I  I    E  I  T  N  S  N  D  L  C  S    Q  I  F  D  Q  L  K  D  M  Q
2821  ACCATTGAGATGATAACCCAAATAGTGGAG  AAAGATTTCTGCACTTCTTGTTTGCAAAAC  AACAACCAAAAGATAGATGATAATTACATC  970
       T  I  E  M  I  T  Q  I  V  E    K  D  F  C  T  S  C  L  Q  N    N  N  Q  K  I  D  D  N  Y  I
2911  GTTGTGGTGATCGAGATTATAACGTCATTA  TCGATGAGGTTTCAAAGAGAAACTTCTGT  ATGATAGTTATTTCCATGGAGAACTATCAT  1000
       V  V  V  I  E  I  I  T  S  L    S  M  R  F  Q  R  E  T  S  G    M  I  V  I  S  M  E  N  Y  H
3001  TTACTAATAAGATCATAAGACAATTAAGT  GAACTGAACGAAGGAAATTTATCTAAGACA  GAAATCCAAATAGATGCCGTCTTGAAAATT  1030
       L  L  I  K  I  I  R  Q  L  S    E  L  N  E  G  N  L  S  K  R    E  I  Q  I  D  A  V  L  K  I
3091  TTTAGCTTTCATCAGGATTCCATTTTCCAA  CGCATCATCGCTGATTATCAGCTGATAAA  CCCACAAGTCCATTCATTGATAGCATATGC  1060
       F  S  F  H  Q  D  S  I  F  Q    R  I  I  A  D  L  S  A  D  K    P  T  S  P  F  I  D  S  I  C
3181  AAGCTGTTTGATAAAATATCATTTAATTTA  AGATTGAAGCTGTTCTTGTACGAAAATTTG  TCTTCATTGAAATCATTCGCCATCTATTCA  1090
       K  L  F  D  K  I  S  F  N  L    R  L  K  L  F  L  Y  E  I  L    S  S  L  K  S  F  A  I  Y  S
3271  TCCACAATTGATGCCCCAGCATTCCACACA  AGCGGTAAGGTCGAACTACCGAAGAAATTG  CTGAACTTACCACCATTCCAAGTGTCCCTCT  1120
       S  T  I  D  A  P  A  F  H  T    S  G  K  V  E  L  P  K  K  L    L  N  L  P  P  F  Q  V  S  S
3361  TTCGTTAAGGAAACAAAACTTCATAGTGGC  GACTACGGGGAAGAAGATGCAGACCAA    GAAGAATCGTTTAGTTTAAATTTAGGAATC  1150
       F  V  K  E  T  K  L  H  S  G    D  Y  G  E  E  D  A  D  Q      E  E  S  F  S  L  N  L  G  I
3451  GGCATAGTTGAAATAGCGCACGAAAACGAA  CAGAAATGGCTCATTTATGACAAGAAGAT  CATAAATATGTCTGCACATTTTCCATGGAG  1180
       G  I  V  E  I  A  H  E  N  E    Q  K  W  L  I  Y  D  K  K  D    H  K  Y  V  C  T  F  S  M  E
3541  CCGTACCACTTCATCTCCAACTATAATACC  AAGTACACAGATGACATGGCTACAGGCAGT  AATGATACGACTGCGTTTAACGATTCCTGT  1210
       P  Y  H  F  I  S  N  Y  N  T    K  Y  T  D  D  M  A  T  G  S    N  D  T  T  A  F  N  D  S  C
3631  GTAAACCTGAGTCTTTTTGATGCTCGGTTT  GAGAGGAAAAATCCACATTGATCTCAGAAT  ATATCCAAATGGATAAATTATAAATTACC  1226
       V  N  L  S  L  F  D  A  R  F    E  R  K  N  P  H
3721  AATAACAGTAATTATGTGTCAGTTTTAATA  CCCAACCAATTG   3761
```

FIG. 21A

```
-147  GATCAAGTAGTGTAGTATTTATTGTAGTACACTCTTACAACAACCCTTTAAGACGAATGGTGTGAAATCGGAAAT
 -72  TACTTTGTTGAAGTAAGGTGTAACTATATATTTTAAGACGTTTAAGCTGGATATCAAGATCTGAGGAGTAGTATG
                                                                              M
   4  AGTTCTGACGCTTCCACGTACAGACTTGAGGATGTGTTTATCCAGCTTCTATAGAGTGGAGAAAATCAAAAGATC
      S S D A S T Y R L E D V L S S F Y R V E K I K K I
  79  AACTATCATCAGTACATTTCTAAAGCCCAAAACGATCAATGGTCTATCCAAATGGAATTCATGCTACGGAAGCAG
      N Y H Q Y I S K A Q N D Q W S I Q M E F M L R K Q
 154  GATCCAAAGACTCTAGTGCGCTGCTTTCAAGGGATTTATGGTGTTTCAGTATAAATGATGATCCGGTACCGACA
      D P K T L V A L L S R D L W C F S I N D D P V P T
 229  CCTCCTGCGATAGAACATAAACCAGTGAGCCCAGATAAAATCGGAACTTTCACTGCCGATTATCAAAGCCAAAC
      P P A I E H K P V S P D K I G T F T A D Y S K P N
 304  TTACCGCCACACTATGCTCTCTTTTTTTAAAAGCTTTAAGAAGAAAATTACATTAATTTGGCATTAGGTTCACAC
      L P P H Y A L F L K A L R R K I Y I N L A L G S H
 379  AATAAGCTAATACAATTTGGGAATGCCTGCATATCATTAAGCGGAGTGCCAAATTATCTCGTACAGCTAGAACCA
      N K L I Q F G N A C I S L S G V P N Y L V Q E P
 454  CACCTTTTTGTAAACGGAGATCTCACAGTGTCGTTATGTGCCAAGAACATGGGATTAGTACCAATGAAGGAGGAA
      H L F V N G D L T V S L C A K N M G L V P M K E E
```

FIG. 21B

```
529  AATTGGAAGAATCTTTCCTTTCAAAGCATGCGCTTTATTTAGCACCATCTGGAATAAGGATGCATTGGCCCCT
     N  L  E  E  S  F  L  S  K  H  A  L  Y  L  A  P  S  G  I  R  M  H  L  A  P

604  GCTTCCAAGCAAGGATACTTGATAACGCCACCAAAACATACAGAACTTCTCTTGACGACGTTAAGTGTATCTCAT
     A  S  K  Q  G  Y  L  I  T  P  P  K  H  T  E  L  L  L  T  T  L  S  V  S  H

679  GGTATAAACTTACAAATAAAAAAATTTGAAATGGGTTGCTGTGTTCCTGACTTAGGACATCTCAACGGCCAC
     G  I  N  L  Q  N  K  K  N  L  K  W  V  A  V  V  P  D  L  G  H  L  N  G  H

754  ACACCTACTATAGCTTCGTATTTAACTCCCTTACTTGAAGCAAAGAAGCTAGTATGGCCGCTGCATTTAATCTTC
     T  P  T  I  A  S  Y  L  T  P  L  L  E  A  K  K  L  V  W  P  L  H  L  I  F

829  GCCCAACCAGTAGCTGATATAGAAAATTCTACTTCCGGAGATCCATCAGAATTTCACTGTTTGCAAGATGCTCTG
     A  Q  P  V  A  D  I  E  N  S  T  S  G  D  P  S  E  F  H  C  L  Q  D  A  L

904  GATGCCATTGATGATTTCATACAATTAAAGCAAACAGCTGCCTATAGGACTCCAGGAAGTTCCGGGCGTATTGAGC
     D  A  I  D  D  F  I  Q  L  K  Q  T  A  A  Y  R  T  P  G  S  S  G  V  L  S

979  AGTAATATTGCTGGTACAAATCCCTTAAGCTCAGATGGAGCATATACAGAACAGTTTCAACATTATAAGAACAAC
     S  N  I  A  G  T  N  P  L  S  S  D  G  A  Y  T  E  Q  F  Q  H  Y  K  N  N

1054 TCAATTAGTTCTCAACCCGCTTCTTATCATTCTGTCCAAGAAACTAATAAGATATCTCCGAAAGATTTCTCCCCT
     S  I  S  S  Q  P  A  S  Y  H  S  V  Q  E  T  N  K  I  S  P  K  D  F  S  P
```

FIG. 21C

```
1129  AATTCACAGGCATTGATAAATTAATGCTGTCGCCCAGCGATCAATTGCTCCAGCTTTCTTAAATACCCCTAAT
       N  F  T  G  I  D  K  L  M  L  S  P  S  D  Q  F  A  P  A  F  L  N  T  P  N

1204  AATAACATCAATGAGAATGAATTATTTAATGATAGGAACAACTACAGTATCAAATGACTTAGAGAACAGCCCA
       N  N  I  N  E  N  E  L  F  N  D  R  K  Q  T  T  V  S  N  D  L  E  N  S  P

1279  CTGAAAACGGAACTGGAGGCAAATGGTAGATCACTCGAAAAGTAAATAATTCCGTGAGCAAGACAGGAAGCGTA
       L  K  T  E  L  E  A  N  G  R  S  L  E  K  V  N  N  S  V  S  K  T  G  S  V

1354  GACACACTTCATAATAAAGAGGGAACACTGGAACAGAACAGAACGAAAATCTGCCAAGTGATAAAGTGAC
       D  T  L  H  N  K  E  G  T  L  E  Q  R  E  Q  N  E  N  L  P  S  D  K  S  D

1429  TCTATGGTAGACAAGGAATTGTTTGGTGAGGATGAGGAAGATTATTGGCGATAGCAATAAATCGAATTCT
       S  M  V  D  K  E  L  F  G  E  D  E  D  E  D  L  F  G  D  S  N  K  S  N  S

1504  ACAAACGAATCGAACAAAAGTATATCGGACGAAATTACCGAGGATATGTTCGAAATGTCTGATGAAGAAGAAAAT
       T  N  E  S  N  K  S  I  S  D  E  I  T  E  D  M  F  E  M  S  D  E  E  E  N

1579  AATAACAATAAAGCATTAATAAAATAACAAGGAAATGCATACTGATCTTGGTAAAGATATTCCATTTTTCCC
       N  N  K  S  I  N  K  N  K  E  M  H  T  D  L  G  K  D  I  P  F  F  P

1654  TCATCTGAAAAACCGAATATCCGTACGATGAGCGGAACTACAAAAAGATTAAATGGAAAGAGGAAATATTTGGAT
       S  S  E  K  P  N  I  R  T  M  S  G  T  T  K  R  L  N  G  K  R  K  Y  L  D
```

FIG. 2ID

```
1729  ATTCCGATAGATGAAATGACCTTGCCAACGAGTCCATTATATATGGACCCAGGTGCGCCACTCCCTGTGGAAACA
       I  P  I  D  E  M  T  L  P  T  S  P  L  Y  M  D  P  G  A  P  L  P  V  E  T

1804  CCCCGCGATAGACGCAAAAGTGTGTTCGCTCCACTGAATTTTAACCCCATAATAGAAAACAATGTTGATAACAAA
       P  R  D  R  R  K  S  V  F  A  P  L  N  F  N  P  I  I  E  N  N  V  D  N  K

1879  TACAAAATCTGGAGGGAAATTTCCTTCAGTCCGTTGCAAAAGGAGGAAGCATTAAACTTTGATATTTCTATGGCG
       Y  K  S  G  G  K  F  S  F  S  P  L  Q  K  E  E  A  L  N  F  D  I  S  M  A

1954  GATCTTTCTAGCTCTGAAGAGGAAGAGGAAGAAGAGAACGGTAGCAGCGATGAGGATCTAAAGTCATTGAAC
       D  L  S  S  S  E  E  E  E  E  D  E  E  E  N  G  S  S  D  E  D  L  K  S  L  N

2029  GTACGGGACGACATGAAACCTTCTGATAACATCAGTACTAATACTAATATTCATGAGCCTCAATACATAAATTAC
       V  R  D  D  M  K  P  S  D  N  I  S  T  N  T  N  I  H  E  P  Q  Y  I  N  Y

2104  TCTTCGATCCCAAGTCTACAAGACTCTATTATAAAGCAAGAAAATTTCAATTCAGTAAACGATGCTAATATCACT
       S  S  I  P  S  L  Q  D  S  I  I  K  Q  E  N  F  N  S  V  N  D  A  N  I  T

2179  AGCAATAAGGAAGGCTTCAACTCTATTTGGAAAATTCCTCAAAATGATATACCACAGACCGAGTCACCACTGAAG
       S  N  K  E  G  F  N  S  I  W  K  I  P  Q  N  D  I  P  Q  T  E  S  P  L  K
```

FIG. 21E

```
2254  ACCGTTGATTCATCTATTCAACCCATAGAATCCAATATAAAGATGACCTTGGAAGATAATAATGTTACCAGTAAT
       T  V  D  S  S  I  Q  P  I  E  S  N  I  K  M  T  L  E  D  N  N  V  T  S  N

2329  CCGTCCGAATTTACGCCGAATATGGTAAATTCTGAAATTCTAACCTACCAAAGGACAAGAGTGGTATCCCCGAA
       P  S  E  F  T  P  N  M  V  N  S  E  I  S  N  L  P  K  D  K  S  G  I  P  E

2404  TTCACACCGGCGGACCCCAATTTATCTTTTGAATCATCAAGTAGTCTACCGTTTCTATTGAGACACATGCCGCTA
       F  T  P  A  D  P  N  L  S  F  E  S  S  S  L  P  F  L  R  H  M  P  L

2479  GCATCTATACCGGACATTTTCATCACGCCTACTCCCGTTGTTACAATTTCAGAAAAAGAACAAGACATCTTAGAT
       A  S  I  P  D  I  F  I  T  P  T  P  V  V  T  I  S  E  K  E  Q  D  I  L  D

2554  TTAATTGCAGAACAAGTCGTCACTGATTATATATCTTAGGAAACCTCGGTATTCCAAAGATCGCCTATAGGGGA
       L  I  A  E  Q  V  V  T  D  Y  N  I  L  G  N  L  G  I  P  K  I  A  Y  R  G

2629  GTTAAAGATTGCCAAGAAGGTTTAATAACAACCACAATGTTACAGTTATTTCCACTTCGGATAGATTAAATGGC
       V  K  D  C  Q  E  G  L  I  T  T  M  L  Q  L  F  S  T  F  D  R  L  N  G

2704  AATGATACGATCTCCAAATTCTATAACATGAAGCAGCCGTATGTTTTTGTAAAGAAACATCGAACTAATCAAA
       N  D  T  I  S  K  F  Y  N  M  K  Q  P  Y  V  F  V  K  K  H  H  E  L  I  K

2779  GTCAAACACGACTCTCAGCCATTTATTAAGTTCCTCAATTTCGCCCTCCAAATGAATAAAAAACTTCAAATCC
       V  K  H  D  S  Q  P  F  I  K  F  L  N  F  R  P  P  N  G  I  K  N  F  K  S
```

FIG. 21F

```
2854  TTATTATTAAGTTCATCTTTCAAGAAGATTGTCTGTCATTGCGCCAACTCTATCTCAAACATATATTAATCAA
       L  L  L  S  S  F  K  E  D  C  L  S  F  A  P  T  L  S  Q  T  Y  I  N  Q

2929  GAGTTAGGGTTTTGTGAGTTGCTTAAACTAATGAAGACCCCGGACTGATGTACTTGAAGGCATTTGAT
       E  L  G  F  C  E  L  L  K  L  T  N  E  D  P  P  G  L  M  Y  L  K  A  F  D

3004  AAAAACAAGTTACTGTTGTTAGCTGCGCAGATTGTTTCATACTGTTCTAATAATAAGAACTCCATCAAAAACGTG
       K  N  K  L  L  L  A  A  Q  I  V  S  Y  C  S  N  N  K  N  S  I  K  N  V

3079  CCACCAATATTAATAATTTTACCCCTTGGATAATGCAACTCTGACTGAATTAGTAGACAAGGCGAATATTTTCAG
       P  P  I  L  I  I  L  P  L  D  N  A  T  L  T  E  L  V  D  K  A  N  I  F  Q

3154  GTGATCAAGAACGAAGTTTGTGCCAAGATGCCTAACATTGAACTATATTTGAAAGTTATTCCTATGGATTTCATT
       V  I  K  N  E  V  C  A  K  M  P  N  I  E  L  Y  L  K  V  I  P  M  D  F  I

3229  AGAAACGTACTGGTGACAGTGGATCAGTACGTCAACGTAGCAATTTCTATATATAACATGCTGCCGCCAAAATCT
       R  N  V  L  V  T  V  D  Q  Y  V  N  V  A  I  S  I  Y  N  M  L  P  P  K  S

3304  GTAAAGTTCACCCACATTGCGCATACGCTGCCGGAGAAAGTGAATTTCAGAACCATGCAGCAACAGCAAATGCAA
       V  K  F  T  H  I  A  H  T  L  P  E  K  V  N  F  R  T  M  Q  Q  Q  M  Q

3379  CAGCAACAGCAACAGCAACAGCAGCAGCAGAATAACAGTACAGGATCATCTTCTATAATATATTATGACTCGTAC
       Q  Q  Q  Q  Q  Q  Q  Q  Q  N  N  S  T  G  S  S  S  I  I  Y  Y  D  S  Y
```

FIG. 21G

```
3454  ATCCACCTGGCATACTCGCGTAGTGTAGATAAAGAGTGGGTTTTTGCAGTCTCTTTCAGATAGCTATGGACAAGGC
       I  H  L  A  Y  S  R  S  V  D  K  E  W  V  F  A  A  L  S  D  S  Y  G  Q  G

3529  AGCATGACGAAAACGTGGTACGTCGGGAATTCCAGAGGAAAATTTGACGACGCATGTAATCAAATATGAATATC
       S  M  T  K  T  W  Y  V  G  N  S  R  G  K  F  D  D  A  C  N  Q  I  W  N  I

3604  GCCCTAAATTTAGCGTCTAAAAAAATTCGGAAAAATATGTCTAATTTTAACTAGATTGAATGGCATACTGCCGAT
       A  L  N  L  A  S  K  K  F  G  K  I  C  L  I  L  T  R  L  N  G  I  L  P  D

3679  GATGAATTGATGAATTGGAGGAGACTTTCTGGTAGGAATATACATCTTGCTGTGGTGTGTGGATGACAACTCT
       D  E  L  M  N  W  R  R  L  S  G  R  N  I  H  L  A  V  V  C  V  D  D  N  S

3754  AAAATCTCCTTCATAGATGAGGACAAATTGTACCCTAGTTTCAAGCCGATCTACAAAGACACTAGGTTTGGAGGA
       K  I  S  F  I  D  E  D  K  L  Y  P  S  F  K  P  I  Y  K  D  T  R  F  G  G

3829  CGCATGGATATGACCAGATTATACGACTATGAAATAAGGGATATAGACCAGGACATCCATGGAATAGTATTTCAG
       R  M  D  M  T  R  L  Y  D  Y  E  I  R  D  I  D  Q  D  I  H  G  I  V  F  Q

3904  CACCCGTTCCCACTGGCACACTCACAGCATCGCTGTGCTATTAGGAGTGGTGCTTTGATCAAATTCAAAAAATGC
       H  P  F  P  L  A  H  S  Q  H  R  C  A  I  R  S  G  A  L  I  K  F  K  K  C
```

FIG. 21H

```
3979  GACGGTGATACGGTTTGGGACAAATTCGCAGTCAACCTTTTAAACTGTCCACATTCTGATAGTACACAATTGCTG
       D   G   D   T   V   W   D   K   F   A   V   N   L   N   C   P   H   S   D   S   T   Q   L   L

4054  GAAACCATCTTAGAAGAGTTTCGCAACCTGGCTGCTCTAAACGTGTGGTACGGTCTCTCTGATGGCGAAGATGGC
       E   T   I   L   E   E   F   R   N   L   A   A   L   N   V   W   Y   G   L   S   D   G   E   D   G

4129  CATATTCCATGGCATATCCTAGCCGTGAAAAAATGATGAACACTCTTGTGCACCAGAGTAAAAATTGCTAAT
       H   I   P   W   H   I   L   A   V   K   K   M   M   N   T   L   V   H   T   R   V   K   I   A   N
```

FIG. 22

```
4204  ACTTCCGCCGCTACTGTGCATACCGCTACTTCTTCATCAATTATTCTCTCGGATAAATAAACTTTTCCGGCAAC
       T  S  A  A  T  V  H  T  A  T  S  S  I  I  L  S  D  K

4279  GTTTTCCTGCTCATCTGTAGCCCTATTACCAGTTTTGGTTTTAGTATTATTCCGGGGTGTAAACCCAGAAGTCT
4354  ATTTCTCCAGTCGGATTTATAAAAACAAAAACCGGAAGCGGGGGCGGTACGGCATTTTCACTGGTGATGCACGCCCA
4429  GCGTGTAGTCCGAGACAATTCCACAGAACGCGAATGAGATTGCGTTTAAGGCTGTATTTCAAGGCACACGAAG
4504  CGGCCACGTGGGTCTGCGATGGTGTTGATGATGTCAAGAATGGTATCATACTCCGTATAAGGTTATGTAATCG
4579  GAAGTCGGATTCTTTTTCAATTTTCTTTTTTATTTTTTTTTCCAGTTTTTTTCGTCTCTGCGATGGAAAATTGTTG
4654  AAGTTCTTCTTGATTAGCAAGTAGTTCTTACATCGCAGGAATCTTATGTT  4702
```

FIG. 23A

SRB10

```
-240  TGATCATAGAAAGGAAACGTGGTTGCATGA ATTGAGATTCGTCTCACACTTCGACTGGTC AAAATTGGCAAGTTTATACCTCACGGCTTG  -151
-150  AAAAGAAGGCAAGTCATCGAGCAGTGCTAT TTAAAATTTATACCATTGAAAAGGGCGATT TGGTTGATAAAGTGCTGCTATTTTATCGAA  -61
-60   TGGAAATCGAACCAGAAAAGAAGAGGTCA  AATGCTGCTGGGCCAGATGATGCCATTTCC ATGCACCTGCTAAAGACTGACGCGATACC    29
 100                                                                                         M H L L K D W T D T  189
       TTTGTATACATCCTGGAAAGCTCATCTTT  GATATGACAAATCACTATAACGATTCTCAA CAACTGCGTACGTGGAAGAGGCAGATTCT    119
  30   F V Y I L E K L I F              D M T N H Y N D S Q              Q L R T W K R Q I S           279
       TATTTTTAAAACTTTTGGGAATTGCTAC   TCACTAAGATTGATCAATAAGGAAATCTTT CATCATTGGCTTGTAGAGTTTATAAATAAG   209
 120   Y F K L L G N C Y                S L R L I N K E I F              H H W L V E F I N K           369
       ATGGAAAACTTCGAATTTTGCCATTATCT  TTACATATTTGATGATTTTTGGAACGAC   ATCTGCCAAATTGATACAAATGCTCCTGTT   299
 210   M E N F E F L P L S              L H I L M I F W N D              I C Q I D T N A P V           459
       GCGGCTACAATAACATCAAGTCAAAAAGAG CCCTTCTTCTCGTAACAAATCACTGAT    ATGCTATTGCACAAATATATATTGTTTCC    389
 300   A A T I T S S Q K E              P F F L V T K I T D              M L L H K Y Y I V S           549
       AGCAGCAAATCAAATGATAACGAGAAC    TACATCATCAATGATATAAAGAAAACAAC  AAGATAAAGTTGAATATTCTCAAAATATTA   479
 390   S S K S M I N D E N              Y I I N D I K K N N              K I K L N I L K I L           639
       TCCAGTTTAATTTTGAAAATTTTTCAAGAA CAATCTTTAGAGGTGTTTATATTTCCCACA TCTAACTGGGAAATTACAAGCCCTTACTT    569
 480   S S L I L K I F Q E              Q S L E V F I F P T              S N W E I Y K P L L           729
       TTTGAAATAGTCTCAAACGCCGACACTAAT CAAAATTCTGATATGAAGAAAATTAGAG   TTAATTAGTTACAGAAACGAGTCATTGAAG   659
 570   F E I V S N A D T N              Q N S D M K K K L E              L I S Y R N E S L K           819
       AATAATTCTCTATACGAAACGTAATAATG  TCTGCCAGCAACGCAAATGACTTTCAATTA ACTATCGTCACCTGTAAACAATTCCAAAA    749
 660   N N S S I R N V I M              S A S N A N D F Q L              T I V T C K Q F P K           909
       CTATCATGCATTCAATTAAATTGTATAGAT ACTCAGTTCACCAAGCTACTGGACGATAAC CCTACAGAATTCGATTGGCCCACTTACGTT   839
 750   L S C I Q L N C I D              T Q F T K L L D D N              P T E F D W P T Y V           999
       GACCAAAATCCCCTTACAATGCATAAAATT ATTCAATTAATTCTCTGTTCCATACATCCA TCAAGGCAATTTGATCACTATGAATCTAAT   929
 840   D Q N P L T M H K I              I Q L I L W S I H P              S R Q F D H Y E S N          1089
       CAACTGGTAGCGAAATTATTACTATTGCGA ATAAATTCAACAGATGAGGATTGCACGAA  TTCCAGATAGAAGATGCCATTTGGTCATTG  1019
 930   Q L V A K L L L R                I N S T D E D L H E              F Q I E D A I W S L          1179
1020   GTTTTCCAATTAGCCAAAAATTTTTCGGCC                                 TCTTTGTATCGCCTGCTTAATATACTAATT  1109
```

```
2370  ATTTTAATAACTTATGGTCATCTCCCAAA  TTACTTGCAACATCTACAAAAATCATTATG  TTGTTATTGAATGATAGCGTGAAAACTCA  2459
       I  L  I  T  Y  G  S  S  P  K    L  L  A  T  S  T  K  I  I  M    L  L  L  N  D  S  V  E  N  S
2530  TCTAATATTTTGGAGGATATTTGTACTAC  TCAACTTGTCCGTCGGAAACCGATCTTAAC  GATATTCCATTGGTAGTGGACAACCAGAC  2619
       S  N  I  L  E  D  I  L  Y  Y    S  T  C  P  S  E  T  D  L  N    D  I  P  L  G  S  G  Q  P  D
2460  AATGACACTGTTGTAACCAACGATGATAAA  AGTGACGATGATGATCACACAGTCGACGAA  ATTGATCATGTAGAATATTACGTTATGATG  2549
       N  D  T  V  V  T  N  D  D  K    S  D  D  D  H  T  V  D  E    I  D  H  V  E  Y  Y  V  M  M
2620  GACTTTGCCAATCTTTGGGTTTTCCAAGCG  TTTACCTGTTTCTGCATCAAAAAAATCATG  GAGAATAATGAGCCAGCAATGGCAATGGAA  2709
       D  F  A  N  L  W  V  F  Q  A    F  T  C  F  C  I  K  K  I  M    E  N  N  E  P  A  M  A  M  E
2550  GACTTGAAGAACTTCATATTCCAAATTATC  GAAATAACTAATTCTAATGATTTATGTTCA  CAAATATTTGACCAACTGAAGGATATGCAG  2639
       D  L  K  N  F  I  F  Q  I  I    E  I  T  N  S  N  D  L  C  S    Q  I  F  D  Q  L  K  D  M  Q
2710  ACCATTGAGATGATAACCCAAATAGTGGAG  AAAGATTTCTGCACTTCTTGTTGCAAAAC  AACAACCAAAAGATAGATGATAATTACATC  2799
       T  I  E  M  I  T  Q  I  V  E    K  D  F  C  T  S  C  L  Q  N    N  N  Q  K  I  D  D  N  Y  I
2640  GTTGTGGTGATCGAGATTATAACGTCATTA  TCGAAGAGGTTTCAAAGAGAAACTTCTGGT  ATGATAGTTATTTCCATGGAGAACTATCAT  2889
       V  V  V  I  E  I  I  T  S  L    S  M  R  F  Q  R  E  T  S  G    M  I  V  I  S  M  E  N  Y  H
2800  TTACTAATAAAGATCATAAGACAATTAAGT  GAACTGAACGAAGAAATTATCTAAGAGA  GAAATCAAATAGATCGCCGTCTTGAAAATT  2819
       L  L  I  K  I  I  R  Q  L  S    E  L  N  E  G  N  L  S  K  R    E  I  Q  I  D  A  V  L  K  I
2730  TTTAGCTTTCATCAGATTCCATTTTCCAA  CGCATCATGCTGATTATCCAGCTGATAAA  CCCACAAGTCCATTCATTGATAGCATATGC  2979
       F  S  F  H  Q  D  S  I  F  Q    R  I  I  A  D  L  S  A  D  K    P  T  S  P  F  I  D  S  I  C
2890  AAGCTGTTTGATAAAATCATCATTAATTTA  AGATTGAAGCTGTTCTCTGTACGAAATTTG  TCTTCATTGAAATCATTCGCCATCTATTCA  2909
       K  L  F  D  K  I  S  F  N  L    R  L  K  L  F  L  F  L  Y  E  I  L    S  S  L  K  S  F  A  I  Y  S
2820  TCCACAATTGATGCCCAGCATTCCACACA  AGCGGTAAGTCGAACTACCGAAGAAATTG  CTGAACTTACCACCATTCCAAGTGTCTCT  3429
       S  T  I  D  A  P  A  F  H  T    S  G  K  V  E  L  P  K  K  L    L  N  L  P  P  F  Q  V  S  S
2980  TTCGTTAAGGAACAAACTTCATAGTGGC  GACTACGGGGAAGAAGATGCAGACCAA  GAAGAATCGTTTAGTTTAAATTTAGGAATC  3519
       F  V  K  E  T  K  L  H  S  G    D  Y  G  E  E  E  D  A  D  Q    E  E  S  F  S  L  N  L  G  I
2910  GGCATAGTTGAAATAGCGCACGAAACGAA  CAGAAATGGCTCATTTATGACAAGAAAGAT  CATAAATATGTCTGCACATTTCCATGGAG  3449
       G  I  V  E  I  A  H  E  N  E    Q  K  W  L  I  Y  D  K  K  D    H  K  Y  V  C  T  F  S  M  E
3070  CCGTACCACTTCATCTCCAACTATAATACC  AAGTACACAGATGACATGGCTACAGGCAGT  AATGATACGACTGCGTTTAACGATTCCTGT  3609
       P  Y  H  F  I  S  N  Y  N  T    K  Y  T  D  D  M  A  T  G  S    N  D  T  T  A  F  N  D  S  C
3000  GTAAACCTGAGTCTTTTTGATGCTCGGTTT  GAGAGGAAAAATCCACATTGATCTCAGAAT  ATATCCAAATGATAAATTATAAATTTACC  3539
       V  N  L  S  L  F  D  A  R  F    E  R  K  N  P  H
3160  AATAACAGTAATTATGTCAGTTTAATA  CCCAACCAATTG  3761
3090
3250
3180
3340
3270
3430
3360
3520
3450
3610
3540
3700
3630
3790
3720
```

FIG. 24A

```
GGTACCAGGTCAAGAAGCAGAATACCCAAGGGCATCCTCCTCCTTAATGAGTTGATTTAAACAATTTAAATCTCATTACGTTTT      90

CCGCATACGAATTGGTGGGAGACTTTCAACCCAAAGCATATATTACTGAGTAAAAAAAATTTTACTCCATTTGTAAGCTTCGATTTGTGAC    180

GATTCTTGGTCATGGATTGAAGAACTTTAAACGAGAAGAAATTAGAAAACAGGTGAAGACCACTATTAGTTCTTACCGCAACATAGG    270

ATAAACAAAGTTATTTCTTACTCCTTTATATATTTGAAAAATATAAATCCACGGAAAAACATCGAAAATTCATTTTTCATGAAGGAA    360

AATTAGGGTTCATACAGGAGTAGAGTTCATTGATGTGGTAGCAACCTTGTTAGCACTCATATTGTTCGAACAAAAAATGCCCTCTCAAAC    450

TTTAGTTGAAGAGCGATAAGGCATCTGAATCTCAAAGTTAGACATGTCGGGGAGCTTCTGGACATCTACACAAGGCATCATTGGCAAT    540
                                        Met Ser Gly Ser Phe Trp Thr Ser Thr Gln Arg His His Trp Gln

ATACCAAGGCATCATTGGCTAAAGAGAGGCAGAAGTTATGGCTATTGGAGTGCCAGCTGTTCCTCAAGGTTTGAATATTGTAATGGATT    630
Tyr Thr Lys Ala Ser Leu Ala Lys Glu Arg Gln Lys Leu Trp Leu Leu Glu Cys Gln Leu Phe Pro Gln Gly Leu Asn Ile Val Met Asp

CGAAGCAAAACGGCATCGAACAATCCAATAACTCACCGAGACTTACACTATGATAAAGATTATAATCTAAGGA    720
Ser Lys Gln Asn Gly Ile Glu Gln Ser Ile Thr Lys Asn Ile Pro Ile Thr His Arg Asp Leu His Tyr Asp Lys Asp Tyr Asn Leu Arg

TCTACTGCTATTTCCTGATAATGAAGCTTGGAAGGAGACTAAATATAAGACAGTATGCACTGGCTACAGCACATATTTATCTATCAAGGT    810
Ile Tyr Cys Tyr Phe Leu Ile Met Lys Leu Gly Arg Arg Leu Asn Ile Arg Gln Tyr Ala Leu Ala Thr Ala His Ile Tyr Leu Ser Arg

TTTTAATAAAGGCTTCAGTTAGAGAAATAAACCTATATGCTGGTTACTACGTGTATATTAGCATGCAAAGTTGAAGAATGCCCGC    900
Phe Leu Ile Lys Ala Ser Val Arg Glu Ile Asn Leu Tyr Met Leu Val Thr Thr Cys Val Tyr Leu Ala Cys Lys Val Glu Glu Cys Pro

```
A
AATATATCAGAACTTTGGTAAGTGAAGCCCGTACCTTATGGCCCGAATTTATTCCTCCTGACCCTACTAAAGTTACTGAGTTTGAGTTCT    990
Gln Tyr Ile Arg Thr Leu Val Ser Glu Ala Arg Thr Leu Trp Pro Glu Phe Ile Pro Pro Asp Pro Thr Lys Val Thr Glu Phe Glu Phe

ACTTACTAGAAGAATTGGAAAGTTACTTAATTGTCCACCACCCTTATCAATCCTTAAAGCAAATTGTTCAAGTCTTAAAGCAACGCCAT   1080
Tyr Leu Leu Glu Glu Leu Glu Ser Tyr Leu Ile Val His His Pro Tyr Gln Ser Leu Lys Gln Ile Val Gln Val Leu Lys Gln Pro Pro

TTCAAATAACACTATCGTCAGATGATCTACAAAACTGTTGGTCCTTAATCAACGACAGTTATATAAATGATGTTCATTTGCTTTACCCTC   1170
Phe Gln Ile Thr Leu Ser Ser Asp Asp Leu Gln Asn Cys Trp Ser Leu Ile Asn Asp Ser Tyr Ile Asn Asp Val His Leu Leu Tyr Pro

CTCATATTATCGCTGTTGCATGTTTATTCATTACGATTTCCATTCATGGGAAACCAACCAAAGGATCATCGTTAGCATCTGCGGCTTCTG   1260
Pro His Ile Ile Ala Val Ala Cys Leu Phe Ile Thr Ile Ser Ile His Gly Lys Pro Thr Lys Gly Ser Ser Leu Ala Ser Ala Ala Ser

AAGCCATCAGAGATCCTAAAAATTCTAGTTCTCCTGTTCAAATAGCTTTTAATCGTTTTATGGCAGAATCTCTTGTAGATCTTGAGGAGG   1350
Glu Ala Ile Arg Asp Pro Lys Asn Ser Ser Ser Pro Val Gln Ile Ala Phe Asn Arg Phe Met Ala Glu Ser Leu Val Asp Leu Glu Glu

TTATGGATACGATTCAAGAGCAAATTACATTATACGATCATTGGGACAAGTACCACGAACAATGGATAAAGTTTCTGCTACATACTTTGT   1440
Val Met Asp Thr Ile Gln Glu Gln Ile Thr Leu Tyr Asp His Trp Asp Lys Tyr His Gln Trp Ile Lys Phe Leu Leu His Thr Leu

ATCTTAGACCAGCATCTGCAATTTAATCATGCGAAGAATAAATTTAAAAACCGTTAAGCCTGTAAATTCAATCATTATGGTGGTGATGAT   1530
Tyr Leu Arg Pro Ala Ser Ala Ile

CCGTTTTGGAAATGTTTCGTCCTTGACTACCTTTGTTTAACATGATATTGGAACGTCAAGACATATTGAGAATAGGTACC             1610
```

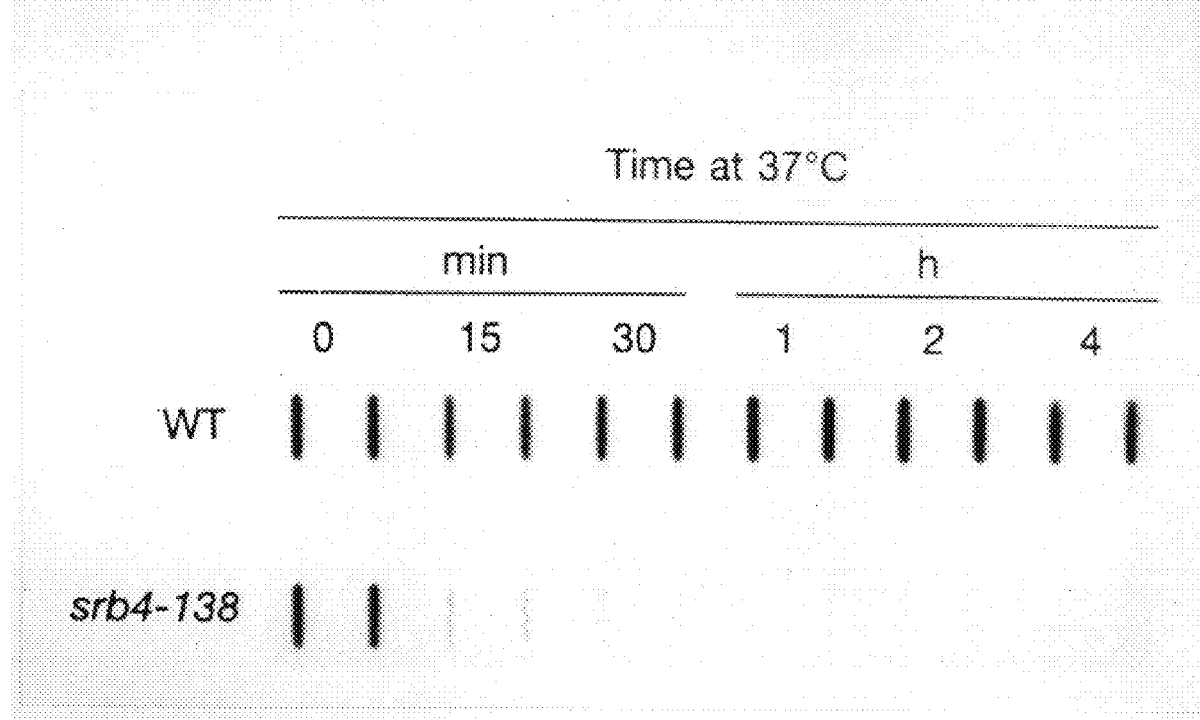

FIG. 31

RNA POLYMERASE II HOLOENZYME FROM SACCHAROMYCES CEREVISIAE

GOVERNMENT SUPPORT

The invention described herein was supported in whole, or in part by Grant Nos. GM 34365 and GM 49911 from the National Institute of Health. The government has certain rights in the invention.

BACKGROUND OF THE INVENTION

The regulation of cellular gene expression occurs primarily at the level of transcription initiation by RNA polymerase. Regulated transcription initiation by RNA polymerase II in higher eukaryotes involves the formation of a complex with general transcription factors at promoters (Sawadogo, M. and Sentenac, A., Ann. Rev. Biochem. 59:711–754 (1990). One of these factors, transcription factor IID (TFIID), contains the TATA-binding protein (TBP), which is able to bind directly to promoter DNA. The remaining components of the transcription initiation complex include RNA polymerase II and the initiation factors TFIIA, TFIIB, TFIIE, TFIIF, TFIIH, and TFIIJ. These components associate with TFIID-bound promoter DNA to form a transcription initiation complex. Sequence-specific DNA-binding proteins appear to regulate the establishment and activity of transcription initiation complexes, possibly through interactions with TFIIB and TBP and additional factors that make up TFIID.

Several high molecular weight complexes containing TBP have been identified in extracts from human and Drosophila cells (Gill, G, and Tjian, R., Curr. Opin. Gen. Dev. 2:236–242 (1992); Sharp, P. A., Cell 68:819–821 (1992)). One of these complexes is TFIID, which contains at least eight TBP-associated factors (TAFs) (Pugh B. F., and Tjian, R. J. Genes Dev. 5:1935–1945 (1991)). A second complex is the RNA polymerase I promoter selectivity factor, SL1, which contains TBP and three TAFs (Comai, L., et al., Cell 68:965–976 (1992)). A third complex is a component of the RNA polymerase III factor TFIIIB, which consists of TBP and two TAFs (Taggart, A. K. P., et al., Cell 71:1015–1028 (1992)). Some of the TAFs associated with these complexes appear to function as transcriptional coactivators by providing a functional link between sequence-specific regulators and TBP (Dynlacht, B. D., et al., Cell 66:563–576 (1991)).

The RNA polymerase II carboxy-terminal domain (CTD) is another component of the transcription apparatus that can bind to TBP (Usheva, A., et al., Cell 69:871–881 (1992)). The CTD is a highly conserved and apparently unique feature of the largest subunit of RNA polymerase II (Young, R. A., Ann. Rev. Biochem. 60:689–715 (1991)). The CTD contains 26–52 repeats, depending on the organism, of the consensus heptapeptide sequence, Tyr-Ser-Pro-Thr-Ser-Pro-Ser. Deletion mutations that remove most or all of the CTD are lethal to cells (Nonet, M., et al., Cell 50:909–915 (1987)). CTD partial truncation mutations cause defects in growth and inducible gene expression in vivo and produce substantial defects in transcription initiation in vitro (Liao, S. M., et al., Genes Dev. 5:2431–2440 (1991)).

An important feature of RNA polymerase II molecules recruited into the initiation complex is their association with RNA polymerase-associated proteins (RAPs) (Conaway, J. W., et al., J. Biol. Chem. 266:17721–17724 (1991)). Two mammalian proteins, RAP30 and RAP74, have been identified as components of the general transcription factor TFIIF (Flores, O., et al., J. Biol. Chem. 263:10812–10816 (1988)).

Despite this knowledge of the components of the RNA polymerase II transcription initiation complex, two major questions have not been addressed until now. First, how do RNA polymerase II and the general initiation factors interact with one another in vivo? For example, it is not clear whether RNA polymerase II and general factors assemble in a sequential manner on promoter DNA, or whether a large complex of these components assembles prior to association with DNA. Second, how do transcriptional regulators interact with the transcription initiation complex? Thus, we do not know whether interactions occur only between regulators and the subunit of TFIID, or whether there are additional interactions with other components of the initiation complex.

SUMMARY OF THE INVENTION

The present invention relates to the discovery of an RNA polymerase II holoenzyme complex. The RNA polymerase II holoenzyme complex is a multisubunit complex containing RNA polymerase II, general transcription factors and regulatory proteins. The RNA polymerase II holoenzyme described herein plays a key role in the initiation of transcription in all eukaryotic cellular organisms. DNA transcription by the RNA polymerase II holoenzyme is stimulated by an activator protein, a feature not observed with purified RNA polymerase II and general transcription factors alone. Specifically, the regulatory proteins, identified herein as SRB2, SRB4, SRB5, SRB6, SRB7, SRB8, SRB9, SRB10 and SRB11 (wherein SRB refers to "suppressor of RNA polymerase B"), act as positive and negative regulators of the activity of RNA polymerase II. Encompassed by this invention are SRB proteins SRB2, SRB4, SRB5, SRB6, SRB7, SRB8, SRB9, SRB10 and SRB11, the amino acids encoding these SRB proteins, and variants or derivatives (e.g., mutant SRB proteins) thereof, and antibodies reactive with the SRB proteins.

Also encompassed by this invention are the DNA sequences encoding the SRB proteins and the complementary strands of these DNA sequences. Also encompassed are DNA sequences, and nucleic acid probes that are substantially complementary to a SRB DNA sequence to selectively hybridize to that SRB DNA sequence.

This invention further relates to methods of modifying gene transcription by substances that bind to, or interact with, SRB proteins and either prevent, or enhance, the formation of the RNA polymerase II holoenzyme, or, if the holoenzyme complex is formed, prevent, or enhance, the function of the holoenzyme as an initiator of transcription. Substances that bind to the SRB proteins may also modify the influence the SRB proteins have on RNA polymerase II, or on other transcription factors essential to gene transcription. This invention also relates to a method of in vitro transcription employing the purified RNA polymerase II holoenzyme and to the use of this method to identify substances, both naturally-occurring, and synthetic, that modify gene transcription.

This invention further relates to methods of detecting SRB genes and gene products in a cell or in biological fluids using nucleic acid probes which hybridize to DNA encoding the SRB protein, or antibodies which bind to the SRB gene product.

BRIEF DESCRIPTION OF THE DRAWINGS

FIG. 2A–B shows the DNA sequence of the 1.95 kb BstEII-EcoRI DNA fragment containing the SRB2 gene (SEQ ID NO: 1) and the deduced sequence of the SRB2 protein (SEQ ID NO: 2) is shown below the sequence of the gene. The transcription initiation site is indicated by the horizontal arrow. The splice donor and splice acceptor sites are underlined. The TGCTAACA splice branch point site is boxed. The SRB2-1 mutation is a C to A transversion (nt 768) that changes as 14 from Pro to His.

FIGS. 5A–E, 6A–C and 7A–B shows the DNA sequences and predicted amino acid sequences of the SRB4 (SEQ ID NO: 3 and 4), SRB5 (SEQ ID NO: 5 and 6) and SRB6 (SEQ ID NO: 7 and 8) proteins, respectively.

FIGS. 8A–8E shows the results of experiments demonstrating that SRB2 and SRB5 are essential for efficient transcription in vitro.

FIGS. 9A–B and 9C–D shows the results of experiments demonstrating that SRB2 and SRB5 are essential for efficient preinitiation complex formation.

FIGS. 10A–C shows the purification scheme of the SRB complex and results of the purification.

FIG. 13A shows the chromatography scheme used to purify the RNA polymerase II holoenzyme complex and factor a.

FIG. 14 lists yeast RNA polymerase II initiation factors and homologs in other species.

FIGS. 15A–D and 16A–B shows the results of experiments demonstrating that the RNA polymerase II holoenzyme is a complex of RNA polymerase II and initiation factors.

FIGS. 19A–B shows the DNA sequence and predicted amino acid sequence of SRB7 (SEQ ID NO: 9 and 10).

FIGS. 20A–C shows the DNA sequence and predicted amino acid sequence of SRB8 (SEQ ID NO: 11 and 12).

FIGS. 21A–H and 22 shows the DNA sequence and predicted amino acid sequence of SRB9 (SEQ ID NO: 13 and 14).

FIGS. 23A–C shows the DNA sequence and predicted amino acid sequence of SRB10 (SEQ ID NO: 15 and 16).

FIGS. 24A–B shows the DNA sequence and predicted amino acid sequence of SRB11 (SEQ ID NO: 17 and 18).

Figure 29B:
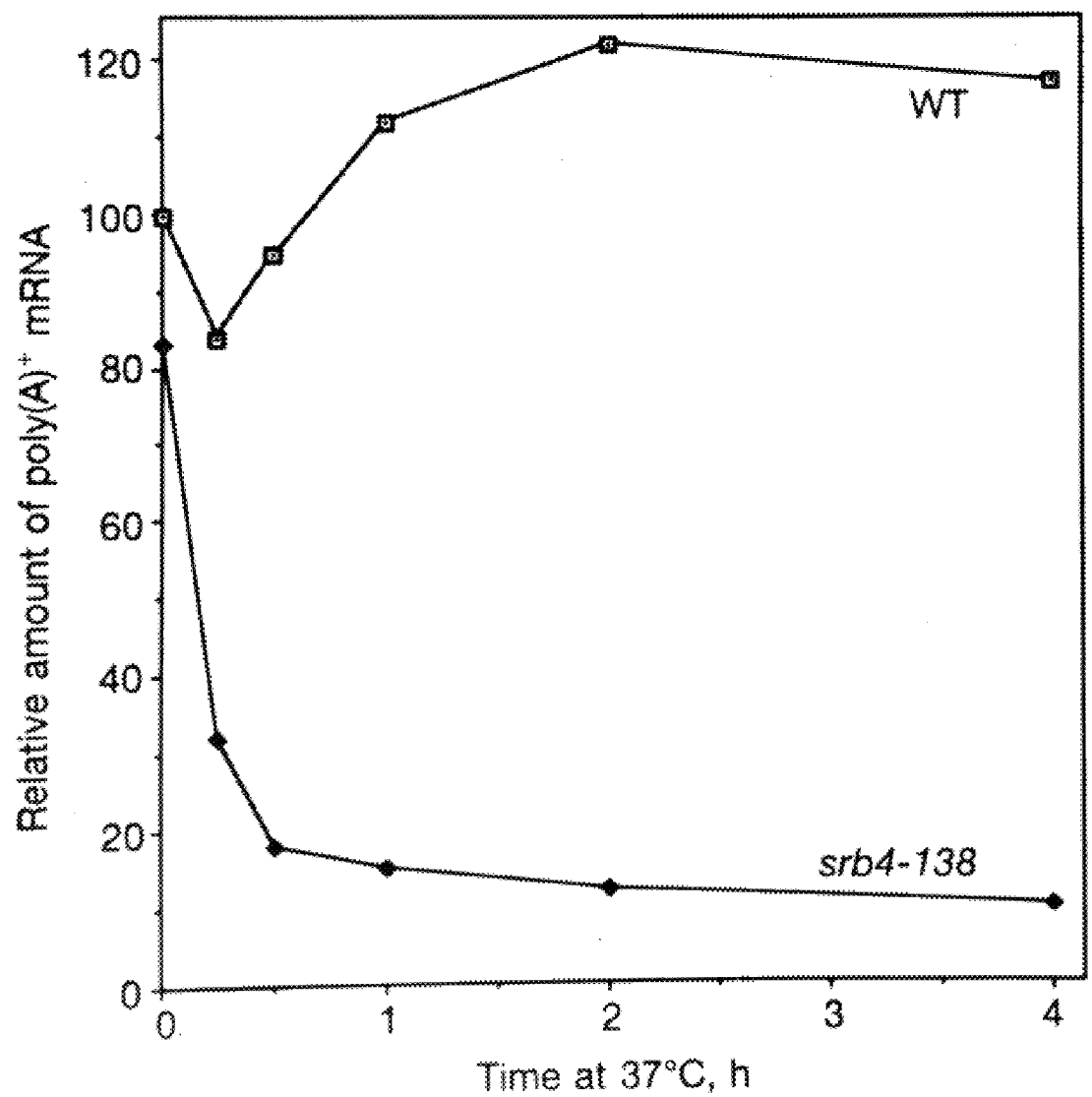

FIGS. 29A–B shows the results of an experiment demonstrating that mRNA levels rapidly decline in srb4-138 cells at the restrictive temperature. At the times indicated, immediately before and following the shift from 30° C. to 37° C., aliquots of cells were removed and total RNA prepared. Equivalent amounts of RNA (2 µg) were slot blotted, in duplicate, onto nitrocellulose and the filter probed with ($^{32}$P)poly(T) (FIG. 29A). The results were quantified using a Fuji Bio-Image Analyzer and plotted (FIG. 29B). Each point represents the average value of the duplicate slots normalized to a value of 100 for wild-type cells at time 0'.

Figure 30:
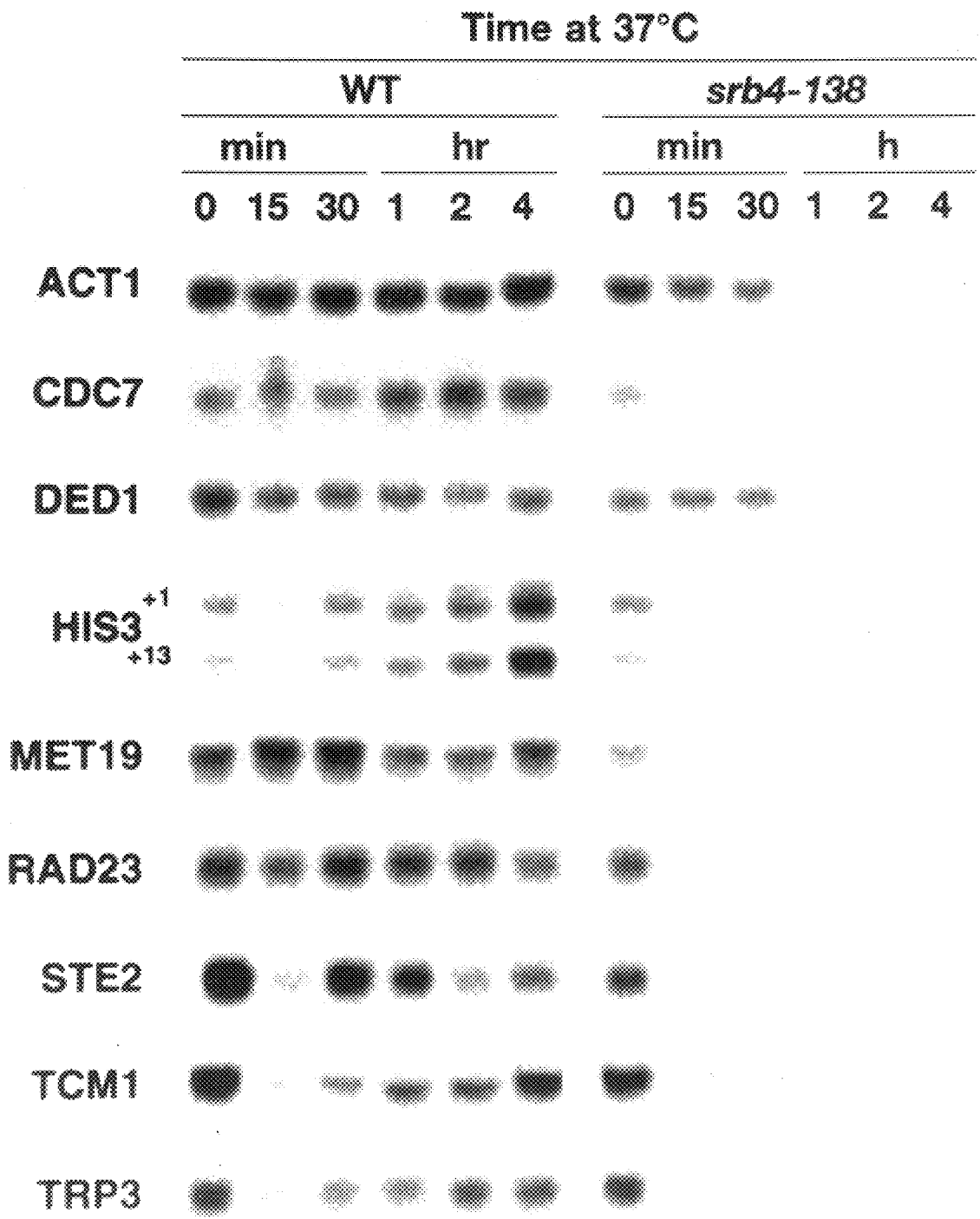

FIG. 30, shows the results of an experiment demonstrating that RNA Polymerase II transcripts are sensitive to loss of SRB4 activity. At the time indicated, immediately before and following the shift from 30° C. to 37° C., aliquots of cells were removed and total RNA prepared. Equivalent amounts of RNA were hybridized with an excess of $^{32}$P-labeled oligonucleotide complementary to the indicated transcripts, treated with S1 nuclease, and subjected to denaturing polyacrylamide gel electrophoresis. The HIS3 oligonucleotide is complementary to the 5' end of the message and detects transcripts initiated from the +1 and +13 sites.

FIG. 31 shows the results of an experiment demonstrating the effect of loss of SRB4 activity on transcription by RNA polymerase I, II, and III. At the times indicated, immediately before and following the shift from 30° C. to 37° C., aliquots of cells were removed and total RNA prepared. Equivalent amounts of RNA were hybridized with an excess of $^{32}$P-labeled oligonucleotide complementary to the indicted transcripts, treated with S1 nuclease, and subjected to denaturing polyacrylamide gel electrophoresis. CTY60 (rpb1-1) is an isogenic strain of CTY233 (WT) and CTY271 (srb4-138).

DETAILED DESCRIPTION OF THE INVENTION

The present invention relates to the discovery of an RNA polymerase II holoenzyme complex capable of site-specific initiation of gene transcription. The RNA polymerase II holoenzyme described in the present invention is a multi-subunit complex that contains RNA polymerase II and transcription factors, typically protein transcription factors. The proteins involved with gene transcription can be divided into three groups, described as follows: 1) subunits of RNA polymerase needed for some or all of the stages of transcription, but are not specific for individual promoters; 2.) transcription factors that bind RNA polymerase before, during, or after it forms an initiation complex, although they are not part of the free enzyme (these factors are likely to be needed for transcription to initiate at all promoters or,for example, to terminate); and 3.) transcription factors that bind specific sequences in the target promoters. (If the sequences were present in all promoters, the factors would be part of the general transcription apparatus. If some sequences are present only in certain classes of promoters, factors that recognize them could be needed specifically to initiate at those promoters.) Transcription factors are also referred to herein as initiation factors. Importantly, as described herein, the RNA polymerase II holoenzyme plays a key role in the initiation of transcription in all eukaryotic organisms.

Specifically, the RNA polymerase II holoenzyme described in the present invention is a high molecular weight multisubunit complex that contains RNA polymerase II, general transcription factors and nine novel regulatory proteins. The general transcription factors are b, e, and g (yeast homologs of TFIIH, TFIIB, and TFIIE). The regulatory proteins, identified herein as SRB2, SRB4, SRB5, SRB6, SRB7, SRB8, SRB9, SRB10 and SRB11, act as positive and negative regulators of the activity of RNA polymerase II. This RNA polymerase II holoenzyme is capable of site-specific initiation of gene transcription when supplemented with factor a (TFIIE) and TATA-binding protein (TBP). Surprisingly, this RNA polymerase II holoenzyme is responsive to activators, such as the GAL4-VP16 activator protein.

Also encompassed by this invention are SRB proteins SRB2, SRB4, SRB5, SRB6, SRB7, SRB8, SRB9, SRB10 and SRB11, the amino acids encoding these SRB proteins, and variants or derivatives thereof. Thus, the present invention is intended to encompass amino acid sequences which encode the SRB proteins but may contain one, or more "silent changes" in the amino acid sequence. Such silent changes in the amino acid sequence may not reflect the exact SRB amino acid sequence described herein, but nevertheless, do not alter the essential function, or activity of the SRB protein, i.e., as a transcriptional regulator. For example, one, or more, amino acid residue(s) may differ in an amino acid sequence from a SRB amino acid sequence described herein, yet still retain the ability to function as an activator of gene transcription.

Also encompassed by this invention are the DNA sequences encoding the SRB proteins and the complementary strands to these DNA sequences. Also encompassed are nucleic acid sequences (e.g., nucleic acid probes) that are substantially complementary to a SRB DNA sequence to selectively hybridize to that SRB DNA sequence. Substantially complementary is defined herein to mean that the nucleic acid sequence may not reflect the exact sequence described herein, but must be sufficiently complementary to hybridize to the DNA sequence encoding the SRB protein. For example, non-complementary bases, or longer or shorter sequences, can be interspersed in the SRB DNA sequence provided that the DNA sequence has sufficient complementarity to hybridize to the SRB sequence therewith.

This invention further relates to methods of modifying gene transcription by substances that bind to, or interact with, SRB proteins and, thus, modify the influence of the SRB proteins on RNA polymerase II, or on other transcription factors essential to gene transcription. Substances that bind to, or interact with, one, or more SRB proteins can prevent or enhance the formation of the RNA polymerase II holoenzyme complex, thus, inhibiting or enhancing gene transcription. Alternatively, even though the holoenzyme complex is formed, substances that bind to, or interact with the SRB proteins, can prevent or enhance the function of the complex in the transcription process. These substances include antibodies that are reactive with, or bind to the SRB proteins.

This invention also relates to a method of in vitro transcription employing the purified RNA polymerase II holoenzyme and to the use of this method to identify substances, both naturally-occurring, and synthetic, that modify gene transcription. This invention further relates to methods of identifying substances that modify gene transcription, and methods of treating disease conditions resulting from insufficient, or increased, production of, SRB proteins, or production of abnormal SRB proteins. These methods include the use of substances that bind to, or interact with, the SRB proteins, wild type (naturally occurring and biologically active) SRB proteins, and genetically altered SRB proteins.

The discovery of these novel SRB protein factors which modify gene transcription was made possible by a combination of genetic and biochemical selection techniques designed to identify transcription factors involved in CTD function. Most, if not all, of these factors are tightly associated with the RNA polymerase II holoenzyme. Among the SRB proteins are both positive and negative regulators, indicating a dual role for CTD-associated factors in the initiation of transcription.

The CTD is a highly conserved and apparently unique feature of the largest subunit of RNA polymerase II. Depending on the organism, the CTD contains 26 to 52 repeats of the consensus heptapeptide sequence Tyr-Ser-Pro-Thr-Ser-Pro-Ser. A subset of the RNA polymerase II molecules in yeast and mammalian cells have highly phosphorylated CTDs, and RNA polymerase II molecules lacking phosphorylation on the CTD are preferentially recruited into the initiation complex. Deletion mutations that remove most, or all, of the CTD are lethal to cells. CTD partial truncation mutations, however, cause defects in growth and gene expression in vivo and produce substantial defects in transcription initiation at multiple promoters in vitro. Thus, suppression analysis of conditional CTD truncation mutations in yeast can be used to identify factors which influence CTD function.

Cloning and Sequence Analysis of SRB2

Figure 1:
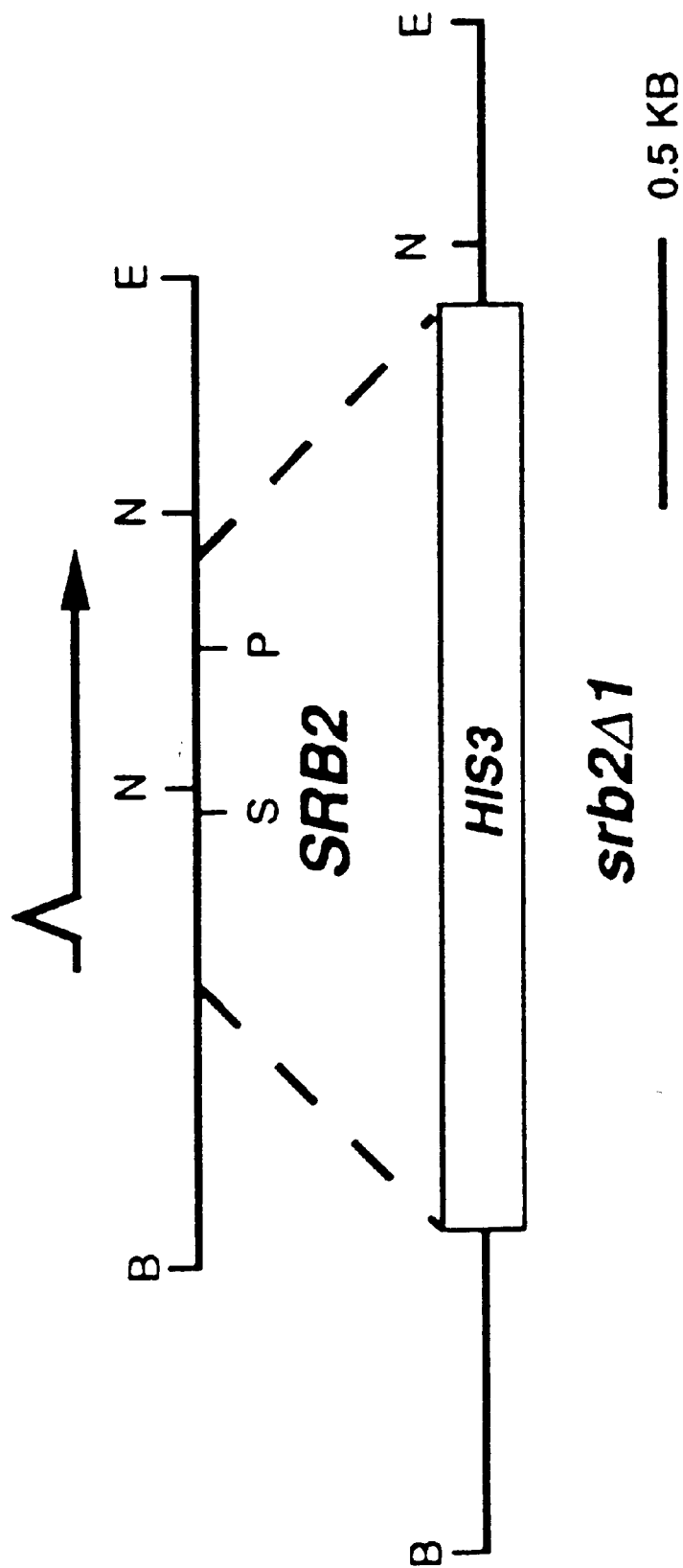
FIG. 1 shows the restriction map of a 1.95 kb BstEII-EcoRI DNA fragment from pCT21 containing the SRB2 gene (B, BstEII; E, EcoRI; N, NcoI; P, PstI; S, SacII). The SRB2 transcript is indicated above the map. The entire coding region of SRB2 was replaced with a 1.75 kb BamHI DNA fragment containing the HIS3 gene to create the deletion allele srb2 Δ1.
Figure 28A:
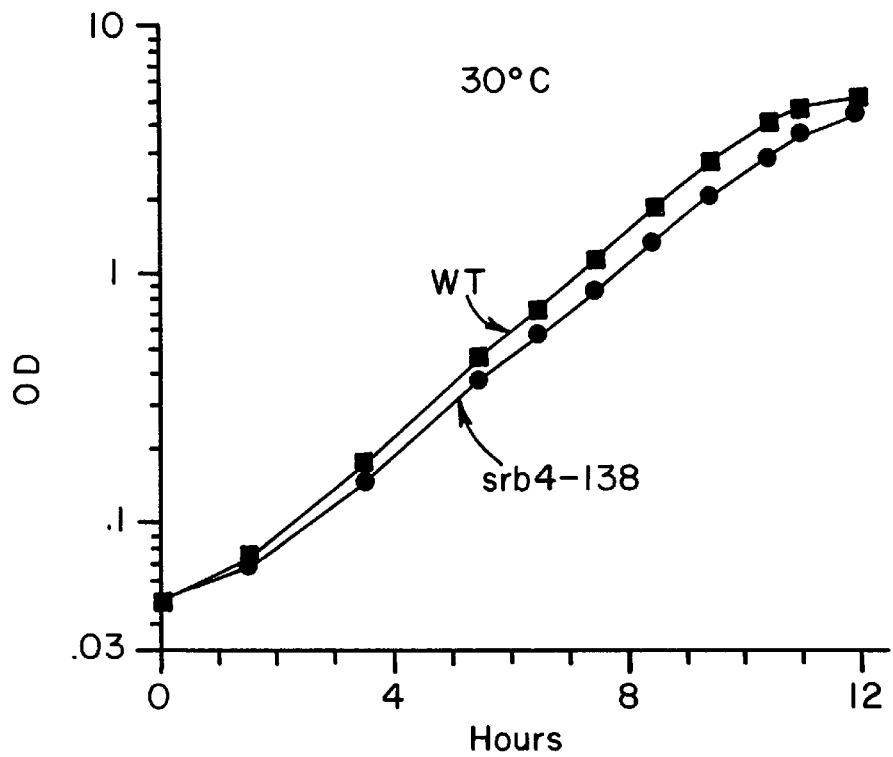
FIGS. 28A–B shows two graphs depicting the results of an experiment demonstrating that a conditional srb4 mutant rapidly ceases growth. The growth of wild-type and srb4-138 strains in YPD medium was determined by measuring $OD_{600}$ at various times. At the time indicated by the arrow, cultures growing at 30° C. were divided and half the culture was left at 30° C. (28A) while the other half was shifted to 37° C. (28B).
Figure 28B:
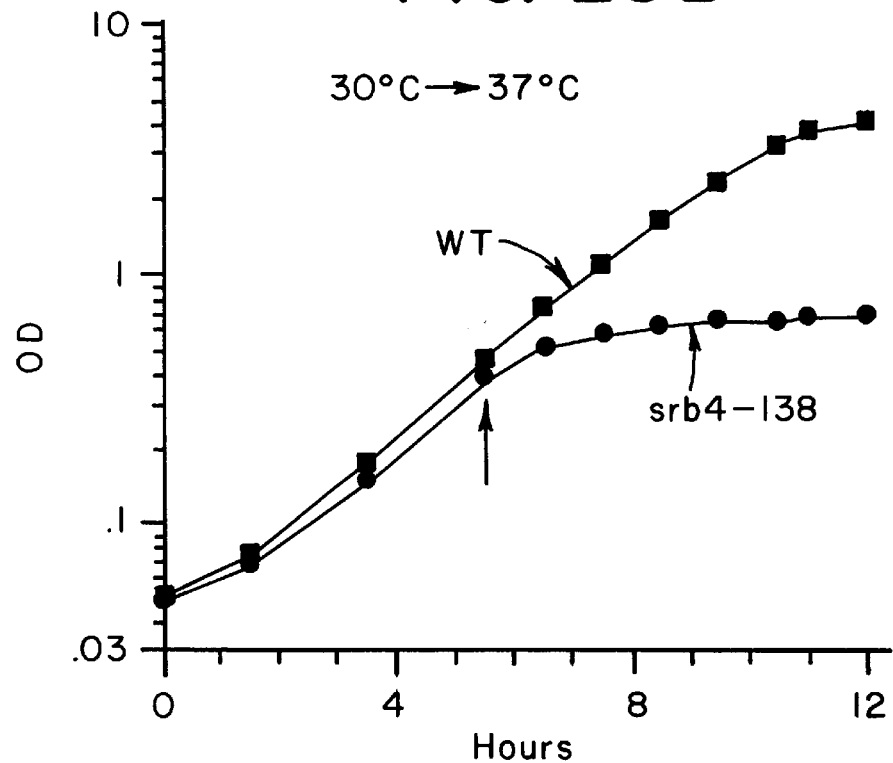

The isolation of suppressors of *Saccharomyces cerevisiae* RNA polymerase II CTD truncation mutations led to the identification of a dominant suppressing allele, SRB2-1, and the isolation of DNA clones containing SRB2-1 and its wild type counterpart, SRB2 (Nonet, M. L. and Young, R. A., *Genetics* 123:715–724 (1989)). The position of SRB2 within a genomic DNA clone is shown in FIG. 1. The sequence was determined for SRB2 and its surrounding DNA, as shown in FIG. 28A–B (SEQ ID NO: 1). The SRB2 gene was shown to encode a TBP-binding protein. (Koleske, A. J., et al., *Cell* 69:883–894 (1992)). The predicted SRB2 protein is 210 amino acids long (SEQ ID NO: 2) and has a molecular mass of 23 Kd. It is a hydrophilic protein rich in serine, threonine and tyrosine residues, and it is acidic, with a predicted $PK_a$ of 5.2. (See Example 1).

The SRB2 gene was identified through analysis of extragenic suppressors of CTD truncation mutations, as described in Example 1. The dominant, gain-of-function mutation SRB2-1 specifically suppresses CTD truncation mutations. Cells lacking SRB2 and cells lacking a large portion of the CTD exhibit the same set of conditional growth phenotypes and have the same defects in gene expression. (See FIG. 3). While the presence of SRB2-1 causes cells with severe CTD truncations to behave as if the CTD was longer, the loss of SRB2 has the opposite effect. The allele specificity of the SRB2 suppressor, the identical behavior of cells with CTD truncations and cells lacking SRB2 all indicate that SRB2 and CTD are involved in the same process during initiation.

To identify additional components of the transcription apparatus that affect CTD function, extragenic suppressors of a Saccharomyces cerevisiae RNA polymerase II CTD truncation mutant were isolated, as described in Example 2. The cold-sensitive phenotype of cells containing RNA polymerase II CTDs with only 11 intact heptapeptide repeats (rpb1Δ104) was exploited to obtain 85 independent suppressing isolates, of which approximately one-third were dominant and two-thirds recessive. The dominant suppressing isolates were chosen for further study. Genetic analysis revealed that all of the dominant mutations occurred in four SRB genes: SRB2, SRB4, SRB5, and SRB6. Additional analysis revealed that SRB4, SRB5, and SRB6 were newly identified genes.

Figure 4A:
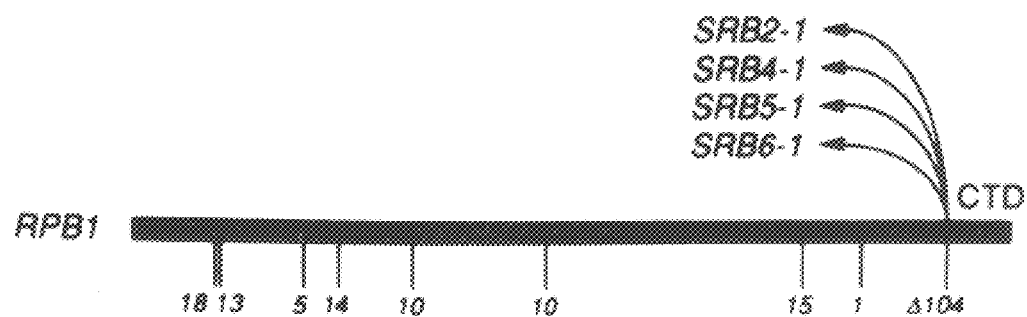
FIG. 4A is a diagramic representation of conditional mutations used to isolate and characterize suppressors of rpb1Δ104 mutations. The positions of the conditional mutations utilized in this study are indicated, except for those of rpb1-4, rpb1-6, and rpb1-12, which have not been determined.
Figure 4B:
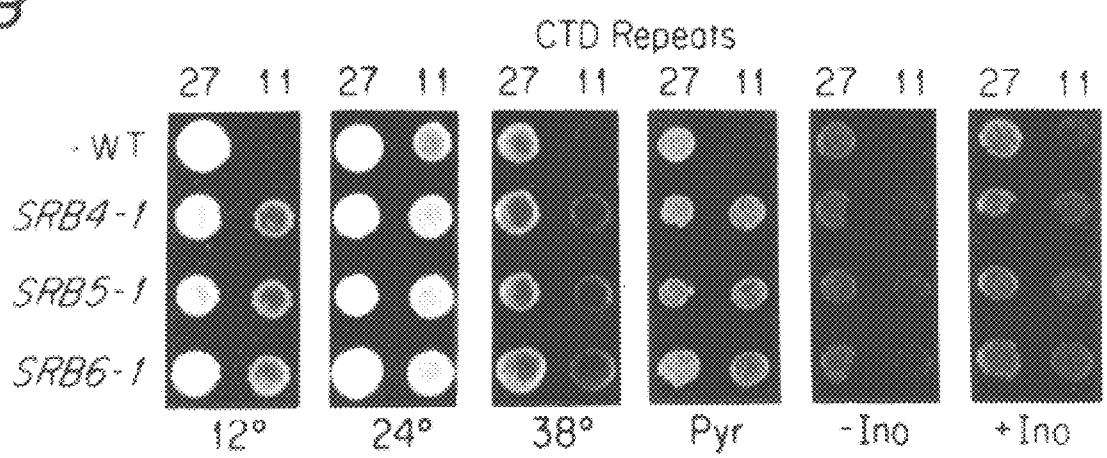
FIGS. 4B–4C shows growth phenotypes of cells containing an RPB1 CTD truncation mutation and SRB4–1, SRB5-1, and SRB6-1. Cells were spotted on YEPD medium and incubated at 12° C., 24° C., and 38° C. (panels 1–3), on SC medium containing pyruvate as a sole carbon source (panel 4), and in minimal medium with or without inositol (panels 5 and 6). Isogenic wild-type, SRB4-1, SRB5-1 and SRB6-1 backgrounds contained either wild-type RPB1 (27 repeat CTD) or rpb1Δ104 (11 repeat CTD). Isogenic wild-type, SRB4-1, SRB5-1, and SRB6-1 backgrounds containing RPB1 alleles indicated on the left were assayed for growth by spotting on YEPD medium and incubating at 12° C., 24° C. and 38° C. Similar experiments revealed that SRB4-1, SRB5-1, and SRB6-1 do not suppress the growth defects of cells containing rpb1-10, rpb1-12, or rpb1-18.
Figure 4C:
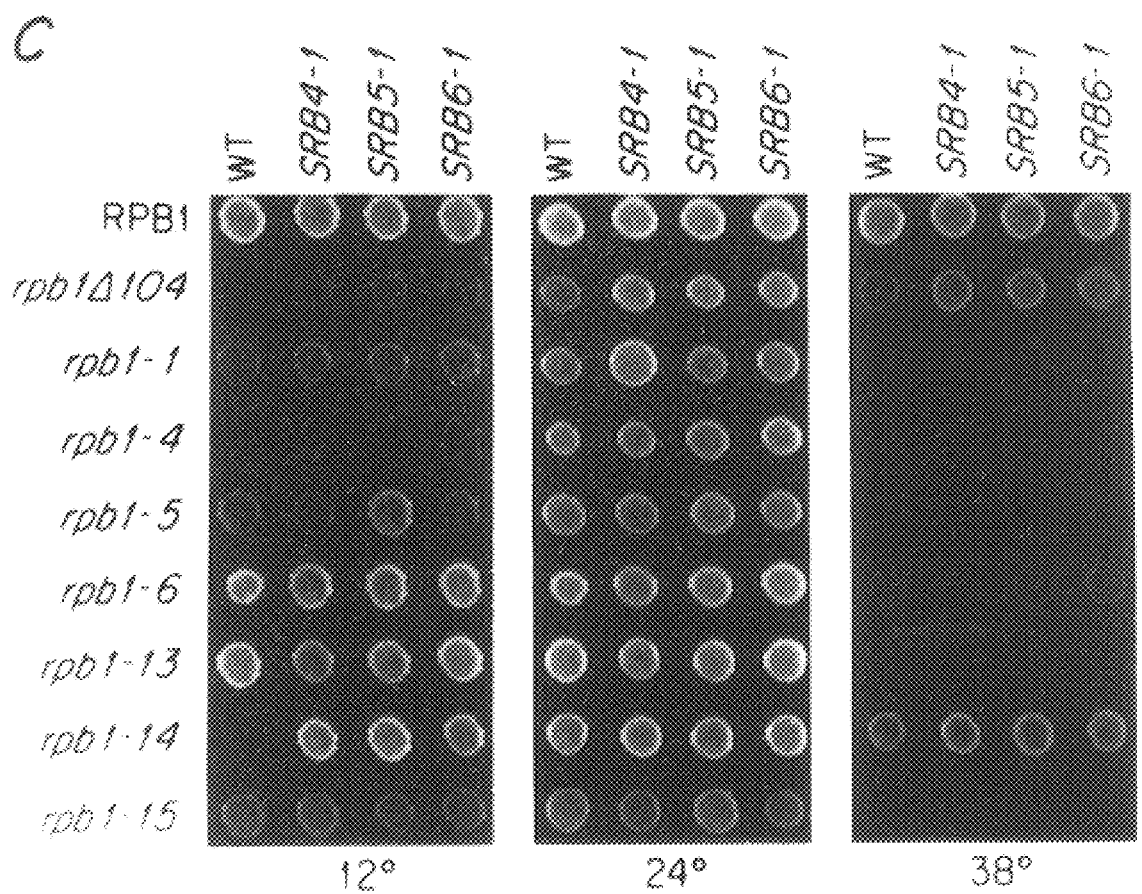

Two genetic assays were performed to obtain support for a functional relationship between the new SRB gene products and the CTD (FIG. 4A, 4B and 4C). The ability of the suppressing alleles of SRB4, SRB5, and SRB6 to suppress all of the phenotypes associated with the CTD truncation mutation rpb1Δ104 was investigated. These phenotypes include cold- and temperature-sensitive growth, inositol auxotrophy, and the inability to utilize pyruvate as a carbon source. Cells containing either SRB4-1, SRB5-1, or SRB6-1 suppress all of these defective phenotypes (FIG. 4B), as does SRB2-1.

To assess whether the suppressing activities of SRB4-1, SRB5-1, and SRB6-1 are specific to CTD mutations, the ability of the SRB alleles to suppress the conditional phenotypes associated with mutations elsewhere in RNA polymerase II was investigated (FIG. 4C). SRB4-1, SRB5-1, and SRB6-1 generally do not suppress the conditional and auxotrophic phenotypes associated with rpb1 point mutations. SRB4-1, SRB5-1, and SRB6-1 do suppress the cold-sensitive phenotype of the rpb1-14 mutation. This is the same type of suppression specificity shown by SRB2-1, and this argues that SRB2, SRB4, SRB5, SRB6, and the CTD are involved in the same process in transcription initiation.

Cloning and Sequence Analysis of SRB4, SRB5, and SRB6

Genomic DNA clones containing SRB4-1, SRB5-1, and SRB6-1 were isolated by taking advantage of their ability to suppress dominantly the cold-sensitive phenotype of a cell containing the CTD truncation mutation rpb1Δ104. Genomic DNA was isolated from strains containing the dominant suppressing alleles of SRB4, SRB5, and SRB6. Libraries were constructed in a yeast centromeric plasmid containing the URA3 gene as a selectable marker. These libraries were transformed into yeast cells containing cold-sensitive CTD truncation mutation, and genomic clones were isolated from Ura$^+$ transformants able to grow at 12° C. The mutant genes were further localized by constructing subgenomic libraries with fragments of the SRB4-1, SRB5-1, and SRB6-1 genomic inserts and again selecting for Ura$^+$ transformants able to grow at 12° C. Genomic clones with the smallest inserts were identified and sequenced.

The wild-type allele of SRB4 was cloned from a wild-type genomic DNA library. Wild-type SRB5 and SRB6 alleles were obtained by plasmid gap repair in vivo. Plasmids containing the wild-type SRB4, SRB5, and SRB6 genes did not suppress the cold-sensitive phenotype of CTD truncation mutants, confirming that in each case the correct locus was cloned. SRB4, SRB5, and SRB6 were physically mapped using the prime clone grid filters of the yeast genome (provided by L. Riles and M. Olson, Washington University). SRB4 maps to the right arm of chromosome V, approximately 40 kb from the centromere (λ clones 5961 and 6224). SRB5 maps to the right arm of chromosome VII, approximately 30 kb centromere proximal to SPT6 (λ clones 5146 and 4624). SRB6 maps to the right arm of chromosome II, approximately 75 kb centromere distal to CDC28 (λ clone 4796).

DNA fragments containing SRB4 (SEQ ID NO: 3), SRB5 (SEQ ID NO: 5), and SRB6 (SEQ ID NO: 7) were sequenced, and the open reading frames were established by unidirectional deletion analysis and identification of the suppressing mutations. The predicted SRB4 protein is 687 amino acids long (SEQ ID NO: 4) and has a molecular mass of 78 kd (FIGS. 5A–E). SRB5 is predicted to be 307 amino acids in length (SEQ ID NO: 6) with a molecular mass of 34 kd (FIGS. 6A–C). The predicted SRB6 protein is 121 amino acids long (SEQ ID NO: 8) and has a molecular mass of 14 kd (FIGS. 7A–B). A search of sequence data banks revealed that SRB4, SRB5, and SRB6 did not have significant sequence similarity to previously identified proteins. One notable feature of the SRB proteins is their acidic content. The predicted pK values of SRB2, SRB4, SRB5, and SRB6 are 5.2, 5.1, 4.7, and 4.6, respectively.

The suppressing mutations in all three genes were identified by comparing the complete sequences of the cloned wild-type and suppressing alleles of SRB4, SRB5, and SRB6. In each case, the alterations were singlepoint, missense mutations. The mutation in SRB4-1 changes glycine 353 to cysteine. The SRB5-1 mutation changes threonine 22 to isoleucine, and the SRB6-1 mutation changes asparagine 86 to lysine.

To determine whether the SRB genes are essential for cell viability, the entire coding region of each of the SRB genes was deleted to produce srb4Δ2, srb5Δ1, and srb6Δ1. SRB4 and SRB6 are essential. SRB5, like SRB2, is not essential, but cells lacking the gene exhibit the slow growth, cold-sensitive, and temperature-sensitive phenotypes characteristic of CTD truncations.

SRB2 and SRB5 Are Required for Efficient Transcription In Vitro

Although yeast cells lacking SRB4 or SRB6 are not viable, cells lacking SRB2 or SRB5 are viable despite striking defects in growth, and it is this feature that facilitates investigation of the transcriptional activity of SRB2 and SRB5 proteins using nuclear extracts in vitro. Previous studies had revealed that SRB2 is required for efficient basal and activated transcription initiation in vitro. The role of SRB5 was investigated similarly and was also found to be required for efficient basal and activated transcription initiation in vitro as described in Example 2 (See FIG. 8A). Nuclear extracts were prepared from wild-type and srb5Δ1 cells and tested for their ability to synthesize a specific transcript in the presence and absence of purified recombinant SRB5 and GAL4-VP16 proteins. Extracts from wild-type cells produced two specific transcripts of 375 and 350 nt, and the addition of GAL4-VP16 produced a 35-fold increase in the levels of these transcripts. Extracts from srb5Δ1 cells required additional factors in order to synthesize significant levels of specific transcripts, in both the presence and the absence of GAL4-VP16 (FIGS. 8B and 8C). Complementation of the srb5Δ1 extract required both purified recombinant SRB2 and SRB5; the addition of SRB5 alone failed to complement. Western blot analysis revealed that the level of SRB2 protein is greatly reduced in extracts prepared from srb5Δ1 cells.

To confirm and extend these results additional transcription assays were performed using nuclear extracts prepared from cells lacking SRB2 and SRB5 (FIGS. 8D and 8E). The results obtained using extracts from cells lacking both SRB proteins were identical to those obtained with extracts from srb5Δ1 cells. These extracts exhibited no defects in promoter-independent transcription elongation assays. These results indicate that both SRB2 and SRB5 are required for efficient basal and activated transcription initiation in vitro.

Formation of a Stable Preinitiation Complex Involves SRB2 and SRB5

A template commitment assay was used to investigate whether both SRB2 and SRB5 participate in the formation of a transcription initiation complex (FIGS. 9A–B and 9C–D). Extracts prepared from cells lacking SRB2 and SRB5 were used for performing this assay. Two templates were employed that contained identical promoters but differed in G-less cassette length. Specific transcripts of 375 and 350 nt were produced from the long template, while transcripts of 275 and 250 nt were produced from the short template.

Figures 9A, 9C:
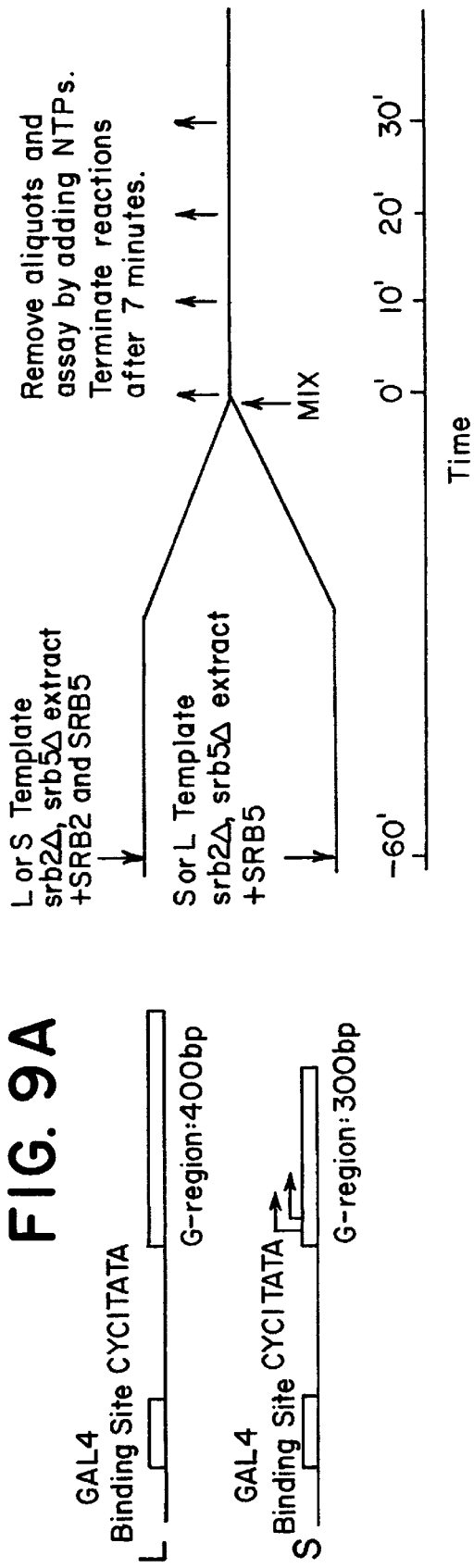

An experiment was first performed to confirm that SRB2 is required for efficient formation of a stable preinitiation complex (FIGS. 9A–B), as described above. The two templates were incubated separately with nuclear extract and SRB5, and a limiting amount of SRB2 protein was added to 1 of the 2 reaction mixtures. After a 60 min preincubation, the 2 reactions were mixed together. Immediately after mixing and every 10 min thereafter, aliquots were removed and nucleotide triphosphates were added to permit RNA synthesis. The reaction was stopped after 7 min to minimize multiple rounds of transcription. Control experiments are shown in lanes 1–4. When srb2Δ1, srb5Δ1 extracts were preincubated with SRB2 and SRB5 along with either the long template (FIG. 9B, lane 1) or short template (FIG. 9B, lane 2), transcripts of the predicted size were produced. When both long and short templates were present in the preincubation mixture, similar levels of long and short transcripts were obtained (FIG. 9B, lane 3). Virtually no transcript was detected when both templates were preincubated with the extract in the presence of SRB5 alone (FIG. 9B, lane 4). When SRB2 was added to the long template mixture, long transcripts were predominant after the two extracts were mixed (FIG. 9B, lanes 5–8). There was no appreciable increase in signal from the short template after 30 min of mixing with the long template. Similarly, when SRB2 was added to the short template mixture, transcripts were produced predominantly from the short template with no appreciable increase in signal from the long template after 30 min of mixing (FIG. 9B, lanes 9–12).

To determine whether SRB5 is required for efficient preinitiation complex formation, a similar experiment was performed (FIG. 9D). This time, the two templates were incubated separately with extract and SRB2, and a limiting amount of SRB5 was added to 1 of the 2 reaction mixtures. The remaining steps were performed as described above. The results of the controls (FIG. 9D, lanes 1–4) were identical to those in FIG. 9D. Lanes 5–12 in FIG. 9D show that transcripts were predominantly obtained from the template that was preincubated in the presence of SRB5 and that there was no significant increase in signal, even after 30 min, from the template incubated in the absence of SRB5.

The template commitment assay results indicate that both SRB2 and SRB5 are required for formation of a stable preinitiation complex and that SRB2 and SRB5 act stoichiometrically in the initiation reaction. These conclusions are based upon two observations. First, the template preincubated in the presence of all necessary factors was preferentially transcribed, upon mixing, relative to the other template, which was incubated in the absence of either SRB2 or SRB5. Second, following mixing, there was no appreciable increase in signal from the template incubated in the absence of either SRB2 or SRB5. If SRB2 or SRB5 acted subsequent to initiation, the templates would be transcribed equally well; since up to 30 min of incubation was allowed after template mixing, there was ample time for any catalytic activity to be carried out on the second template. The observation of little to no increase in second template transcription, even after 30 min, indicates that SRB2 and SRB5 became stably associated with the first template during preincubation.

When the experiment in FIG. 9A was performed using excess SRB2 in the preinitiation step, transcription increased with time from the template that was preincubated in the absence of SRB2. Similarly, when the experiment in FIG. 9C was performed using excess SRB5 in the preincubation step, transcription increased with time from the template that was preincubated in the absence of SRB5. This indicates that much of the template that was preincubated in the absence of SRB2 or SRB5 was still available for transcription and that SRB2 and SRB5 continued to be active for an extended period in the reaction mixture. These data suggest that SRB2 and SRB5 are integral components of the preinitiation complex.

SRB Proteins. TBP. and RNA Polymerase Are Components of a 1.2 Md Complex

The ability of mutations in SRB2, SRB4, SRB5, and SRB6 to specifically suppress the growth phenotypes of cells with CTD truncations indicates that the products of these genes are involved in the same functional process as the CTD. Template commitment assays suggest that SRB2 and SRB5 are components of the transcription initiation complex. These functional studies led to the investigation of whether the SRB proteins interact physically with one another. Cells were constructed that produce functional, epitope-tagged SRB4, SRB5, or SRB6 proteins, and transcriptionally competent nuclear extracts were prepared from these cells. When SRB4, SRB5, or SRB6 were immunoprecipitated, SRB2 and 5%–10% of the TBP in the extract were coprecipitated, as revealed by immunoblotting. This observation suggested that the four SRB proteins and TBP are components of a multisubunit complex which led to an attempt of purification of the SRB proteins from wild-type cells by conventional chromatography.

Figure 10A:
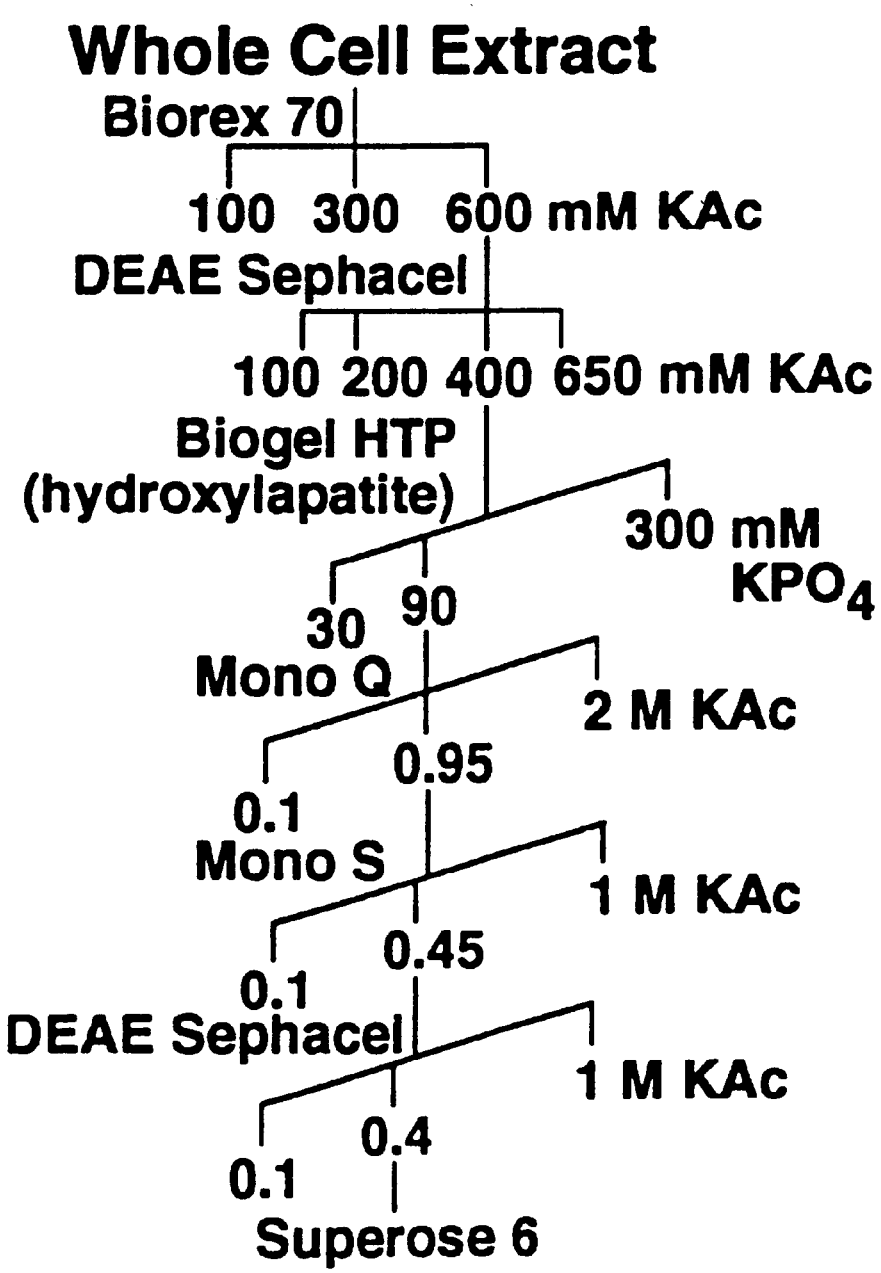

Whole-cell extracts from wild-type cells were fractionated through a series of seven chromatography columns, and rabbit polyclonal antibodies generated against recombinant SRB2, SRB4, SRB5, and SRB6 and against recombinant TBP were used to monitor these proteins during purification (FIG. 10A). Essentially all of the SRB2, SRB4, SRB5, and SRB6 in the whole-cell extract cofractionated through the seven purification steps. Approximately 20 additional polypeptides, including a portion of the TBP in the extract, cofractionated with the four SRB proteins. A subset of these additional polypeptides was identified as RNA polymerase II subunits by Western blot analysis.

Figure 10C:
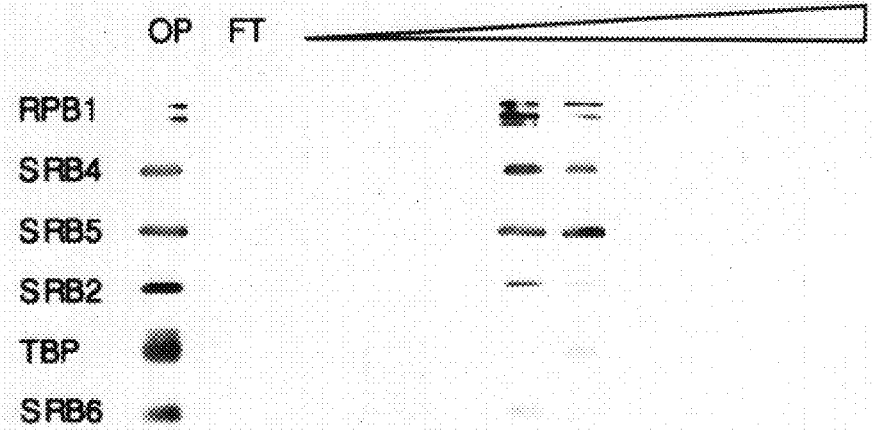

The high molecular weight complex containing TBP, SRB proteins and RNA polymerase II appeared to be quite stable. The proteins in this complex remained tightly associated in fractions exposed to a variety of strong ion exchangers at salt concentrations up to 1.1M potassium acetate and upon gel filtration in buffers containing 400 mM potassium acetate. FIG. 10C shows, for example, the elution profile of TBP, SRB proteins, and RNA polymerase II from the Mono S column. It is estimated that the complex was purified approximately 10,000-fold by quantitative Western blot analysis. The complex appeared to be purified to near homogeneity, since the composition of the complex did not change on chromatography subsequent to the Mono S column.

Gel filtration on Superose 6 revealed that these approximately two dozen polypeptides comigrate as a complex at a position corresponding to a native molecular mass of about 1.2 Md. The sum of the apparent molecular weights of the polypeptide bands that appear to be components of the complex is 1.4 Md, consistent with the size predicted by gel filtration. Since RNA polymerase II accounts for approximately 0.5 Md, the remaining complex has a mass of 0.7–0.9 Md.

Figure 11:
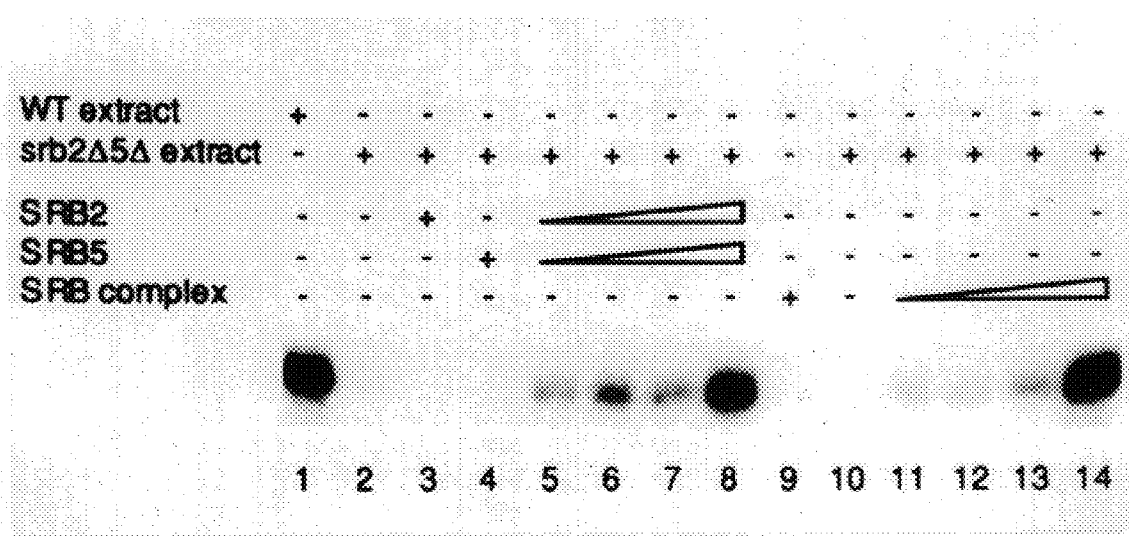
FIG. 11 shows the results of experiments using nuclear extracts from wild-type (Z561) or srb2Δ1, srb5Δ1cells (Z563), tested for their ability to synthesize specific transcripts from the pGAL4CG⁻ template in the presence of recombinant GAL4-VP16 fusion protein (150 ng). Recombinant SRB2 and SRB5 were added to reactions as follows: lane 3, 500 ng of SRB2; lane 4, 500 ng of SRB5; lane 5, 62.5 ng of both SRB2 and SRB5; lane 6, 125 ng of SRB2 and SRB5; lane 7, 250 ng of SRB2 and SRB5; lane 8, 500 ng of SRB2 and SRB5. Purified holoenzyme complex was added to reactions as follows: lane 9, 250 ng; lane 11, 62.5 ng; lane 12 125 ng; lane 13, 250 ng; lane 14, 500 ng. One microgram of holoenzyme complex contained approximately 20 ng of SRB2 and 25 ng of SRB5, as estimated by quantitative Western analysis with known amounts of recombinant SRB2 and SRB5 proteins.

The components of the 1.2 Md complex have both SRB and RNA polymerase activities in vitro. FIG. 11 shows that the 1.2 Md complex can complement a nuclear extract lacking SRB2 and SRB5. The specific activity of native SRB2 and SRB5 in the complex was 100-fold that of recombinant SRB2 and SRB5 proteins In this assay. The RNA polymerase activity of the complex is comparable to that obtained with similar amounts of the purified enzyme in nonspecific transcription assays.

A CTD Column Specifically Retains a TBP-Containing Multisubunit Complex

Figure 12:
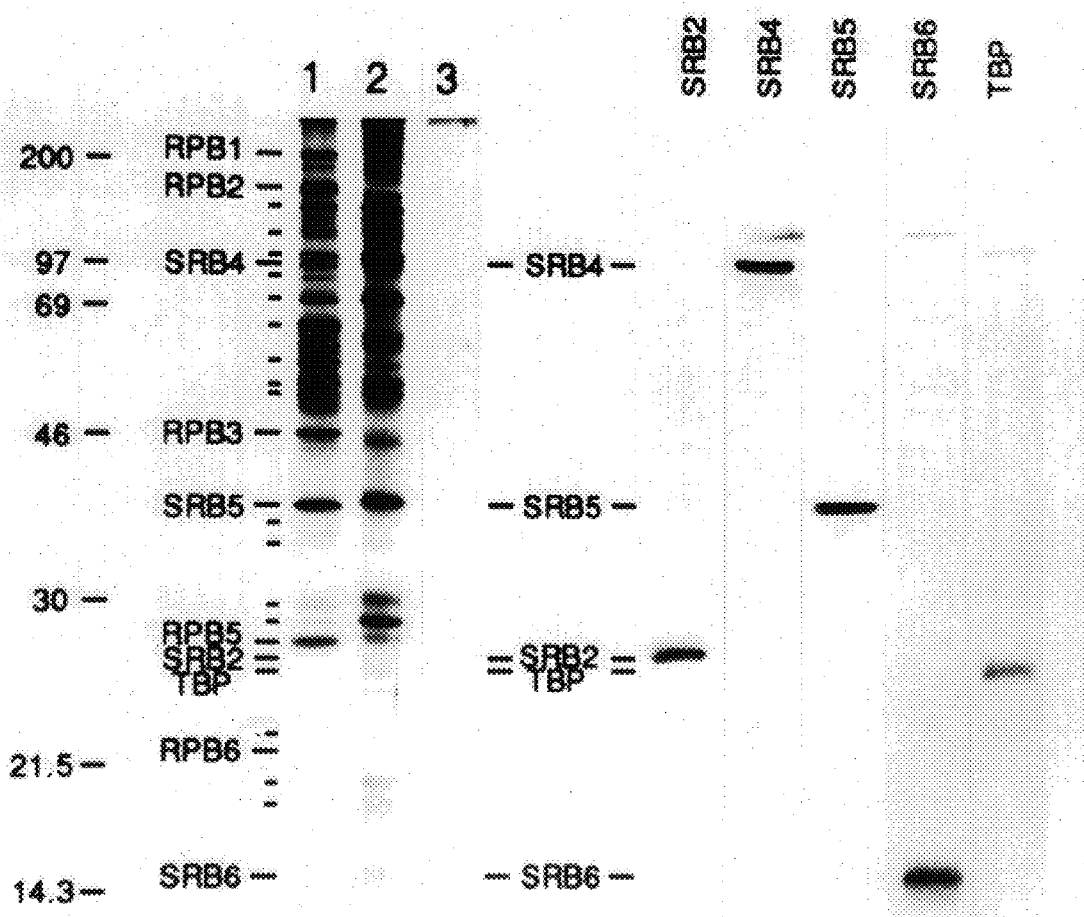
FIG. 12 shows the results of an experiment demonstrating that a TBP-associated complex binds to the RNA polymerase II CTD. (Left panel) Silver-stained SDS-polyacrylamide (15%) gel containing the TBP-containing complex purified by conventional chromatography (lane 1) and proteins in a TBP-containing complex purified by CTD affinity chromatography (lane 2). Yeast whole-cell extract was loaded on GST-CTD and GST control (lane 3) columns, the columns were washed, and proteins were eluted with 0.2M guanidine hydrochloride. The positions of RNA polymerase II subunits, SRB proteins, TBP, and additional polypeptides that are candidate subunits of the complex purified by conventional chromatography are indicated. (Right panel) Western blot analysis of proteins isolated by CTD affinity chromatography. The antibody probes were: lane 1, polyclonal anti-SRB2; lane 2, polyclonal anti-SRB4; lane 3, polyclonal anti-SRB5; lane 4, polyclonal anti-SRB6; lane 5, polyclonal anti-TBP.

The presence of RNA polymerase II and SRB proteins in a TBP-containing multisubunit complex, together with evidence that the CTD interacts with TBP suggested that the SRB-TBP complex may physically interact with RNA polymerase II via the CTD. To investigate this possibility, yeast whole-cell extract was loaded onto columns containing recombinant glutathione S-transferase (GST)-CTD fusion protein or GST alone. The columns were washed extensively, and bound protein was eluted with low concentrations of guanidine hydrochloride (FIG. 12). Guanidine hydrochloride (0.3M) was used for elution because proteins specifically bound to the GST-CTD column could not be eluted with buffers containing high salt concentrations (2M potassium acetate). The proteins that specifically bound the GST-CTD affinity column include the four SRB polypeptides, TBP, and at least a dozen additional polypeptides. Many of these proteins appear to be components of the TBP-containing multisubunit complex purified by conventional chromatography.

An RNA Polymerase II Holoenzyme Responsive to Activators

Figure 13A:
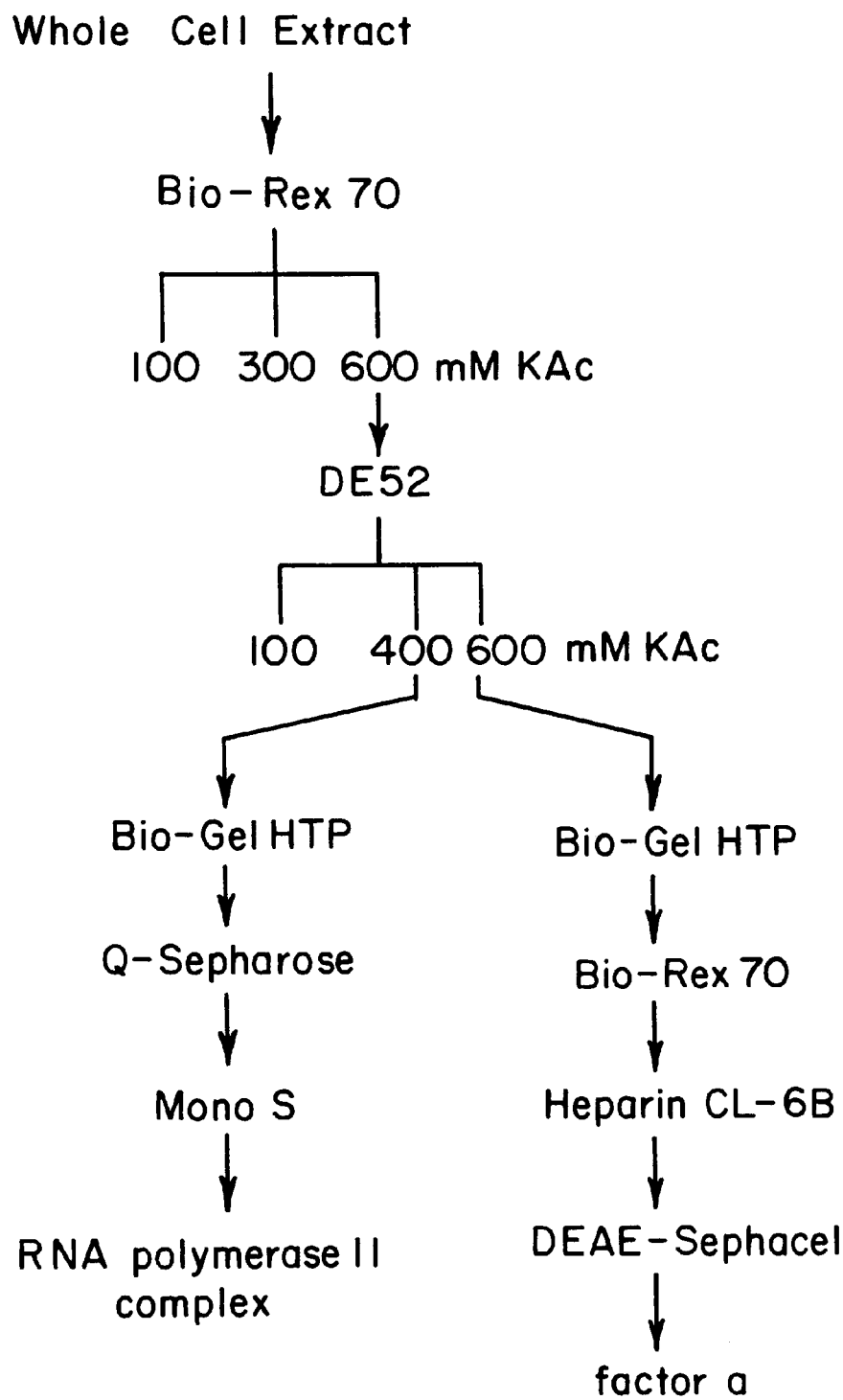

The SRB proteins, which play essential roles in transcription initiation in vivo and in vitro, copurify with RNA polymerase II and additional unidentified polypeptides in a high molecular weight complex. To further investigate the role of the RNA polymerase II-containing complex in transcription initiation, a search was made for additional components needed for selective transcription in vitro. The RNA polymerase II holoenzyme and factor a were purified as described in Example 2, and as described in Sayre, M. H., et al., *J. Biol. Chem.* 267:23383–23387 (1992) (FIG. 13A). Because the complex contains similar amounts of RNA polymerase II and SRB protein molecules, but substoichiometric amounts of TBP, TBP levels needed to be supplemented to support in vitro transcription. (See Example 3). Specific transcription of promoter-containing DNA was obtained following the addition of recombinant TBP and a fraction from a yeast whole cell extract to the RNA polymerase II-containing complex. Purification of this activity revealed that it is composed of two polypeptides (FIG. 13B) whose chromatographic behavior and size (66 kD and 43 kD) are identical to that described for factor a, the yeast homologue of TFIIE (FIG. 14A). Thus, the RNA polymerase II-containing complex represents a novel form of the enzyme that is capable of site-specific initiation when supplemented with yeast TBP and transcription factor a (FIG. 14). Since purified RNA polymerase II requires the assistance of multiple general transcription factors for selective transcription initiation, these results suggested that the high molecular weight RNA polymerase II complex might contain some of these general factors preassembled into the complex, producing an RNA polymerase II holoenzyme.

Figure 15A:
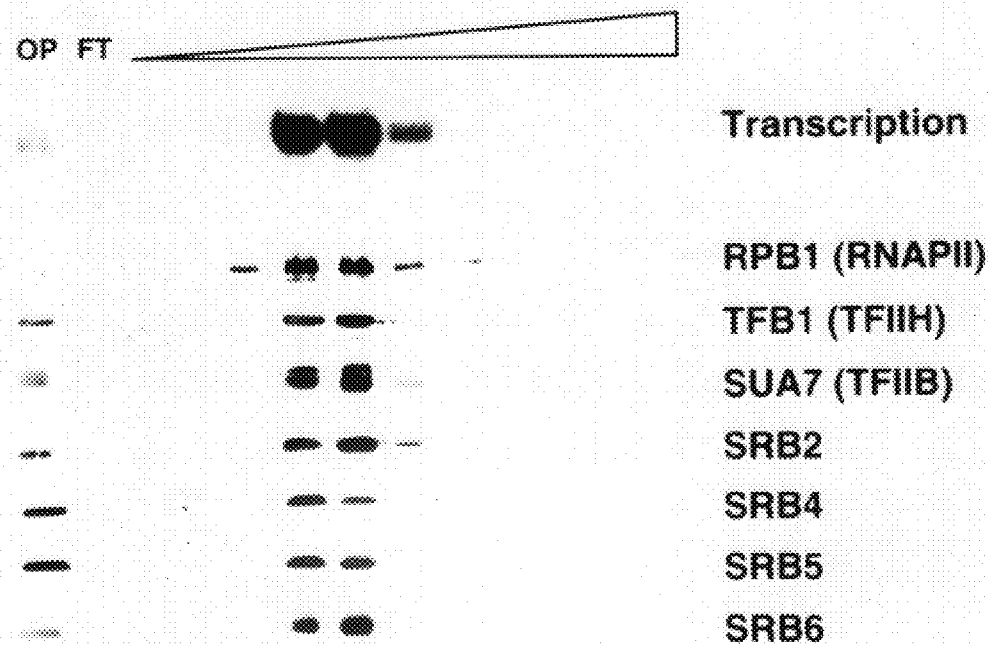
Figure 15B:
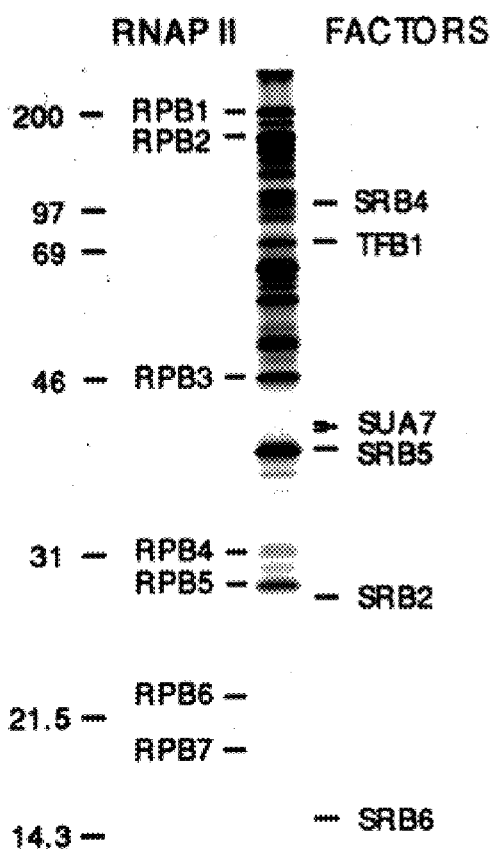

It was further investigated whether a subset of the general transcription factors are associated with RNA polymerase II and SRB proteins in the high molecular weight complex. The general transcription factors bind to common promoter elements such as TATA or initiation motifs. These protein factors include, but are not limited to, TFIIA, TFIIB, TFIID, TFIIE, TFIIF, TFIIG and TFIIH. Five general factors (a, b, d, e, and g) are sufficient to allow yeast RNA polymerase II to accurately initiate transcription in vitro. Column fractions from the final purification step of the RNA polymerase II holoenzyme were tested in reconstituted transcription reactions and subjected to western blot analysis with antisera specific to yeast initiation factors (FIG. 15). Transcription activity coeluted with RNA polymerase II and the SRB2, SRB4, SRB5, and SRB6 proteins. The activity also coeluted with the 41 Kd yeast factor e (TFIIB) protein and the 73 kD TFB1 subunit of yeast factor b (TFIIH). Although specific antisera are not yet available for factor g (TFIIF), the purified complex (FIG. 15B) contains 3 polypeptides whose sizes coincide with those reported for subunits of purified factor g (105, 55, and 30 Kd). Furthermore, TFIIF and TFIIH are essential for the transcription of linear templates by human RNA polymerase II, and it was found that the RNA polymerase II holoenzyme can transcribe linear templates, supporting the inference that the holoenzyme contains activities homologous to TFIIF and TFIIH. Taken together, these results indicate that the purified complex represents a form of RNA polymerase II that is tightly associated with multiple SRB proteins and with factors b, e, and g (TFIIH, TFIIB, and TFIIF), and that this form of RNA polymerase II holoenzyme can accurately initiate transcription when supplemented with factor a (TFIIE) and TBP.

Figure 15C:
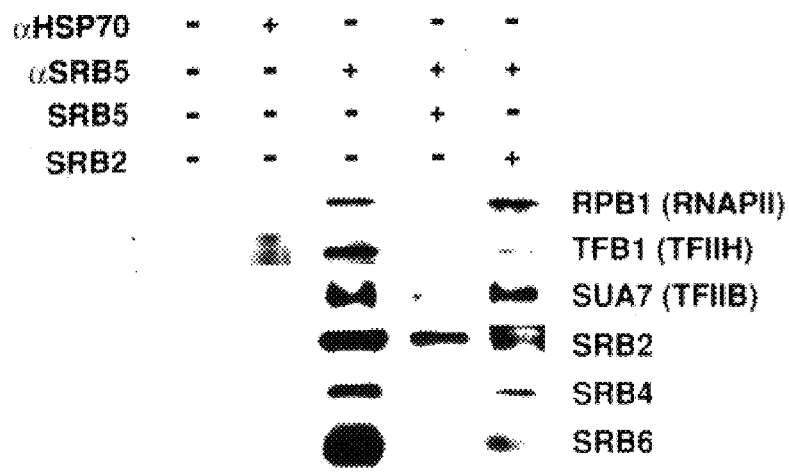

The RNA polymerase II holoenzyme is a highly stable complex; it remains intact upon chromatography through six ion exchange columns and migrates as a single 1.2 Md complex upon gel filtration. To confirm that the holoenzyme consists of a single multisubunit complex, immunoprecipitation experiments were performed. The four SRB proteins, factor e (TFIIB), the TFB1 subunit of factor b (TFIIH), and RNA polymerase II were all found to specifically coimmunoprecipitate from purified preparations of the RNA polymerase II holoenzyme using anti-SRB5 antibodies (FIG. 15C). Similar results were obtained when the complex was immunoprecipitated with antibodies against other holoenzyme components.

The holoenzyme preparation contains approximately equimolar amounts of SRB2, SRB5, factor e (TFIIB) and RNA polymerase II (FIG. 15D and 16A–B). The highly purified holoenzyme does not contain significant amounts of TBP or the TOA1 subunit of yeast TFIIA (FIG. 15D). Although previously shown that some TBP is associated with the multisubunit complex, the highly purified holoenzyme contains less than one molecule of TBP per fifty molecules of RNA polymerase II, consistent with the observation that transcription by the holoenzyme is absolutely dependent on the addition of purified recombinant TBP. At each step in the purification of the holoenzyme, a portion of TBP coelutes from the column with the holoenzyme, while a portion of the TBP elutes as free TBP. This behavior may reflect a weak interaction of TBP with the holoenzyme complex in the absence of DNA, as the purified holoenzyme contains no detectable DNA. TBP can bind to SRB2, SRB5, and the RNA polymerase II CTD on affinity columns, suggesting that TBP may interact physically with these components of the holoenzyme.

Figure 13B:
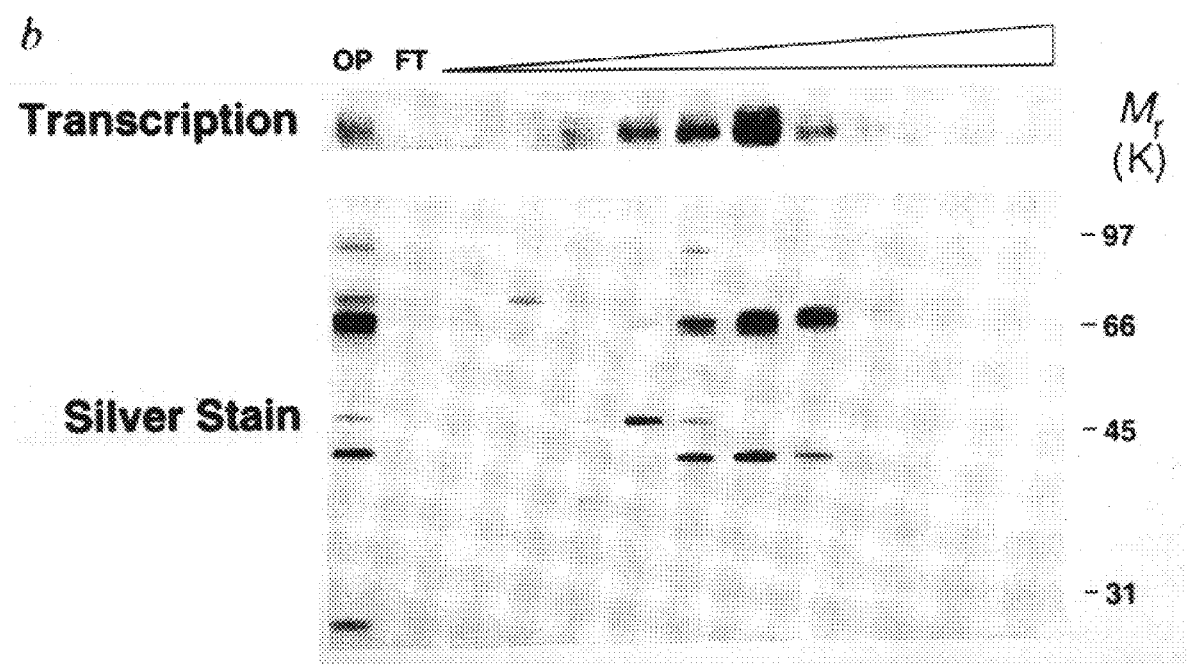
FIG. 13B shows the results of an experiment demonstrating that factor a is required, in addition to TBP and the RNA polymerase II complex, for in vitro transcription.
Figure 17A:
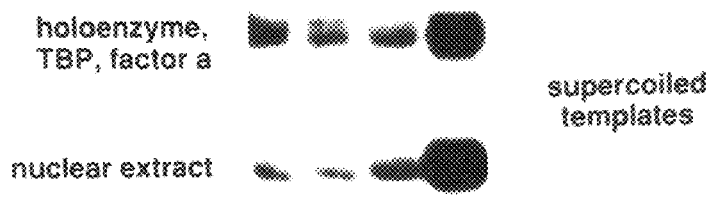
FIGS. 17A and 17B shows the results of experiments demonstrating that transcription by the RNA polymerase II holoenzyme is stimulated by GAL4-VP16.

The ability of the RNA polymerase II holoenzyme to respond to transcriptional activators was also investigated. Purified yeast RNA polymerase II and general transcription factors alone are unable to respond to transcriptional activators. Transcription of supercoiled templates could be stimulated 5-fold by the transcriptional activator GAL4-VP16 in reactions reconstituted with the RNA polymerase holoenzyme, TBP, and factor a (FIG. 17A). Similar results were obtained when linearized templates were used for in vitro transcription (FIG. 13B). For comparison, GAL4-VP16 stimulated transcription of a supercoiled template in crude yeast nuclear extracts 10-fold under the same conditions (FIG. 17A). These data indicate that one or more components of the holoenzyme are able to respond to activation signals from GAL4-VP16.

The presence of an RNA polymerase II holoenzyme probably escaped earlier detection because of its low abundance relative to free RNA polymerase II. While most of the SRB protein in whole cell extracts is complexed with RNA polymerase II, only 6% of RNA polymerase II and 12% of TFIIB is found in the holoenzyme. The nuclear RNA polymerases were originally purified using nonspecific transcription assays, and the general factors that are necessary to direct selective initiation by the purified enzymes were subsequently identified. In contrast, the discovery of a holoenzyme began with a genetic search for factors involved in RNA polymerase 11 transcription in vivo. The genetic experiments demonstrated a physiological role for the SRB proteins in transcription by RNA polymerase in vivo. The biochemical analysis revealed that the SRB proteins are essential transcription initiation factors, and that most of the SRB protein in cells is contained within the holoenzyme.

It is estimated that yeast haploid cells contain approximately 1000 molecules of the holoenzyme, adequate amounts to initiate transcription at active promoters. However, the proportion of active promoters that are transcribed by the holoenzyme is not yet known. It is possible that the holoenzyme is preferentially utilized at some promoters, while free RNA polymerase II and general factors are recruited in a stepwise fashion to others. A significant fraction of cellular RNA polymerase II is involved in elongation of nascent transcripts, and accounts for at least a portion of the enzyme that is not complexed with SRB proteins.

The existence of an RNA polymerase II holoenzyme preassembled with a subset of general initiation factors has implications for the mechanisms involved in the regulation of transcription. Activators appear to function, at least in part, through interactions with multisubunit TFIID. The holoenzyme may be efficiently recruited to promoters through interactions with gene activators and promoter-bound TFIID. The level of activation in crude extracts is more than two-fold greater than the level of activation obtained with the purified holoenzyme. This difference may reflect the absence of TAFs in the reactions reconstituted with the holoenzyme.

The SRB proteins may have multiple roles in the holoenzyme. The SRBs appear to act as a regulatory "glue" that stabilizes interactions between RNA polymerase II and transcription factors. They may also confer some degree of responsiveness to transcriptional activators, perhaps serving the holoenzyme in a manner functionally analogous to TAFs in TFIID. Furthermore, the SRBs may regulate events subsequent to initiation complex formation, for example, phosphorylation of the CTD and promoter clearance.

Suppressors of RNA Polymerase II CTD Truncation Mutations

Figure 18:
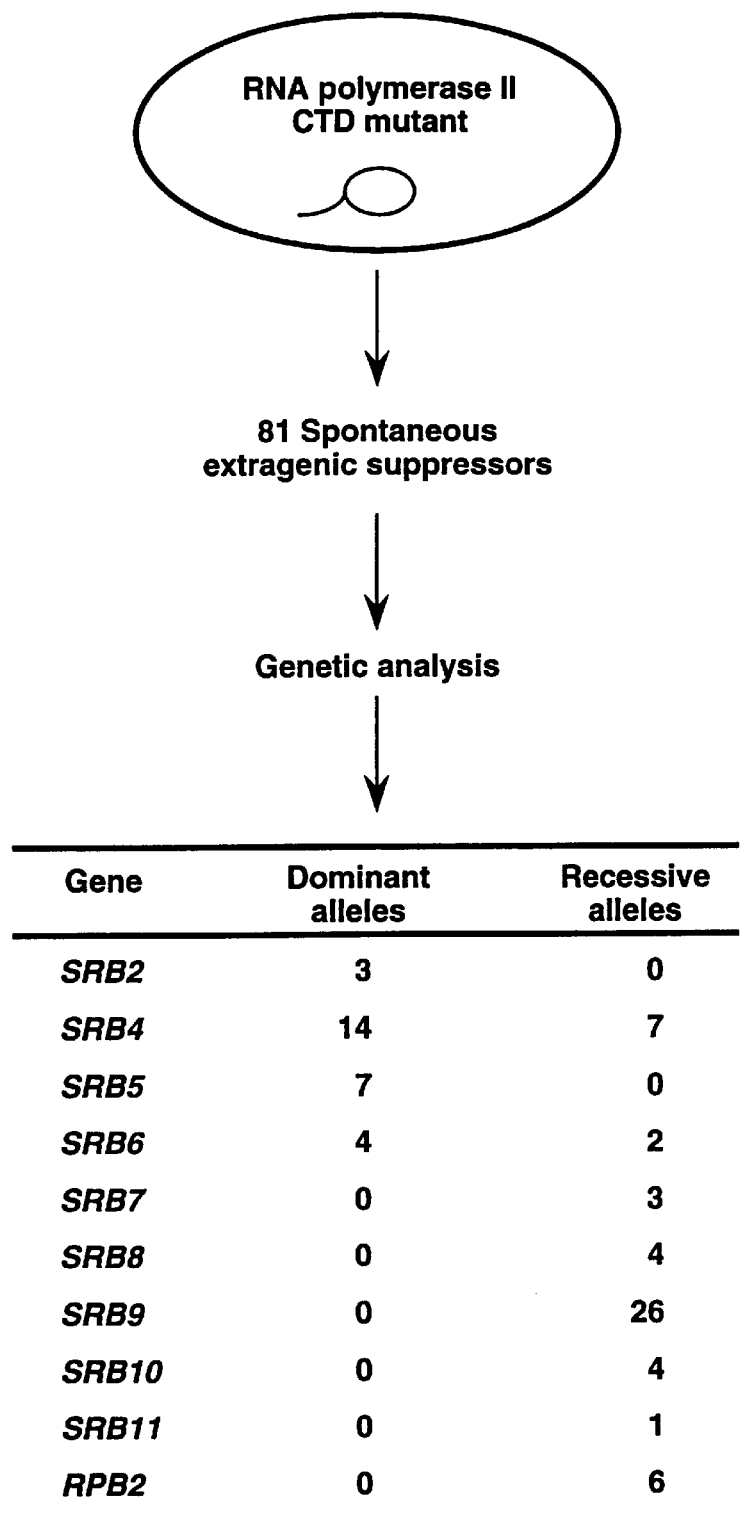
FIG. 18 summarizes extragenic suppressors of CTD truncation mutants.

Extragenic suppressors of a *Saccharomyces cerevisiae* RNA polymerase II CTD truncation mutant were isolated to identify additional components of the transcription apparatus that affect CTD function. (FIG. 18). The cold-sensitive phenotype of cells containing RNA polymerase II CTDs with only 11 intact heptapeptide repeats (rpb1Δ104) was exploited to obtain 81 independent suppressing isolates, of which approximately one third were dominant and two-thirds recessive. Genetic analysis has revealed that mutations in at least ten genes will suppress growth defects of cells containing a truncated CTD. As described above, dominant mutations have been found in four genes, designated SRB2, SRB4, SRB5, and SRB6. Using genetic and molecular complementation analysis, recessive suppressing mutations in six additional genes: SRB7, SRB8, SRB9, SRB10, SRB11, and RPB2 have been identified. Recessive suppressing alleles of SRB4 and SRB6 were also identified.

This selection appears to be nearly saturated since, with the exception of SRB11, more than one independent isolate of each of the ten genes has been identified. The characterization and cloning of the genes containing recessive suppressing mutations is presented in Example 4. SRB7, SRB8, SRB9, SRB10 and SRB11 are newly identified genes, whereas RPB2 is the gene encoding the second largest subunit of RNA polymerase II.

Genetic Analysis of SRB7, SRB8, SRB9, and RPB2

The ability of suppressing alleles of SRB7, SRB8 SRB9, and RPB2 (srb7-1, srb8-1, srb9-1 and rpb2-551, respectively) to suppress conditional phenotypes associated with the CTD truncation mutation rpb1Δ104 was further investigated. These phenotypes include cold- and temperature-sensitive growth and the inability to utilize pyruvate as a carbon source. Growth phenotypes of cells containing an RPB1 CTD truncation mutation and srb7-1, srb8-1, srb9-1, or rpb2-551. Cells were spotted on YEPD medium and incubated at 12° C., 30° C. and 38° C. and on SC medium containing pyruvate as a sole carbon source. Isogonic wild-type, srb7-1, srb8-1, srb9-1, and rpb2-551 backgrounds contained either wild-type RPB1 (27 repeat CTD) or rpb1Δ104 (11 repeat CTD).

The srb7-1, srb8-1, srb9-1, or rpb2-551 alleles permit growth of rpb1Δ104 cells at 12° C. and on media containing pyruvate as a sole carbon source. Cells containing these suppressing alleles, however, do not suppress the temperature-sensitivity associated with the CTD truncation mutation.

These srb and rpb2 alleles do not suppress the conditional phenotypes of other mutations in RPB1 that have been tested. This specificity of suppression argues that SRB7, SRB8, SRB9, RPB2, and the CTD are involved in the same process in transcription initiation.

Cloning and Sequence Analysis of SRB7, SRB8, SRB9, and RPB2

Genomic DNA clones containing SRB7, SRB8, SRB9, and RPB2 were isolated by exploiting their ability to reverse the suppressing phenotype of the recessive srb or rpb2 alleles. A wild-type genomic DNA library constructed in a yeast URA3 centromeric plasmid was transformed into yeast cells containing the CTD truncation mutation rpb1Δ104 and srb7-1, srb8-1, srb9-1, or rpb2-551. Ura$^+$ transformants were then screened for lack of growth at 12° C. and on pyruvate media. When necessary, the wild-type genes were further localized by subcloning fragments of the genomic inserts and again screening Ura$^+$ transformants unable to grow at 12° C. and on pyruvate media. The clones with the smallest inserts were sequenced.

The predicted SRB7 protein is 140 amino acids long (SEQ ID NO: 10) and has a molecular mass of 16 Kd (FIG. 19A–B). SRB8 is predicted to be 1226 amino acids in length (SEQ ID NO: 12) with a molecular mass of 144 Kd (FIG. 20A–C). Partial sequence analysis of SRB8 revealed that it is ORF YCR81W (Oliver, S. G., et al., Nature 357:38–46 (1992)). The predicted SRB9 protein is 1420 amino acids long (SEQ ID NO: 14) and has a molecular mass of 160 Kd (FIG. 21A–H and FIG. 22). Partial sequence analysis of the fourth clone identified RPB2 as a suppressor of CTD truncations. A search of the sequence data banks revealed that SRB7, SRB8, and SRB9 do not have significant sequence similarity to previously identified proteins. SRB9 does, however, contain a single polyglutamine stretch of 16 residues from amino acids 1121 to 1136. The DNA sequences and predicted amino acid sequences for SRB10 (SEQ ID NO: 15 and 16) and SRB11 (SEQ ID NO: 17 and 18) are shown in FIG. 24A–C and FIG. 24A–B, respectively.

SRB7 and SRB9 were physically mapped using the prime λ, clone grid filters of the yeast genome (provided by L. Riles and M. Olson, Washington University). SRB7 maps to the right arm of chromosome IV, approximately 45 kb centromere distal to GCN2 (λ clone 6118). SRB9 also maps to the right arm of chromosome IV, approximately 35 kb centromere distal to ADE8 (λ clone 5513). SRB8 maps to the right arm of chromosome III, approximately 5 kb centromere proximal to TUP1.

The srb7-1 and rpb2-551 mutant alleles were obtained by plasmid gap repair in vivo. Plasmids containing these mutant alleles did not prevent growth at 12° C., unlike their wild-type counterparts, when transformed into yeast cells containing the CTD truncation mutation rpb1Δ104 and srb7-1 or rpb2-551, respectively. This confirms that in each case the correct locus was cloned. The identification of the correct open reading frame is further supported by identification of the suppressing mutations of srb7-1 and rpb2-551, identified by comparing the complete sequences of the cloned wild-type and suppressing alleles. In each case, the alterations were single-point, missense mutations. The mutation in srb7-1 changes alanine 21 to threonine. The rpb2-551 mutation changes alanine 1200 to valine.

SRB8 and SRB9 are Negative Regulators of CTD Function

To determine whether the SRB genes are essential for cell viability, most, if not the entire coding region of each of the SRB genes was deleted to produce srb7Δ1, srb8Δ1, and srb9Δ1. SRB7, like RPB2, is essential. SRB8 and SRB9 are not essential, but cells lacking either one of these genes flocculate and exhibit mild cold- and temperature-sensitive phenotypes. Significantly, null alleles of SRB8 and SRB9 partially suppress the conditional phenotypes associated with CTD truncations. Phenotypes exhibited by deletions of SRB8 or SRB9 are very similar to those phenotypes exhibited by the suppressing mutant alleles of these genes, indicating that we have cloned and identified the correct gene.

Figure 25:
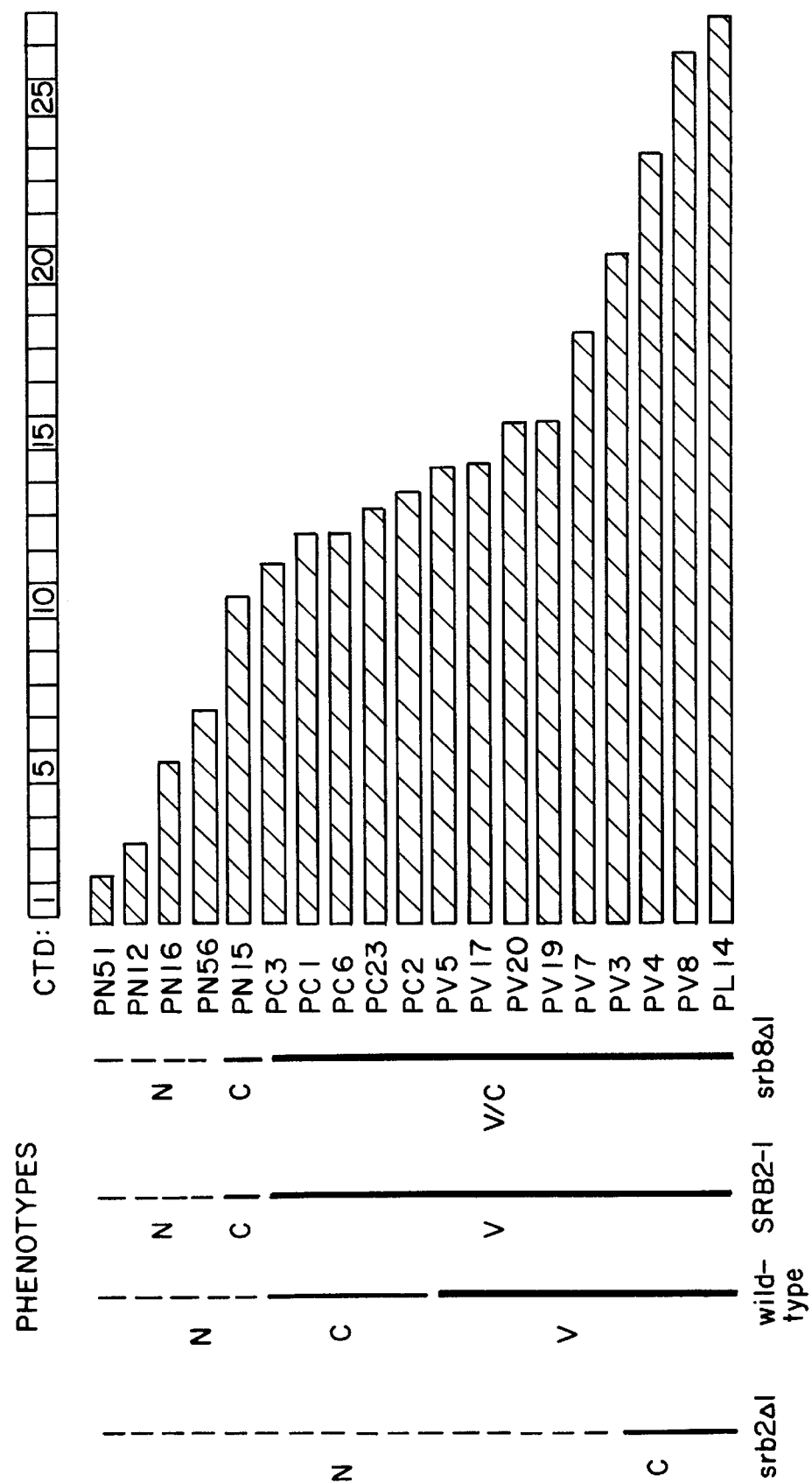
FIG. 25 shows the influence of SRB2 and SRB8 alleles on growth phenotypes of RNA polymerase II CTD truncation mutants.

The influence of srb8Δ1 and srb9Δ1 on RNA polymerase II CTD function was further investigated by examining the effect of these deletion alleles on the growth phenotypes of cells containing a spectrum of CTD truncation mutations. (FIG. 25). Yeast cells lacking SRB8 partially suppressed the conditional phenotypes associated with CTD truncations containing 10–12 complete heptapeptide repeats. Moreover, the lack of SRB8 allowed cells with only nine heptapeptide repeats to survive; thus, loss of SRB8 counters the defects associated with CTD truncation. This pattern of suppression is opposite to that observed with SRB2 alleles. The dominant, gain-of-function SRB2-1 allele produces the same suppression phenotype as the recessive, loss-of-function srb8Δ1 allele. In contrast, the recessive, loss-of-function srb2Δ1 allele, increases the severity of the defects associated with CTD truncation. The influence of srb9Δ1 on the phenotypes of cells containing CTD truncations is similar to that of srb8Δ1. SRB8 and SRB9, therefore, behave as negative regulators of CTD function, while SRB2 behaves as a positive regulator of CTD function.

SRB7, SRB8, and SRB9 are Components of an RNA Polymerase II Holoenzyme

Figure 26A:
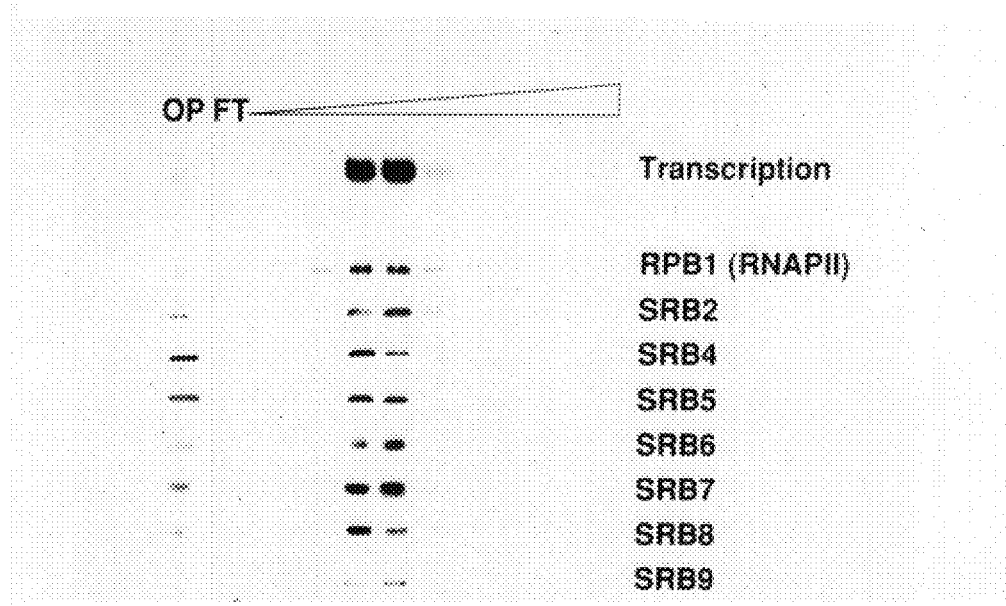
FIGS. 26A–B shows that SRB2 and SRB4-SRB9 are components of an RNA polymerase II holoenzyme.
Figure 26B:
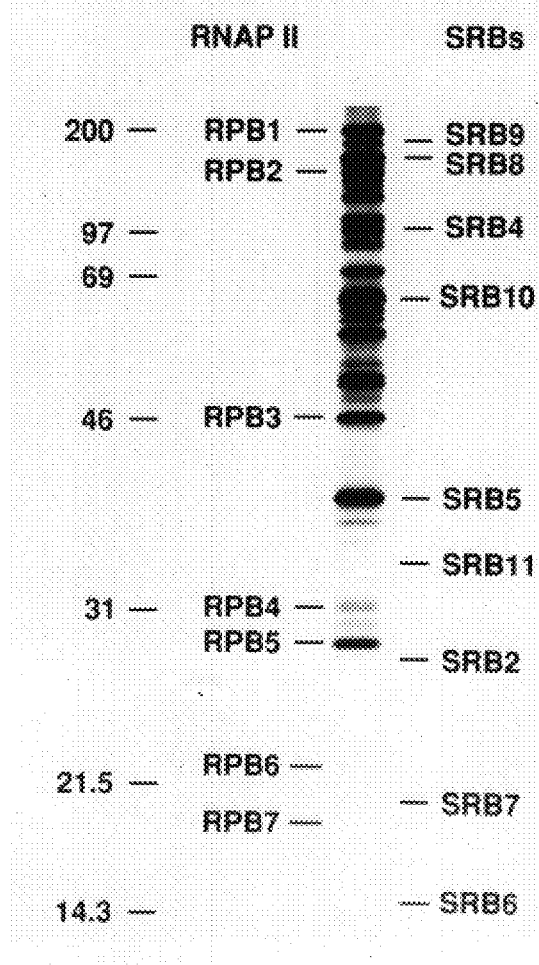

It was investigated whether SRB7, SRB8, and SRB9 are also components of the RNA Polymerase II holoenzyme. Rabbit polyclonal antibodies were generated against recombinant SRB7, SRB8, and SRB9. Column fractions from the final purification step of the RNA polymerase II holoenzyme were tested in reconstituted transcription reactions and subject to Western blot analysis with antisera specific to RNA polymerase II and SRB proteins (FIG. 26A and 26B). Transcription activity coeluted with RNA polymerase II and the SRB2, SRB4, SRB5, SRB6, SRB7, SRB8, and SRB9 proteins.

Multiple Factors Influence CTD Activity

In order to better define the role of the CTD of RNA polymerase II in transcription initiation, extragenic suppressors of a CTD truncation mutant have been isolated Ten genes; SRB2, SRB4SRB11, and RPB2, have now been identified in this selection. The observation that the suppressing mutations in these genes suppress the conditional and auxotrophic phenotypes associated with CTD truncations, but not similar phenotypes associated with point mutations outside of the CTD, argues that these gene products and the CTD are involved in the same process in transcription initiation. Genomic DNA for the genes identified in this selection has been cloned and sequenced. These SRB factors are necessary for yeast cells to grow at wild-type rates and for survival throughout the normal temperature range for cell growth (See Table 1).

TABLE 1

SRB genes

| Gene | SDS-PAGE mobility (kDa) | Protein mass (kDa) | pI | Chromosomal Location[a] | Deletion viability | References[c] |
|---|---|---|---|---|---|---|
| SRB2 | 27 | 23 | 5.2 | VIII | conditional | 1,2,3,4 |
| SRB4 | 98 | 78 | 5.1 | V | inviable | 3,4 |
| SRB5 | 38 | 34 | 4.7 | VII | conditional | 3,4 |
| SRB6 | 15 | 15 | 4.5 | II | inviable | 3,4 |
| SRB7 | 19 | 16 | 4.8 | IV | inviable | |
| SRB8 | 160 | 144 | 5.7 | III | conditional[b] | |
| SRB9 | 180 | 160 | 5.5 | IV | conditional[b] | |
| RPB2 | 145 | 139 | 6.9 | XV | inviable | 5 |

[a]precise map locations have been determined
[b]null alleles partially suppress conditional phenotypes associated with CTD truncations
[c]1) Nonet and Young 1989, 2) Koleske et al. 1992, 3) Thompson et al. 1993, 4) Koleske and Young 1994, 5) Sweetser et al. 1987

SRB genes encode positive and negative regulators of CTD function. Dominant, gain-of-function mutations in SRB2 and SRB5 suppress CTD truncation mutations. Furthermore, cells lacking SRB2 can survive only if the CTD is nearly wild-type in length. In contrast, it is the absence of SRB8 or SRB9 which suppress CTD truncation mutations. SRB8 and SRB9 proteins, therefore, appear to repress CTD activity while SRB2 and SRB5 proteins enhance CTD activity.

Figure 27:
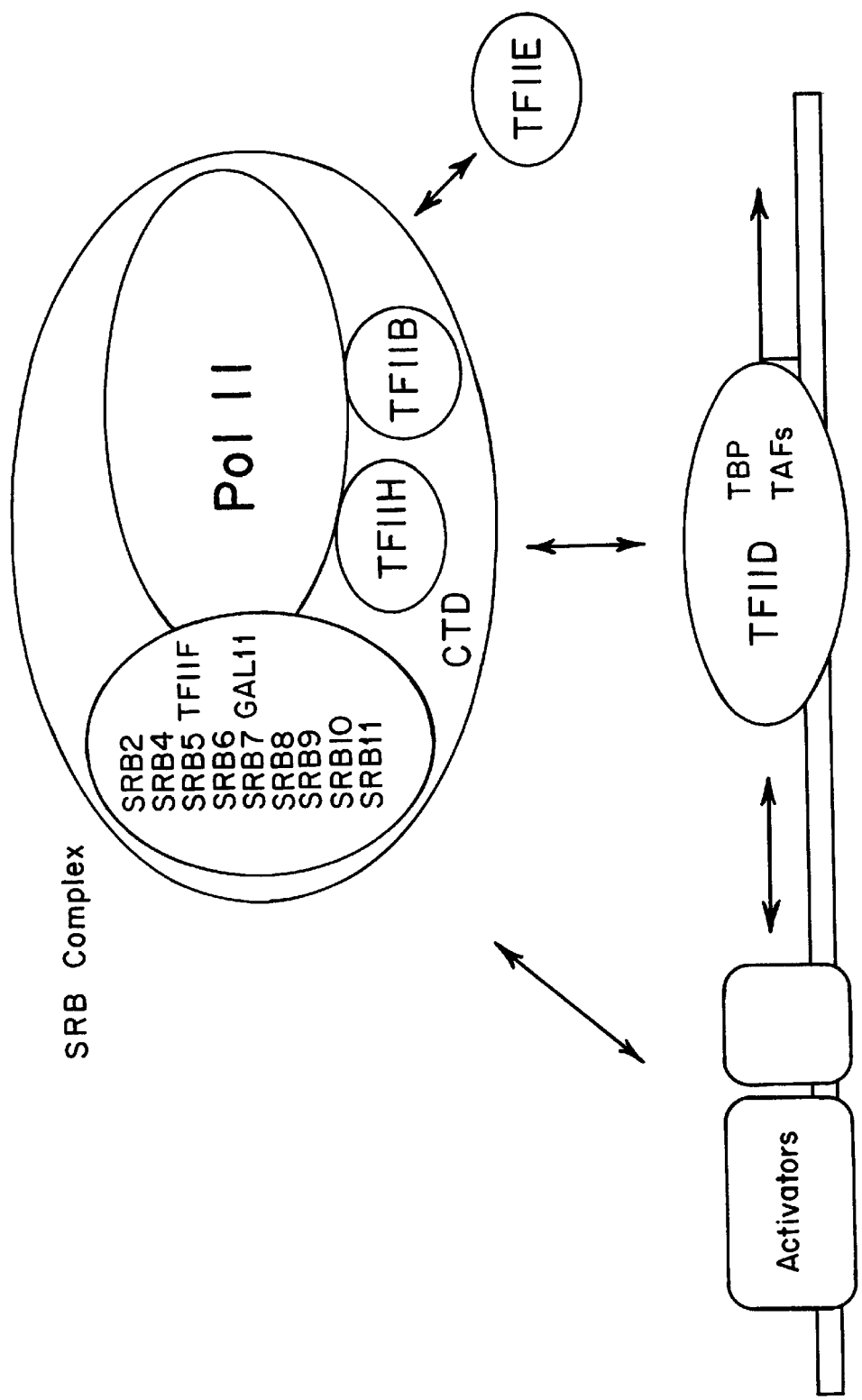
FIG. 27 depicts the RNA Polymerase II holoenzyme model.

FIG. 27 depicts the RNA Polymerase II holoenzyme model. The initiation factors b, e, and g (yeast homologs of TFIIH, TFIIB, and TFIIF) and the SRB proteins are tightly associated with RNA polymerase II to form a holoenzyme. The dotted lines indicate incoming regulatory signals. This holoenzyme and factor a (TFIIE) associate with a complex of TATA-binding protein (TBP) and DNA to form an initiation complex. The SRBs may influence the stability of the holoenzyme or the recruitment of the holoenzyme into a preinitiation complex, possibly in response to regulatory factors.

The RNA Polymerase II Holoenzyme Is The Predominant Form of The Enzyme In The Cell Recruited to Promoters A set of experiments were performed to demonstrate a general requirement for the SRBs in RNA polymerase II transcription in vivo. These data suggest that the RNA polymerase II holoenzyme is the predominant form of the enzyme recruited to promoters in the cell.

A PCR-based mutagenesis strategy was used to construct a mutagenized library of the SRB4 gene and plasmid shuffle techniques were then used to identify a recessive ts allele, srb4-138. The effect of the srb4-138 mutation on cell growth was investigated (FIG. 28A–B). Mutant cells grew normally at the permissive temperature of 30° C. but failed to grow at the restrictive temperature of 37° C. Upon shifting a growing culture of srb4-138 cells to the restrictive temperature, growth rapidly decreased, failing to double before growth ceased altogether. Sequence analysis of srb4-138 revealed multiple point mutations in the open reading frame. The mutation causing the ts phenotype was not determined.

The effect of the srb4-138 mutation on mRNA synthesis was investigated by growing wild-type and mutant cells at the permissive temperature, then shifting the cultures to the restrictive temperature. Aliquots were taken immediately before and at various times after the shift and total RNA was prepared. The amount of poly(A)+ mRNA for each sample was determined by slot blot analysis (FIG. 29A–B). Equal amounts of total RNA were blotted and probed with labeled poly(T). Following the shift to the restrictive temperature there is a dramatic and rapid decline in mRNA in mutant cells while wild-type cells are largely unaffected, indicating a general defect in RNA polymerase II transcription at the restrictive temperature in srb4-138 cells.

To investigate the defect in RNA polymerase II transcription in more detail, synthesis of specific mRNAs was investigated. Equal amounts of total RNA prepared from each sample were hybridized with an excess of labeled complementary oligonucleotide to the ACT1, CDC7, DED1, HIS3, MET19, RAD23, STE2, TCM1, and TRP3 transcripts, and the resulting products were treated with S1 nuclease and subjected to denaturing polyacrylamide gel electrophoresis (FIG. 30). These nine messages represent a broad spectrum of genes affecting diverse cellular processes. Since this approach measures steady-state levels of mRNAs, in the absence of new mRNA synthesis, the rate of reduction is a function of mRNA decay rate. All nine of these messages are sensitive to loss of SRB4 activity. Wild-type cells, on the other hand, continue to synthesize these transcripts throughout the entire 4-hour period at 37° C. The transient decrease in the levels of some of the transcripts from wild-type cells is due to a mild heat shock response (Nicolet, C. M. and Craig, E. A., Meth. Enzymol. 194:710 (1991)).

The influence of the srb4-138 mutation on tRNA synthesis by RNA polymerase III was also investigated. tRNAs are extremely stable, but their transcripts contain introns which are rapidly processed with half-lives of less than 3 minutes (Cormack B. P., and Struhl, K. Cell 69:685 (1992); Knapp, G. et al., Cell 14:221 (1978)). S1 nuclease analysis with an oligonucleotide complementary to the 5' intron-exon junction of the tryptophan family of tRNA transcripts was used to measure RNA polymerase III activity (FIG. 31). There is no appreciable effect on the RNA polymerase III synthesis of tRNA by the srb4-138 mutant.

rRNA synthesis by RNA polymerase I was similarly investigated using S1 nuclease analysis with an oligonucleotide complimentary to the 3' processing junction of the short lived ribosomal precursor RNA (FIG. 31) (Cormack B. P., and Struhl, K. Cell 69:685 (1992); Kempers-Veenstra, A. E. et al., EMBO J. 5:2703 (1986)). There is a substantial decrease in synthesis of the precursor rRNA transcript in the srb4-138 mutant. This decrease in RNA polymerase I activity is similar to that observed in cells containing the ts rpb1-1 allele of RPB1, the gene encoding the largest subunit of RNA polymerase II. (Cormack B. P., and Struhl, K. *Cell* 69:685 (1992); (Nonet, M. et al., *Mol. Cell. Biol.* 7:1602 (1987)). RNA polymerases II and III activities in srb4-138 and rpb1-1 cells are also nearly identical. At the restrictive temperature the synthesis of MET19 and RAD23 transcripts is dramatically reduced while the synthesis of tRNA is largely unaffected. The shutdown of rRNA synthesis in rpb1-1 and srb4-138 cells may be a consequence of a stringent response that shuts off rRNA synthesis under conditions when gene expression is affected (Nonet, M. et al., *Mol. Cell. Biol.* 7:1602 (1987)). While a role for SRB4 in RNA polymerase I transcription can not be completely eliminated, it is very unlikely. The SRBs were identified by the ability of mutations in these genes to specifically suppress conditional and auxotrophic phenotypes associated with truncations of the carboxy-terminal domain (CTD) of RNA polymerase II and, as discussed above, the vast majority of SRB protein in the cell is tightly associated with RNA polymerase II.

The general cessation of mRNA synthesis in srb4-138 cells is unlikely due to indirect effects of metabolic mayhem at 37° C. or loss of a highly unstable protein that is encoded by an unstable RNA whose synthesis is dependent on SRB4. Similar temperature-shift experiments conducted by Cormack, B. P. and Struhl, K. (*Cell* 69:685 (1992)) using a strain containing a ts mutation in CDC28, the gene encoding the cyclin-associated protein kinase that mediates entry into the cell cycle, showed no appreciable effects on RNA polymerase II transcription. In the same study these investigators examined the effects of cycloheximide, a potent inhibitor of cellular translation, on transcription of a subset of messages in wild-type cells and found no effect on the synthesis of these transcripts.

It was previously estimated that approximately 6% of the RNA polymerase II in the cell was in the holoenzyme, adequate amounts to initiate transcription at active promoters. It was unclear, however, if the holoenzyme was preferentially recruited to some promoters, while free RNA polymerase II and general factors were recruited in a step-wise fashion to others. It appears now that the holoenzyme is the form of RNA polymerase II utilized at most promoters. This conclusion is based upon the above demonstration that SRB4 plays a general role in RNA polymerase II transcription and that the majority of SRB4 in the cell is tightly associated with RNA polymerase II in the holoenzyme.

These results have important implications for the regulation of transcription initiation. A fraction of RNA polymerase II is involved in elongation of nascent transcripts, accounting for at least some of the enzyme not complexed with SRB proteins. Thus, remaining RNA polymerase II and general factors would be competing for limited amounts of SRBs. The SRBs, therefore, can play a key regulatory role in RNA polymerase holoenzyme formation leading to initiation complex assembly.

Methods Of Modifyinc Gene Transcription

As described herein, Applicants have identified nine genes encoding nine SRB proteins which act as positive and negative regulators of gene transcription via interaction with RNA polymerase II. In particular, Applicants have demonstrated that SRB2 and SRB5 positively regulate CTD function and that SRB8 and SRB9 negatively regulate CTD function. In addition, Applicants have shown that the SRB proteins are an integral part of a multisubunit holoenzyme complex comprising SRB proteins, general transcription factors b, e, and g (homologies of TFIIH, TFIIB, and TFIIF, respectively) and RNA polymerase II. This RNA polymerase II holoenzyme is preassembled and readily recruited to a DNA promoter, and, when supplemented with factor a (TFIIE) and TATA-binding protein, is capable of site-specific gene transcription. Importantly, the RNA polymerase II holoenzyme described herein is responsive to transcriptional activators, such as GAL4-VP16, unlike purified RNA polymerase II combined with previously known transcription factors. Thus, the SRB proteins contained in the RNA polymerase II holoenzyme act as signal processors which confer responsiveness to both positive and negative activators, most likely through interaction with RNA polymerase II.

Because of the critical role the SRB proteins play in the regulation of gene transcription, it is apparent that modification, or alteration, of one, or more, of the SRB proteins results in the modification, or alteration, of the RNA polymerase II holoenzyme and thus, modify, or alter, gene transcription. Based on this model of an RNA polymerase II holoenzyme, it is reasonable to propose methods of modifying gene transcription in a cell by modifying the initiation of transcription by the RNA polymerase II holoenzyme.

Modification of the RNA polymerase II holoenzyme can be accomplished in a number of ways. One, or more, SRB proteins can be prevented from associating with other SRB proteins, thus, preventing the formation of the holoenzyme complex. One, or more, SRB proteins can be modified such that, even though the holoenzyme complex is formed, the holoenzyme is not functional, e.g., it no longer has the ability to initiate gene transcription). Modification of the RNA polymerase holoenzyme can also be accomplished by modifying the SRB regulatory proteins such that the signals sent to the RNA polymerase II holoenzyme are altered, leading to either a stimulation or suppression of transcription. This can be accomplished by the use of a substance that specifically interacts with a component of the RNA poymerase II holoenzyme. Substances used in the methods described herein can be proteinaceous in nature, such as peptides (comprised of natural and non-natural amino acids) and peptide analogs (comprised of peptide and non-peptide components), or can be non-proteinaceous in nature, such as small organic molecules. The substance can also be a genetically engineered SRB protein with an altered amino acid sequence. These substances would be designed to bind to, or interact with the SRB protein based on the DNA or amino acid sequences of the SRB proteins described herein, or the antibodies reactive with the SRB proteins described herein.

For example, a substance can be identified, or designed, that specifically interferes with the interaction of one, or more SRB proteins in the holoenzyme complex. These substances would mimic a site on at least one SRB protein (e.g., a binding site on the SRB protein) that interacts with another SRB protein, thus preventing, or inhibiting, the association of at least one SRB protein as part of the holoenzyme complex. Thus, formation of the RNA polymerase II holoenzyme is prevented. By preventing the holoenzyme from forming, transcription would be inhibited. Alternatively, these substances would mimic a site on the RNA polymerase II which interacts with, or binds to, at least one SRB protein, again preventing, or inhibiting an SRB protein from interacting with the RNA polymerase II CTD. Thus, the RNA polymerase II holoenzyme complex would be formed, but it would not be a functional holoenzyme complex, capable of initiating transcription. Monoclonal or polyclonal antibodies (e.g, the polyclonal antibodies described herein) specific for one, or more, of the SRB proteins can also be used to prevent, or inhibit, the SRB proteins from participating in the initiation of gene transcription. The antibody would react with, or bind to, the SRB protein and, for example, prevent the SRB protein from associating with other SRB proteins and forming the holoenzyme complex. Thus, gene transcription is inhibited.

The RNA polymerase II holoenzyme is unusual in that it can respond to transcriptional activators, whereas RNA polymerase II or transcriptional factors alone cannot.

Thus, the SRB proteins act as sort of a "regulatory glue" to hold the transcriptional complex together and confer responsiveness to the activator on the holoenzyme. Because of the presence of the SRB proteins, gene transcription can be up-regulated or down-regulated. Thus, substances, including antibodies, that bind to one or more SRB proteins in the holoenzyme complex, would result in up-regulation or down-regulation of gene transcription. For example, SRB2 and SRB5 have been shown to positively regulate gene transcription. Thus, a substance which interacts with either the SRB2 or SRB5 proteins, or both proteins, can decrease, or reduce, the activation of gene transcription. In contrast, substance that interacts with SRB8 or SRB9, which have been shown to negatively regulate gene transcription, can stimulate gene transcription. Alternatively, a mutant SRB protein can be introduced into the cell which is incapable of processing regulatory signals, thus preventing gene transription.

Certain of the SRB proteins also contain amino acid sequences characteristic of protein kinase domains, thus, indicating that they have kinase activity. It is reasonable to predict that these SRB proteins play a role in the phosphorylation of SRB proteins, or other proteins or factors involved with the transcription machinery. Thus, modifying, or altering the kinase activity of one, or more, SRB proteins can also modify, or alter, gene transcription by e.g., preventing the phosphorylation of another transcription factor.

The substances described in the present invention can be identified and tested for their ability to modify gene transcription using an in vitro transcription assay. For example, DNA of interest (i.e., DNA to be transcribed) can be admixed with purified RNA polymerase II, the SRB proteins, transcription factors b, e, g or a (or homologies thereof), TBP and the substance to be tested and maintained under conditions sufficient for DNA transcription to occur. The resulting combination is referred to as a test mixture. DNA transcription can be assessed by determining the quantity of mRNA produced, or by phenotypic evaluation, such as the alteration of yeast growth characteristics as described in the Examples. DNA transcription is determined in the presence of the substance being tested and compared to DNA transcription in the absence of the test substance taking place under identical conditions (e.g., a control mixture). If DNA transcription occurs to a lesser extent in the test mixture (i.e., in the presence of the substance being evaluated) than in the control mixture, the substance has interacted with one, or more SRB proteins in such a manner as to inhibit DNA transcription. If DNA transcription occurs to a greater extent in the test mixture than in the control mixture, the substance has interacted with one, or more, SRB proteins in such a manner as to stimulate DNA transcription.

The SRB proteins can also be genetically altered, such as by site directed mutagenesis, resulting in a SRB protein with altered activity. Genetically altered SRB proteins would affect gene transcription. For example, one, or more genetically altered SRB proteins may be introduced into a cell via a liposome, or linked to a carrier protein known to cross the cell membrane. Alternatively, DNA encoding such a protein may be introduced into the cell using for example, a vector containing the DNA sequence via standard laboratory procedures. These genetically altered SRB proteins would be impaired in their ability to interact with naturally occurring (i.e., unmodified) SRB proteins, thus inhibiting, the formation of the RNA polymerase II holoenzyme, or inhibiting the formation of a functional holoenzyme, thus inhibiting gene transcription. In addition, DNA encoding a wild-type SRB protein with biological activity (i.e., being capable of participating in gene transcription) may be introduced into the cell to supplement a diminished supply of endogenous SRB protein. The wild-type SRB protein would be expressed in the cell, thus increasing the level of SRB protein in the cell, resulting in an increased amount of RNA polymerase II holoenzyme being formed, and, thus, increasing gene transcription.

The ability to modify gene transcription is useful in three categories of human disease: 1) inherited, or genetic, disease; 2) acquired disease, not of infectious origin; and 3) acquired disease, of infectious origin. Changes in gene transcription in these three situations will contribute to changes in the manifestation of the disease.

For example, in an inherited disease, the level of expression of a critical gene is altered relative to the expression of the gene in an individual who does not manifest the disease. If the amount of gene product produced is inadequate, the introduction of a substance into a cell which interacts with at least one SRB protein, resulting, for example, in stimulating gene transcription will result in increased gene product, thus, improving the condition of the individual.

In the example of an acquired disease that is not of infectious origin, such as cancer, modifying gene transcription will also modify the disease state. Typically a cancer is the result of the loss of growth control concomitant with increased transcriptional activity, in a particular cell type. In this case, a substance that interacts with one, or more SRB proteins, thus decreasing gene transcription, will improve the condition of the individual. Because cancer cells have an extraordinarily high rate of gene transcription, the substances will significantly affect the rate of gene transcription in cancer cells, (i.e., rapidly growing cells) but insignificantly affect the rate of gene transcription in normal cells (analogous to the use of anti-metabolites in the treatment of cancer).

In the case of acquired disease where the disease is the result of an infectious agent, such as a bacteria or a virus, an increase in the transcription of genes encoding proteins involved in the immune response would result in the improvement of the condition of the individual. For example, in HIV infection, a substance which interacts with SRB8 or SRB9, which negatively regulate gene transcription, could be targeted for delivery to lymphocytic cells, resulting in the increase of transcription of important lymphocytic proteins. Also, in the case of some virus infections, such as vaccinia virus, host cell gene transcription is completely shut down by the virus. A substance as described above, targeted to the virally infected cells, would turn on the host cell's transcription machinery. Alternatively, for some viruses, i.e., adenovirus, it may be advantageous to turn down the host cell's transcription machinery (as described above for cancer).

It is important to note that only the modification, or alteration, of gene transcription is necessary to see an effect. The inhibition or stimulation of gene transcription may be partial inhibition or partial stimulation. Complete inhibition, or complete stimulation of gene transcription is not necessary. All that is needed is to diminish or enhance gene transcription relative to the rate of gene transcription in a cell that does not have the substance introduced in to it. Thus, as defined herein, an effective amount of a substance to modify gene transcription is that amount of the substance necessary to diminish or enhance gene transcription relative to the rate of gene transcription in a cell that does not have the substance introduced into it.

Introduction of a substance into the cell may be by any conventional means, such as the use of a carrier protein which will interact with the cell membrane; attachment to an antibody which reacts with a cell surface antigen; or encapsulation in a liposome. If the substance is proteinaceous in nature, e.g., a peptide, DNA encoding the substance can be introduced into the cell, and the substance can be genetically expressed in the cell. Alternatively, the DNA can be directly introduced into a cell, e.g., an epidermal cell, via a "gene gun", or other electroporation technique. Other methods of cell targeting known to those of skill in the art may also be used.

According to this invention, the substances can be formulated into pharmaceutical compositions containing a pharmaceutically acceptable carrier and/or other excipients using conventional materials and means. They can be administered using conventional routes such as parenteral, oral, inhalation and the like, using appropriate formulations. Other methods of passive or active transport of small molecules known to those of skill in the art can also be employed.

Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxymethycellulose, polyvinyl pyrrolidone, etc. For parenteral application, particularly suitable are injectable, sterile solutions, preferably oily or aqueous solutions, as well as suspensions, emulsions, or implants, including suppositories.

It will be appreciated that the actual preferred effective amounts of substance in a specific case will vary according to the specific substance being utilized, the particular compositions formulated, the mode of application, the particular situs of application, and the organism being treated. If administered to an individual, dosages for a given recipient will be determined on the basis of individual characteristics, such as body size, weight, age and the type and severity of the condition being treated.

Also encompassed by the present invention are methods of diagnosing disease conditions in humans resulting from abnormalities in the production of, or in the SRB proteins themselves. These methods are based on the detection, and/or quantification, of SRB proteins in the cell, or in a biological sample. A biological sample includes biological fluids such as blood, urine, feces, tissue samples or cells isolated from these sources.

For example, a method of detecting SRB DNA in a biological sample can be accomplished by obtaining a sample and isolating the DNA by known laboratory procedures resulting in DNA available for hybridization with a DNA probe. The DNA probe would be a nucleic acid probe having a nucleic acid sequence of sufficient complementarity to a SRB DNA sequence such that it is capable of selectively hybridizing with SRB DNA under standard hybridization conditions. These conditions may be conditions of high stringency as determined by one of skill in the art. Detection and quantitification of SRB DNA can be determined using standard techniques of detection, such as flourescence detection, if flourescent-tagged probes are used.

An immunoassay can also be used to detect, or quantify, the amount of SRB protein present in a cell. Alternatively, an immunoassay can also be used to determine the biological activity of a SRB protein. For example, a biological sample can be obtained and reacted with an antibody under conditions suitable for binding of the antibody to a SRB protein. If the sample contains SRB protein, the antibody will bind to the protein, forming an antibody/SRB protein complex. This antibody/SRB complex can be detected using, for example, a second antibody which is detectably-tagged and which would bind to this complex as is known to those of skill in the art.

The present invention is illustrated by the following examples, which are not intended to be limited in any way.

EXAMPLES

Example 1: The SRB2 Gene and Encoded Protein
Molecular Analysis of SRB2 pCT21 contains the SRB2 gene within a 6.2 kb Sacl-BamHI DNA fragment from pCT19 (Nonet, M. L, and Young, R. A., *Genetics* 123: 715–724 (1989), inserted into the Sacl-BamHI sites of the pUC18 poly-linker. A set of nested deletions of pCT21 was created as described previously (Nonet, M. L., et al., *Mol. Cell Biol.* 7:16021611 (1987), and SRB2 and surrounding DNA sequenced from double-stranded plasmid DNAs. pCT20 is a pUC18 plasmid that contains the 6.2 kb Sacl-BamHI DNA fragment from pCT1 inserted into the Sacl-BamHI sites of the poly-linker. The SRB2-1 mutation was deduced by sequencing double-stranded pCT20 DNA using a set of six 20 bp oligonucleotide primers:

CT100=ACTACAATCCGGGCTTATCC (SEQ ID NO: 19);

CT101=TCTTGGTCTCAAACTCGCCC (SEQ ID NO: 20);

CT102=GTTGTCCTTGATTAGCACGG (SEQ ID NO: 21);

CT200=CCAAAGTGAAATTTTACTGG (SEQ ID NO: 22);

CT201=TAGACTTTCGGACGTACCGG (SEQ ID NO: 23);

CT202=CGGTGAGACGTTGATCTTGG (SEQ ID NO: 24);

Total RNA was isolated from wild-type and from rna2 yeast cells, and poly(A)$^+$ RNA was purified from these preparations, utilizing procedures described in Elder et al., *Proc. Natl. Acad. Sci. USA* 80:2432–2436 (1993). Northern analysis were performed as described in Nonet et al., (1987). The 550 bp Ncol DNA fragment from pCT21 was nick-translated and used as a probe. In addition, strandspecific probes were generated and used to identify the orientation of the SRB2 transcript. Oligonucleotides were synthesized complementary to sequences 932–952 and 1206–1226 and used for primer extension analysis with poly(A)$^+$ RNA to locate the 5' end of the SRB2 transcript.

DNA Constructs

All DNA manipulations were performed according to Sambrook et al., Molecular Cloning: A Laboratory Manual (Cold Spring Harbor Laboratory 1989). Site-directed mutagenesis was performed as described in Kunkel, T. A., et al., *Meth. Enzymol.* 154:367–382 (1987). The entire coding region of SRB2 was deleted from pCT29 using the primer GAAGGAAGGGGCAGGTGGTTACGCGGTG-TATACGTATAG (SEQ ID NO: 25). This replaced the coding sequence of SRB2 with an Hpal site, creating pCM28-2. To introduce HIS3 into the HpaI site, the 1.75 kb BamHI DNA fragment from pRB328 was blunt-ended by treatment with Klenow and ligated into pCM28-2 to produce pTK33 (containing the deletion allele srb2Δ1::HIS3).

The 12CA5 epitope coding sequence (Kolodziej, P. A., et al., *Mol. Cell. Biol.* 10:1915–1929 (1990)) was introduced contiguous to the carboxyl terminus of the SRB2 protein coding sequence of pCT29 using the primer AGCATTCG-TAAGAACTCAAGCGTAGTCTGG-GACGTCGTATGGGTACAGCTCCAGAGCA CGAAC (SEQ ID NO: 26), producing pTK2. The epitope-tagged SRB2 is fully able to complement the deletion allele srb2Δ1.

The intron of SRB2 was removed from the gene on pTK2, using the oligomer TCCACGAATATAACAGCT-GATTTTCCCATG (SEQ ID NO: 27), to generate pTK21. Two primers, TCGGCATATGGGAAAATCAGCTGTTAT (SEQ ID NO: 28) and CCGTGGATCCTCACAGCTCCA-GAGCACGAA (SEQ ID NO: 29), were used to PCR amplify the coding region of the epitope-tagged SRB2 gene of pTK21 for insertion into the NdeI-BamHI sites of the bacterial expression vector pET3a (Studier, F. W. and Moffatt, B. A., *J. Mol. Biol.* 189:113–130, (1986)), forming pTK27.

To construct isogenic strains for analyzing the growth phenotypes of strains containing various SRB2 alleles, pTK44 and pTK45 were constructed by inserting the 2.5 kb XbaI-SalI fragment from pCT25 (SRB2-1) or pCT27 (SRB2) into YCp405, pCT25 is identical to pCT27 except that it contains the SRB2-1 mutation.

Several plasmid DNAs were used as templates for in vitro transcription. pSL187, a gift of Sha-Mei Liao (Whitehead Institute), is identical to pGAL4CG-(Chasman, D. I., et al., *Nature* 339:679–684 (1989)) except that the GAL4 binding site has been removed. pJJ460 was a kind gift of Michael Woontner and Judith Jaehning (Wootner, M., et al. *Mol. Cell. Biol.* 11:4555–4560 (1991)).

Genetic Analysis

Analysis of the growth phenotypes of cells containing CTD truncation mutations in SRB2 wild-type cells has been described previously (Nonet et al. (1987); Nonet and Young, (1989)), and the experiments described here were performed similarly. To create strains for analysis of CTD length requirements in an srb2Δ1 back-ground, strain Z426 was transformed with the 3.3 kb EcoRI fragment containing srb2 Δ1::HIS3 from pTK33. Z426 has a genomic deletion of RPB1 covered by a wild-type copy of RPB1 on a URA3 CEN plasmid (Table 2). A His$^+$ colony confirmed to have SRB2 replaced by srb2Δ1::His by Southern analysis was designated Z404. The viability of cells containing CTD truncations in combination with the srb2Δ1 allele was assayed by plasmid shuffle with strain Z404 (Boeke et al., (1987)). Plasmids containing the various CTD truncations have been described (Nonet et al., (1987)). Surviving strains were tested for temperature sensitivity at 38° C., cold sensitivity at 12° C., and inositol auxotrophy was previously described (Nonet and Young, (1989)). Strains were previously constructed for analysis of CTD length requirements in an SRB2-1 background (Nonet and Young, (1989)).

TABLE 2

Strain List

| Strain | Common Name | Genotype |
|---|---|---|
| Z494 | YTK54 | Mat α ura-352 his3Δ200 leu2-77 ade2-101 lys2-801 trp1-901 tyr1-501 gal4-542 gal80-538 rpb1Δ182 srb2Δ1::HIS3 [pRP112 (URA3 RPB1)] |
| Z405 | RY1 | Mat α rna2-1 ura1 ade1 his 7 lys2 tyr1 gal |

TABLE 2-continued

Strain List

| Strain | Common Name | Genotype |
|---|---|---|
| Z406 | YTK35 | Mat α ura3-52 his3Δ200 leu2-77 ade2-101 lys2-801 trp1901 tyr1-501 gal4-542 gal80-538 rpb1Δ182 srb2Δ1::HIS3 [pC6(rpb1-104 LEU2) pTK44 (SRB2 LYS2)] |
| Z407 | YTK34 | Mat α ura3-52 his3Δ200 leu2-77 ade2-101 lys2-801 trp1901 tyr1-501 gal4-542 gal80-538 rpb1Δ182 srb2Δ1::HIS3 [pC6(rpb1-104 LEU2) pTK45 (SRB2 LYS2)] |
| Z408 | YTK36 | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 LEU2) YCP405 (LYS2)] |
| Z409 | YTK38 | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 LEU2) pTK44 (SRB2-1 LYS2)] |
| Z410 | YTK37 | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 LEU2) [pRP114 (RPB1 LEU2) pTK45 (SRB2 LYS2)] |
| Z411 | YTK13 | YTK54 [pV17 (LEU2 rpb1-115)] |
| Z412 | YTK14 | YTK54 [pV8 (LEU2 rpb1-112)] |
| Z413 | YTK15 | YTK54 [pV4 (LEU2 rpb1-109)] |
| Z414 | YTK16 | YTK54 [pC23 (LEU2 rpb1-105)] |
| Z415 | YTK17 | YTK54 [pC3 (LEU2 rpb1-103)) |
| Z416 | YTK18 | YTK54 [pV5 (LEU2 rpb1-110)] |
| Z417 | YTK19 | YTK54 [pV3 (LEU2 rpb1-108)] |
| Z418 | YTK20 | YTK54 [pV7 (LEU2 rpb1-111)] |
| Z419 | YTK21 | YTK54 [pV19 (LEU2 rpb1-117)] |
| Z420 | YTK22 | YTK54 [pC1 (LEU2 rpb1-101)] |
| Z421 | YTK23 | YTK54 [pC2 (LEU2 rpb1-102)] |
| Z422 | YTK24 | YTK54 [pC6 (LEU2 rpb1-104)] |
| Z423 | YTK25 | YTK54 [pV20 (LEU2 rpb1-118)] |
| Z424 | YTK72 | Mat α his3Δ200 leu2-3 leu2-112 ura3-52 trp1Δ1 ade2-101 |
| Z425 | YTK73 | Mat α his3Δ200 leu2-3 leu2-112 yra3-52 trp1Δ1 lys2-801 srb2Δ1::HIS3 |
| Z426 | N402 | Mat α ura3-52 his3Δ200 leu2-77 ade2-101 lys 2-801 trp1-901 tyr1-501 gal4-542 gal80-583 rpb1Δ182 [pRP112(URA3 RPB1)] |
| Z427 | CM94 | Mat a/Mat α his3Δ200/his3Δ200 leu 2-3/leu2-112/ leu2-112 ura3-52/ura3-52 trp1Δ1/trp1Δ1 ADE2/ade2 LYS2/lys2-801 |

Figure 3:
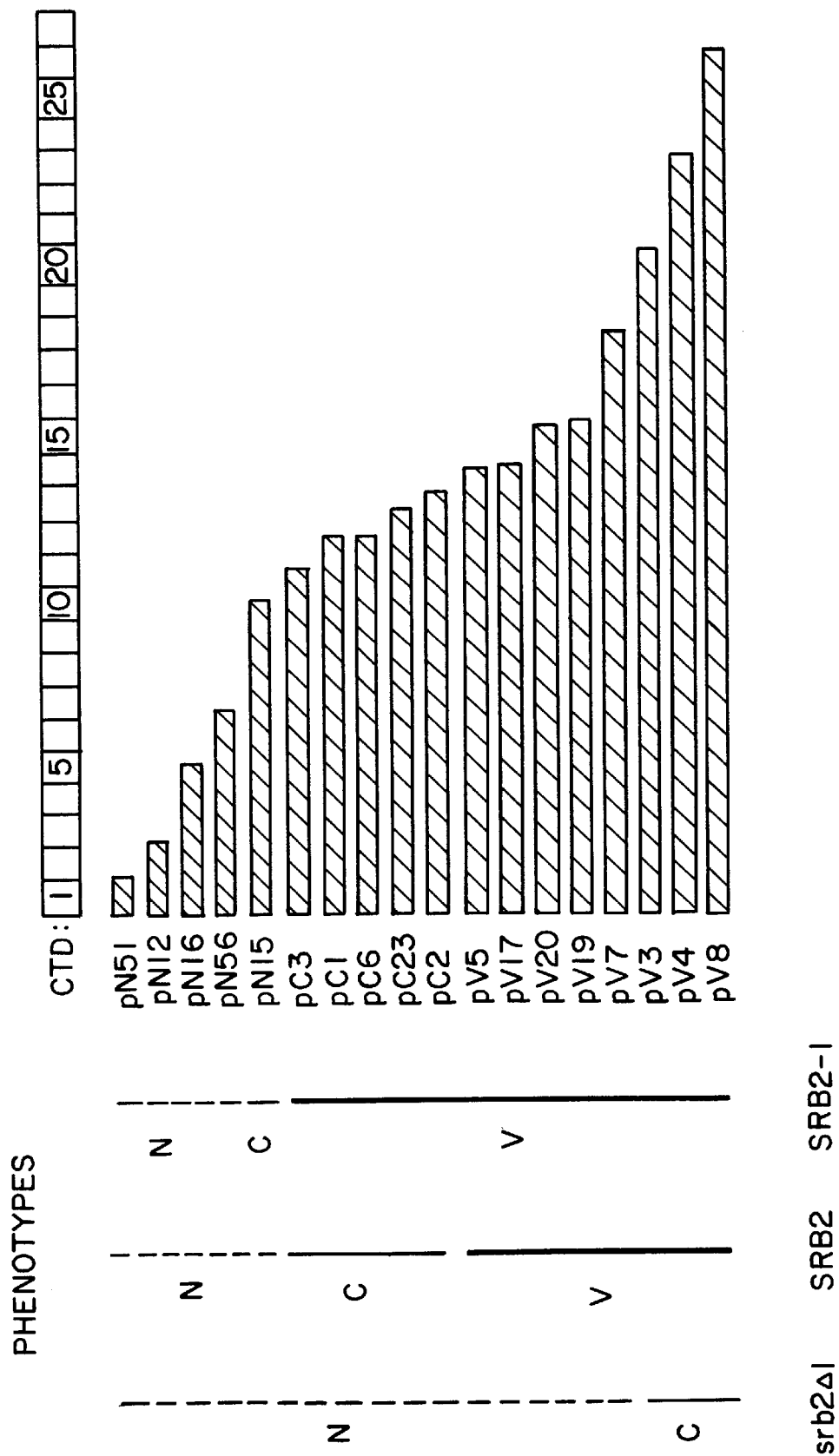
FIG. 3 is a graph showing the influence of SRB2 alleles on growth phenotypes of RNA polymerase II CTD truncation mutants.

Strains containing combinations of SRB2 alleles and CTD truncation alleles were assayed for growth at 38° C., 25° C., and 12° C. and for their ability to grow on minimal medium lacking inositol, as shown in FIG. 3. The degree of CTD truncation is shown for each mutant on the horizontal axis, and the plasmid carrying each CTD truncation allele is indicated (i.e., pN51). The phenotypes exhibited by each of the CTD truncation mutants in the presence of SRB2, the deletion allele srb2Δ1, or the suppressing allele SRB2-1 are shown on the left. Nonviable strains (N) are indicated by a dashed line, conditional strains (C) that were sensitive to hot (38° C.) and cold temperatures (12° C.) and failed to grow on minimal medium lacking inositol are indicated by a thin solid line, and viable (V) strains that exhibit wild-type growth characteristics under all conditions tested are indicated by a heavy solid line.

Example 2: The SRB4, SRB5, SRB6 Genes and Encoded Proteins

Yeast strains and plasmids are listed in Tables 3 and 4, respectively. Yeast medium was prepared as described (Nonet and Young, 1989), except pyruvate medium, which consists of synthetic complete (SC) medium with 2% pyruvic acid (Sigma) as a carbon source. Yeast transformations were done using a lithium acetate procedure (Schiestl, R. H. and Gietz, R. D., *Curr. Genet.* 16:339–346 (1989)). Plasmid shuffle techniques were performed as described by Boeke, J., et al. *Meth. Enzymol.* 154:164–175 (1987)), using 5-fluoroorotic acid (5-FOA) as a selective agent against URA3 plasmids.

TABLE 3

Yeast Strains

| Strain | Alias | Genotype |
|---|---|---|
| BJ926 | | Mat a/Mat α trp1/TRP1 prc1-126/prc1-126 pep4-3/pep4-3 prp1-1122/prbl-1122 can1/can1 |
| Z22 | N114 | Mat α ura3-52 his3Δ200 leu2-3, 112 |
| Z26 | N247 | Mat α ura3-52 his3Δ200 leu2-3, 112 rpb1Δ187::HIS3 (pRP112[URA3 RPB1]) |
| Z28 | RY4 | Mat a/MAT α mal-/mal-gal2/gal2 |
| Z425 | YTK73 | Mat a his3Δ200 leu2-3, 112 ura3-52 trp1Δ1 lys2-801 srb2Δ1::HIS3 |
| Z551 | N400 | Mat a ura3-52 his3Δ200 leu2-3, 112 rpb1Δ187::HIS3 (pC6[LEU2 rpb1Δ104]) |
| Z552 | CTY3 | Mat a ura3-52 his3Δ200 leu2-3, 112 rpb1Δ187::HIS3 SRB4-1 (pC6[LEU2 rpb1Δ104]) |
| Z553 | CTY8 | Mat a ura3-52 his3Δ200 leu2-3, 112 rpb1Δ187::HIS3 SRB5-1 (pC6[LEU2 rpb1Δ104]) |
| Z554 | CTY9 | Mat a ura3-52 his3Δ200 leu2-3, 112 rpb1Δ187::HIS3 SRB6-1 (pC6[LEU2 rpb1Δ104]) |
| Z555 | CTY15 | Mat a ura3-52 his3Δ200 leu2-3, 112 rpb1Δ187::HIS3 SRB4-1 (pRP112[URA3 RPB1]) |
| Z556 | CTY20 | Mat a ura3-52 his3Δ200 leu2-3, 112 rpb1Δ187::HIS3 SRB5-1 (pRP112[URA3 RPB1]) |
| Z557 | CTY21 | Mat a ura3-52 his3Δ200 leu2-3, 112 rpb1Δ187::HIS3 SRB6-1 (pRP112[URA3 RPB1]) |
| Z558 | CTY143 | Mat a/MAT α ura3-52/ura3-52 his3Δ200/his3Δ200 leu2-3, 112/leu2-3, 112 |
| Z559 | CTY144 | Mat a/MAT α ura3-52/ura3-52 his3Δ200/his3Δ200 leu2-3, 112/leu2-3, 112 srb5Δ1::URA3hisG/SRB5 |
| Z560 | CTY148 | MAT α ura3-52 his3Δ200 leu2-3, 112 srb5Δ1::URA3hisG |
| Z561 | CTY151 | MAT a ura3-52 his3Δ200 leu2-3, 112 lys2-801 |
| Z562 | CTY153 | Mat a ura3-52 his3Δ200 leu2-3, 112 lys2-801 srb5Δ1::URA3hisG |
| Z563 | CTY154 | Mat a ura3-52 his3Δ200 leu2-3, 112 lys2-801 srb2Δ1::HIS3 srb5Δ1::URA3 hisG |
| Z564 | CTY158 | Mat a/Mat α ura3-52/ura3-52 his3Δ200/his3Δ200 leu2-3, 112/leu2-3, 112 srb6Δ1::URA3hisG/SRB6 |
| Z565 | CTY176 | Mat a/Mat α ura3-52/ura3-52 his3Δ200/his3Δ200 leu2-3, 112/leu2-3, 112 srb4Δ2::HIS3/SRB4 |
| Z566 | CTY184 | Mat a ura3-52 his3Δ200 leu2-3, 112 srb6Δ1::hisG (pCT66[LEU2 SRB6]) |

TABLE 4

Plasmids

| Plasmid | Description |
|---|---|
| pCT3 | URA3 CEN plasmid. pUN55 (Elledge and Davis, 1988) with Hpal-Nael fragment removed, XhoI site in polylinker SalI-SalI destroyed by digestion and blunting, and XhoI linker (CCGCTCGAGCGG) inserted into SmaI site of polylinker |
| pCT108 | pGAL4CG (Leu et al., 1989) with 300 bp G-less cassette created by ligating SmaI G-less cassette from pJJ460 (Woontner et al., 1991) with SmaI vector fragment of pGAL4CG. |
| pDC127 | pQE9 (Qiagen) with 6xHIS-GST-12CA5 fusion. An oligonucleotide encoding the 12CA5 epitope flanked by a BglII and a BamHI site was cloned into same of pSP72 (Promega), followed by insertion into BamHI of pGEX-2T (Pharmacia). GST-12CA5 fusion was amplified by PCR and inserted into BamHI-SalI-digested pSP72. GST-12CA5 fusion was then cloned into pQE9. |
| pDC130 | pQE9 (Qiagen) with 6xHIS-GST-12CA5-CTD fusion. A KpnI RPB1 containing fragment from pV14 (Nonet et al., 1987b) was inserted into same of pSP72 (Promega), followed by insertion of the |

TABLE 4-continued

Plasmids

| Plasmid | Description |
|---|---|
| | BamHI fragment encoding the CTD and 98 N-terminal adjoining amino acids of RPB1 into pDC127. |
| SRB4 | |
| pCT4 | pCT3 with 9 kb genomic (Z28) Sau3a fragment containing SRB4 inserted at XhoI site. |
| pCT8 | pCT3 with 8 kb genomic (Z552) Sau3A fragment containing SRB4-1 inserted at XhoI site. |
| pCT15 | pCT3 with 2.5 kb subgenomic (pCT4) Sau3A fragment containing SRB4 inserted at XhoI site. |
| pCT16 | pCT3 with 2.8 kb subgenomic (pCT4) Sau3A fragment containing SRB4 inserted at XhoI site. |
| PCT48 | pCT15 with BstXI-SnaBI SRB4-1 C-terminus fragment from pCT8 replacing some SRB4 fragment. |
| pCT54 | srb4Δ2::HIS3, created by ligation of SRB4 SalI-BamHI from pCT16 with SalI-BamHI of pSP72 (Promega), followed by PCR with the oligonucleotides TAATATCCTGAGTCACTCCT and TATGGCTTTTAAGCTGCTTA and ligation of PCR product with SmaI HIS3 kan fragment from B2179 (G. R. Fink, Whitehead). |
| pCT107 | pGEX-2T (Smith and Johnson, 1988) with GST-SRB4 fusion. NdeI site at ATG of SRB4 created by ligation of SRB4 SalI-XbaI from pCT15 with SalI-XbaI of pBSIISK(−) (Stratagene), followed by site-directed mutagenesis. NdeI (partial/blunt)-SnaBI SRB4 containing fragment was then ligated with BamHI (blunt)-digested pGEX-2T. |
| SRB5 | |
| pcT14 | pCT3 with 9 kb genomic (Z553) Sau3A fragment containing SRB5-1 inserted at XhoI site. |
| pCT20 | pCT3 with 1.9 kb subgenomic (pCT14) Sau3A fragment containing SRB-1 inserted at XhoI site. |
| pCT32 | pcT20 with unique SacI site in insert, created by removal of NarI (blunt)-SacII (blunt) fragment from vector. |
| pCT37 | srb5Δ1::URA3hisG, created by ligation of SRB5-1 EcoRI-BamHI from pCT20 with EcoRI-BamHI of pSP72 (Promega), followed by PCR with the oligonucleotides TAATCATTGGCACCTGGGCA and CTTTTCTTCTTAATATGGAA and ligation of PCR product with BglIII (blunt)-BamHI (blunt) URA3 kan hisG cassette from B2178 (G. R. Fink). |
| pCT39 | pcT32 containing SRB5, obtained by gap repair of vector containing fragment of pCT32 SacI-XhoI digest. |
| pCT98 | pET-3a (Studier and Moffat, 1986) with SRB5. NdeI site at ATG of SRB5 created by ligation of SRB5 EcoRI-BamHI from pCT39 with EcoRI-BamHI of pBSIISK(−) (Stratagene), followed by site-directed mutagenesis. NdeI-EcoRI (blunt) SRB5-containing fragment was then ligated with NdeI-BamHI (blunt)-digested pET-3a. |
| SRB6 | |
| pCT26 | pCT3 with 3 kb genomic (Z554) Sau3A fragment containing SRB6-1 inserted at XhoI site. |
| pCT29 | pCT3 with 1.0 kb subgenomic (pCT26) Sau3A fragment containing SRB6-1 inserted at XhoI site. |
| pCT38 | srb6Δ1::URA3hisG, created by ligation of SRB6-1 EcoRI-BamHI from pCT29 with EcoRI-BamHI of pSP72 (Promega), followed by PRC with oligonucleotides TAAAAAGGCGGTATTTATCT and CATATAGTGCCTGGTTGCTC and ligation of PRC product with BglIII (blunt)-BamHI (blunt) URA3 kan hisG cassette from B2178 (G. R. Fink). |
| pCT40 | pCT29 with SRB6, obtained by gap repair of vector containing fragment of pCT29 BalI-SphI digest. |
| pCT66 | LEU2 CEN pUN105 (Elledge and Davis, 1988) with SRB6, created by ligation of SRB6 BamHI (blunt)-SalI (blunt) from pCT40 with SmaI-digested pUN105. |
| pCT116 | pGEX-2T (Smith and Johnson, 1988) with GST-SRB6 fusion. NdeI site at ATG of SRB6 created by ligation of SRB6 SalI-XbaI from pCT40 with SalI-XbaI of pBSIISK(+) (Stratagene), followed by site-directed mutagenesis. NdeI (blunt)-XbaI SRB6-containing fragment was then ligated with BamHI (blunt)-digested pGEX-2T. |

Extragenic suppressors of the cold-sensitive phenotype of Z551 were isolated as previously described (Nonet and Young, 1989). Dominant suppressors were identified by mating to Z26, selecting against the presence of pRP112 using 5-FOA and assaying growth at 12° C. on YEPD. Diploids able to grow at 12° C. contained a dominant suppressor. Isogenic wild-type, SRB4-1, SRB5 1, and SRB6-1 strains containing various RPB1 alleles (rpb1-4, rpb1-5, rpb1-6, rpb1-10, rpb1-12, rpb1-13, rpb1-14, rpb1-15, and rpb1-18) on LEU2 CEN plasmids were constructed using Z26, Z555, Z556, and Z557 and plasmid shuffle techniques. Isogenic wildtype, SRB4-1, SRB5-1, and SRB6-1 strains containing rpb1-1 on a URA3 CEN plasmid, pRP1-1 [U] were constructed by transforming Z551, Z552, Z553, and Z554 with pRP1-1[U], followed by growth in SC-Ura medium to permit loss of pC6. Growth assays were performed by suspending similar numbers of cells in water and transferring equal volumes to agar plates with a 48 prong apparatus.

Deletions of SRB4, SRB5, and SRB6 were created by a single step disruption method (Rothstein, R., *Meth. Enzymol.* 194:281–301 (1991)). Z558 was transformed with the desired DNA fragment and plated on the proper selective medium. Southern analysis was used 10 confirm that a single copy of the desired SRB gene had been deleted. The diploid was sporulated and tetrads (more than 20) were dissected on YEPD plates and scored for nutritional auxotrophies and growth at a variety of temperatures. Z565 was created by transformation with the EcoRl-Xbal fragment of pCT54 containing the srb4Δ2::HIS3 fragment and plating on SC-His medium. Two spores or fewer from each tetrad were viable, and these were all histidine auxotrophs, indicating that SRB4 is essential. To confirm that SRB4 is essential, Z565 was transformed with pCT15 (URA3 SRB4), tetrads were dissected, and His$^+$ Ura$^+$ segregants were streaked to 5-FOA plates. They were unable to grow on 5-FOA-containing medium, confirming that SRB4 is essential. Z559 was created by transformation with the EcoRI-Sphl fragment of pCT37 containing the srb5Δ1::URA3-hisG fragment and plating on SC-Ura medium. Segregants scored 2:2 for uracil prototrophy and air uracil prototrophs exhibited cold-sensitive, temperature-sensitive, and slow growth phenotypes, indicating that SRB5 deletion strains are conditionally viable. Z564 was created by transformation with the Bglll-BamHl fragment of pCT38 containing the srb6Δ1::URA3-hisG fragment and plating on SC-Ura medium. Two spores of fewer from each tetrad were viable, and these spores were all uracil auxotrophs, indicating that SRB6 is essential. To confirm that SRB6 is essential, Z564 was transformed with pCT66 (LEU2 SRB6) tetrads were dissected and Z566 was created by placing a Ura$^+$ Leu$^+$ segregant onto 5-FOA to select for the excision of the URA3 gene. Z566 was transformed with pCT40 (URA3 SRB6), grown in SC-Ura medium to permit loss of pCT66, and then tested for growth on 5-FOA plates. No growth was observed on 5-FOA. Confirming that SRB6 is essential.

Several strains were constructed for producing yeast nuclear extracts for in vitro transcription assays. Z425 was mated to Z560, and tetrads were dissected to produce the wild-type Z561, srb5Δ1::URA3-hisG strain Z562, and srb2Δ1::HIS3, srb5Δ1:URA3-hisG strain Z563, Z562 and Z563 displayed identical temperature-sensitive, cold-sensitive and slow growth phenotypes.

DNA Methods

DNA manipulations were performed according to Sambrook et al. (1989). Site directed mutagenesis was performed as described in Kunkel et al., (1987). Polymerase chain reaction (PCR) amplifications to produce pCT54 (srb4Δ2), pCT37 (srb5Δ1) and pCT38 (srb6Δ1) were performed with Taq DNA polymerase (Perkin Elmer) in 100 μl of buffer (provided by the manufacturer) supplemented with 1.0 mM MgCl$_2$ and 200 μM dNTP for a total of 25 cycles. Primer concentrations were 0.5 μM with 50 ng of DNA and cycling was at 94° C. (1.0 min), 50° C. (1.0 min), and 72° C. (2.5 min).

Library Construction and Cloning

Yeast genomic DNA libraries were prepared from strains Z28 (wild type), Z552 (SRB4-1), Z553 (SRB5-1), and Z554 (SRB6-1). Genomic DNA was isolated partially digested with Sau3A and separated on a 0.7% agarose gel, 6–12 kb fragments were purified by electroelution, and the ends were partially filled in with d(AG)TP using Klenow. The URA3 centromeric plasmid pCT3 was digested with Xhol, and the ends were partially filled in with d(CT)TP to make them compatible with the ends of the Sau3A digested genomic DNA. Following ligation, DH5α cells made competent by the method of Hanahan (Hanahan, D., et al., *Meth. Enzymol.* 204:63–113 (1991)) were transformed. Libraries contained approximately 150,000 individual recombinants with an average insert size of approximately 10 kb. Subgenomic DNA libraries were prepared from pCT4 (SRB4), pCT14 (SRB5-1), and pCT26 (SRB6-1) in a manner similar to that described above for the genomic DNA libraries. Plasmid insert DNA was partially digested with Sau3A and separated on a 1.5% agarose gel, and 1–3 kb fragments were purified by gene clean (BIO 101), and the ends were partially filled in with d(AG)TP using Klenow.

Fragments were ligated with pCT3 prepared as described above and transformed into DH5α cells. Subgenomic libraries contained approximately 20,000 individual recombinants with an average insert size of 2 kb.

Genomic clones of SRB4-1 (pCT8). SRB5-1 (pCT14), and SRB6-1 (pCT26) were isolated by transformation of the respective genomic library into Z551, plating to SC-Ura medium and placing plates at 12° C. following a 12 hr recovery period at 30° C. Approximately 1 in 2000 primary transformants was able to grow at 12° C. For each library transformed, the genomic clone was isolated by the method of Hoffman, C. S. and Winston, F., *Gene* 57:267–272 (1987), from over 12 Ura colonies able to grow at 12° C., and was retested for the ability to suppress the cold-sensitive phenotype of Z551. A genomic clone of SRB4 (pCT4) was isolated from the wild-type Z28 library using a recessive SRB4 allele, which has a tight temperature-sensitive phenotype in combination with a CTD truncation allele of 11 repeats. The presence of pCT4 restores a leaky temperature-sensitive phenotype to this strain at 38° C. Subgenomic clones made from pCT4 (SRB4), pCT14 (SRB5-1), and pCT26 (SRB6-1) were selected as described above in order to isolate pCT15 and pCT16 (SRB4), pCT20 (SRB5-1), and pCT29 (SRB6-1), respectively. pCT15 and pCT16 differ only in the amount of DNA downstream of SRB4. pCT39 was created from pCT32 in vivo by transforming Z22 with Sacl-Xhol-digested pCT32 DNA and isolating the plasmid from a Ura$^+$ transformant that had repaired the plasmid with wild-type SRB5 sequences from the chromosome (Rothstein. 1991). Similarly, SRB6 was isolated using Ball-Sphl-digested pCT29 DNA to create pCT40.

Sequence Analysis

Insert DNAs from pCT15, pCT20, and pCT29 (containing SRB4. SRB5-1, and SRB6-1, respectively) were completely sequenced on each strand. Unidirectional deletions were constructed using the Erase-a-Base system (Promega), and double-stranded sequencing with dideoxy-nucleotides and Sequenase (US Biochemical) was carried out as described by the manufacturer, using T3 and T7 promoter primers. The suppressing mutations in SRB4, SRB5, and SRB6 were deduced by sequencing using oligonucleotide primers that spanned the entire open reading frames. Positive numbering of the DNA begins with the predicted start site of translation. pCT15 (SRB4) and pCT48 (SRB4-1) were sequenced, and the SRB4-1 mutation was identified as a G to T transversion (nucleotide 1057) that changed amino acid 353 from Gly to Cys.pCT39 (SRB5) and pCT32 (SRB5-1) were sequenced, and the SRB5-1 mutation was identified as a C to T transition (nucleotide 65) that changed amino acid 22 from Thr to Ile.pCT40 (SRB6) and pCT29 (SRB6-1) were sequenced, and the SRB6-1 mutation was identified as a C to G transversion (nucleotide 258) that changed amino acid 86 from Asn to Lys. Sequence comparison analysis was performed at the National Center for Biotechnology Information using the BLAST network service.

Purification of Recombinant Proteins

Purification of SRB2 has been previously described. SRB5 protein was purified from the bacterial strain BL21 (DE3) pLysS (Studier and Moffatt, 1986) carrying the plasmid pCT98 in the same manner in which SRB2 was purified. SRB4 and SRB6 were purified as fusions to GST from DH5α carrying pCT107 and pCT116, respectively, according to the method of Smith and Johnson (1988). GAL4(1-147)-VP16 protein was purified as described by Chasman et al. (1989) from XA90 carrying pJL2. GST-fusion proteins for CTD affinity purification were purified from DH5α, carrying pDC127 or pDC130 by affinity chromatography on glutathione-agarose (Sigma) and Ni-NTA agarose (Qiagen), and then by ion exchange chromatography on SP Sepharose (Pharmacia) to an approximate purity of 95%.

In vitro Transcription

Promoter-dependent in vitro transcription was carried out as described by Liao, S. M. et al., *Genes. Dev.* 5:2431–2440 (1991). Three hundred nanograms of template were used for promoter-dependent in vitro transcription reactions, except the template commitment assays, in which 600 ng of template was used per reaction. Optimal activity was obtained using 100 μg of Z561 protein, 150 μg of Z562 protein, and 150 μg of Z563 protein. Transcripts were quantified using a Fuji Bio-image analyzer, promoter-independent transcription assays were performed according to Nonet et al. (1987). Purified SRB complex used in in vitro transcription assays was purified as described below. Eluate from the second Biorex 70 column was dialyzed in buffer A(50) (buffer A containing 50 MM potassium acetate) and concentrated 4-fold by centrifugation through Centricon 10 filter units (Amicon).

FIG. 8A shows the template pGAL4CG⁻ contains a CYC1 TATA element downstream of a single GAL4 binding site that directs expression of a G-less transcript.

FIGs. 8B and 8C shows nuclear extracts made from wild-type cells (Z561) or srb5Δ mutant cells (Z562) were tested for their ability to synthesize specific transcripts from the pGAL4CG⁻ template in the presence or absence of recombinant SRB2 (250 ng) and/or SRB5 (250 ng). Transcription reactions were carried out in the absence (B) or presence (C) of recombinant GAL4-VP16 (150 ng). The film shown in (B) was exposed five times longer than that in (C). Quantitation of the results indicates that the level of specific transcripts produced by srb5Δ extracts is 50-fold less than that produced by wild-type extracts in the absence of added SRB proteins. Addition of both SRB2 and SRB5 to srb5Δ extracts restored transcript levels to approximately 40% of those observed in wild-type extracts.

FIGS. 8D and 8E shows nuclear extracts made from wild-type cells (Z561) or srb2Δ1, srb5Δ1 mutant cells (Z563) were tested for their ability to synthesize specific transcripts from the pGAL4CG⁻ template in the presence or absence of recombinant SRB2 (250 ng) and/or SRB5 (250 ng). Transcription reactions were carried out in the absence (D) or presence (E) of recombinant GAL4-VP16 (150 ng). The film shown in (D) was exposed five times longer than that in (E). Quantitation of the results indicates that the level of specific transcripts produced by srb2Δ, srb5Δ extracts is 50-fold less than that produced by wild-type extracts in the absence of added SRB proteins. Addition of both SRB2 and SRB5 to srb2Δ, srb5Δ extracts restored transcript levels to approximately 40% of those observed in wild-type extracts.

Template Commitment Assay

As shown in FIGs. 9A–9D, SRB2 and SRB5 are essential for efficient preinitiation complex formation. (A) SRB2 is necessary for formation of stable preinitiation complex. The templates used in the template commitment assay each contained in a CYC1 TATA element downstream of a single GAL4-binding site that directs expression of a G-less transcript. The long (L) template (pGAL4CG) contained in a G-less cassette of 400 nt, and the short (S) template (pCT108) contained a G-less cassette of 300 nt. The two templates were incubated separately with nuclear extracts from srb2Δ1, srb5Δ1 cells (Z563), SRB5 (250 ng) and GAL4-VP16 (150 ng). A limiting amount of SRB2 protein (25 ng) was added to 1 of the 2 reaction mixtures. After a 60 min preincubation, the 2 reactions were mixed together, and aliquots were removed at 10 min intervals and transcriptionally competent complexes were assayed by the addition of nucleoside triphosphates. The reactions were terminated after 7 min to minimize reinitiation. Control experiments are shown in lanes 1–4. Extracts from srb2Δ1, srb5Δ1 cells were preincubated with SRB2, SRB5 and GAL4-VP16 along with short and long template, individually (lanes 1–2) or in combination (lane 3). In lane 4, both templates were incubated in the presence of SRB5 and GAL4-VP16 but in the absence of SRB2. After mixing of preincubation reactions, aliquots were removed and nucleoside triphosphates were added at the indicated times (lanes 5–12).

(B) SRB5 is necessary for formation of a stable preinitiation complex. The template commitment assay was performed as in (A), except that preincubations were performed in the presence or absence of limiting amounts of SRB5 (75 ng) and excess of SRB2 (250 ng).

Purification of SRB Complex

An outline of the purification scheme is shown in FIG. 10A. Yeast strain BJ926 (Buchman, A. R. et al., *Mol. Cell. Biol.* 8:5086–5099 (1988)) was grown at 30° C. to $OD_{600}$ of 4.0–4.5 in 1 x YNB medium (0.15% Difco yeast nitrogen base, 0.5% ammonium sulfate, 200 μM inositol, 2% glucose). The level of the SRB complex appeared to be elevated in cells grown in minimal medium, and this observation was exploited to facilitate purification of the TBP containing SRB complex. Cells were collected by centrifugation and washed in ice cold buffer (20 mM HEPES KOH (pH 7.5), 10% glycerol, 50 mM potassium acetate, 1 mM dithiothreitol (DTT), and 1 mM EDTA). Whole-cell extract was prepared from 480 g of cell paste as described by Sayre, M. H. et al. *J. Biol. Chem.* 267:23376–23382 (1992). Protease inhibitors used where indicated were: 1 mM phenylmethylsufonyl fluoride, 2 mM benzamidine, 2 μM pepstatin A, 0.6 μM leupeptin, 2 μg/ml chymostatin. 5 μg/ml antipain HCl (Sigma).

During purification, the SRB complex was monitored by Western blot using antibodies to SRB2, SRB4, SRB5, and SRB6. Silver staining of gels was performed as per Blum, H. et al. *Electrophoresis* 8:93–99 (1987), with minor modifications. The gels were fixed for a minimum of 4 hr, and the impregnation with silver nitrate was performed for 40 min.

Whole-cell extract (8 g of protein in 390 ml) was diluted 1:5 in buffer A (20% glycerol, 20 mM HEPES KOH (pH 7.5), 1 mM DTT, 1 mM EDTA. and protease inhibitors). The extract was loaded onto a 5 cm×17 cm Biorex 70 (Bio Rad Laboratories) column at a flow rate of 5 ml/min. The column was washed with buffer A (100) until no further protein could be eluted from the column. The column was then eluted with step washes of buffer A (300) and buffer A (600). The SRB complex eluted in the 600 mM potassium acetate step.

The Biorex 70 (600) fraction (250 mg in 120 ml) was diluted 1:6 with buffer B (20% glycerol, 20 mM Trisacetate (pH 7.9), 1 mM DTT, 1 mM EDTA. 0.01% Nonidet P-40, and protease inhibitors and was loaded onto a 2.5 cm×8.5 cm diethylaminoethyl (DEAE)-Sephacel column (Pharmacia) at a flow rate of 4 ml/min. The column was washed extensively with buffer B (100) and then eluted with step washes of buffer B (400) and buffer 6 (650). The SRB complex eluted from this column in the 400 mM potassium acetate step.

The DEAE-Sephacel (400) fraction (48 ml) was dialyzed into buffer C (20% glycerol, 10 mM potassium phosphate (pH 7.7), 100 mM potassium acetate, 1 mM DTT, 0.25 mM EDTA, 0.01% Nonidet P-40, and protease inhibitors). The dialysate was spun in a Sorvall SS34 rotor at 10,000 rpm for 20 min and the supernatant (50 mg of protein in 50 ml) was loaded onto a 1.5 cm×6.5 cm Bio-Gel HTP Hydroxylapatite at a flow rate of 1 ml/min. The column was washed with 20 ml of loading buffer and eluted with a 120 ml linear gradient of buffer C to buffer D (buffer D is identical to buffer C except that it contains 300 mM potassium phosphate (pH 7.71). The SRB complex eluted from this column in a peak corresponding to 68–112 mM potassium phosphate.

The 20 ml of eluate from the Bio-Gel HTP (Bio-Rad Laboratories) was dialyzed against buffer E (same as buffer B except 0.25 mM EDTA) containing 100 mM potassium acetate. The dialyzed material was spun in a Sorvall SS34 rotor at 10,000 rpm for 20 min. and the supernatant (11 mg protein in 20 ml) was loaded onto a Mono Q HR 5/5 fast protein liquid chromatography column (Pharmacia) and eluted with a 15 ml linear gradient from buffer E (100) to buffer E (2000) at a flow rate of 0.5 ml/min. The SRB complex eluted from this column at 0.95M potassium acetate.

Peak fractions containing SRB activity were diluted 1:6 with buffer F (same as buffer A except 0.25 mM EDTA).

This material (1.1 mg of protein in 10 ml) was loaded onto a Mono S HR 0.5/5 FPLC column (Pharmacia) and eluted with a 10 ml gradient from buffer F (100) to buffer F (1000) at a flow rate of 0.5 ml/min. The SRB complex eluted from this column at 450 mM potassium acetate. This material (0.6 mg of protein in 8 ml) was diluted 1:4 in buffer E (0) and loaded onto a 1.5 um×1.5 cm DEAE-Sephacel column and eluted with a 20 ml gradient from buffer E (100) to buffer E (1000) at a flow rate of 0.3 ml/min. The SRB complex eluted from this column at 400 mM potassium acetate. (Further chromatography revealed that this material was approximately 90% pure.) This material (0.5 mg of protein in 2 ml) was diluted 1:4 in buffer F (0) and loaded onto a 1.5 cm×1 cm Biorex 70 column and was eluted with a 10 ml gradient from buffer F (100) to buffer F (1000). The SRB complex eluted from this column at 600 mM potassium acetate and was approximately 95% pure. The total yield of the SRB complex was 0.5 mg, and purification was estimated to be 10,000-fold.

The SRB complex was subjected to gel filtration chromatography in buffer F (400) on a Superose 6 HR 10/30 FPLC column (Pharmacia). The estimated molecular size of the SRB complex was determined by extrapolation of a calibration curve performed with thyroglobulin (669 kd), apoferritin (443 kd), bovine serum albumin (132 kd, 66 kd) and carbonic anhydrase.

CTD Affinity Purification

Whole-cell extracts were prepared by adding 1.61 of 4% glucose to 800 g of Red Star dry yeast, incubating the mixture at room temperature for 45 min, and adding 800 ml of disruption buffer (1.2M ammonium sulfate, 0.16M K-HEPES (pH 7.3), 4 mM DTT, and protease inhibitors [as in the conventional purification above]). Aliquots (200 ml) were frozen dropwise in liquid nitrogen and blended for 5–10 min in a Waring blender. After thawing at 55° C., viscosity was reduced by brief blending. Disrupted cells were centrifuged for 30 min at 12,000 rpm in a Sorvall GSA rotor, and the clarified supernatant was filtered through cheesecloth. One-twentieth volume of a 10% solution of Polymin P was added, the extract was incubated on ice for 30 min. and the solution was centrifuged for 30 min at 12,000 rpm in a Sorvall GSA rotor. The supernatant was collected and brought to 70% saturation with solid ammonium sulfate and stored at 4° C.

An aliquot of the suspension was removed from storage and centrifuged at 12,000 rpm in a Sorvall GSA rotor for 30 min. The pellet was resuspended in 1.5 vol of 1×transcription buffer (Liao et al., 1991) plus protease inhibitors and centrifuged at 17,000 rpm in a Sorvall SS34 rotor for 20 min. The supernatant was then diluted 1:6 in 1×transcription buffer plus protease inhibitors and centrifuged at 12,000 rpm in a Sorvall GSA rotor for 30 min. The supernatant was incubated with 10 g/100 milliliters of cell debris remover (Whatman Labsales) for 15 min. The cell debris remover was removed by centrifugation and filtration. The cleared supernatant was then centrifuged at 40,000 rpm in a Beckman 50.2Ti rotor for 1–2 hr.

GST fusion proteins were coupled to Pharmacia activated CH Sepharose according to the manufacturers directions at a concentration of 5 milligrams of protein per milliliter of matrix. The affinity matrices were washed with 6M guanidine hydrochloride followed by 1×transcription buffer before use. Twenty milliliters of yeast whole-cell extract were mixed with 1/10 vol of 1×transcription buffer plus 10% Triton X-100 and applied to 100 $\mu$l of either GST-Sepharose or GST-CTD Sepharose. The columns were washed with 20 ml of 1×transcription buffer plus 1% Triton X-100, followed by 5 ml of 1×transcription buffer without Triton X-100. Bound proteins were eluted with 1×transcription buffer containing various concentrations of guanidine hydrochloride.

Western Blot Analysis

Western blotting of fractions was performed with polyclonal rabbit antisera raised against whole TBP, SRB2, and SRB5 proteins. A GST-SRB4 fusion protein, or a GST-SRB6 fusion protein, by standard methods. RPB1 was detected via the CTD with 8WG16 monoclonal antibody ascites fluid (Thompson, N. E. et al., *J. Biol. Chem.* 164:11511–11520 (1989)). Polyclonal anti-TBP, anti-SRB2, anti-GST-SRB4, and anti-SRB5 antisera were diluted 1:1000. Anti-GST-SRB6 antiserum was diluted 1:200. A 1:1000 dilution of 8WG16 monoclonal antibody ascites fluid was used. In all cases, bands were visualized by secondary probing with alkaline phosphatase conjugate secondary antibodies (Promega).

FIG. 10B, left panel, shows a liver-stained SDS-polyacrylamide (15%) gel containing approximately 1 $\mu$g of protein from each fraction of the SRB complex purification.

Lane 1, whole-cell extract; lane 2, biorex 70; lane 3, DEAE-Sephacel; lane 4, hydroxylapatite; lane 5, Mono Q; lane 6, Mono S; lane 7, DEAE-Sephacel. The positions of RNA polymerase II subunits, SRB proteins, TBP, and additional polypeptides that are candidate subunits of the complex are indicated, M, markers.

FIG. 10B, right panel, shows Western blot analysis of 1 μg of SRB complex protein from the DEAE-Sephacel fraction loaded onto a SDS-polyacrylamide (15%) gel and probed with antibodies against SRB and TBP proteins. The antibody probes were: lane 1, polyclonal anti-SRB2; lane 2, polyclonal anti-SRB4; lane 3, polyclonal anti-SRB5; lane 4, polyclonal anti-SRB6; and lane 5, polyclonal anti-TBP.

FIG. 10C shows that Western blot analysis reveals that SRB proteins, RNA polymerase II and TBP coelute from a Mono S column, Semipurified SRB complex (0.8 mg of total protein) from the Mono Q column was loaded onto a Mono S column and eluted with a 0.1–1.0M gradient of potassium acetate as described in Experimental Procedures. The onput and flow-through material (1/25) and every other eluate fraction (1/50) were analyzed by Western blot for the presence of RPB1, SRB4, SRB5, SRB2, TBP, and SRB6. The SRB complex eluted in a peak corresponding to approximately 0.4M potassium acetate.

Example 3: RNA Polymerase II Holoenzyme Activity

In Vitro Transcription Activity of the RNA Polymerase II Holoenzyme

The RNA polymerase II holoenzyme was purified as described in Example 2.

As shown in FIG. 13B, factor a is required in addition to TBP and the RNA polymerase II complex for in vitro transcription Sayre, M. H. et al., J. Biol. Chem. 267:23383–23387 (1992). Semipurified factor a (300 μg protein in 2 ml) eluted from the Heparin-CL6B column was loaded onto a DEAE-Sephacel column and eluted with a 0.15–1.0M gradient of potassium acetate. The onput (OP) and flow-through (FT) and a portion of every other fraction eluting from this column between 0.32 and 1.0M potassium acetate were analyzed for transcriptional activity (top panel) and for the presence of polypeptides by SDS-PAGE (bottom panel). Top panel, assays were performed using pGAL4G-template (300 ng), RNA polymerase II complex (1 μg), recombinant TBP (40 ng), and 1 μl of the OP, FT, and every other fraction from the column. Bottom panel, 2.5 μl of the OP, FT, and every other column fraction was subjected to electrophoresis on a 12% SDS-PAGE gel, and the gel was stained with silver using standard protocols. The positions of molecular weight standards are shown on the right of the panel.

Figure 13C:
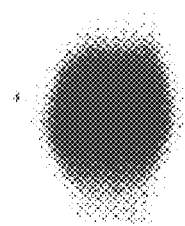
FIG. 13C shows the results of an experiment demonstrating that the RNA polymerase II holoenzyme, factor a, and TBP are sufficient for in vitro transcription.

As shown in FIG. 13C, the holoenzyme, factor a, and TBP are sufficient for in vitro transcription. Transcription reactions were performed using the pGAL4G-template (300 ng) and standard conditions, 30 The holoenzyme (1 μg), factor a (40 ng), and recombinant TBP (40 ng) were added to reactions as indicated. This and other figures in this application were prepared from digital replicas of primary data scanned using a UMax UC80 Max Vision digital scanner.

The Holoenzyme is a Complex of RNA Polymerase II and Initiation Factors

Semipurified holoenzyme that eluted from the Q-Sepharose column (FIG. 15A) was loaded onto a Mono S column and eluted with a 0.1–1.0M gradient of potassium acetate. The onput (OP) and flow-through (FT) and a portion of every other fraction eluting between 0.1 and 0.9M potassium acetate were analyzed for holoenzyme activity (top panel). These samples were also analyzed by western blot for the presence of RNA polymerase II and transcription factors (bottom panels). Top panel, Transcription assays were performed using the pGAL4G- template (300 ng), Factor a (40 ng), recombinant TBP (40 ng), and 1 μl of the OP, FT, and every other fraction from the Mono S column. Bottom panels, one μl of the same fractions were also separated on an SDS-polyacrylamide gel and blotted to nitrocellulose. The blots were probed with polyclonal antibodies specific to the 73 kD subunit of factor b (TFB1), factor e (SUA7), SRB2, SRB4, SRB5, and SRB6 and monoclonal specific to the largest subunit of RNA polymerase II (RPBI).

FIG. 15B shows the polypeptide composition of RNA polymerase holoenzyme. One microgram of purified holoenzyme was subjected to SDS-PAGE and stained with silver. Western blots of purified holoenzyme were performed on samples run on adjacent lanes of the gel with antiserum used in FIG. 15A to identify subunits of the SRB complex. Proteins in the holoenzyme preparation that correspond in size to subunits of RNA polymerase II SRB proteins, or subunits of initiation factors are indicated. The sizes of protein molecular weight standards are indicated in kD.

FIG. 15C shows coimmunoprecipitation of holoenzyme components with SRB5. Fifteen micrograms of the purified RNA polymerase II were diluted in 0.5 ml of transcription buffer containing potassium acetate instead of potassium glutamate, 0.01% NP40, and 0.1 mg/ml BSA. One microgram of affinity purified anti-HSP70 or anti-SRB5 antibodies, and five micrograms of recombinant SRB2 or SRB5 protein were added as indicated. Immunoprecipitated material was analyzed by western blot as indicated in (B) for the presence of transcription factor subunits and RNA polymerase II.

FIG. 15D shows quantitation of holoenzyme components. Samples of whole cell extract, nuclear extract, and purified holoenzyme together with standard amounts of purified RNA polymerase II and recombinant transcription factor subunits were quantitated by western blotting. Each gel contained the following: 25 μg yeast whole cell extract (lane 1), 25 μg yeast nuclear extract (lane 2), 1 μg purified holoenzyme (lane 3), and 0.2 μg purified holoenzyme (lane 4). The gels also contained purified standard proteins in lanes 5–7 in following amounts: 8, 40, and 200 ng RNA polymerase II; 4, 20, and 100 ng 6His-tagged factor e (SUA7); 3.2, 16, and 80 ng SRB2; 4, 20, and 100 ng SRB5; 3.2, 16, and 80 ng TOA1; 3.2, 16, and 80 ng TBP. Epitope-tagged SRB2 and 6His-tagged factor e (SUA7) used in this analysis exhibit slightly lower mobility on gels than their untagged counterparts. The RNA polymerase II CTD in the holoenzyme is the hypophosphorylated form (IIA).

FIG. 16A–B shows a summary of holoenzyme components. The amount of each holoenzyme component in 1 μg of the holoenzyme was determined by comparison with standard amounts in (D). Taking the molecular weight of each component into account, the stoichiometry of each factor per RNA polymerase II molecule is presented.

Transcription by the Holoenzyme is Stimulated by GAL4-VP16

As shown in FIG. 17A, transcription reactions were performed using either a template containing a CYCI TATA element that directs transcription of a G-less cassette (−GAL4 Site template) or a template that contained in addition a single consensus DNA binding site for the GAL4 protein upstream of the TATA element (+GAL4 Site template). GAL4-VP16 (150 ng) was added to reactions as indicated. Top panel, reactions were performed with the holoenzyme (1 μg), factor a (40 ng), recombinant TBP (40 ng), and each template (100 ng) as indicated. Bottom panel, reactions were performed with yeast nuclear extract protein (150 μg). Transcription in reactions containing nuclear extract is stimulated 10-fold by GAL4-VP16. Transcription by the holoenzyme is stimulated 5-fold by GAL4-VP16. The +GAL4 site template is pGAL4G-. The GAL4 site template is pSL187. The exposure in the top panel was 5 times longer than the exposure in the bottom panel. Levels of transcript were quantitated using a Fuji Bio-image Analyzer.

Figure 17B:
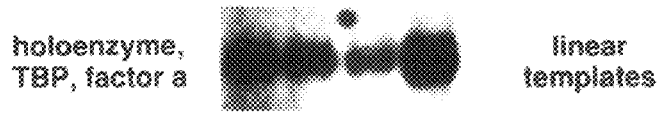

As shown in FIG. 17B, reactions were performed with the holoenzyme as detailed above except 225 ng of template, linearized by digestion with PvuII restriction endonuclease, was used. This exposure was 3 times longer than the holoenzyme panel in (A).

Example 4: SRB7, SRB8, SRB9, SRB10, SRB11 Genes and Their Encoded Proteins

Yeast strains and plasmids are listed in Table 5 and 6, respectively.

TABLE 5

Yeast Strains

| Strain | Alias | Genotype |
|---|---|---|
| Z26 | N247 | Mat α ura3-52 his3Δ200 leu2-3, 112 rpb1Δ187::HIS3[pRP112(URA3 RPB1)] |
| Z551 | N400 | MAT a ura3-52 his3Δ204 leu2-3, 112 rpb1Δ187::HIS3[pC6(LEU2 rpb1Δ104)] |
| Z558 | CTY143 | Mat a/Mat α ura3-52/ura3-52 his3Δ200/his3Δ200 leu2-3, 112/leu2-3, 112 |
| Z567 | S242 | Mat a ura3-52 his3Δ200 leu2-3, 112 rpb1Δ187::HIS3 srb7-1[pC6(LEU2 rpb1Δ104)] |
| Z568 | S358 | Mat a ura3-52 his3Δ200 leu2-3, 112 rpb1Δ187::HIS3 srb8-1[pC6(LEU2 rpb1Δ104)] |
| Z569 | S363 | Mat a ura3-52 his3Δ200 leu2-3, 112 rpb1Δ187::HIS3 srb9-1[pC6(LEU2 rpb1Δ104)] |
| Z570 | S456 | Mat a ura3-52 his3Δ200 leu2-3, 112 rpb1Δ187::HIS3 rpb2-551[pC6(LEU2 rpb1Δ104)] |
| Z571 | CHY1 | Mat a ura3-52 his3Δ200 leu2-3, 112 rpb1Δ187::HIS3 srb7-1[pRP112(URA3 RPB1)] |
| Z572 | SLY63 | Mat a ura3-52 his3Δ200 leu2-3, 112 rpb1Δ187::HIS3 srb8-1[pRP114(LEU2 RPB1)] |
| Z573 | CHY3 | Mat a ura3-52 his3Δ200 leu2-3, 112 rpb1Δ187::HIS3 srb9-1[pRP112(URA3 RPB1)] |
| Z574 | SLY64 | Mat a ura3-52 his3Δ200 leu2-3, 112 rpb1Δ187::HIS3 rpb2-551[pRP114(LEU2 RPB1)] |
| Z575 | CHY102 | Mat a/Mat α ura3-52/ura3-52 his3Δ200/his3Δ200 leu2-3, 112/leu2-3, 112 srb7Δ1::URA3hisG/SRB7 |
| Z576 | SLY35 | Mat a/Mat α ura3-52/ura3-52 his3Δ200/his3Δ200 leu2-3, 112/leu2-3, 112 srb8Δ1::URA3hisG/SRB8 |
| Z577 | CHY105 | Mat a/Mat α ura3-52/ura3-52 his3Δ200/his3Δ200 leu2-3, 112/leu2-3, 112 srb9Δ1::URA3hisG/SRB9 |
| Z578 | SLY61 | MAT α ura3-52 his3Δ200 leu2-3, 112 rpb1Δ187::HIS3 srb8Δ1::hisG[pRP114(LUE2 RPB1)] |
| Z579 | SLY76 | MAT α ura3-52 his3Δ200 leu2-3, 112 rpb1Δ187::HIS3 srb8Δ1::hisG[pC6(LEU2 rpb1Δ104)] |
| Z580 | CHY113 | MAT α ura3-52 his3Δ200 leu2-3, 112 rpb1Δ187::HIS3 srb9Δ1::hisG[pRP114(LUE2 RPB1)] |
| Z581 | CHY116 | MAT α ura3-52 his3Δ200 leu2-3, 112 rpb1Δ187::HIS3 srb9Δ1::hisG[pC6U(URA3 rpb1Δ104)] |

TABLE 6

Plasmids

| Plasmid | Description |
|---|---|
| SRB7 | |
| pCH2 | SRB7 (6.7 kb) URA3 CEN. |
| PCH7 | SRB7 (2.0 kb) URA3 CEN. |

TABLE 6-continued

Plasmids

| Plasmid | Description |
|---|---|
| PCH36 | srb7-1 URA3 CEN. |
| pCH34 | SRB7 in pET-3a (Studier and Moffat, 1986). |
| pCH46 | srb7Δ1::URA3hisG in pSP72 (Promega). |
| SRB8 | |
| pSL301 | SRB8 (9.0 kb) URA3 CEN. |
| pSL311 | SRB8 (6.0 kb) URA3 CEN. |
| pSL307 | SRB8 (encoding aa 868 to 1226) in pET-3a (Studier and Moffat, 1986) |
| pSL315 | srb8Δ1::URA3hisG in pBSIISK (+) (Stratagene). |
| SRB9 | |
| pCH47 | SRB9 (7.3 kb) URA3 CEN. |
| pCH64 | SRB9 (encoding aa 45 to 501) in pGEX-1 (Smith and Johnson, 1988). |
| pCH66 | SRB9Δ1::URA3hisG in pSP72 (Promega). |
| RPB2 | |
| pSL401 | RPB2 (10 kb) URA3 CEN. |
| pSL411 | rpb2-551 URA3 CEN. |

Yeast media was prepared as described (Thompson et al., 1993). Yeast transformations were done using a lithium acetate procedure (Schiestl and Gietz, 1989). Plasmid shuffle techniques were performed as described by Boeke et al. (1987) using 5-fluoro-orotic acid (5-FOA) as a selective agent against URA3 plasmids. Plasmids were recovered from yeast as described by Hoffman and Winston (1987). Growth assays were performed by suspending similar numbers of cells in water and transferring equal volumes to agar plates with a 48-prong apparatus. To reduce flocculation of some strains, cells were first washed in 100 mM EGTA, 10 mM Tris-HCl 7.5.

Extragenic suppressors of the cold sensitive phenotype of Z551 were isolated as previously described (Nonet and Young, 1989). Dominant and recessive suppressors were identified by mating to Z26, selecting against the presence of pRP112 (Nonet et al., 1987) using 5-FOA and assaying growth at 12° C. on YEPD. Diploids able to grow at 12° C. contained a dominant suppressor. Diploids unable to grow at 12° C. contained a recessive suppressor.

Yeast strains of the opposite mating type of approximately half of the dominant suppressors and half of the recessive suppressors were generated by inducing a mating type switch by expression of the HO gene placed on a plasmid under the control of a galactose inducible promoter. Random spore analysis of the dominantly suppressing mutations was used to determine if two independent isolates were likely to contain mutations in the same gene. Haploids were mated to each other, each containing the CTD truncation mutation rpb1Δ104 and an independently isolated SRB mutation, to form diploids. These diploids were sporulated on plates and a small quantity of spores scraped off and shaken overnight at 30° C. in 0.5 ml 30 mM β-mercaptoethanol and 100 ng/ml Zymolase 100 T (ICN). 0.5 ml of 1.5% NP-40 and 0.4 g glass beads were added and the mixture held on ice for 15 min. The suspension was then vortexed 3 min, held on ice 5 min, vortexed 2 min, and the glass beads allowed to settle for 10 min at room temperature. The supernatant was removed, spun 2 min, the pellet washed once in water, then resuspended in water and a portion plated onto YEPD. Approximately fifty of the haploid offspring were assayed for their ability to grow at 12° C. If all haploids were able to grow at 12° C. then the two SRB isolates were assumed to contain mutations in the same gone. Genetic complementation of the recessive alleles involved mating haploids to each other, each containing the CTD truncation mutation rpb1 Δ1 and an independently isolated srb mutation, to form diploids and assessing the ability of these diploids to grow at 12° C. Diploids able to grow at 12° C. were assumed to contain srb mutations in the same gene. Genomic clones of each complementation group were used to confirm the identity of each member of the complementation group and to identify additional members. Cells containing the CTD truncation mutation rpb1Δ104 and a recessive srb allele were unable to grow at 12° C. and on pyruvate media when transformed with the corresponding wild-type SRB allele.

Deletions of SRB7, SRB8 and SRB9 were created by a single step disruption method (Rothstein, 1991). Z558 was transformed with the desired DNA fragment and plated on SC-Ura media. Southern analysis was used to confirm that a single copy of the desired SRB gene had been deleted. The diploid was sporulated and tetrads dissected (>20) on YEPD plates and scored for nutritional auxotrophies and growth at a variety of temperatures. Z575 was created by transformation with the srb7Δ1::URA3hisG fragment from pCH46. Two or less spores from each tetrad were viable and these spores were uracil auxotrophs, indicating that SRB7 is essential. Z576 was created by transformation with the srb8Δ1::URA3hisG fragment from pSL315 and Z577 was created by transformation with the srb9Δ1::URA3hisG fragment from pCH66. In each case segregants scored 2:2 for uracil prototrophy and all uracil prototrophs exhibited mild cold-sensitive, temperature-sensitive, and slow growth phenotypes, indicating that SRB8 and SRB9 deletion strains are conditionally viable. srb8AΔ1 and srb9Δ1 strains are also flocculent as are the suppressing isolates of SRB8 and SRB9. Strains containing unmarked deletions of SRB8 and SRB9 were created by selecting for excision of the URA3 gene by growth on 5-FOA (Alani, E. et al., *Genetics* 116:541–545 (1987)).

FIG. 20 shows the influence of SRB2 and SRB8 alleles on growth phenotypes of RNA polymerase II CTD truncation mutants. Strains containing combinations of SRB2 or SRB8 alleles and CTD truncation alleles were assayed for growth on YEPD medium at 12° C., 30° C., and 38° C. and on SC medium containing pyruvate as a sole carbon source. The degree of CTD truncation is shown for each mutant on the horizontal axis, and the plasmid carrying each CTD truncation allele is indicated (i.e., pN51). The phenotypes exhibited by each of the CTD truncation mutants in a wild-type, srb2Δ1, SRB2-1, or srb8Δ1 background are shown on left. Nonviable strains (N) are indicated by a dashed line, conditional strains (C) that were extremely sensitive to high (38° C.) and low (12° C.) temperatures and failed to grow on pyruvate media are indicated by a thin solid line, and viable (V) strains that exhibit nearly wild-type growth characteristics under all conditions tested are indicated by a heavy solid line. Viable/conditional srb8Δ1 strains (V/C) were able to grow at low temperatures and on pyruvate medium but were sensitive to high temperatures and are indicted by a solid line. Not every CTD truncation allele was tested in every background, but for each background the phenotypic boundaries are well established.

DNA methods

DNA manipulations were performed according to Sambrook et al. (1989). Site-directed mutagenesis was performed as described in Kunkel et al. (1987). PCR amplifications to produce pCH45 (srb7Δ1), pSL315 (srb8Δ1), and pSL307 (SRB8 in pET-3a) were performed with Taq DNA polymerase (Perkin Elmer) in 100λ of buffer (provided by the manufacturer) supplemented with 200 μM dNTP for a total of 25 cycles. Primer concentrations were 0.5 μM with 50 ng of DNA and cycling was at 94° C. (1.0 min), 50° C. (1.0 min) and 72° C. (2.5 min).

Cloning and Sequence analysis

Genomic clones of SRB7 (pCH2), SRB8 (pSL301), SRB9 (pCH47), and RPB2 (pSL401) were isolated by transformation and complementation of Z567, Z568, Z569, and Z570, respectively. pCH36 was created from pCH7 in vivo by transforming Z567 with linearized pCH7 lacking SRB7 coding DNA and isolating the plasmid from a Ura⁺ transformant which had repaired the plasmid with the mutant srb7-1 sequences from the chromosome (Rothstein, 1991). Similarly, rpb2-551 (pSL411) was isolated from Z570 using pRP212 (Scafe et al., 1990). SRB7 and SRB9 were completely sequenced on each strand using genomic DNA from pCH7 and pCH47, respectively. Unidirectional deletions were constructed using the Erase-a-Base system (Promega) and double stranded sequencing with dideoxynucleotides and Sequenase (US Biochemical) was carried out as described by the manufacturer using T3 and T7 promoter primers. Gaps in the sequence were filled in by sequencing with internal oligonucleotide primers. The suppressing mutations in SRB7 and RPB2 were deduced by sequencing using oligonucleotide primers that spanned the entire open reading frames. Sequence comparison analysis was performed at the National Center for Biotechnology Information using the BLAST network service.

A restriction map of a 2.0 kb DNA fragment from pCH7 containing the SRB7 gene was determined. The entire coding region of SRB7 was replaced with a 5.5 kb DNA fragment containing the URA3 and kanamycin genes flanked by direct repeats of Salmonella hisG DNA to create the deletion allele srb7Δ1::URA3hisG. The predicted 140 aa sequence of the SRB7 protein is shown in FIG. 19A–B. Positive numbering of the DNA begins with the predicted start site of translation. The srb7-1 mutation is a G to A transition (nt 61) that changes aa 21 from Ala to Thr.

A restriction map of a 6.0 kb DNA fragment from pSL311 containing the SRB8 gene was also determined. Approximately 500 bp upstream of SRB8 there is an inversion, relative to the genomic DNA used to sequence that region of chromosome III, encompassing greater than 2 kb. The entire coding region of SRB8 was replaced with a 5.5 kb DNA fragment containing the URA3 and kanamycin genes flanked by direct repeats of Salmonella hisG DNA to reate the deletion allele srb8Δ1::URA3hisG. The DNA sequence SRB8, with its predicted amino acid sequence is shown in FIG. 20A–C.

A restriction map of a 7.3 kb DNA fragment from pCH47 containing the SRB9 gene was also determined. Most of the coding region of SRB9 was replaced with a 5.5 kb DNA fragment containing the URA3 and kanamycin genes flanked by direct repeats of Salmonella hisG DNA to create the deletion allele srb9Δ1::URA3hisG. FIG. 21A–H, and 22 shows the sequence of the 7.3 kb DNA fragment containing the SRB9 gene. The predicted 1420 aa sequence of the SRB9 protein is shown below the sequence of the gene. The DNA sequences and their predicted amino acid sequences for SRB10 and SRB11 are shown in FIGS. 23A–C and 24A–B respectively.

Purification of recombinant proteins

Recombinant proteins were purified for generating polyclonal antibodies in rabbits. SRB7 and a portion of SRB8 (amino acids 868 to 1226) were purified from the bacterial strain BL21 (DE3) pLysS (Studier and Moffatt, 1986) carrying the plasmids pCH34 and pSL307, respectively, in the same manner SRB2 was purified (Koleske et al., 1992). A portion of SRB9 (amino acids 45 to 501) was purified as a fusion to glutathione-S transferase from DH5α carrying pCH64 according to the method of Smith, D. B. and Johnson K. S., *Gene*. 67:31–40 (1988).

In vitro transcription and Western blot analysis

In vitro transcription assay for holoenzyme activity was performed as described above. Western blotting was performed by standard methods. RPB1 was detected via the CTD with 8WG16 monoclonal antibody ascites fluid (Promega). Polyclonal rabbit anti-SRB2, anti-GST-SRB4, anti-SRB5, anti-GST-SRB6, anti-SRB7, anti-SRB8 (aa 868 to 1226), and anti-GST-SRB9 (aa 45 to 501) antiserum were used to detect the SRBs. In all cases, bands were visualized by secondary probing with alkaline phosphatase conjugate secondary antibodies (Promega).

FIG. 26A–B shows that SRB2 and SRB4-SRB9 are components of an RNA polymerase II holoenzyme. (A) semipurified holoenzyme that eluted from the Q-sepharose column as described in Example 3 was loaded onto a Mono S column and eluted with a 0.1–1.0M gradient of potassium acetate. The onput (OP) and flow-through (FT) and a portion of every other fraction eluting between 0.1 and 0.9M potassium acetate were analyzed for holoenzyme activity (top panel). These samples were also analyzed by Western blot for the presence of RNA polymerase II and SRB proteins. This figure was prepared from digital replicas of primary data scanned using a UMAX UC840 Max Vision digital scanner. (B) Polypeptide composition of RNA polymerase II holoenzyme. One microgram of purified holoenzyme was subjected to SDS-PAGE and stained with silver. Proteins in the holoenzyme preparation that correspond in size to subunits of RNA polymerase and SRB proteins are indicated. The sizes of protein molecular weight standards are indicated in kd.

Example 5: General Requirement for RNA Polymerase II Holoenzyme In Vivo

PRC mutagenesis was performed as described by D.W. Leung, E. Chen, D. V. Goeddel, Technique. 1:11 (1989). The plasmid pCT127 (SRB4 LEU2 CEN) contains a unique NdeI site at the SRB4 ATG and a unique XbaI site following the SRB4 stop codon, both created by site-specific mutagenesis (T. A. Kunkel, J. D. Roberts, R. A. Zakour, *Meth. Enzymol*. 154:367 (1987)). PCR of SRB4 from pCT127 with oligonucleotides flanking the ORF was performed in buffer containing 0.1 mM, 0.2 mM, and 0.4 mM $Mn^{2+}$. Reactions were pooled, DNA digested with NdeI-XbaI, ligated with NdeI-XbaI digested pCT127 vector fragment, and transformed into DH5α. Approximately 30,000 transformants were obtained.

Plasmid shuffle techniques were performed as described by J. Boeke, J. Truehart, B. Natsoulis, G. R. Fink, *Meth. Enzymol*. 154:164 (1987), using 5-flouroorotic acid (5-FOA) as a selective agent against URA3 plasmids. Genetic manipulations of yeast were performed as previously described. DNA molecules containing LEU2 and mutagenized SRB4 genes were transformed into a yeast strain (CTY182) deleted for the chromosomal copy of SRB4, but carrying a URA3 centromeric plasmid encoding a wild-type copy of the gene. Approximately 20% of the transformants were unable to grow in the presence of 5-FOA, indicating a lethal mutation in the LEU2 plasmid-borne SRB4 gene. Approximately 0.5% of the transformants were able to grow on 5-FOA plates at 30° C. but not at 37° C., indicating a ts allele in the LEU2 plasmid-borne SRB4 gene. The LEU2 plasmids from these transformants were recovered and reintroduced in CTY182 to verify the ts phenotype. The plasmid pCT181 contains the srb4-138 mutant allele.

Total RNA from cells was isolated using hot acidic phenol extraction (F. M. Ausubel et al., Ed., *Current Protocals in Molecular Biology* (John Wiley and Sons, New York, (1993)). RNA was quantified by absorbance at 260 nm and the integrity of the RNA confirmed by ethidium bromide straining of RNA in agarose gels.

S1 nuclease protection assays were carried out with 5–30 ug of RNA and DED1, HIS3, TRP3, rRNA and $tRNA^W$ oligonucleotide probes as previously described (Cormack & Struhl). The sequences for the other oligonucleotide probes are: ACT1 (GGAAGAGTACAAGGACAAAACGGCTT GGATGGAAA CGTAGAAGGCATTCCA) (SEQ ID NO: 30), CDC7 (GGGGCTACTCTC GAAGATCCCGTCAT-TATGTACAGCAGGTTGAGCAT GCCT) (SEQ ID NO: 31), MET 19 (GCCTTACCGGCACGCATCATGATGGG GACGCCCTCCCAACGCTCGAC ACTT) (SEQ ID NO: 32), RAD23 (GCAGTGGCTGCAGGAGCTGCAG AAGCATCGGTACTGGGGGATGCAATCCA) (SEQ ID NO: 33), STE2 (GTCGACGGGTTCAACTTCTCCCTCT TTGTAACTTGCATCAGCAAACGGATGACA) (SEQ ID NO: 34), AND TCM1 (GGAGTGTCAACAACGGTGA CAGCTTCGAC AACTTCACGCTTGTGGTGAGCT) (SEQ ID NO: 35). Ooligonucleotides are written in the 5' 3' direction and contain 6 residues at their 3' ends that are not complementary to the RNA, permitting distinction between bands due to appropriate RNA-DNA hybrids and undigested probe.

Equivalents

Those skilled in the art will recognize, or be able to ascertain, using no more than routine experimentation, many equivalents to the specific embodiments of the invention described herein. Such equivalents are intended to be encompassed by the following claims:

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
       (A) LENGTH: 1949 base pairs
       (B) TYPE: nucleic acid
       (C) STRANDEDNESS: double
       (D) TOPOLOGY: linear (ii) MOLECULE TYPE: DNA (genomic)

(ix) FEATURE:
    (A) NAME/KEY: CDS
    (B) LOCATION: 743..1357

(xi) SEQUENCE DESCRIPTION: SEQ ID NO:1:

```
GGTGACCACT ACAGGAACGC AAACTTAAGC TACATTGTTC ACCATATTAT ACTATATATA      60

TAACCTCGCG CTGAGCTTTA CAGGTGCGTT TGTCCTCGAA GAACGAAAAG CAGCCCGAAA     120

AAAAAATGCA AAACGATAAA AGCTGGCTGG AGAACAATAG CGGGTTGACC GCTAAACGAG     180

CACACACGTG ATGTGTCGTG AACTGTGATC GTGGTAGTAT GATGCTAGTA TGTAGTGATG     240

GCTGCATGGT ACCAGCGGTG ACGTTCGGTA GACTCTACTC TCCTTTGTTC CCCCGGTGTG     300

CCATCTTTTG AGTTTTGCGT GCGTTATCTA CTGGGAGCAA GGGTCTGGCT CGTACGCATA     360

GAGGCTGAGG ACGAACAGTG TGCGTTTGCA GGCGTGGATA TAGAATACAT AGCTATATAG     420

ATGGGTAGTG CGCATGGGAA AGTGCAATTG AGCGAAGGAA GGGGCAGGTG GACTGTAGAT     480

GTCGCCGCGT GATTTTATCG TTGTTTCTCT TCTTGTGTTT TCTTATGCGT TAGTATGCCA     540

GTTTCGCGGT GTGATTCCCA AAGTGAAATT TTACTGGAAG AGCAAATCTT GTAAGTCGGC     600

GCTCGAAAGC ACAGTAGCAA TCCATCATGG GAAAATCAGC GTATGTAAAG CTGGAGCGTC     660

CTTCGTGGCG CATCGGAATT TCTTCAATTG AACTACCTGT TGCTAACAAC AGTTTTTTTT     720

TTCTCTCTTT TATGTATATA GC GTT ATA TTC GTG GAA AGA GCC ACT CCC GCT     772
                        Val Ile Phe Val Glu Arg Ala Thr Pro Ala
                         1               5                  10

ACA CTA ACG GAA CTG AAG GAT GCT CTC TCG AAT AGT ATC CTG TCC GTG     820
Thr Leu Thr Glu Leu Lys Asp Ala Leu Ser Asn Ser Ile Leu Ser Val
             15                  20                  25

CGA GAC CCT TGG TCG ATA GAC TTT CGG ACG TAC CGG TGC TCT ATC AAG     868
Arg Asp Pro Trp Ser Ile Asp Phe Arg Thr Tyr Arg Cys Ser Ile Lys
         30                  35                  40

AAC CTA CCC GCG GAT GTC TCC AAG CTC ATG TAC TCG ATA ACG TTC CAC     916
Asn Leu Pro Ala Asp Val Ser Lys Leu Met Tyr Ser Ile Thr Phe His
     45                  50                  55

CAC CAT GGC CGG CAG ACC GTG CTA ATC AAG GAC AAC TCA GCG ATG GTG     964
His His Gly Arg Gln Thr Val Leu Ile Lys Asp Asn Ser Ala Met Val
 60                  65                  70

ACG ACT GCC GCA GCG GCG GAT ATC CCT CCG GCG CTG GTG TTC AAT GGC    1012
Thr Thr Ala Ala Ala Ala Asp Ile Pro Pro Ala Leu Val Phe Asn Gly
 75                  80                  85                  90

TCA TCT ACG GGC GTT CCT GAG TCC ATA GAC ACT ATT TTG TCG TCC AAG    1060
Ser Ser Thr Gly Val Pro Glu Ser Ile Asp Thr Ile Leu Ser Ser Lys
             95                 100                 105

CTG TCC AAC ATC TGG ATG CAG AGG CAG CTC ATC AAG GGT GAT GCC GGT    1108
Leu Ser Asn Ile Trp Met Gln Arg Gln Leu Ile Lys Gly Asp Ala Gly
        110                 115                 120

GAG ACG TTG ATC TTG GAC GGG CTC ACC GTG CGA CTC GTC AAC CTC TTC    1156
Glu Thr Leu Ile Leu Asp Gly Leu Thr Val Arg Leu Val Asn Leu Phe
    125                 130                 135

TCC TCC ACT GGG TTC AAG GGT CTC CTG ATA GAA CTG CAG GCG GAC GAA    1204
Ser Ser Thr Gly Phe Lys Gly Leu Leu Ile Glu Leu Gln Ala Asp Glu
140                 145                 150

GCG GGC GAG TTT GAG ACC AAG ATT GCA GGC ATC GAA GGA CAC CTA GCT    1252
Ala Gly Glu Phe Glu Thr Lys Ile Ala Gly Ile Glu Gly His Leu Ala
155                 160                 165                 170

GAA ATC CGG GCC AAG GAG TAC AAA ACC TCA TCC GAC TCG TTG GGG CCG    1300
Glu Ile Arg Ala Lys Glu Tyr Lys Thr Ser Ser Asp Ser Leu Gly Pro
            175                 180                 185
```

```
GAC ACC AGC AAC GAA ATA TGT GAT TTG GCG TAC CAG TAT GTT CGT GCT    1348
Asp Thr Ser Asn Glu Ile Cys Asp Leu Ala Tyr Gln Tyr Val Arg Ala
            190                 195                 200

CTG GAG CTG TGAGTTCTTA CGAATGCTTT TCTTTTTTT TTTTTTCTGT             1397
Leu Glu Leu
        205

TTGTATATTG CGGTGTATAC GTATAGATAG ATAGTCTAAA TAGTAATCTT CAACCTTATG  1457

TATCTCGGCT CATGCAGTGA GGAAATCCAT GGATAAGCCC GGATTGTAGT CATCGTCGCT  1517

GTCGCTGTCG CTGTCGCTGG CGTCCTGTGT TTCCTTCTGT ACAGGTTCTT CTGTCGGTTG  1577

AGAGTCCTCT TCAGCGTCTT CCTCCTCCCT TGCATTGTCA ATAAACTTGT TCAGTGTACT  1637

CGTATGCTCA AGTGGGCGGG GTTCCTGGTG TAGCACCTCG TAGCCCTCTG GTAGGTCGGC  1697

CTCTGTCATG GCAACGAATA TCGTGGGTTT CTCGATCACT GTGGTGTTCT TCAACAATTC  1757

TCCGATGCAT TTCTCATGTA TAGCCAACTC CACCAAGTTT TTTGAATCCA TTATATGCGT  1817

GGTGTTGTAA GGGAACGTTT TCGTGTAGAA TTTGAGCCCA CTCTTCTGTA GGATCTGTGT  1877

TCTTTCCTCT TTGGTCTCCG AACCGTCTTC GCCCTCTATG CAAGAGCTTG TTCCAGCCAA  1937

GCGATAGAAT TC                                                     1949

(2) INFORMATION FOR SEQ ID NO:2:

(i) SEQUENCE CHARACTERISTICS:
        (A) LENGTH: 205 amino acids
        (B) TYPE: amino acid
        (D) TOPOLOGY: linear (ii) MOLECULE TYPE: protein (xi) SEQUENCE DESCRIPTION: SEQ ID NO:2:

Val Ile Phe Val Glu Arg Ala Thr Pro Ala Thr Leu Thr Glu Leu Lys
 1               5                  10                  15

Asp Ala Leu Ser Asn Ser Ile Leu Ser Val Arg Asp Pro Trp Ser Ile
            20                  25                  30

Asp Phe Arg Thr Tyr Arg Cys Ser Ile Lys Asn Leu Pro Ala Asp Val
        35                  40                  45

Ser Lys Leu Met Tyr Ser Ile Thr Phe His His Gly Arg Gln Thr
    50                  55                  60

Val Leu Ile Lys Asp Asn Ser Ala Met Val Thr Thr Ala Ala Ala Ala
65                  70                  75                  80

Asp Ile Pro Pro Ala Leu Val Phe Asn Gly Ser Ser Thr Gly Val Pro
                85                  90                  95

Glu Ser Ile Asp Thr Ile Leu Ser Ser Lys Leu Ser Asn Ile Trp Met
            100                 105                 110

Gln Arg Gln Leu Ile Lys Gly Asp Ala Gly Glu Thr Leu Ile Leu Asp
        115                 120                 125

Gly Leu Thr Val Arg Leu Val Asn Leu Phe Ser Ser Thr Gly Phe Lys
130                 135                 140

Gly Leu Leu Ile Glu Leu Gln Ala Asp Glu Ala Gly Glu Phe Glu Thr
145                 150                 155                 160

Lys Ile Ala Gly Ile Glu Gly His Leu Ala Glu Ile Arg Ala Lys Glu
                165                 170                 175

Tyr Lys Thr Ser Ser Asp Ser Leu Gly Pro Asp Thr Ser Asn Glu Ile
            180                 185                 190

Cys Asp Leu Ala Tyr Gln Tyr Val Arg Ala Leu Glu Leu
        195                 200                 205
```

(2) INFORMATION FOR SEQ ID NO:3:

(i) SEQUENCE CHARACTERISTICS:
        (A) LENGTH: 2473 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 320..2380

(xi) SEQUENCE DESCRIPTION: SEQ ID NO:3:

```
GATCTCGACG ATTTGGGATT CTTATAAGGG CGCATAAAAA ATAAATAACT ACCATTCATA     60

ACAGAAATTC ATTCGTATAT ACATAAAGTT CTCATAAACG TATATATATA TATATATATA    120

TACTTATTGA TATCAAAGTG TGTTACTTTC TACATTCATA GACGGGGAAG AAAAGTGAGG    180

AAAAGTTGTT TTCTCTTGTG CACTGCAGCC CTTTGAAAAA GTAGAACTGC AGAAAAAATA    240

ACTGAACGTA AAGCATTATT TACTTTTCAA AGGCAAAAGA GATAGAGCCA AAAAAATTGT    300

AAGCAGCTTA AAAGCCATA ATG ACA ACG GAA GAT CCA GAT TCA AAT CAC TTA    352
                    Met Thr Thr Glu Asp Pro Asp Ser Asn His Leu
                      1               5                  10

AGT TCC GAA ACT GGC ATT AAA TTG GCA TTG GAC CCG AAC TTA ATT ACA    400
Ser Ser Glu Thr Gly Ile Lys Leu Ala Leu Asp Pro Asn Leu Ile Thr
            15                  20                  25

TTG GCA CTA AGT TCT AAT CCA AAC TCT AGC CTT CAT TCA CCA ACG TCT    448
Leu Ala Leu Ser Ser Asn Pro Asn Ser Ser Leu His Ser Pro Thr Ser
        30                  35                  40

GAT GAA CCC GTA CCT GAA TCT GCA GGA AAA GCA GAT ACT AGT ATT CGA    496
Asp Glu Pro Val Pro Glu Ser Ala Gly Lys Ala Asp Thr Ser Ile Arg
    45                  50                  55

CTA GAA GGT GAT GAG TTA GAG AAT AAA ACT AAG AAA GAC AAT GAT AAG    544
Leu Glu Gly Asp Glu Leu Glu Asn Lys Thr Lys Lys Asp Asn Asp Lys
60                  65                  70                  75

AAC TTA AAA TTT TTG AAG AAT AAA GAT TCT CTA GTC AGT AAT CCA CAC    592
Asn Leu Lys Phe Leu Lys Asn Lys Asp Ser Leu Val Ser Asn Pro His
                80                  85                  90

GAA ATT TAT GGC TCC ATG CCG TTG GAG CAA TTG ATC CCA ATC ATC TTA    640
Glu Ile Tyr Gly Ser Met Pro Leu Glu Gln Leu Ile Pro Ile Ile Leu
            95                 100                 105

AGA CAG CGT GGT CCA GGC TTT AAA TTC GTT GAT TTA AAT GAA AAA GAA    688
Arg Gln Arg Gly Pro Gly Phe Lys Phe Val Asp Leu Asn Glu Lys Glu
       110                 115                 120

TTG CAA AAT GAG ATT AAG CAG CTT GGT AGT GAT AGT AGT GAC GGT CAT    736
Leu Gln Asn Glu Ile Lys Gln Leu Gly Ser Asp Ser Ser Asp Gly His
   125                 130                 135

AAC AGC GAG AAG AAG GAC ACT GAT GGC GCT GAT GAG AAT GTA CAA ATT    784
Asn Ser Glu Lys Lys Asp Thr Asp Gly Ala Asp Glu Asn Val Gln Ile
140                 145                 150                 155

GGA GAA GAT TTC ATG GAA GTG GAT TAT GAA GAT AAA GAT AAT CCA GTG    832
Gly Glu Asp Phe Met Glu Val Asp Tyr Glu Asp Lys Asp Asn Pro Val
                160                 165                 170

GAT TCA CGA AAT GAA ACA GAC CAC AAA ACG AAT GAA AAT GGC GAG ACC    880
Asp Ser Arg Asn Glu Thr Asp His Lys Thr Asn Glu Asn Gly Glu Thr
            175                 180                 185

GAT GAT AAT ATT GAA ACG GTA ATG ACA CAG GAA CAG TTT GTT AAA AGA    928
Asp Asp Asn Ile Glu Thr Val Met Thr Gln Glu Gln Phe Val Lys Arg
       190                 195                 200

AGG AGG GAT ATG CTA GAG CAT ATA AAT CTG GCC ATG AAC GAA TCG TCT    976
```

```
                Arg Arg Asp Met Leu Glu His Ile Asn Leu Ala Met Asn Glu Ser Ser
                205                 210                 215

TTG GCT TTG GAA TTC GTT TCT TTG CTA CTG TCG AGT GTT AAA GAG TCT         1024
Leu Ala Leu Glu Phe Val Ser Leu Leu Leu Ser Ser Val Lys Glu Ser
220                 225                 230                 235

ACA GGT ATG TCA TCA ATG TCA CCA TTT CTT AGG AAA GTT GTT AAA CCT         1072
Thr Gly Met Ser Ser Met Ser Pro Phe Leu Arg Lys Val Val Lys Pro
                240                 245                 250

TCT AGT TTA AAC AGT GAT AAA ATT CCA TAT GTT GCA CCT ACA AAA AAA         1120
Ser Ser Leu Asn Ser Asp Lys Ile Pro Tyr Val Ala Pro Thr Lys Lys
            255                 260                 265

GAA TAT ATC GAG TTG GAT ATA TTG AAT AAG GGA TGG AAG TTA CAA AGT         1168
Glu Tyr Ile Glu Leu Asp Ile Leu Asn Lys Gly Trp Lys Leu Gln Ser
        270                 275                 280

TTA AAC GAA TCT AAA GAT CTC CTA CGC GCA AGT TTT AAT AAA CTG AGT         1216
Leu Asn Glu Ser Lys Asp Leu Leu Arg Ala Ser Phe Asn Lys Leu Ser
285                 290                 295

TCC ATA TTA CAG AAC GAA CAT GAC TAT TGG AAT AAG ATA ATG CAG AGT         1264
Ser Ile Leu Gln Asn Glu His Asp Tyr Trp Asn Lys Ile Met Gln Ser
300                 305                 310                 315

ATT AGC AAC AAG GAT GTT ATT TTT AAG ATT AGG GAC AGG ACT AGT GGT         1312
Ile Ser Asn Lys Asp Val Ile Phe Lys Ile Arg Asp Arg Thr Ser Gly
                320                 325                 330

CAA AAG CTG TTG GCA ATT AAG TAT GGT TAC GAA GAC TCT GGA TCT ACC         1360
Gln Lys Leu Leu Ala Ile Lys Tyr Gly Tyr Glu Asp Ser Gly Ser Thr
                335                 340                 345

TAT AAG CAT GAC AGA GGT ATT GCT AAT ATA AGG AAT AAT ATA GAA TCA         1408
Tyr Lys His Asp Arg Gly Ile Ala Asn Ile Arg Asn Asn Ile Glu Ser
            350                 355                 360

CAA AAT TTG GAT TTG ATA CCC CAC AGT AGT TCA GTG TTC AAA GGC ACT         1456
Gln Asn Leu Asp Leu Ile Pro His Ser Ser Ser Val Phe Lys Gly Thr
        365                 370                 375

GAT TTC GTA CAT TCA GTA AAG AAA TTC TTA AGG GTT CGT ATC TTC ACA         1504
Asp Phe Val His Ser Val Lys Lys Phe Leu Arg Val Arg Ile Phe Thr
380                 385                 390                 395

AAA ATC GAA TCA GAA GAT GAT TAC ATA TTG AGT GGC GAA AGT GTG ATG         1552
Lys Ile Glu Ser Glu Asp Asp Tyr Ile Leu Ser Gly Glu Ser Val Met
                400                 405                 410

GAT AGG GAT AGT GAA AGT GAA GAA GCT GAA ACG AAA GAT ATC AGA AAG         1600
Asp Arg Asp Ser Glu Ser Glu Glu Ala Glu Thr Lys Asp Ile Arg Lys
                415                 420                 425

CAA ATC CAA CTT TTG AAA AAG ATC ATT TTT GAA AAA GAA CTG ATG TAC         1648
Gln Ile Gln Leu Leu Lys Lys Ile Ile Phe Glu Lys Glu Leu Met Tyr
            430                 435                 440

CAA ATA AAG AAA GAA TGC GCT TTG TTG ATT TCC TAT GGT GTC AGT ATT         1696
Gln Ile Lys Lys Glu Cys Ala Leu Leu Ile Ser Tyr Gly Val Ser Ile
        445                 450                 455

GAA AAC GAA AAC AAG GTA ATA ATT GAA CTA CCT AAC GAA AAA TTT GAA         1744
Glu Asn Glu Asn Lys Val Ile Ile Glu Leu Pro Asn Glu Lys Phe Glu
460                 465                 470                 475

ATC GAG TTG TTG TCC CTT GAC GAT GAC TCC ATT GTC AAT CAT GAA CAA         1792
Ile Glu Leu Leu Ser Leu Asp Asp Asp Ser Ile Val Asn His Glu Gln
                480                 485                 490

GAC TTA CCA AAA ATC AAC GAC AAG AGA GCA AAT TTA ATG CTT GTT ATG         1840
Asp Leu Pro Lys Ile Asn Asp Lys Arg Ala Asn Leu Met Leu Val Met
                495                 500                 505

TTG AGA CTA TTA GTC GTT ATA TTC AAG AAA ACA TTA CGA TCG AGA             1888
Leu Arg Leu Leu Val Val Ile Phe Lys Lys Thr Leu Arg Ser Arg
            510                 515                 520

ATA AGC TCA CCC CAC GGA CTG ATC AAT TTG AAT GTT GAC GAT GAT ATC         1936
```

```
Ile Ser Ser Pro His Gly Leu Ile Asn Leu Asn Val Asp Asp Ile
    525             530                 535

TTA ATA ATA CGT CCC ATT CTT GGT AAA GTT CGG TTT GCT AAT TAC AAA        1984
Leu Ile Ile Arg Pro Ile Leu Gly Lys Val Arg Phe Ala Asn Tyr Lys
540             545                 550                 555

CTG TTA CTA AAA AAA ATC ATA AAG GAT TAC GTG CTC GAT ATA GTT CCT        2032
Leu Leu Leu Lys Lys Ile Ile Lys Asp Tyr Val Leu Asp Ile Val Pro
                560                 565                 570

GGC TCA AGT ATA ACA GAA ACG GAA GTT GAG AGA GAA CAA CCT CAA GAA        2080
Gly Ser Ser Ile Thr Glu Thr Glu Val Glu Arg Glu Gln Pro Gln Glu
                575                 580                 585

AAT AAA AAC ATT GAT GAT GAA AAT ATA ACT AAA TTA AAT AAA GAG ATC        2128
Asn Lys Asn Ile Asp Asp Glu Asn Ile Thr Lys Leu Asn Lys Glu Ile
            590                 595                 600

CGT GCC TTC GAT AAA CTA TTG AAT ATA CCT AGA CGT GAA CTC AAA ATA        2176
Arg Ala Phe Asp Lys Leu Leu Asn Ile Pro Arg Arg Glu Leu Lys Ile
            605                 610                 615

AAT CTA CCA TTA ACT GAG CAC AAA AGC CCT AAT CTA AGT TTA ATG CTC        2224
Asn Leu Pro Leu Thr Glu His Lys Ser Pro Asn Leu Ser Leu Met Leu
620             625                 630                 635

GAA AGT CCT AAC TAT TGT AAC GCA CTC ATT CAC ATC AAG TTT TCA GCT        2272
Glu Ser Pro Asn Tyr Cys Asn Ala Leu Ile His Ile Lys Phe Ser Ala
                640                 645                 650

GGT ACG GAA GCC AAC GCA GTG TCC TTT GAC ACA ACA TTT TCT GAT TTT        2320
Gly Thr Glu Ala Asn Ala Val Ser Phe Asp Thr Thr Phe Ser Asp Phe
                655                 660                 665

AAA GAA GTA GAG GAC TTC CTA CAT TTT ATT GTC GCT GAG TAC ATC CAG        2368
Lys Glu Val Glu Asp Phe Leu His Phe Ile Val Ala Glu Tyr Ile Gln
            670                 675                 680

CAA AAG AAG GTG TAATATCCTG AGTCACTCCT TAAACCTACA TACATTGCCA            2420
Gln Lys Lys Val
            685

TAGAATGCCA TTTATTACTA TATAAAGTCG CATACGTACA AAAGGACAAG ATC             2473

(2) INFORMATION FOR SEQ ID NO:4:

(i) SEQUENCE CHARACTERISTICS:
        (A) LENGTH: 687 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Thr Glu Asp Pro Asp Ser Asn His Leu Ser Ser Glu Thr Gly
 1               5                  10                  15

Ile Lys Leu Ala Leu Asp Pro Asn Leu Ile Thr Leu Ala Leu Ser Ser
            20                  25                  30

Asn Pro Asn Ser Ser Leu His Ser Pro Thr Ser Asp Glu Pro Val Pro
        35                  40                  45

Glu Ser Ala Gly Lys Ala Asp Thr Ser Ile Arg Leu Glu Gly Asp Glu
    50                  55                  60

Leu Glu Asn Lys Thr Lys Asp Asn Asp Lys Asn Leu Lys Phe Leu
65                  70                  75                  80

Lys Asn Lys Asp Ser Leu Val Ser Asn Pro His Glu Ile Tyr Gly Ser
                85                  90                  95

Met Pro Leu Glu Gln Leu Ile Pro Ile Ile Leu Arg Gln Arg Gly Pro
            100                 105                 110

Gly Phe Lys Phe Val Asp Leu Asn Glu Lys Glu Leu Gln Asn Glu Ile
        115                 120                 125
```

-continued

```
Lys Gln Leu Gly Ser Asp Ser Asp Gly His Asn Ser Glu Lys Lys
    130                 135                 140

Asp Thr Asp Gly Ala Asp Glu Asn Val Gln Ile Gly Glu Asp Phe Met
145                 150                 155                 160

Glu Val Asp Tyr Glu Asp Lys Asp Asn Pro Val Asp Ser Arg Asn Glu
                165                 170                 175

Thr Asp His Lys Thr Asn Glu Asn Gly Glu Thr Asp Asp Asn Ile Glu
            180                 185                 190

Thr Val Met Thr Gln Glu Gln Phe Val Lys Arg Arg Asp Met Leu
        195                 200                 205

Glu His Ile Asn Leu Ala Met Asn Glu Ser Ser Leu Ala Leu Glu Phe
    210                 215                 220

Val Ser Leu Leu Leu Ser Ser Val Lys Glu Ser Thr Gly Met Ser Ser
225                 230                 235                 240

Met Ser Pro Phe Leu Arg Lys Val Lys Pro Ser Ser Leu Asn Ser
                245                 250                 255

Asp Lys Ile Pro Tyr Val Ala Pro Thr Lys Lys Glu Tyr Ile Glu Leu
            260                 265                 270

Asp Ile Leu Asn Lys Gly Trp Lys Leu Gln Ser Leu Asn Glu Ser Lys
        275                 280                 285

Asp Leu Leu Arg Ala Ser Phe Asn Lys Leu Ser Ser Ile Leu Gln Asn
    290                 295                 300

Glu His Asp Tyr Trp Asn Lys Ile Met Gln Ser Ile Ser Asn Lys Asp
305                 310                 315                 320

Val Ile Phe Lys Ile Arg Asp Arg Thr Ser Gly Gln Lys Leu Leu Ala
                325                 330                 335

Ile Lys Tyr Gly Tyr Glu Asp Ser Gly Ser Thr Tyr Lys His Asp Arg
            340                 345                 350

Gly Ile Ala Asn Ile Arg Asn Asn Ile Glu Ser Gln Asn Leu Asp Leu
        355                 360                 365

Ile Pro His Ser Ser Ser Val Phe Lys Gly Thr Asp Phe Val His Ser
    370                 375                 380

Val Lys Lys Phe Leu Arg Val Arg Ile Phe Thr Lys Ile Glu Ser Glu
385                 390                 395                 400

Asp Asp Tyr Ile Leu Ser Gly Glu Ser Val Met Asp Arg Asp Ser Glu
                405                 410                 415

Ser Glu Glu Ala Glu Thr Lys Asp Ile Arg Lys Gln Ile Gln Leu Leu
            420                 425                 430

Lys Lys Ile Ile Phe Glu Lys Glu Leu Met Tyr Gln Ile Lys Lys Glu
        435                 440                 445

Cys Ala Leu Leu Ile Ser Tyr Gly Val Ser Ile Glu Asn Glu Asn Lys
    450                 455                 460

Val Ile Ile Glu Leu Pro Asn Glu Lys Phe Glu Ile Glu Leu Leu Ser
465                 470                 475                 480

Leu Asp Asp Asp Ser Ile Val Asn His Glu Gln Asp Leu Pro Lys Ile
                485                 490                 495

Asn Asp Lys Arg Ala Asn Leu Met Leu Val Met Leu Arg Leu Leu Leu
            500                 505                 510

Val Val Ile Phe Lys Lys Thr Leu Arg Ser Arg Ile Ser Ser Pro His
        515                 520                 525

Gly Leu Ile Asn Leu Asn Val Asp Asp Ile Leu Ile Ile Arg Pro
    530                 535                 540

Ile Leu Gly Lys Val Arg Phe Ala Asn Tyr Lys Leu Leu Leu Lys Lys
```

-continued

```
545                 550                 555                 560
Ile Ile Lys Asp Tyr Val Leu Asp Ile Val Pro Gly Ser Ser Ile Thr
                565                 570                 575

Glu Thr Glu Val Glu Arg Glu Gln Pro Gln Glu Asn Lys Asn Ile Asp
            580                 585                 590

Asp Glu Asn Ile Thr Lys Leu Asn Lys Glu Ile Arg Ala Phe Asp Lys
        595                 600                 605

Leu Leu Asn Ile Pro Arg Arg Glu Leu Lys Ile Asn Leu Pro Leu Thr
    610                 615                 620

Glu His Lys Ser Pro Asn Leu Ser Leu Met Leu Glu Ser Pro Asn Tyr
625                 630                 635                 640

Cys Asn Ala Leu Ile His Ile Lys Phe Ser Ala Gly Thr Glu Ala Asn
                645                 650                 655

Ala Val Ser Phe Asp Thr Thr Phe Ser Asp Phe Lys Glu Val Glu Asp
            660                 665                 670

Phe Leu His Phe Ile Val Ala Glu Tyr Ile Gln Gln Lys Lys Val
        675                 680                 685
```

(2) INFORMATION FOR SEQ ID NO:5:

(i) SEQUENCE CHARACTERISTICS:
        (A) LENGTH: 1905 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 433..1353

(xi) SEQUENCE DESCRIPTION: SEQ ID NO:5:

```
GATCTTCAGT ATCCTCGCGG AACGCTACAA CAATGTAAAC GATTAGAACA ACATTGGCCA      60

TTGCAGCAGC TAAACCTCCA CTAATTAAGG TATTTGGCGT AAAATTGCTGA ATAATGAAAA    120

AAGTGAGTAC GGGCAGTACC ACCATCGCTG CAGTAAACAG CATAAGTTTA TTAATCACCG     180

CACGAGGAAC ATCTACAGCC ATTATTTGAT TCTTTTGAAG TCTTGGTTAG TTTCTACTAT     240

TGCTTTCCAG TATTGCGTTC ATTTTAGCTT GCAGGTTAGT AATATATAGT GAGAGCTCTT     300

TTGCCTTTCT TTTATTTGAA AAAAATAAAA TAACCTAGAA AATTATCAAA TATCGAAGAC     360

AAACAACCAA AATAAAAAAA AAGGTAGAAA ATTGAATTTT CCAGCCAAGG TATTCCATAT     420

TAAGAAGAAA AG ATG GTT CAG CAA CTA AGC CTT TTT GGA TCT ATT GGT         468
              Met Val Gln Gln Leu Ser Leu Phe Gly Ser Ile Gly
                1               5                   10

GAT GAC GGC TAC GAT TTA CTA ATT TCA ACT TTG ACC ACA ATA TCA GGT       516
Asp Asp Gly Tyr Asp Leu Leu Ile Ser Thr Leu Thr Thr Ile Ser Gly
          15                  20                  25

AAT CCT CCG CTA CTG TAT AAC AGT TTA TGC ACT GTC TGG AAA CCA AAT       564
Asn Pro Pro Leu Leu Tyr Asn Ser Leu Cys Thr Val Trp Lys Pro Asn
     30                  35                  40

CCA TCT TAC GAC GTC GAG AAC GTG AAC TCT AGA AAC CAA TTG GTT GAA       612
Pro Ser Tyr Asp Val Glu Asn Val Asn Ser Arg Asn Gln Leu Val Glu
 45                  50                  55                  60

CCA AAT AGA ATA AAA CTT TCC AAA GAG GTG CCA TTT TCT TAC CTG ATC       660
Pro Asn Arg Ile Lys Leu Ser Lys Glu Val Pro Phe Ser Tyr Leu Ile
                 65                  70                  75

GAT GAA ACA ATG ATG GAT AAG CCA TTA AAC TTT AGA ATC TTG AAA TCT       708
Asp Glu Thr Met Met Asp Lys Pro Leu Asn Phe Arg Ile Leu Lys Ser
             80                  85                  90
```

```
TTT ACA AAC GAT AAA ATC CCG CTT AAC TAT GCT ATG ACA CGG AAT ATC      756
Phe Thr Asn Asp Lys Ile Pro Leu Asn Tyr Ala Met Thr Arg Asn Ile
        95                  100                 105

TTG CAC AAC ACA GTT CCG CAA GTC ACC AAC TTC AAC AGC ACA AAC GAA      804
Leu His Asn Thr Val Pro Gln Val Thr Asn Phe Asn Ser Thr Asn Glu
110                 115                 120

GAT CAA AAC AAC AGT AAG CAT ACA GAA GAT ACT GTA AAT GAA AGT CGA      852
Asp Gln Asn Asn Ser Lys His Thr Glu Asp Thr Val Asn Glu Ser Arg
125                 130                 135                 140

AAC AGC GAT GAC ATC ATA GAT GTC GAC ATG GAT GCA AGT CCC GCC CCT      900
Asn Ser Asp Asp Ile Ile Asp Val Asp Met Asp Ala Ser Pro Ala Pro
                145                 150                 155

TCA AAC GAG TCA TGT TCC CCT TGG TCA TTG CAA ATT TCA GAT ATT CCT      948
Ser Asn Glu Ser Cys Ser Pro Trp Ser Leu Gln Ile Ser Asp Ile Pro
            160                 165                 170

GCT GCA GGA AAC AAT AGA AGT GTT TCA ATG CAA ACG ATA GCT GAG ACT      996
Ala Ala Gly Asn Asn Arg Ser Val Ser Met Gln Thr Ile Ala Glu Thr
        175                 180                 185

ATC ATA TTA TCT TCA GCT GGC AAA AAC TCT TCA GTA TCC TCG CTC ATG     1044
Ile Ile Leu Ser Ser Ala Gly Lys Asn Ser Ser Val Ser Ser Leu Met
190                 195                 200

AAC GGA TTG GGT TAT GTA TTC GAA TTT CAG TAT CTT ACA ATT GGT GTG     1092
Asn Gly Leu Gly Tyr Val Phe Glu Phe Gln Tyr Leu Thr Ile Gly Val
205                 210                 215                 220

AAA TTT TTT ATG AAG CAT GGT TTA ATA CTT GAG TTA CAA AAA ATT TGG     1140
Lys Phe Phe Met Lys His Gly Leu Ile Leu Glu Leu Gln Lys Ile Trp
                225                 230                 235

CAA ATA GAA GAA GCA GGC AAT TCA CAA ATA ACA AGC GGA GGG TTC CTT     1188
Gln Ile Glu Glu Ala Gly Asn Ser Gln Ile Thr Ser Gly Gly Phe Leu
            240                 245                 250

TTA AAA GCA TAC ATC AAT GTT AGT AGG GGG ACC GAT ATC GAT CGT ATA     1236
Leu Lys Ala Tyr Ile Asn Val Ser Arg Gly Thr Asp Ile Asp Arg Ile
        255                 260                 265

AAC TAT ACA GAG ACT GCC TTG ATG AAC TTA AAA AAG GAA CTA CAA GGC     1284
Asn Tyr Thr Glu Thr Ala Leu Met Asn Leu Lys Lys Glu Leu Gln Gly
270                 275                 280

TAT ATA GAG TTA AGT GTA CCC GAT AGA CAG TCA ATG GAC TCG AGG GTA     1332
Tyr Ile Glu Leu Ser Val Pro Asp Arg Gln Ser Met Asp Ser Arg Val
285                 290                 295                 300

GCA CAT GGA AAT ATT CTA ATA TAATCATTGG CACCTGGGCA TATTTTACA         1383
Ala His Gly Asn Ile Leu Ile
                305

AAATTCACTC ATATAGTTAT ACAGAACAAC AGTAACCACT TTTAATGTAC AGGTATTTCT   1443

ATATCTACAA ACAAAAATGT GTAGTTATAT ATCTAATGTT GCTATACCGA GGAATTATAA   1503

AGTAATAAAG ATGTTAAATT AAAAGACAAA ATTTTTGAGA GGCTATTGGA AAAGAAGAGA   1563

AAACTATTTC TTGGAATCTA GTTTATTCAG TTTAGCTTTT TGTTTGGCAA TTTGCTTCTT   1623

TTTCTTTTTT AAGTTCTCAG CTTGTTCCTC CTTTTTAGCA TTAGAATACT TCATTTTTTT   1683

GTAAAGTTTC TTTTGTTTGT TACTCATCAT TATCATTTTC AATTTCTTTT CTTCTTCTTC   1743

TTCATCCACC TTTCTCTTTT TGTTCTTTGA CTTATTGACA TCCTTATCAG CTTCTGAAGT   1803

TTCAGAATAT TTGATACCTT GTGCTTCCAA TTCAAGCTCT TTTTGAGCTT GTAGCTCTTC   1863

GTCATCGTCA TCATCTTCTT CTCCAGCAAC AACTTCTTGA TC                     1905

(2) INFORMATION FOR SEQ ID NO:6:

(i) SEQUENCE CHARACTERISTICS:
        (A) LENGTH: 307 amino acids
```

(B) TYPE: amino acid
            (D) TOPOLOGY: linear (ii) MOLECULE TYPE: protein (xi) SEQUENCE DESCRIPTION: SEQ ID NO:6:

Met Val Gln Gln Leu Ser Leu Phe Gly Ser Ile Gly Asp Asp Gly Tyr
1               5                   10                  15

Asp Leu Leu Ile Ser Thr Leu Thr Thr Ile Ser Gly Asn Pro Pro Leu
                20                  25                  30

Leu Tyr Asn Ser Leu Cys Thr Val Trp Lys Pro Asn Pro Ser Tyr Asp
            35                  40                  45

Val Glu Asn Val Asn Ser Arg Asn Gln Leu Val Glu Pro Asn Arg Ile
        50                  55                  60

Lys Leu Ser Lys Glu Val Pro Phe Ser Tyr Leu Ile Asp Glu Thr Met
65                  70                  75                  80

Met Asp Lys Pro Leu Asn Phe Arg Ile Leu Lys Ser Phe Thr Asn Asp
                85                  90                  95

Lys Ile Pro Leu Asn Tyr Ala Met Thr Arg Asn Ile Leu His Asn Thr
            100                 105                 110

Val Pro Gln Val Thr Asn Phe Asn Ser Thr Asn Glu Asp Gln Asn Asn
        115                 120                 125

Ser Lys His Thr Glu Asp Thr Val Asn Glu Ser Arg Asn Ser Asp Asp
130                 135                 140

Ile Ile Asp Val Asp Met Asp Ala Ser Pro Ala Pro Ser Asn Glu Ser
145                 150                 155                 160

Cys Ser Pro Trp Ser Leu Gln Ile Ser Asp Ile Pro Ala Ala Gly Asn
                165                 170                 175

Asn Arg Ser Val Ser Met Gln Thr Ile Ala Glu Thr Ile Ile Leu Ser
            180                 185                 190

Ser Ala Gly Lys Asn Ser Ser Val Ser Ser Leu Met Asn Gly Leu Gly
        195                 200                 205

Tyr Val Phe Glu Phe Gln Tyr Leu Thr Ile Gly Val Lys Phe Phe Met
210                 215                 220

Lys His Gly Leu Ile Leu Glu Leu Gln Lys Ile Trp Gln Ile Glu Glu
225                 230                 235                 240

Ala Gly Asn Ser Gln Ile Thr Ser Gly Gly Phe Leu Leu Lys Ala Tyr
                245                 250                 255

Ile Asn Val Ser Arg Gly Thr Asp Ile Asp Arg Ile Asn Tyr Thr Glu
            260                 265                 270

Thr Ala Leu Met Asn Leu Lys Lys Glu Leu Gln Gly Tyr Ile Glu Leu
        275                 280                 285

Ser Val Pro Asp Arg Gln Ser Met Asp Ser Arg Val Ala His Gly Asn
290                 295                 300

Ile Leu Ile
305

(2) INFORMATION FOR SEQ ID NO:7:

(i) SEQUENCE CHARACTERISTICS:
        (A) LENGTH: 1004 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS (B) LOCATION: 286..648

(xi) SEQUENCE DESCRIPTION: SEQ ID NO:7:

```
GATCGTTGTT GTAGACTCTC TGGAAGAAAG TGCAAGAGGG GCCGGTGGCT TTGGTAGCAC         60

TGGTAACTAA CTTAGTGTAT ATACTTTGGC ACACTTGTAT AATGTATAAT AAAATCAGGA        120

TAAATCCAGT GTGACCCGGA CTGAATTACT GAAACTTTGA AGTGTTAAGG AAATTGTACT        180

GCCATTTAAC GCATTTACCT ATCACTTAGT AGCATGCATA AGCCATGGGC TAATCATAAC        240

AGATTGTGAT GATAGGCATC CTGTACTCCT TTTTTTTACA AGAAA ATG AGC AAC           294
                                                 Met Ser Asn
                                                  1

CAG GCA CTA TAT GAG AAA CTC GAA CAA ACC AGG ACG ATT CTG TCC GTG         342
Gln Ala Leu Tyr Glu Lys Leu Glu Gln Thr Arg Thr Ile Leu Ser Val
     5                  10                  15

AAG CTG GCG GAA TTG ATA AAT ATG ACT ACG ATA GCC GAT AGA AAT GAT         390
Lys Leu Ala Glu Leu Ile Asn Met Thr Thr Ile Ala Asp Arg Asn Asp
 20                  25                  30                  35

GAT GAC GAG GGT TCA TTC GCA CAA GAA AAT TCT GAG CTC GCT GTG GCC         438
Asp Asp Glu Gly Ser Phe Ala Gln Glu Asn Ser Glu Leu Ala Val Ala
                 40                  45                  50

ACG ACC AGT GTG ATG ATG GTG AAT AAC CAG ACC ATG CAA TTG ATT AAA         486
Thr Thr Ser Val Met Met Val Asn Asn Gln Thr Met Gln Leu Ile Lys
             55                  60                  65

AAT GTT CAA GAC TTG TTG ATC CTG ACC AGA TCG ATA AAA GAG AAA TGG         534
Asn Val Gln Asp Leu Leu Ile Leu Thr Arg Ser Ile Lys Glu Lys Trp
 70                  75                  80

CTA CTG AAC CAA ATT CCT GTA ACG GAA CAC TCA AAA GTG ACT CGT TTT         582
Leu Leu Asn Gln Ile Pro Val Thr Glu His Ser Lys Val Thr Arg Phe
         85                  90                  95

GAC GAG AAG CAG ATA GAG GAA TTA CTG GAT AAC TGT ATA GAA ACG TTC         630
Asp Glu Lys Gln Ile Glu Glu Leu Leu Asp Asn Cys Ile Glu Thr Phe
100                 105                 110                 115

GTG GCG GAA AAA ACT ACG TAAAAAGGCG GTATTTATCT ATTATTTGGC                 678
Val Ala Glu Lys Thr Thr
                120

CAAAAAAAAA AAAAAAATAC ATACTACATA TACATATACG CCATAAAAAA TCTCTGCATC        738

TATCTTATTT CCCATTATTT GGACAAATGC TTACGTGCTA ATGTCCTTAC CCTCGAGTCG        798

AATGCCGGGC TCCTAATAGG GTCTGTAATC TTATAAAACG GGTTCATTAG TGTCTTTACG        858

TATAGTTCGT GTACCTCTTG GTAGAATGAC CTCATATTAT TGTCGTCAAT AACTACGCTA        918

CTGTTGGCTG AGTTCCCATG GATCATCACG AACTTCATCC CACTATAGCT AATATAAGCC        978

GTTATTGCTA GTCCATAAAA ATGATC                                            1004
```

(2) INFORMATION FOR SEQ ID NO:8:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Asn Gln Ala Leu Tyr Glu Lys Leu Glu Gln Thr Arg Thr Ile
 1               5                  10                  15

Leu Ser Val Lys Leu Ala Glu Leu Ile Asn Met Thr Thr Ile Ala Asp
                 20                  25                  30

Arg Asn Asp Asp Asp Glu Gly Ser Phe Ala Gln Glu Asn Ser Glu Leu
             35                  40                  45
```

```
Ala Val Ala Thr Thr Ser Val Met Met Val Asn Asn Gln Thr Met Gln
     50                  55                  60

Leu Ile Lys Asn Val Gln Asp Leu Leu Ile Leu Thr Arg Ser Ile Lys
 65                  70                  75                  80

Glu Lys Trp Leu Leu Asn Gln Ile Pro Val Thr Glu His Ser Lys Val
                 85                  90                  95

Thr Arg Phe Asp Glu Lys Gln Ile Glu Glu Leu Leu Asp Asn Cys Ile
            100                 105                 110

Glu Thr Phe Val Ala Glu Lys Thr Thr
            115                 120
```

(2) INFORMATION FOR SEQ ID NO:9:

(i) SEQUENCE CHARACTERISTICS:
        (A) LENGTH: 1491 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 646..1065

(xi) SEQUENCE DESCRIPTION: SEQ ID NO:9:

```
TCGATGATGT TCTTTATTCT TTCAACCAGC TCGAGCCCCT GCAAACTTAA GCTAAGGACA        60

GAAAAGAAAA AAAAAAAAAA AAAAAATTCA AGAATCAGC TTATAAAACA TATTCAAGGA       120

CCATCTGAAG TATCATTCAT TCGTTTTTTA CTCGTTAATC TCATTCATTC GTTTCCTCAT      180

TCTTTTTTCT TTGTTCTTTA TTTCGGCTAT TTTTTCACTA TTAAAATAAC TAGAGCTAAC      240

AATATTATTT CTTCTGCTTT AGTTACAAAA CAAGGACATT CATTTAACTT GGCGTTATCC      300

CATACATTCG TTTATTATAT CTTCTTTAAA ACACAATTTC TTTTACAGTT AAACTTTTCT      360

GATTTATTAT ATATTACTTA AGATTGTTCA TATAACTAAC ATTTATAGCT TATATGCGTG      420

AAGTGCGCTT TTGTAGAACA TGTGGCTGTT TCTGTAGAAG CCTTGTCTTT CTCTGTAATC      480

CTTTAAAGGC CAACCGTACG TGCTTAATTA CAAGCTTTGT TCGCATTGCA AGAAAGTTAG      540

AAAAAAAATC AATTCTGAAA GATAATTATA ATTCAAACGG TAAACCATTG GTTAAAAGAG      600

GGACATAACA TTTCACTAGT TCAATACATT ATATGCTCTT TAACA ATG ACA GAT          654
                                                Met Thr Asp
                                                  1

AGA TTA ACA CAA TTG CAG ATA TGT TTA GAC CAA ATG ACG GAG CAA TTC        702
Arg Leu Thr Gln Leu Gln Ile Cys Leu Asp Gln Met Thr Glu Gln Phe
      5                  10                  15

TGT GCT ACT TTA AAC TAC ATA GAT AAG AAC CAT GGT TTT GAA CGA TTG        750
Cys Ala Thr Leu Asn Tyr Ile Asp Lys Asn His Gly Phe Glu Arg Leu
 20                  25                  30                  35

ACC GTA AAT GAA CCT CAG ATG TCC GAT AAG CAT GCC ACA GTA GTA CCT        798
Thr Val Asn Glu Pro Gln Met Ser Asp Lys His Ala Thr Val Val Pro
              40                  45                  50

CCT GAG GAA TTT TCT AAC ACG ATA GAT GAG CTA TCC ACG GAC ATT ATA        846
Pro Glu Glu Phe Ser Asn Thr Ile Asp Glu Leu Ser Thr Asp Ile Ile
         55                  60                  65

CTT AAA ACA AGA CAG ATA AAC AAG CTT ATT GAC TCG TTA CCT GGT GTT        894
Leu Lys Thr Arg Gln Ile Asn Lys Leu Ile Asp Ser Leu Pro Gly Val
     70                  75                  80

GAC GTT TCA GCT GAA GAG CAA TTA AGG AAG ATT GAT ATG TTG CAG AAA        942
Asp Val Ser Ala Glu Glu Gln Leu Arg Lys Ile Asp Met Leu Gln Lys
 85                  90                  95
```

```
AAG CTA GTT GAA GTG GAA GAC GAA AAA ATT GAG GCC ATC AAA AAG AAG        990
Lys Leu Val Glu Val Glu Asp Glu Lys Ile Glu Ala Ile Lys Lys Lys
100                 105                 110                 115

GAG AAA CTT TTA AGG CAC GTT GAT TCT TTA ATT GAA GAT TTT GTA GAT       1038
Glu Lys Leu Leu Arg His Val Asp Ser Leu Ile Glu Asp Phe Val Asp
            120                 125                 130

GGC ATT GCA AAC TCA AAA AAG AGC ACA TAAACTTAAG TTTTACAAAG             1085
Gly Ile Ala Asn Ser Lys Lys Ser Thr
                135                 140

AAATTTGCGA ACAGAGGACA GAAAATGTAC TATAGTTATA TGGCAGAGTT AAGCGTATGT     1145

ATGTTATTCT TATAAATAAT TGTGCTACTC TATTTGTACC GGAGAATTAT TGAAGCAATG     1205

GGAGAAAAAT CATAATGGAG AAAATCTTTC TACGAGTTAC TTTGCAAGGC AATCTAACGA     1265

TTCTAAAAGA CACAATACAC TAAAGAAAAA ACTTTGGAAG TACAGTTTTT TCCCCAAGTT     1325

GAAGTGTGGA CTCATTGTGA AGATGTAAAA ATGTAAAAAC CAACCGACAA TGCACTCCCA     1385

GCCAAATTCA TTGTAGACCT CCCATTTGAT AGAAAAGGAA GGTTCAGCAG TTGTCCACGG     1445

ATTCCAAGAT ATCATTCTCT TACATTGCAC GCACATGAAA ATGATC                    1491

(2) INFORMATION FOR SEQ ID NO:10:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:10:

Met Thr Asp Arg Leu Thr Gln Leu Gln Ile Cys Leu Asp Gln Met Thr
1               5                   10                  15

Glu Gln Phe Cys Ala Thr Leu Asn Tyr Ile Asp Lys Asn His Gly Phe
            20                  25                  30

Glu Arg Leu Thr Val Asn Glu Pro Gln Met Ser Asp Lys His Ala Thr
        35                  40                  45

Val Val Pro Pro Glu Glu Phe Ser Asn Thr Ile Asp Glu Leu Ser Thr
    50                  55                  60

Asp Ile Ile Leu Lys Thr Arg Gln Ile Asn Lys Leu Ile Asp Ser Leu
65                  70                  75                  80

Pro Gly Val Asp Val Ser Ala Glu Glu Gln Leu Arg Lys Ile Asp Met
                85                  90                  95

Leu Gln Lys Lys Leu Val Glu Val Glu Asp Glu Lys Ile Glu Ala Ile
            100                 105                 110

Lys Lys Lys Glu Lys Leu Leu Arg His Val Asp Ser Leu Ile Glu Asp
        115                 120                 125

Phe Val Asp Gly Ile Ala Asn Ser Lys Lys Ser Thr
    130                 135                 140

(2) INFORMATION FOR SEQ ID NO:11:

(i) SEQUENCE CHARACTERISTICS:
        (A) LENGTH: 4002 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 241..3918
```

(xi) SEQUENCE DESCRIPTION: SEQ ID NO:11:

```
TGATCATAGA AAGGAAACGT GGTTGCATGA ATTGAGATTC GTCTCACACT TCGACTGGTC        60

AAAATTGGCA AGTTTATACC TCACGGCTTG AAAAGAAGGC AAGTCATCGA GCAGTGCTAT       120

TTAAAATTTA TACCATTGAA AAGGGCGATT TGGTTGATAA AGTGCTGCTA TTTTATCGAA       180

TGGAAATCGA ACCAGAAAAA GAAGAGGTCA ATGCTGCTG GGGCAGATGA TGCCATTTCC        240
```

| | | | | | | | | | | | | | | | | |
|---|---|---|---|---|---|---|---|---|---|---|---|---|---|---|---|---|
| ATG | CAC | CTG | CTA | AAG | GAC | TGG | ACG | GAT | ACC | TTT | GTA | TAC | ATC | CTG | GAA | 288 |
| Met | His | Leu | Leu | Lys | Asp | Trp | Thr | Asp | Thr | Phe | Val | Tyr | Ile | Leu | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAG | CTC | ATC | TTT | GAT | ATG | ACA | AAT | CAC | TAT | AAC | GAT | TCT | CAA | CAA | CTG | 336 |
| Lys | Leu | Ile | Phe | Asp | Met | Thr | Asn | His | Tyr | Asn | Asp | Ser | Gln | Gln | Leu | |
| | | | | 20 | | | | | 25 | | | | | 30 | | |

| | | | | | | | | | | | | | | | | |
|---|---|---|---|---|---|---|---|---|---|---|---|---|---|---|---|---|
| CGT | ACG | TGG | AAG | AGG | CAG | ATT | TCT | TAT | TTT | TTA | AAA | CTT | TTG | GGG | AAT | 384 |
| Arg | Thr | Trp | Lys | Arg | Gln | Ile | Ser | Tyr | Phe | Leu | Lys | Leu | Leu | Gly | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| TGC | TAC | TCA | CTA | AGA | TTG | ATC | AAT | AAG | GAA | ATC | TTT | CAT | CAT | TGG | CTT | 432 |
| Cys | Tyr | Ser | Leu | Arg | Leu | Ile | Asn | Lys | Glu | Ile | Phe | His | His | Trp | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| GTA | GAG | TTT | ATA | AAT | AAG | ATG | GAA | AAC | TTC | GAA | TTT | TTG | CCA | TTA | TCT | 480 |
| Val | Glu | Phe | Ile | Asn | Lys | Met | Glu | Asn | Phe | Glu | Phe | Leu | Pro | Leu | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TTA | CAT | ATT | TTG | ATG | ATT | TTT | TGG | AAC | GAC | ATC | TGC | CAA | ATT | GAT | ACA | 528 |
| Leu | His | Ile | Leu | Met | Ile | Phe | Trp | Asn | Asp | Ile | Cys | Gln | Ile | Asp | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| AAT | GCT | CCT | GTT | GCG | GCT | ACA | ATA | ACA | TCA | AGT | CAA | AAA | GAG | CCC | TTC | 576 |
| Asn | Ala | Pro | Val | Ala | Ala | Thr | Ile | Thr | Ser | Ser | Gln | Lys | Glu | Pro | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| TTT | CTG | GTA | ACA | AAA | ATC | ACT | GAT | ATG | CTA | TTG | CAC | AAA | TAT | TAT | ATT | 624 |
| Phe | Leu | Val | Thr | Lys | Ile | Thr | Asp | Met | Leu | Leu | His | Lys | Tyr | Tyr | Ile | |
| | | | 115 | | | | | 120 | | | | | 125 | | | |

| | | | | | | | | | | | | | | | | |
|---|---|---|---|---|---|---|---|---|---|---|---|---|---|---|---|---|
| GTT | TCC | AGC | AGC | AAA | TCA | ATG | ATA | AAT | GAC | GAG | AAC | TAC | ATC | ATC | AAT | 672 |
| Val | Ser | Ser | Ser | Lys | Ser | Met | Ile | Asn | Asp | Glu | Asn | Tyr | Ile | Ile | Asn | |
| | | | 130 | | | | | 135 | | | | | 140 | | | |

| | | | | | | | | | | | | | | | | |
|---|---|---|---|---|---|---|---|---|---|---|---|---|---|---|---|---|
| GAT | ATA | AAG | AAA | AAC | AAC | AAG | ATA | AAG | TTG | AAT | ATT | CTC | AAA | ATA | TTA | 720 |
| Asp | Ile | Lys | Lys | Asn | Asn | Lys | Ile | Lys | Leu | Asn | Ile | Leu | Lys | Ile | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TCC | AGT | TTA | ATT | TTG | AAA | ATT | TTT | CAA | GAA | CAA | TCT | TTA | GAG | GTG | TTT | 768 |
| Ser | Ser | Leu | Ile | Leu | Lys | Ile | Phe | Gln | Glu | Gln | Ser | Leu | Glu | Val | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| ATA | TTT | CCC | ACA | TCT | AAC | TGG | GAA | ATT | TAC | AAG | CCC | TTA | CTT | TTT | GAA | 816 |
| Ile | Phe | Pro | Thr | Ser | Asn | Trp | Glu | Ile | Tyr | Lys | Pro | Leu | Leu | Phe | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| ATA | GTC | TCA | AAC | GCC | GAC | ACT | AAT | CAA | AAT | TCT | GAT | ATG | AAG | AAA | AAA | 864 |
| Ile | Val | Ser | Asn | Ala | Asp | Thr | Asn | Gln | Asn | Ser | Asp | Met | Lys | Lys | Lys | |
| | | | 195 | | | | | 200 | | | | | 205 | | | |

| | | | | | | | | | | | | | | | | |
|---|---|---|---|---|---|---|---|---|---|---|---|---|---|---|---|---|
| TTA | GAG | TTA | ATT | AGT | TAC | AGA | AAC | GAG | TCA | TTG | AAG | AAT | AAT | TCT | TCT | 912 |
| Leu | Glu | Leu | Ile | Ser | Tyr | Arg | Asn | Glu | Ser | Leu | Lys | Asn | Asn | Ser | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| ATA | CGA | AAC | GTA | ATA | ATG | TCT | GCC | AGC | AAC | GCA | AAT | GAC | TTT | CAA | TTA | 960 |
| Ile | Arg | Asn | Val | Ile | Met | Ser | Ala | Ser | Asn | Ala | Asn | Asp | Phe | Gln | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ACT | ATC | GTC | ACC | TGT | AAA | CAA | TTT | CCA | AAA | CTA | TCA | TGC | ATT | CAA | TTA | 1008 |
| Thr | Ile | Val | Thr | Cys | Lys | Gln | Phe | Pro | Lys | Leu | Ser | Cys | Ile | Gln | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| AAT | TGT | ATA | GAT | ACT | CAG | TTC | ACC | AAG | CTA | CTG | GAC | GAT | AAC | CCT | ACA | 1056 |
| Asn | Cys | Ile | Asp | Thr | Gln | Phe | Thr | Lys | Leu | Leu | Asp | Asp | Asn | Pro | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| GAA | TTC | GAT | TGG | CCC | ACT | TAC | GTT | GAC | CAA | AAT | CCC | CTT | ACA | ATG | CAT | 1104 |

```
               Glu Phe Asp Trp Pro Thr Tyr Val Asp Gln Asn Pro Leu Thr Met His
                   275                 280                 285

AAA ATT ATT CAA TTA ATT CTC TGG TCC ATA CAT CCA TCA AGG CAA TTT              1152
Lys Ile Ile Gln Leu Ile Leu Trp Ser Ile His Pro Ser Arg Gln Phe
        290                 295                 300

GAT CAC TAT GAA TCT AAT CAA CTG GTA GCG AAA TTA TTA CTA TTG CGA              1200
Asp His Tyr Glu Ser Asn Gln Leu Val Ala Lys Leu Leu Leu Leu Arg
305                 310                 315                 320

ATA AAT TCA ACA GAT GAG GAT TTG CAC GAA TTC CAG ATA GAA GAT GCC              1248
Ile Asn Ser Thr Asp Glu Asp Leu His Glu Phe Gln Ile Glu Asp Ala
                325                 330                 335

ATT TGG TCA TTG GTT TTC CAA TTA GCC AAA AAT TTT TCG GCC CAA AAG              1296
Ile Trp Ser Leu Val Phe Gln Leu Ala Lys Asn Phe Ser Ala Gln Lys
        340                 345                 350

AGG GTG GTA TCA TAT ATG ATG CCT TCT TTG TAT CGC CTG CTT AAT ATA              1344
Arg Val Val Ser Tyr Met Met Pro Ser Leu Tyr Arg Leu Leu Asn Ile
                355                 360                 365

CTA ATT ACT TAT GGC ATC ATT AAG GTC CCT ACG TAT ATC AGA AAG CTA              1392
Leu Ile Thr Tyr Gly Ile Ile Lys Val Pro Thr Tyr Ile Arg Lys Leu
370                 375                 380

ATC AGT TCC GGC CTA CTT TAT CTC CAA GAT TCC AAT GAT AAG TTT GTG              1440
Ile Ser Ser Gly Leu Leu Tyr Leu Gln Asp Ser Asn Asp Lys Phe Val
385                 390                 395                 400

CAT GTC CAG CTG TTA ATT AAC TTG AAA ATT TCA CCG TTG ATG AAA AGT              1488
His Val Gln Leu Leu Ile Asn Leu Lys Ile Ser Pro Leu Met Lys Ser
                405                 410                 415

CAA TAC AAT ATG GTA TTG AGG AAC GTT ATG GAA TAT GAC GTT AAA TTT              1536
Gln Tyr Asn Met Val Leu Arg Asn Val Met Glu Tyr Asp Val Lys Phe
        420                 425                 430

TAT GAA ATT TTT AAT TTC GAC CAA CTC GTG GAA ATC ACA GAA CAA ATC              1584
Tyr Glu Ile Phe Asn Phe Asp Gln Leu Val Glu Ile Thr Glu Gln Ile
                435                 440                 445

AAA ATG CGA ATA CTC TCC AAT GAT ATA ACT AAT TTG CAA CTG TCG AAA              1632
Lys Met Arg Ile Leu Ser Asn Asp Ile Thr Asn Leu Gln Leu Ser Lys
        450                 455                 460

ACT CCT CTG AGC ATT AAA ATC ATG GTT GCA GAA TGG TAC TTA TCA CAT              1680
Thr Pro Leu Ser Ile Lys Ile Met Val Ala Glu Trp Tyr Leu Ser His
465                 470                 475                 480

TTA TGT TCC GGT ATT TTA TCT AGT GTT AAC CGC ACA GTG TTG CTA AAA              1728
Leu Cys Ser Gly Ile Leu Ser Ser Val Asn Arg Thr Val Leu Leu Lys
                485                 490                 495

ATA TTC AAG ATT TTT TGT ATC GAT CTG GAG GTT TTC CAC CAC TTT TTT              1776
Ile Phe Lys Ile Phe Cys Ile Asp Leu Glu Val Phe His His Phe Phe
        500                 505                 510

AAG TGG ATC GAG TTT ATT GTC TAC CAT CAA TTG CTA AGT GAT ATA GAA              1824
Lys Trp Ile Glu Phe Ile Val Tyr His Gln Leu Leu Ser Asp Ile Glu
        515                 520                 525

TCT CTG GAG GCA TTG ATG GAC ATC TTG CTA TGC TAC CAA AAA TTG TTC              1872
Ser Leu Glu Ala Leu Met Asp Ile Leu Leu Cys Tyr Gln Lys Leu Phe
        530                 535                 540

TCA CAA TTC ATT AAT GAC CAT ATT CTT TTT ACG AAG ACG TTA ATA TTC              1920
Ser Gln Phe Ile Asn Asp His Ile Leu Phe Thr Lys Thr Leu Ile Phe
545                 550                 555                 560

ATT TAC AAG AAA GTT TTG AAA GAA AAA GAC GTG CCT GCT TAT AAT GTG              1968
Ile Tyr Lys Lys Val Leu Lys Glu Lys Asp Val Pro Ala Tyr Asn Val
                565                 570                 575

ACT TCA TTT ATG CCA TTC TGG AAA TTT TTT ATG AAA AAC TTC CCT TTT              2016
Thr Ser Phe Met Pro Phe Trp Lys Phe Phe Met Lys Asn Phe Pro Phe
                580                 585                 590

GTT TTA AAG GTG GAT AAC GAT TTA AGG ATT GAG TTA CAA TCT GTT TAC              2064
```

```
Val Leu Lys Val Asp Asn Asp Leu Arg Ile Glu Leu Gln Ser Val Tyr
        595                 600                 605

AAT GAT GAG AAA TTG AAA ACT GAG AAG CTG AAG AAT GAT AAA TCA GAA        2112
Asn Asp Glu Lys Leu Lys Thr Glu Lys Leu Lys Asn Asp Lys Ser Glu
            610                 615                 620

GTC TTG AAG GTG TAT TCC ATG ATC AAT AAT TCA AAC CAA GCT GTT GGA        2160
Val Leu Lys Val Tyr Ser Met Ile Asn Asn Ser Asn Gln Ala Val Gly
625                 630                 635                 640

CAG ACT TGG AAT TTT CCC GAG GTG TTT CAA GTA AAC ATC AGG TTT CTA        2208
Gln Thr Trp Asn Phe Pro Glu Val Phe Gln Val Asn Ile Arg Phe Leu
                645                 650                 655

CTA CAC AAC TCC GAG ATC ATT GAT ACA AAT ACA AGC AAA CAG TTC CAG        2256
Leu His Asn Ser Glu Ile Ile Asp Thr Asn Thr Ser Lys Gln Phe Gln
            660                 665                 670

AAA GCA CGA AAC AAT GTC ATG CTT TTG ATT GCC ACT AAC TTG AAG GAG        2304
Lys Ala Arg Asn Asn Val Met Leu Leu Ile Ala Thr Asn Leu Lys Glu
        675                 680                 685

TAC ATT AAA TTT ATG TCC ATT TTC TTG AAA AGG AAA GAC TTT ACT AAC        2352
Tyr Ile Lys Phe Met Ser Ile Phe Leu Lys Arg Lys Asp Phe Thr Asn
690                 695                 700

AAA AAT TTA ATT CAA TTG ATC TCT CTA AAA CTT CTA ACT TTT GAA GTG        2400
Lys Asn Leu Ile Gln Leu Ile Ser Leu Lys Leu Leu Thr Phe Glu Val
705                 710                 715                 720

ACG CAG AAT GTG TTG GGG CTC GAG TAT ATT ATT CGA TTA TTA CCA ATA        2448
Thr Gln Asn Val Leu Gly Leu Glu Tyr Ile Ile Arg Leu Leu Pro Ile
                725                 730                 735

AAC TTG GAA AAT AAT GAC GGC TCA TAT GGT CTG TTT TTG AAG TAT CAT        2496
Asn Leu Glu Asn Asn Asp Gly Ser Tyr Gly Leu Phe Leu Lys Tyr His
            740                 745                 750

AAA GAA CAA TTC ATA AAG TCA AAT TTT GAG AAA ATT TTA CTT ACA TGT        2544
Lys Glu Gln Phe Ile Lys Ser Asn Phe Glu Lys Ile Leu Leu Thr Cys
        755                 760                 765

TAT GAA TTA GAA AAA AAA TAT CAT GGC AAC GAA TGT GAA ATA AAT TAT        2592
Tyr Glu Leu Glu Lys Lys Tyr His Gly Asn Glu Cys Glu Ile Asn Tyr
770                 775                 780

TAT GAG ATC CTA TTG AAA ATT TTA ATA ACT TAT GGG TCA TCT CCC AAA        2640
Tyr Glu Ile Leu Leu Lys Ile Leu Ile Thr Tyr Gly Ser Ser Pro Lys
785                 790                 795                 800

TTA CTT GCA ACA TCT ACA AAA ATC ATT ATG TTG TTA TTG AAT GAT AGC        2688
Leu Leu Ala Thr Ser Thr Lys Ile Ile Met Leu Leu Leu Asn Asp Ser
                805                 810                 815

GTG GAA AAC TCA TCT AAT ATT TTG GAG GAT ATT TTG TAC TAC TCA ACT        2736
Val Glu Asn Ser Ser Asn Ile Leu Glu Asp Ile Leu Tyr Tyr Ser Thr
            820                 825                 830

TGT CCG TCG GAA ACC GAT CTT AAC GAT ATT CCA TTG GGT AGT GGA CAA        2784
Cys Pro Ser Glu Thr Asp Leu Asn Asp Ile Pro Leu Gly Ser Gly Gln
        835                 840                 845

CCA GAC AAT GAC ACT GTT GTA ACC AAC GAT GAT AAA AGT GAC GAT GAT        2832
Pro Asp Asn Asp Thr Val Val Thr Asn Asp Asp Lys Ser Asp Asp Asp
850                 855                 860

GAT CAC ACA GTC GAC GAA ATT GAT CAT GTA GAA TAT TAC GTT ATG ATG        2880
Asp His Thr Val Asp Glu Ile Asp His Val Glu Tyr Tyr Val Met Met
865                 870                 875                 880

GAC TTT GCC AAT CTT TGG GTT TTC CAA GCG TTT ACC TGT TTC TGC ATC        2928
Asp Phe Ala Asn Leu Trp Val Phe Gln Ala Phe Thr Cys Phe Cys Ile
                885                 890                 895

AAA AAA ATC ATG GAG AAT AAT GAG CCA GCA ATG GCA ATG GAA GAC TTG        2976
Lys Lys Ile Met Glu Asn Asn Glu Pro Ala Met Ala Met Glu Asp Leu
            900                 905                 910

AAG AAC TTC ATA TTC CAA ATT ATC GAA ATA ACT AAT TCT AAT GAT TTA        3024
```

```
                    -continued

Lys Asn Phe Ile Phe Gln Ile Ile Glu Ile Thr Asn Ser Asn Asp Leu
            915                 920                 925

TGT TCA CAA ATA TTT GAC CAA CTG AAG GAT ATG CAG ACC ATT GAG ATG      3072
Cys Ser Gln Ile Phe Asp Gln Leu Lys Asp Met Gln Thr Ile Glu Met
        930                 935                 940

ATA ACC CAA ATA GTG GAG AAA GAT TTC TGC ACT TCT TGT TTG CAA AAC      3120
Ile Thr Gln Ile Val Glu Lys Asp Phe Cys Thr Ser Cys Leu Gln Asn
945                 950                 955                 960

AAC AAC CAA AAG ATA GAT GAT AAT TAC ATC GTT GTG GTG ATC GAG ATT      3168
Asn Asn Gln Lys Ile Asp Asp Asn Tyr Ile Val Val Val Ile Glu Ile
                965                 970                 975

ATA ACG TCA TTA TCG ATG AGG TTT CAA AGA GAA ACT TCT GGT ATG ATA      3216
Ile Thr Ser Leu Ser Met Arg Phe Gln Arg Glu Thr Ser Gly Met Ile
            980                 985                 990

GTT ATT TCC ATG GAG AAC TAT CAT TTA CTA ATA AAG ATC ATA AGA CAA      3264
Val Ile Ser Met Glu Asn Tyr His Leu Leu Ile Lys Ile Ile Arg Gln
        995                 1000                1005

TTA AGT GAA CTG AAC GAA GGA AAT TTA TCT AAG AGA GAA ATC CAA ATA      3312
Leu Ser Glu Leu Asn Glu Gly Asn Leu Ser Lys Arg Glu Ile Gln Ile
    1010                1015                1020

GAT GCC GTC TTG AAA ATT TTT AGC TTT CAT CAG GAT TCC ATT TTC CAA      3360
Asp Ala Val Leu Lys Ile Phe Ser Phe His Gln Asp Ser Ile Phe Gln
1025                1030                1035                1040

CGC ATC ATC GCT GAT TTA TCA GCT GAT AAA CCC ACA AGT CCA TTC ATT      3408
Arg Ile Ile Ala Asp Leu Ser Ala Asp Lys Pro Thr Ser Pro Phe Ile
                1045                1050                1055

GAT AGC ATA TGC AAG CTG TTT GAT AAA ATA TCA TTT AAT TTA AGA TTG      3456
Asp Ser Ile Cys Lys Leu Phe Asp Lys Ile Ser Phe Asn Leu Arg Leu
            1060                1065                1070

AAG CTG TTC TTG TAC GAA ATT TTG TCT TCA TTG AAA TCA TTC GCC ATC      3504
Lys Leu Phe Leu Tyr Glu Ile Leu Ser Ser Leu Lys Ser Phe Ala Ile
        1075                1080                1085

TAT TCA TCC ACA ATT GAT GCC CCA GCA TTC CAC ACA AGC GGT AAG GTC      3552
Tyr Ser Ser Thr Ile Asp Ala Pro Ala Phe His Thr Ser Gly Lys Val
    1090                1095                1100

GAA CTA CCG AAG AAA TTG CTG AAC TTA CCA CCA TTC CAA GTG TCC TCT      3600
Glu Leu Pro Lys Lys Leu Leu Asn Leu Pro Pro Phe Gln Val Ser Ser
1105                1110                1115                1120

TTC GTT AAG GAA ACA AAA CTT CAT AGT GGC GAC TAC GGG GAA GAA GAA      3648
Phe Val Lys Glu Thr Lys Leu His Ser Gly Asp Tyr Gly Glu Glu Glu
                1125                1130                1135

GAT GCA GAC CAA GAA GAA TCG TTT AGT TTA AAT TTA GGA ATC GGC ATA      3696
Asp Ala Asp Gln Glu Glu Ser Phe Ser Leu Asn Leu Gly Ile Gly Ile
            1140                1145                1150

GTT GAA ATA GCG CAC GAA AAC GAA CAG AAA TGG CTC ATT TAT GAC AAG      3744
Val Glu Ile Ala His Glu Asn Glu Gln Lys Trp Leu Ile Tyr Asp Lys
        1155                1160                1165

AAA GAT CAT AAA TAT GTC TGC ACA TTT TCC ATG GAG CCG TAC CAC TTC      3792
Lys Asp His Lys Tyr Val Cys Thr Phe Ser Met Glu Pro Tyr His Phe
    1170                1175                1180

ATC TCC AAC TAT AAT ACC AAG TAC ACA GAT GAC ATG GCT ACA GGC AGT      3840
Ile Ser Asn Tyr Asn Thr Lys Tyr Thr Asp Asp Met Ala Thr Gly Ser
1185                1190                1195                1200

AAT GAT ACG ACT GCG TTT AAC GAT TCC TGT GTA AAC CTG AGT CTT TTT      3888
Asn Asp Thr Thr Ala Phe Asn Asp Ser Cys Val Asn Leu Ser Leu Phe
                1205                1210                1215

GAT GCT CGG TTT GAG AGG AAA AAT CCA CAT TGATCTCAGA ATATATCCAA        3938
Asp Ala Arg Phe Glu Arg Lys Asn Pro His
            1220                1225

ATGGATAAAT TATAAATTTA CCAATAACAG TAATTATGTG TCAGTTTTAA TACCCAACCA    3998
```

```
                                               ATTG                                                          4002
```

(2) INFORMATION FOR SEQ ID NO:12:

(i) SEQUENCE CHARACTERISTICS:
        (A) LENGTH: 1226 amino acids
        (B) TYPE: amino acid
        (D) TOPOLOGY: linear (ii) MOLECULE TYPE: protein (xi) SEQUENCE DESCRIPTION: SEQ ID NO:12:

```
Met His Leu Leu Lys Asp Trp Thr Asp Thr Phe Val Tyr Ile Leu Glu
 1               5                  10                  15

Lys Leu Ile Phe Asp Met Thr Asn His Tyr Asn Asp Ser Gln Gln Leu
            20                  25                  30

Arg Thr Trp Lys Arg Gln Ile Ser Tyr Phe Leu Lys Leu Leu Gly Asn
        35                  40                  45

Cys Tyr Ser Leu Arg Leu Ile Asn Lys Glu Ile Phe His His Trp Leu
    50                  55                  60

Val Glu Phe Ile Asn Lys Met Glu Asn Phe Glu Leu Pro Leu Leu Ser
65                  70                  75                  80

Leu His Ile Leu Met Ile Phe Trp Asn Asp Ile Cys Gln Ile Asp Thr
                85                  90                  95

Asn Ala Pro Val Ala Ala Thr Ile Thr Ser Ser Gln Lys Glu Pro Phe
            100                 105                 110

Phe Leu Val Thr Lys Ile Thr Asp Met Leu Leu His Lys Tyr Tyr Ile
        115                 120                 125

Val Ser Ser Ser Lys Ser Met Ile Asn Asp Glu Asn Tyr Ile Ile Asn
    130                 135                 140

Asp Ile Lys Lys Asn Asn Lys Ile Lys Leu Asn Ile Leu Lys Ile Leu
145                 150                 155                 160

Ser Ser Leu Ile Leu Lys Ile Phe Gln Glu Gln Ser Leu Glu Val Phe
                165                 170                 175

Ile Phe Pro Thr Ser Asn Trp Glu Ile Tyr Lys Pro Leu Leu Phe Glu
            180                 185                 190

Ile Val Ser Asn Ala Asp Thr Asn Gln Asn Ser Asp Met Lys Lys Lys
        195                 200                 205

Leu Glu Leu Ile Ser Tyr Arg Asn Glu Ser Leu Lys Asn Asn Ser Ser
    210                 215                 220

Ile Arg Asn Val Ile Met Ser Ala Ser Asn Ala Asn Asp Phe Gln Leu
225                 230                 235                 240

Thr Ile Val Thr Cys Lys Gln Phe Pro Lys Leu Ser Cys Ile Gln Leu
                245                 250                 255

Asn Cys Ile Asp Thr Gln Phe Thr Lys Leu Leu Asp Asp Asn Pro Thr
            260                 265                 270

Glu Phe Asp Trp Pro Thr Tyr Val Asp Gln Asn Pro Leu Thr Met His
        275                 280                 285

Lys Ile Ile Gln Leu Ile Leu Trp Ser Ile His Pro Ser Arg Gln Phe
    290                 295                 300

Asp His Tyr Glu Ser Asn Gln Leu Val Ala Lys Leu Leu Leu Leu Arg
305                 310                 315                 320

Ile Asn Ser Thr Asp Glu Asp Leu His Glu Phe Gln Ile Glu Asp Ala
                325                 330                 335

Ile Trp Ser Leu Val Phe Gln Leu Ala Lys Asn Phe Ser Ala Gln Lys
            340                 345                 350
```

-continued

```
Arg Val Val Ser Tyr Met Met Pro Ser Leu Tyr Arg Leu Leu Asn Ile
        355                 360                 365
Leu Ile Thr Tyr Gly Ile Ile Lys Val Pro Thr Tyr Ile Arg Lys Leu
    370                 375                 380
Ile Ser Ser Gly Leu Leu Tyr Leu Gln Asp Ser Asn Asp Lys Phe Val
385                 390                 395                 400
His Val Gln Leu Leu Ile Asn Leu Lys Ile Ser Pro Leu Met Lys Ser
                405                 410                 415
Gln Tyr Asn Met Val Leu Arg Asn Val Met Glu Tyr Asp Val Lys Phe
            420                 425                 430
Tyr Glu Ile Phe Asn Phe Asp Gln Leu Val Glu Ile Thr Glu Gln Ile
        435                 440                 445
Lys Met Arg Ile Leu Ser Asn Asp Ile Thr Asn Leu Gln Leu Ser Lys
    450                 455                 460
Thr Pro Leu Ser Ile Lys Ile Met Val Ala Glu Trp Tyr Leu Ser His
465                 470                 475                 480
Leu Cys Ser Gly Ile Leu Ser Ser Val Asn Arg Thr Val Leu Leu Lys
                485                 490                 495
Ile Phe Lys Ile Phe Cys Ile Asp Leu Glu Val Phe His His Phe Phe
            500                 505                 510
Lys Trp Ile Glu Phe Ile Val Tyr His Gln Leu Leu Ser Asp Ile Glu
        515                 520                 525
Ser Leu Glu Ala Leu Met Asp Ile Leu Leu Cys Tyr Gln Lys Leu Phe
    530                 535                 540
Ser Gln Phe Ile Asn Asp His Ile Leu Phe Thr Lys Thr Phe Ile Phe
545                 550                 555                 560
Ile Tyr Lys Lys Val Leu Lys Glu Lys Asp Val Pro Ala Tyr Asn Val
                565                 570                 575
Thr Ser Phe Met Pro Phe Trp Lys Phe Phe Met Lys Asn Phe Pro Phe
            580                 585                 590
Val Leu Lys Val Asp Asn Asp Leu Arg Ile Glu Leu Gln Ser Val Tyr
        595                 600                 605
Asn Asp Glu Lys Leu Lys Thr Glu Lys Leu Lys Asn Asp Lys Ser Glu
    610                 615                 620
Val Leu Lys Val Tyr Ser Met Ile Asn Asn Ser Asn Gln Ala Val Gly
625                 630                 635                 640
Gln Thr Trp Asn Phe Pro Glu Val Phe Gln Val Asn Ile Arg Phe Leu
                645                 650                 655
Leu His Asn Ser Glu Ile Ile Asp Thr Asn Thr Ser Lys Gln Phe Gln
            660                 665                 670
Lys Ala Arg Asn Asn Val Met Leu Leu Ile Ala Thr Asn Leu Lys Glu
        675                 680                 685
Tyr Ile Lys Phe Met Ser Ile Phe Leu Lys Arg Lys Asp Phe Thr Asn
    690                 695                 700
Lys Asn Leu Ile Gln Leu Ile Ser Leu Lys Leu Leu Thr Phe Glu Val
705                 710                 715                 720
Thr Gln Asn Val Leu Gly Leu Glu Tyr Ile Ile Arg Leu Leu Pro Ile
                725                 730                 735
Asn Leu Glu Asn Asn Asp Gly Ser Tyr Gly Leu Phe Leu Lys Tyr His
            740                 745                 750
Lys Glu Gln Phe Ile Lys Ser Asn Phe Glu Lys Ile Leu Leu Thr Cys
        755                 760                 765
Tyr Glu Leu Glu Lys Lys Tyr His Gly Asn Glu Cys Glu Ile Asn Tyr
```

-continued

```
            770                 775                 780
Tyr Glu Ile Leu Leu Lys Ile Leu Ile Thr Tyr Gly Ser Ser Pro Lys
785                 790                 795                 800

Leu Leu Ala Thr Ser Thr Lys Ile Ile Met Leu Leu Leu Asn Asp Ser
                805                 810                 815

Val Glu Asn Ser Ser Asn Ile Leu Glu Asp Ile Leu Tyr Tyr Ser Thr
            820                 825                 830

Cys Pro Ser Glu Thr Asp Leu Asn Asp Ile Pro Leu Gly Ser Gly Gln
            835                 840                 845

Pro Asp Asn Asp Thr Val Val Thr Asn Asp Asp Lys Ser Asp Asp Asp
        850                 855                 860

Asp His Thr Val Asp Glu Ile Asp His Val Glu Tyr Tyr Val Met Met
865                 870                 875                 880

Asp Phe Ala Asn Leu Trp Val Phe Gln Ala Phe Thr Cys Phe Cys Ile
                885                 890                 895

Lys Lys Ile Met Glu Asn Asn Glu Pro Ala Met Ala Met Glu Asp Leu
                900                 905                 910

Lys Asn Phe Ile Phe Gln Ile Ile Glu Ile Thr Asn Ser Asn Asp Leu
            915                 920                 925

Cys Ser Gln Ile Phe Asp Gln Leu Lys Asp Met Gln Thr Ile Glu Met
        930                 935                 940

Ile Thr Gln Ile Val Glu Lys Asp Phe Cys Thr Ser Cys Leu Gln Asn
945                 950                 955                 960

Asn Asn Gln Lys Ile Asp Asp Asn Tyr Ile Val Val Ile Glu Ile
                965                 970                 975

Ile Thr Ser Leu Ser Met Arg Phe Gln Arg Glu Thr Ser Gly Met Ile
            980                 985                 990

Val Ile Ser Met Glu Asn Tyr His Leu Leu Ile Lys Ile Ile Arg Gln
        995                 1000                1005

Leu Ser Glu Leu Asn Glu Gly Asn Leu Ser Lys Arg Glu Ile Gln Ile
        1010                1015                1020

Asp Ala Val Leu Lys Ile Phe Ser Phe His Gln Asp Ser Ile Phe Gln
1025                1030                1035                1040

Arg Ile Ile Ala Asp Leu Ser Ala Asp Lys Pro Thr Ser Pro Phe Ile
                1045                1050                1055

Asp Ser Ile Cys Lys Leu Phe Asp Lys Ile Ser Phe Asn Leu Arg Leu
            1060                1065                1070

Lys Leu Phe Leu Tyr Glu Ile Leu Ser Ser Leu Lys Ser Phe Ala Ile
        1075                1080                1085

Tyr Ser Ser Thr Ile Asp Ala Pro Ala Phe His Thr Ser Gly Lys Val
        1090                1095                1100

Glu Leu Pro Lys Lys Leu Leu Asn Leu Pro Pro Phe Gln Val Ser Ser
1105                1110                1115                1120

Phe Val Lys Glu Thr Lys Leu His Ser Gly Asp Tyr Gly Glu Glu Glu
                1125                1130                1135

Asp Ala Asp Gln Glu Glu Ser Phe Ser Leu Asn Leu Gly Ile Gly Ile
            1140                1145                1150

Val Glu Ile Ala His Glu Asn Glu Gln Lys Trp Leu Ile Tyr Asp Lys
        1155                1160                1165

Lys Asp His Lys Tyr Val Cys Thr Phe Ser Met Glu Pro Tyr His Phe
        1170                1175                1180

Ile Ser Asn Tyr Asn Thr Lys Tyr Thr Asp Met Ala Thr Gly Ser
1185                1190                1195                1200
```

```
Asn Asp Thr Thr Ala Phe Asn Asp Ser Cys Val Asn Leu Ser Leu Phe
            1205                1210                1215

Asp Ala Arg Phe Glu Arg Lys Asn Pro His
            1220            1225
```

(2) INFORMATION FOR SEQ ID NO:13:

(i) SEQUENCE CHARACTERISTICS:
        (A) LENGTH: 4849 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 148..4407

(xi) SEQUENCE DESCRIPTION: SEQ ID NO:13:

```
GATCAAGTAG TGTAGTATTT ATTGTAGTAC ACTCTTACAA CAACCCTTTA AGACGAATGG      60

TGTGAAATCG GAAATTACTT TGTTGAAGTA AGGTGTAACT ATATTTTAAG AACGTTTAAG     120

CTGGATATCA AGATCTGAGG AGGTAGT ATG AGT TCT GAC GCT TCC ACG TAC         171
                              Met Ser Ser Asp Ala Ser Thr Tyr
                                1               5

AGA CTT GAG GAT GTT TTA TCC AGC TTC TAT AGA GTG GAG AAA ATC AAA       219
Arg Leu Glu Asp Val Leu Ser Ser Phe Tyr Arg Val Glu Lys Ile Lys
        10                  15                  20

AAG ATC AAC TAT CAT CAG TAC ATT TCT AAA GCC CAA AAC GAT CAA TGG       267
Lys Ile Asn Tyr His Gln Tyr Ile Ser Lys Ala Gln Asn Asp Gln Trp
 25              30                  35                  40

TCT ATC CAA ATG GAA TTC ATG CTA CGG AAG CAG GAT CCA AAG ACT CTA       315
Ser Ile Gln Met Glu Phe Met Leu Arg Lys Gln Asp Pro Lys Thr Leu
                45                  50                  55

GTT GCG CTG CTT TCA AGG GAT TTA TGG TGT TTC AGT ATA AAT GAT GAT       363
Val Ala Leu Leu Ser Arg Asp Leu Trp Cys Phe Ser Ile Asn Asp Asp
            60                  65                  70

CCG GTA CCG ACA CCT CCT GCG ATA GAA CAT AAA CCA GTG AGC CCA GAT       411
Pro Val Pro Thr Pro Pro Ala Ile Glu His Lys Pro Val Ser Pro Asp
        75                  80                  85

AAA ATC GGA ACT TTC ACT GCC GAT TAT TCA AAG CCA AAC TTA CCG CCA       459
Lys Ile Gly Thr Phe Thr Ala Asp Tyr Ser Lys Pro Asn Leu Pro Pro
 90                  95                 100

CAC TAT GCT CTT TTT TTA AAA GCT TTA AGA AGG AAA ATT TAC ATT AAT       507
His Tyr Ala Leu Phe Leu Lys Ala Leu Arg Arg Lys Ile Tyr Ile Asn
105                 110                 115                 120

TTG GCA TTA GGT TCA CAC AAT AAG CTA ATA CAA TTT GGG AAT GCC TGC       555
Leu Ala Leu Gly Ser His Asn Lys Leu Ile Gln Phe Gly Asn Ala Cys
                125                 130                 135

ATA TCA TTA AGC GGA GTG CCA AAT TAT CTC GTA CAG CTA GAA CCA CAC       603
Ile Ser Leu Ser Gly Val Pro Asn Tyr Leu Val Gln Leu Glu Pro His
            140                 145                 150

CTT TTT GTA AAC GGA GAT CTC ACA GTG TCG TTA TGT GCC AAG AAC ATG       651
Leu Phe Val Asn Gly Asp Leu Thr Val Ser Leu Cys Ala Lys Asn Met
        155                 160                 165

GGA TTA GTA CCA ATG AAG GAG GAA AAT TTG GAA GAA TCT TTC CTT TCA       699
Gly Leu Val Pro Met Lys Glu Glu Asn Leu Glu Glu Ser Phe Leu Ser
170                 175                 180

AAG CAT GCG CTT TAT TTA GCA CCA TCT GGA ATA AGG ATG CAT TTG GCC       747
Lys His Ala Leu Tyr Leu Ala Pro Ser Gly Ile Arg Met His Leu Ala
185                 190                 195                 200

CCT GCT TCC AAG CAA GGA TAC TTG ATA ACG CCA CCA AAA CAT ACA GAA       795
```

|     |     |     |     |     |     |     |     |     |     |     |     |     |
| --- | --- | --- | --- | --- | --- | --- | --- | --- | --- | --- | --- | --- |
| Pro | Ala | Ser | Lys | Gln | Gly | Tyr | Leu | Ile | Thr | Pro | Pro | Lys | His | Thr | Glu |
|     |     |     |     | 205 |     |     |     |     | 210 |     |     |     | 215 |

```
CTT CTC TTG ACG ACG TTA AGT GTA TCT CAT GGT ATA AAC TTA CAA AAT          843
Leu Leu Leu Thr Thr Leu Ser Val Ser His Gly Ile Asn Leu Gln Asn
            220                 225                 230

AAA AAA AAT TTG AAA TGG GTT GCT GTT GTT CCT GAC TTA GGA CAT CTC          891
Lys Lys Asn Leu Lys Trp Val Ala Val Val Pro Asp Leu Gly His Leu
            235                 240                 245

AAC GGC CAC ACA CCT ACT ATA GCT TCG TAT TTA ACT CCC TTA CTT GAA          939
Asn Gly His Thr Pro Thr Ile Ala Ser Tyr Leu Thr Pro Leu Leu Glu
250                 255                 260

GCA AAG AAG CTA GTA TGG CCG CTG CAT TTA ATC TTC GCC CAA CCA GTA          987
Ala Lys Lys Leu Val Trp Pro Leu His Leu Ile Phe Ala Gln Pro Val
265                 270                 275                 280

GCT GAT ATA GAA AAT TCT ACT TCC GGA GAT CCA TCA GAA TTT CAC TGT         1035
Ala Asp Ile Glu Asn Ser Thr Ser Gly Asp Pro Ser Glu Phe His Cys
            285                 290                 295

TTG CAA GAT GCT CTG GAT GCC ATT GAT GAT TTC ATA CAA TTA AAG CAA         1083
Leu Gln Asp Ala Leu Asp Ala Ile Asp Asp Phe Ile Gln Leu Lys Gln
            300                 305                 310

ACA GCT GCC TAT AGG ACT CCA GGA AGT TCC GGC GTA TTG AGC AGT AAT         1131
Thr Ala Ala Tyr Arg Thr Pro Gly Ser Ser Gly Val Leu Ser Ser Asn
            315                 320                 325

ATT GCT GGT ACA AAT CCC TTA AGC TCA GAT GGA GCA TAT ACA GAA CAG         1179
Ile Ala Gly Thr Asn Pro Leu Ser Ser Asp Gly Ala Tyr Thr Glu Gln
330                 335                 340

TTT CAA CAT TAT AAG AAC AAC TCA ATT AGT TCT CAA CCC GCT TCT TAT         1227
Phe Gln His Tyr Lys Asn Asn Ser Ile Ser Ser Gln Pro Ala Ser Tyr
345                 350                 355                 360

CAT TCT GTC CAA GAA ACT AAT AAG ATA TCT CCG AAA GAT TTC TCC CCT         1275
His Ser Val Gln Glu Thr Asn Lys Ile Ser Pro Lys Asp Phe Ser Pro
            365                 370                 375

AAT TTC ACA GGC ATT GAT AAA TTA ATG CTG TCG CCC AGC GAT CAA TTT         1323
Asn Phe Thr Gly Ile Asp Lys Leu Met Leu Ser Pro Ser Asp Gln Phe
            380                 385                 390

GCT CCA GCT TTC TTA AAT ACC CCT AAT AAT AAC ATC AAT GAG AAT GAA         1371
Ala Pro Ala Phe Leu Asn Thr Pro Asn Asn Asn Ile Asn Glu Asn Glu
            395                 400                 405

TTA TTT AAT GAT AGG AAA CAA ACT ACA GTA TCA AAT GAC TTA GAG AAC         1419
Leu Phe Asn Asp Arg Lys Gln Thr Thr Val Ser Asn Asp Leu Glu Asn
410                 415                 420

AGC CCA CTG AAA ACG GAA CTG GAG GCA AAT GGT AGA TCA CTC GAA AAG         1467
Ser Pro Leu Lys Thr Glu Leu Glu Ala Asn Gly Arg Ser Leu Glu Lys
425                 430                 435                 440

GTA AAT AAT TCC GTG AGC AAG ACA GGA AGC GTA GAC ACA CTT CAT AAT         1515
Val Asn Asn Ser Val Ser Lys Thr Gly Ser Val Asp Thr Leu His Asn
            445                 450                 455

AAA GAG GGA ACA CTG GAA CAA CGA GAA CAG AAC GAA AAT CTG CCA AGT         1563
Lys Glu Gly Thr Leu Glu Gln Arg Glu Gln Asn Glu Asn Leu Pro Ser
            460                 465                 470

GAT AAA AGT GAC TCT ATG GTA GAC AAG GAA TTG TTT GGT GAG GAT GAG         1611
Asp Lys Ser Asp Ser Met Val Asp Lys Glu Leu Phe Gly Glu Asp Glu
            475                 480                 485

GAT GAG GAT TTA TTT GGC GAT AGC AAT AAA TCG AAT TCT ACA AAC GAA         1659
Asp Glu Asp Leu Phe Gly Asp Ser Asn Lys Ser Asn Ser Thr Asn Glu
            490                 495                 500

TCG AAC AAA AGT ATA TCG GAC GAA ATT ACC GAG GAT ATG TTC GAA ATG         1707
Ser Asn Lys Ser Ile Ser Asp Glu Ile Thr Glu Asp Met Phe Glu Met
505                 510                 515                 520

TCT GAT GAA GAA GAA AAT AAT AAC AAT AAA AGC ATT AAT AAA AAT AAC         1755
```

-continued

```
Ser Asp Glu Glu Glu Asn Asn Asn Asn Lys Ser Ile Asn Lys Asn Asn
            525                 530                 535

AAG GAA ATG CAT ACT GAT CTT GGT AAA GAT ATT CCA TTT TTT CCC TCA      1803
Lys Glu Met His Thr Asp Leu Gly Lys Asp Ile Pro Phe Phe Pro Ser
            540                 545                 550

TCT GAA AAA CCG AAT ATC CGT ACG ATG AGC GGA ACT ACA AAA AGA TTA      1851
Ser Glu Lys Pro Asn Ile Arg Thr Met Ser Gly Thr Thr Lys Arg Leu
            555                 560                 565

AAT GGA AAG AGG AAA TAT TTG GAT ATT CCG ATA GAT GAA ATG ACC TTG      1899
Asn Gly Lys Arg Lys Tyr Leu Asp Ile Pro Ile Asp Glu Met Thr Leu
            570                 575                 580

CCA ACG AGT CCA TTA TAT ATG GAC CCA GGT GCG CCA CTC CCT GTG GAA      1947
Pro Thr Ser Pro Leu Tyr Met Asp Pro Gly Ala Pro Leu Pro Val Glu
585                 590                 595                 600

ACA CCC CGC GAT AGA CGC AAA AGT GTG TTC GCT CCA CTG AAT TTT AAC      1995
Thr Pro Arg Asp Arg Arg Lys Ser Val Phe Ala Pro Leu Asn Phe Asn
                605                 610                 615

CCC ATA ATA GAA AAC AAT GTT GAT AAC AAA TAC AAA TCT GGA GGG AAA      2043
Pro Ile Ile Glu Asn Asn Val Asp Asn Lys Tyr Lys Ser Gly Gly Lys
            620                 625                 630

TTT TCC TTC AGT CCG TTG CAA AAG GAG GAA GCA TTA AAC TTT GAT ATT      2091
Phe Ser Phe Ser Pro Leu Gln Lys Glu Glu Ala Leu Asn Phe Asp Ile
            635                 640                 645

TCT ATG GCG GAT CTT TCT AGC TCT GAA GAG GAA GAG GAT GAA GAA GAG      2139
Ser Met Ala Asp Leu Ser Ser Ser Glu Glu Glu Glu Asp Glu Glu Glu
            650                 655                 660

AAC GGT AGC AGC GAT GAG GAT CTA AAG TCA TTG AAC GTA CGC GAC GAC      2187
Asn Gly Ser Ser Asp Glu Asp Leu Lys Ser Leu Asn Val Arg Asp Asp
665                 670                 675                 680

ATG AAA CCT TCT GAT AAC ATC AGT ACT AAT ACT AAT ATT CAT GAG CCT      2235
Met Lys Pro Ser Asp Asn Ile Ser Thr Asn Thr Asn Ile His Glu Pro
                685                 690                 695

CAA TAC ATA AAT TAC TCT TCG ATC CCA AGT CTA CAA GAC TCT ATT ATA      2283
Gln Tyr Ile Asn Tyr Ser Ser Ile Pro Ser Leu Gln Asp Ser Ile Ile
            700                 705                 710

AAG CAA GAA AAT TTC AAT TCA GTA AAC GAT GCT AAT ATC ACT AGC AAT      2331
Lys Gln Glu Asn Phe Asn Ser Val Asn Asp Ala Asn Ile Thr Ser Asn
            715                 720                 725

AAG GAA GGC TTC AAC TCT ATT TGG AAA ATT CCT CAA AAT GAT ATA CCA      2379
Lys Glu Gly Phe Asn Ser Ile Trp Lys Ile Pro Gln Asn Asp Ile Pro
            730                 735                 740

CAG ACC GAG TCA CCA CTG AAG ACC GTT GAT TCA TCT ATT CAA CCC ATA      2427
Gln Thr Glu Ser Pro Leu Lys Thr Val Asp Ser Ser Ile Gln Pro Ile
745                 750                 755                 760

GAA TCC AAT ATA AAG ATG ACC TTG GAA GAT AAT AAT GTT ACC AGT AAT      2475
Glu Ser Asn Ile Lys Met Thr Leu Glu Asp Asn Asn Val Thr Ser Asn
                765                 770                 775

CCG TCC GAA TTT ACG CCG AAT ATG GTA AAT TCT CAA ATT TCT AAC CTA      2523
Pro Ser Glu Phe Thr Pro Asn Met Val Asn Ser Gln Ile Ser Asn Leu
            780                 785                 790

CCA AAG GAC AAG AGT GGT ATC CCC GAA TTC ACA CCG GCG GAC CCC AAT      2571
Pro Lys Asp Lys Ser Gly Ile Pro Glu Phe Thr Pro Ala Asp Pro Asn
            795                 800                 805

TTA TCT TTT GAA TCA TCA AGT AGT CTA CCG TTT CTA TTG AGA CAC ATG      2619
Leu Ser Phe Glu Ser Ser Ser Ser Leu Pro Phe Leu Leu Arg His Met
            810                 815                 820

CCG CTA GCA TCT ATA CCG GAC ATT TTC ATC ACG CCT ACT CCC GTT GTT      2667
Pro Leu Ala Ser Ile Pro Asp Ile Phe Ile Thr Pro Thr Pro Val Val
825                 830                 835                 840

ACA ATT TCA GAA AAA GAA CAA GAC ATC TTA GAT TTA ATT GCA GAA CAA      2715
```

```
                                                    -continued

Thr Ile Ser Glu Lys Glu Gln Asp Ile Leu Asp Leu Ile Ala Glu Gln
            845                 850                 855
GTC GTC ACT GAT TAT AAT ATC TTA GGA AAC CTC GGT ATT CCA AAG ATC      2763
Val Val Thr Asp Tyr Asn Ile Leu Gly Asn Leu Gly Ile Pro Lys Ile
            860                 865                 870
GCC TAT AGG GGA GTT AAA GAT TGC CAA GAA GGT TTA ATA ACA ACC ACA      2811
Ala Tyr Arg Gly Val Lys Asp Cys Gln Glu Gly Leu Ile Thr Thr Thr
            875                 880                 885
ATG TTA CAG TTA TTT TCC ACT TCG GAT AGA TTA AAT GGC AAT GAT ACG      2859
Met Leu Gln Leu Phe Ser Thr Ser Asp Arg Leu Asn Gly Asn Asp Thr
            890                 895                 900
ATC TCC AAA TTC TAT AAC ATG AAG CAG CCG TAC GTT TTT GTA AAG AAA      2907
Ile Ser Lys Phe Tyr Asn Met Lys Gln Pro Tyr Val Phe Val Lys Lys
905                 910                 915                 920
CAT CAC GAA CTA ATC AAA GTC AAA CAC GAC TCT CAG CCA TTT ATT AAG      2955
His His Glu Leu Ile Lys Val Lys His Asp Ser Gln Pro Phe Ile Lys
            925                 930                 935
TTC CTC AAT TTT CGC CCT CCA AAT GGA ATA AAA AAC TTC AAA TCC TTA      3003
Phe Leu Asn Phe Arg Pro Pro Asn Gly Ile Lys Asn Phe Lys Ser Leu
            940                 945                 950
TTA TTA AGT TCA TCT TTC AAA GAA GAT TGT CTG TCA TTT GCG CCA ACT      3051
Leu Leu Ser Ser Ser Phe Lys Glu Asp Cys Leu Ser Phe Ala Pro Thr
            955                 960                 965
CTA TCT CAA ACA TAT ATT AAT CAA GAG TTA GGG TTT TGT GAG TTG CTT      3099
Leu Ser Gln Thr Tyr Ile Asn Gln Glu Leu Gly Phe Cys Glu Leu Leu
            970                 975                 980
AAA CTA ACT AAT GAA GAC CCG CCC GGA CTG ATG TAC TTG AAG GCA TTT      3147
Lys Leu Thr Asn Glu Asp Pro Pro Gly Leu Met Tyr Leu Lys Ala Phe
985                 990                 995                 1000
GAT AAA AAC AAG TTA CTG TTG TTA GCT GCG CAG ATT GTT TCA TAC TGT      3195
Asp Lys Asn Lys Leu Leu Leu Ala Ala Gln Ile Val Ser Tyr Cys
            1005                1010                1015
TCT AAT AAT AAG AAC TCC ATC AAA AAC GTG CCA CCA ATA TTA ATA ATT      3243
Ser Asn Asn Lys Asn Ser Ile Lys Asn Val Pro Pro Ile Leu Ile Ile
            1020                1025                1030
TTA CCC TTG GAT AAT GCA ACT CTG ACT GAA TTA GTA GAC AAG GCG AAT      3291
Leu Pro Leu Asp Asn Ala Thr Leu Thr Glu Leu Val Asp Lys Ala Asn
            1035                1040                1045
ATT TTT CAG GTG ATC AAG AAC GAA GTT TGT GCC AAG ATG CCT AAC ATT      3339
Ile Phe Gln Val Ile Lys Asn Glu Val Cys Ala Lys Met Pro Asn Ile
            1050                1055                1060
GAA CTA TAT TTG AAA GTT ATT CCT ATG GAT TTC ATT AGA AAC GTA CTG      3387
Glu Leu Tyr Leu Lys Val Ile Pro Met Asp Phe Ile Arg Asn Val Leu
1065                1070                1075                1080
GTG ACA GTG GAT CAG TAC GTC AAC GTA GCA ATT TCT ATA TAT AAC ATG      3435
Val Thr Val Asp Gln Tyr Val Asn Val Ala Ile Ser Ile Tyr Asn Met
            1085                1090                1095
CTG CCG CCA AAA TCT GTA AAG TTC ACC CAC ATT GCG CAT ACG CTG CCG      3483
Leu Pro Pro Lys Ser Val Lys Phe Thr His Ile Ala His Thr Leu Pro
            1100                1105                1110
GAG AAA GTG AAT TTC AGA ACC ATG CAG CAA CAG CAA ATG CAA CAG CAA      3531
Glu Lys Val Asn Phe Arg Thr Met Gln Gln Gln Gln Met Gln Gln Gln
            1115                1120                1125
CAG CAA CAG CAA CAG CAG CAG CAG AAT AAC AGT ACA GGA TCA TCT TCT      3579
Gln Gln Gln Gln Gln Gln Gln Gln Asn Asn Ser Thr Gly Ser Ser Ser
            1130                1135                1140
ATA ATA TAT TAT GAC TCG TAC ATC CAC CTG GCA TAC TCG CGT AGT GTA      3627
Ile Ile Tyr Tyr Asp Ser Tyr Ile His Leu Ala Tyr Ser Arg Ser Val
1145                1150                1155                1160
GAT AAA GAG TGG GTT TTT GCA GCT CTT TCA GAT AGC TAT GGA CAA GGC      3675
```

```
Asp Lys Glu Trp Val Phe Ala Ala Leu Ser Asp Ser Tyr Gly Gln Gly
            1165                1170                1175

AGC ATG ACG AAA ACG TGG TAC GTC GGG AAT TCC AGA GGA AAA TTT GAC      3723
Ser Met Thr Lys Thr Trp Tyr Val Gly Asn Ser Arg Gly Lys Phe Asp
            1180                1185                1190

GAC GCA TGT AAT CAA ATA TGG AAT ATC GCC CTA AAT TTA GCG TCT AAA      3771
Asp Ala Cys Asn Gln Ile Trp Asn Ile Ala Leu Asn Leu Ala Ser Lys
            1195                1200                1205

AAA TTC GGA AAA ATA TGT CTA ATT TTA ACT AGA TTG AAT GGC ATA CTG      3819
Lys Phe Gly Lys Ile Cys Leu Ile Leu Thr Arg Leu Asn Gly Ile Leu
            1210                1215                1220

CCG GAT GAT GAA TTG ATG AAT TGG AGG AGA CTT TCT GGT AGG AAT ATA      3867
Pro Asp Asp Glu Leu Met Asn Trp Arg Arg Leu Ser Gly Arg Asn Ile
1225                1230                1235                1240

CAT CTT GCT GTG GTG TGT GTG GAT GAC AAC TCT AAA ATC TCC TTC ATA      3915
His Leu Ala Val Val Cys Val Asp Asp Asn Ser Lys Ile Ser Phe Ile
                1245                1250                1255

GAT GAG GAC AAA TTG TAC CCT AGT TTC AAG CCG ATC TAC AAA GAC ACT      3963
Asp Glu Asp Lys Leu Tyr Pro Ser Phe Lys Pro Ile Tyr Lys Asp Thr
            1260                1265                1270

AGG TTT GGA GGA CGC ATG GAT ATG ACC AGA TTA TAC GAC TAT GAA ATA      4011
Arg Phe Gly Gly Arg Met Asp Met Thr Arg Leu Tyr Asp Tyr Glu Ile
            1275                1280                1285

AGG GAT ATA GAC CAG GAC ATC CAT GGA ATA GTA TTT CAG CAC CCG TTC      4059
Arg Asp Ile Asp Gln Asp Ile His Gly Ile Val Phe Gln His Pro Phe
            1290                1295                1300

CCA CTG GCA CAC TCA CAG CAT CGC TGT GCT ATT AGG AGT GGT GCT TTG      4107
Pro Leu Ala His Ser Gln His Arg Cys Ala Ile Arg Ser Gly Ala Leu
1305                1310                1315                1320

ATC AAA TTC AAA AAA TGC GAC GGT GAT ACG GTT TGG GAC AAA TTC GCA      4155
Ile Lys Phe Lys Lys Cys Asp Gly Asp Thr Val Trp Asp Lys Phe Ala
            1325                1330                1335

GTC AAC CTT TTA AAC TGT CCA CAT TCT GAT AGT ACA CAA TTG CTG GAA      4203
Val Asn Leu Leu Asn Cys Pro His Ser Asp Ser Thr Gln Leu Leu Glu
            1340                1345                1350

ACC ATC TTA GAA GAG TTT CGC AAC CTG GCT GCT CTA AAC GTG TGG TAC      4251
Thr Ile Leu Glu Glu Phe Arg Asn Leu Ala Ala Leu Asn Val Trp Tyr
            1355                1360                1365

GGT CTC TCT GAT GGC GAA GAT GGC CAT ATT CCA TGG CAT ATC CTA GCC      4299
Gly Leu Ser Asp Gly Glu Asp Gly His Ile Pro Trp His Ile Leu Ala
            1370                1375                1380

GTG AAA AAA ATG ATG AAC ACT CTT GTG CAC ACC AGA GTA AAA ATT GCT      4347
Val Lys Lys Met Met Asn Thr Leu Val His Thr Arg Val Lys Ile Ala
1385                1390                1395                1400

AAT ACT TCC GCC GCT ACT GTG CAT ACC GCT ACT TCT TCA TCA ATT ATT      4395
Asn Thr Ser Ala Ala Thr Val His Thr Ala Thr Ser Ser Ser Ile Ile
            1405                1410                1415

CTC TCG GAT AAA TAAACTTTTT CCGGCAACGT TTTCCTGCTC ATCTGTAGCC          4447
Leu Ser Asp Lys
            1420

CTATTTACCA GTTTTGGTTT TAGTATTATT CCGGGGTGTA AACCCAGAAG TCTATTTCTC    4507

CAGTCGGATT TATAAAAACA AAACCGGAAG CGGGGCGGTA CGGCATTTTC ACTGGTGATG    4567

CACGCCCAGC GTGTAGTCCG AGACAATTTC CACAGAACGC GAATGAGATT GCGTTTAAGG    4627

CTGTATTTTC AAGGCACACG AAGCGGCCAC GTGGGTCTGC GATGGTGTGT TGATGATGTC    4687

AAGAATGGTA TCATACTCCG TATAAGGTTA TGTAATCGGA AGTCGCGATT CTTTTTCAAT    4747

TTTTTCTTTT TATTTTTTTC CAGTTTTTTC GTCTCTGCGA TGGAAAATTG TTGAAGTTCT    4807

CTTGATTAGC AAGTAGTTCT TACATCGCAG GAATCTTATG TT                      4849
```

(2) INFORMATION FOR SEQ ID NO:14:

(i) SEQUENCE CHARACTERISTICS:
        (A) LENGTH: 1420 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Ser Asp Ala Ser Thr Tyr Arg Leu Glu Asp Val Leu Ser Ser
 1               5                  10                  15

Phe Tyr Arg Val Glu Lys Ile Lys Lys Ile Asn Tyr His Gln Tyr Ile
                20                  25                  30

Ser Lys Ala Gln Asn Asp Gln Trp Ser Ile Gln Met Glu Phe Met Leu
            35                  40                  45

Arg Lys Gln Asp Pro Lys Thr Leu Val Ala Leu Leu Ser Arg Asp Leu
        50                  55                  60

Trp Cys Phe Ser Ile Asn Asp Asp Pro Val Pro Thr Pro Pro Ala Ile
 65                 70                  75                  80

Glu His Lys Pro Val Ser Pro Asp Lys Ile Gly Thr Phe Thr Ala Asp
                85                  90                  95

Tyr Ser Lys Pro Asn Leu Pro Pro His Tyr Ala Leu Phe Leu Lys Ala
               100                 105                 110

Leu Arg Arg Lys Ile Tyr Ile Asn Leu Ala Leu Gly Ser His Asn Lys
           115                 120                 125

Leu Ile Gln Phe Gly Asn Ala Cys Ile Ser Leu Ser Gly Val Pro Asn
       130                 135                 140

Tyr Leu Val Gln Leu Glu Pro His Leu Phe Val Asn Gly Asp Leu Thr
145                 150                 155                 160

Val Ser Leu Cys Ala Lys Asn Met Gly Leu Val Pro Met Lys Glu Glu
               165                 170                 175

Asn Leu Glu Glu Ser Phe Leu Ser Lys His Ala Leu Tyr Leu Ala Pro
           180                 185                 190

Ser Gly Ile Arg Met His Leu Ala Pro Ala Ser Lys Gln Gly Tyr Leu
       195                 200                 205

Ile Thr Pro Pro Lys His Thr Glu Leu Leu Leu Thr Thr Leu Ser Val
210                 215                 220

Ser His Gly Ile Asn Leu Gln Asn Lys Lys Asn Leu Lys Trp Val Ala
225                 230                 235                 240

Val Val Pro Asp Leu Gly His Leu Asn Gly His Thr Pro Thr Ile Ala
               245                 250                 255

Ser Tyr Leu Thr Pro Leu Leu Glu Ala Lys Lys Leu Val Trp Pro Leu
           260                 265                 270

His Leu Ile Phe Ala Gln Pro Val Ala Asp Ile Glu Asn Ser Thr Ser
       275                 280                 285

Gly Asp Pro Ser Glu Phe His Cys Leu Gln Asp Ala Leu Asp Ala Ile
       290                 295                 300

Asp Asp Phe Ile Gln Leu Lys Gln Thr Ala Ala Tyr Arg Thr Pro Gly
305                 310                 315                 320

Ser Ser Gly Val Leu Ser Ser Asn Ile Ala Gly Thr Asn Pro Leu Ser
               325                 330                 335

Ser Asp Gly Ala Tyr Thr Glu Gly Phe Gln His Tyr Lys Asn Asn Ser
           340                 345                 350

Ile Ser Ser Gln Pro Ala Ser Tyr His Ser Val Gln Glu Thr Asn Lys
```

```
              355                 360                 365
Ile Ser Pro Lys Asp Phe Ser Pro Asn Phe Thr Gly Ile Asp Lys Leu
        370                 375                 380
Met Leu Ser Pro Ser Asp Gln Phe Ala Pro Ala Phe Leu Asn Thr Pro
385                 390                 395                 400
Asn Asn Asn Ile Asn Glu Asn Glu Leu Phe Asn Asp Arg Lys Gln Thr
                405                 410                 415
Thr Val Ser Asn Asp Leu Glu Asn Ser Pro Leu Lys Thr Glu Leu Glu
                420                 425                 430
Ala Asn Gly Arg Ser Leu Glu Lys Val Asn Asn Ser Val Ser Lys Thr
                435                 440                 445
Gly Ser Val Asp Thr Leu His Asn Lys Glu Gly Thr Leu Glu Gln Arg
        450                 455                 460
Glu Gln Asn Glu Asn Leu Pro Ser Asp Lys Ser Asp Ser Met Val Asp
465                 470                 475                 480
Lys Glu Leu Phe Gly Glu Asp Glu Asp Leu Phe Gly Asp Ser
                485                 490                 495
Asn Lys Ser Asn Ser Thr Asn Glu Ser Asn Lys Ser Ile Ser Asp Glu
                500                 505                 510
Ile Thr Glu Asp Met Phe Glu Met Ser Asp Glu Glu Asn Asn Asn
                515                 520                 525
Asn Lys Ser Ile Asn Lys Asn Lys Glu Met His Thr Asp Leu Gly
        530                 535                 540
Lys Asp Ile Pro Phe Phe Pro Ser Ser Lys Pro Asn Ile Arg Thr
545                 550                 555                 560
Met Ser Gly Thr Thr Lys Arg Leu Asn Gly Lys Arg Lys Tyr Leu Asp
                565                 570                 575
Ile Pro Ile Asp Glu Met Thr Leu Pro Thr Ser Pro Leu Tyr Met Asp
                580                 585                 590
Pro Gly Ala Pro Leu Pro Val Glu Thr Pro Arg Asp Arg Arg Lys Ser
                595                 600                 605
Val Phe Ala Pro Leu Asn Phe Asn Pro Ile Ile Glu Asn Asn Val Asp
        610                 615                 620
Asn Lys Tyr Lys Ser Gly Gly Lys Phe Ser Phe Ser Pro Leu Gln Lys
625                 630                 635                 640
Glu Glu Ala Leu Asn Phe Asp Ile Ser Met Ala Asp Leu Ser Ser Ser
                645                 650                 655
Glu Glu Glu Glu Asp Glu Glu Asn Gly Ser Ser Asp Glu Asp Leu
                660                 665                 670
Lys Ser Leu Asn Val Arg Asp Asp Met Lys Pro Ser Asp Asn Ile Ser
        675                 680                 685
Thr Asn Thr Asn Ile His Glu Pro Gln Tyr Ile Asn Tyr Ser Ser Ile
        690                 695                 700
Pro Ser Leu Gln Asp Ser Ile Ile Lys Gln Glu Asn Phe Asn Ser Val
705                 710                 715                 720
Asn Asp Ala Asn Ile Thr Ser Asn Lys Glu Gly Phe Asn Ser Ile Trp
                725                 730                 735
Lys Ile Pro Gln Asn Asp Ile Pro Gln Thr Glu Ser Pro Leu Lys Thr
                740                 745                 750
Val Asp Ser Ser Ile Gln Pro Ile Glu Ser Asn Ile Lys Met Thr Leu
                755                 760                 765
Glu Asp Asn Asn Val Thr Ser Asn Pro Ser Glu Phe Thr Pro Asn Met
        770                 775                 780
```

```
Val Asn Ser Gln Ile Ser Asn Leu Pro Lys Asp Lys Ser Gly Ile Pro
785                 790                 795                 800

Glu Phe Thr Pro Ala Asp Pro Asn Leu Ser Phe Glu Ser Ser Ser Ser
                805                 810                 815

Leu Pro Phe Leu Leu Arg His Met Pro Leu Ala Ser Ile Pro Asp Ile
            820                 825                 830

Phe Ile Thr Pro Thr Pro Val Val Thr Ile Ser Glu Lys Glu Gln Asp
        835                 840                 845

Ile Leu Asp Leu Ile Ala Glu Gln Val Val Thr Asp Tyr Asn Ile Leu
850                 855                 860

Gly Asn Leu Gly Ile Pro Lys Ile Ala Tyr Arg Gly Val Lys Asp Cys
865                 870                 875                 880

Gln Glu Gly Leu Ile Thr Thr Met Leu Gln Leu Phe Ser Thr Ser
                885                 890                 895

Asp Arg Leu Asn Gly Asn Asp Thr Ile Ser Lys Phe Tyr Asn Met Lys
            900                 905                 910

Gln Pro Tyr Val Phe Val Lys Lys His His Glu Leu Ile Lys Val Lys
        915                 920                 925

His Asp Ser Gln Pro Phe Ile Lys Phe Leu Asn Phe Arg Pro Pro Asn
    930                 935                 940

Gly Ile Lys Asn Phe Lys Ser Leu Leu Leu Ser Ser Ser Phe Lys Glu
945                 950                 955                 960

Asp Cys Leu Ser Phe Ala Pro Thr Leu Ser Gln Thr Tyr Ile Asn Gln
                965                 970                 975

Glu Leu Gly Phe Cys Glu Leu Leu Lys Leu Thr Asn Glu Asp Pro Pro
            980                 985                 990

Gly Leu Met Tyr Leu Lys Ala Phe Asp Lys Asn Lys Leu Leu Leu Leu
        995                 1000                1005

Ala Ala Gln Ile Val Ser Tyr Cys Ser Asn Asn Lys Asn Ser Ile Lys
    1010                1015                1020

Asn Val Pro Pro Ile Leu Ile Leu Pro Leu Asp Asn Ala Thr Leu
1025                1030                1035                1040

Thr Glu Leu Val Asp Lys Ala Asn Ile Phe Gln Val Ile Lys Asn Glu
                1045                1050                1055

Val Cys Ala Lys Met Pro Asn Ile Glu Leu Tyr Leu Val Ile Pro
            1060                1065                1070

Met Asp Phe Ile Arg Asn Val Leu Val Thr Val Asp Gln Tyr Val Asn
        1075                1080                1085

Val Ala Ile Ser Ile Tyr Asn Met Leu Pro Pro Lys Ser Val Lys Phe
    1090                1095                1100

Thr His Ile Ala His Thr Leu Pro Glu Lys Val Asn Phe Arg Thr Met
1105                1110                1115                1120

Gln Gln Gln Gln Met Gln Gln Gln Gln Gln Gln Gln Gln Gln
                1125                1130                1135

Asn Asn Ser Thr Gly Ser Ser Ile Ile Tyr Tyr Asp Ser Tyr Ile
            1140                1145                1150

His Leu Ala Tyr Ser Arg Ser Val Asp Lys Glu Trp Val Phe Ala Ala
        1155                1160                1165

Leu Ser Asp Ser Tyr Gly Gln Gly Ser Met Thr Lys Thr Trp Tyr Val
    1170                1175                1180

Gly Asn Ser Arg Gly Lys Phe Asp Asp Ala Cys Asn Gln Ile Trp Asn
1185                1190                1195                1200

Ile Ala Leu Asn Leu Ala Ser Lys Lys Phe Gly Lys Ile Cys Leu Ile
                1205                1210                1215
```

```
Leu Thr Arg Leu Asn Gly Ile Leu Pro Asp Asp Glu Leu Met Asn Trp
    1220                1225                1230

Arg Arg Leu Ser Gly Arg Asn Ile His Leu Ala Val Val Cys Val Asp
        1235                1240                1245

Asp Asn Ser Lys Ile Ser Phe Ile Asp Glu Asp Lys Leu Tyr Pro Ser
    1250                1255                1260

Phe Lys Pro Ile Tyr Lys Asp Thr Arg Phe Gly Gly Arg Met Asp Met
1265                1270                1275                1280

Thr Arg Leu Tyr Asp Tyr Glu Ile Arg Asp Ile Asp Gln Asp Ile His
        1285                1290                1295

Gly Ile Val Phe Gln His Pro Phe Pro Leu Ala His Ser Gln His Arg
    1300                1305                1310

Cys Ala Ile Arg Ser Gly Ala Leu Ile Lys Phe Lys Lys Cys Asp Gly
    1315                1320                1325

Asp Thr Val Trp Asp Lys Phe Ala Val Asn Leu Leu Asn Cys Pro His
    1330                1335                1340

Ser Asp Ser Thr Gln Leu Leu Glu Thr Ile Leu Glu Glu Phe Arg Asn
1345                1350                1355                1360

Leu Ala Ala Leu Asn Val Trp Tyr Gly Leu Ser Asp Gly Glu Asp Gly
        1365                1370                1375

His Ile Pro Trp His Ile Leu Ala Val Lys Lys Met Met Asn Thr Leu
    1380                1385                1390

Val His Thr Arg Val Lys Ile Ala Asn Thr Ser Ala Ala Thr Val His
        1395                1400                1405

Thr Ala Thr Ser Ser Ser Ile Ile Leu Ser Asp Lys
    1410                1415                1420

(2) INFORMATION FOR SEQ ID NO:15:

(i) SEQUENCE CHARACTERISTICS:
        (A) LENGTH: 2434 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 421..2043

(xi) SEQUENCE DESCRIPTION: SEQ ID NO:15:

AGACGGATTA TTGTTTTCAG TTGAAGTTGC GCACTCGGCA TATGATTTAT AGATTCCCAA      60

TATATTGTAC TTCGTTATAT ATGTGTTACG AATATTTTTG ATTTCGTTTT AGAGAGTTTT     120

GATTAGAGGA AATTATAGCT TTTTTTAACA GTGAAATAAA TATCATACAT CAAAAGTCTT     180

CAAGAATTAC GTGGTGTGGC TTAAGTTGCG TTTCATTTTC CCGCTTCAAT ACTTGAAAGT     240

TATCCCACAA TCACTGCTGA CAAAAAGGAT ACAAGAAAGG TTTATAGGAA AGAAAAAAGG     300

CGGAAGGGTA TACTGAAGTT AGTAATTTTG CTTCCCAATT GAATTAAGGC CGCCTAGTTT     360

TGACGGGAGG AGAGAGAAAT GTATAATGGC AAGGATAGAG CACAAAACTC CTATCAGCCA     420

ATG TAC CAA AGG CCT ATG CAG GTA CAA GGA CAA CAG CAA GCT CAA TCG      468
Met Tyr Gln Arg Pro Met Gln Val Gln Gly Gln Gln Gln Ala Gln Ser
  1               5                  10                  15

TTC GTT GGA AAG AAA AAC ACA ATC GGA AGT GTG CAT GGA AAA GCC CCG      516
Phe Val Gly Lys Lys Asn Thr Ile Gly Ser Val His Gly Lys Ala Pro
             20                  25                  30

ATG CTA ATG GCC AAT AAT GAT GTT TTT ACT ATT GGA CCT TAT AGG GCA      564
```

```
            Met Leu Met Ala Asn Asn Asp Val Phe Thr Ile Gly Pro Tyr Arg Ala
                    35                  40                  45

AGA AAA GAT AGA ATG CGG GTA TCT GTC TTA GAA AAG TAC GAA GTT ATT            612
Arg Lys Asp Arg Met Arg Val Ser Val Leu Glu Lys Tyr Glu Val Ile
         50                  55                  60

GGC TAC ATT GCT GCG GGC ACA TAT GGT AAA GTT TAC AAA GCG AAA AGA            660
Gly Tyr Ile Ala Ala Gly Thr Tyr Gly Lys Val Tyr Lys Ala Lys Arg
 65              70                  75                  80

CAA ATC AAC TCC GGT ACC AAT TCC GCT AAT GGT TCT AGT CTG AAT GGT            708
Gln Ile Asn Ser Gly Thr Asn Ser Ala Asn Gly Ser Ser Leu Asn Gly
                     85                  90                  95

ACC AAT GCG AAA ATT CCG CAG TTT GAC AGC ACG CAA CCA AAA TCA AGC            756
Thr Asn Ala Lys Ile Pro Gln Phe Asp Ser Thr Gln Pro Lys Ser Ser
             100                 105                 110

TCT TCA ATG GAC ATG CAG GCA AAT ACA AAC GCA TTA AGA AGA AAC TTG            804
Ser Ser Met Asp Met Gln Ala Asn Thr Asn Ala Leu Arg Arg Asn Leu
         115                 120                 125

TTA AAG GAT GAA GGA GTG ACC CCC GGA AGA ATA CGA ACT ACG AGG GAA            852
Leu Lys Asp Glu Gly Val Thr Pro Gly Arg Ile Arg Thr Thr Arg Glu
 130                 135                 140

GAT GTA TCC CCG CAC TAT AAT TCC CAA AAA CAA ACC CTC ATT AAA AAA            900
Asp Val Ser Pro His Tyr Asn Ser Gln Lys Gln Thr Leu Ile Lys Lys
145                 150                 155                 160

CCG CTG ACG GTA TTT TAT GCC ATT AAA AAG TTC AAG ACA GAG AAG GAT            948
Pro Leu Thr Val Phe Tyr Ala Ile Lys Lys Phe Lys Thr Glu Lys Asp
                 165                 170                 175

GGC GTC GAA CAA TTG CAT TAT ACG GGA ATA TCT CAG AGT GCC TGT AGA            996
Gly Val Glu Gln Leu His Tyr Thr Gly Ile Ser Gln Ser Ala Cys Arg
             180                 185                 190

GAA ATG GCA TTA TGT CGA GAA TTG CAC AAC AAG CAT TTA ACC ACA TTA           1044
Glu Met Ala Leu Cys Arg Glu Leu His Asn Lys His Leu Thr Thr Leu
         195                 200                 205

GTG GAA ATT TTT TTG GAA AGG AAA TGT GTC CAT ATG GTA TAC GAA TAT           1092
Val Glu Ile Phe Leu Glu Arg Lys Cys Val His Met Val Tyr Glu Tyr
 210                 215                 220

GCG GAG CAT GAT CTG CTA CAA ATT ATC CAC TTC CAT TCC CAT CCC GAA           1140
Ala Glu His Asp Leu Leu Gln Ile Ile His Phe His Ser His Pro Glu
225                 230                 235                 240

AAA AGG ATG ATA CCA CCA AGA ATG GTT CGG TCT ATT ATG TGG CAG CTT           1188
Lys Arg Met Ile Pro Pro Arg Met Val Arg Ser Ile Met Trp Gln Leu
                 245                 250                 255

TTA GAC GGC GTA TCG TAT CTT CAT CAA AAT TGG GTG CTT CAT CGA GAT           1236
Leu Asp Gly Val Ser Tyr Leu His Gln Asn Trp Val Leu His Arg Asp
             260                 265                 270

TTG AAA CCC GCA AAT ATA ATG GTG ACC ATA GAT GGA TGT GTT AAA ATT           1284
Leu Lys Pro Ala Asn Ile Met Val Thr Ile Asp Gly Cys Val Lys Ile
         275                 280                 285

GGT GAT TTA GGT TTG GCC AGA AAA TTT CAT AAT ATG CTG CAA ACC CTC           1332
Gly Asp Leu Gly Leu Ala Arg Lys Phe His Asn Met Leu Gln Thr Leu
 290                 295                 300

TAT ACT GGG GAT AAA GTG GTT GTC ACT ATA TGG TAC CGT GCA CCT GAG           1380
Tyr Thr Gly Asp Lys Val Val Val Thr Ile Trp Tyr Arg Ala Pro Glu
305                 310                 315                 320

TTG CTA TTG GGA GCA CGG CAC TAT ACC CCT GCG GTT GAT TTA TGG TCC           1428
Leu Leu Leu Gly Ala Arg His Tyr Thr Pro Ala Val Asp Leu Trp Ser
                 325                 330                 335

GTT GGC TGC ATT TTT GCA GAA CTG ATA GGA TTA CAG CCC ATA TTT AAA           1476
Val Gly Cys Ile Phe Ala Glu Leu Ile Gly Leu Gln Pro Ile Phe Lys
             340                 345                 350

GGT GAA GAA GCT AAA CTA GAC TCT AAA AAG ACT GTT CCA TTT CAA GTG           1524
```

```
Gly Glu Glu Ala Lys Leu Asp Ser Lys Lys Thr Val Pro Phe Gln Val
        355                 360                 365

AAT CAA CTA CAG AGA ATT TTG GAA GTT CTT GGC ACT CCC GAT CAA AAA      1572
Asn Gln Leu Gln Arg Ile Leu Glu Val Leu Gly Thr Pro Asp Gln Lys
    370                 375                 380

ATT TGG CCT TAT TTG GAG AAG TAT CCA GAA TAT GAT CAA ATT ACG AAG      1620
Ile Trp Pro Tyr Leu Glu Lys Tyr Pro Glu Tyr Asp Gln Ile Thr Lys
385                 390                 395                 400

TTT CCA AAG TAT AGG GAT AAC CTT GCT ACA TGG TAT CAT TCC GCG GGA      1668
Phe Pro Lys Tyr Arg Asp Asn Leu Ala Thr Trp Tyr His Ser Ala Gly
                405                 410                 415

GGA AGG GAC AAG CAT GCT TTA AGC TTA CTT TAC CAC TTG TTA AAT TAT      1716
Gly Arg Asp Lys His Ala Leu Ser Leu Leu Tyr His Leu Leu Asn Tyr
            420                 425                 430

GAT CCA ATT AAA AGA ATA GAT GCA TTT AAT GCG TTG GAA CAT AAG TAC      1764
Asp Pro Ile Lys Arg Ile Asp Ala Phe Asn Ala Leu Glu His Lys Tyr
        435                 440                 445

TTC ACA GAA AGT GAT ATT CCT GTT AGT GAA AAT GTA TTT GAA GGT CTA      1812
Phe Thr Glu Ser Asp Ile Pro Val Ser Glu Asn Val Phe Glu Gly Leu
    450                 455                 460

ACT TAC AAA TAC CCG GCA AGA AGA ATT CAC ACG AAC GAT AAT GAC ATC      1860
Thr Tyr Lys Tyr Pro Ala Arg Arg Ile His Thr Asn Asp Asn Asp Ile
465                 470                 475                 480

ATG AAT CTT GGA TCA AGA ACG AAA AAC AAT ACA CAA GCT TCA GGA ATC      1908
Met Asn Leu Gly Ser Arg Thr Lys Asn Asn Thr Gln Ala Ser Gly Ile
                485                 490                 495

ACC GCA GGT GCC GCT GCA AAT GCG TTA GGT GGG CTT GGT GTT AAC CGT      1956
Thr Ala Gly Ala Ala Ala Asn Ala Leu Gly Gly Leu Gly Val Asn Arg
            500                 505                 510

AGA ATT CTG GCC GCG GCA GCA GCC GCT GCT GCG GTG TCA GGA AAC           2004
Arg Ile Leu Ala Ala Ala Ala Ala Ala Ala Val Ser Gly Asn
        515                 520                 525

AAT GCA TCA GAT GAG CCA TCT CGA AAG AAA AAC AGA AGA TAGGCTTCTA       2053
Asn Ala Ser Asp Glu Pro Ser Arg Lys Lys Asn Arg Arg
    530                 535                 540

TTTTTATATA TATTTGGAAT TTTTCATTCC ACAGCACTGT CACTATTATA TTCATTAAAC    2113

TTTTTTTTAT CTTTATAGTA TTTAAATCGG CATACAGTTT CAATTTTTCG CTTTAGAGGC    2173

ACTAAGAATG CAAGTCTGCA ACATTCAGGT AAAATAATGG GTTGATTTTA GGTCGAGCTA    2233

AAACCCTGTT CTCCGCAGAT GTATGCGAAT TCGTCATAA TTCATCTCAA CTAATGGGGC     2293

TTTAAAACAT ATGAATATCT CATGCAAACC CAAAAAGAA GAAAGAAAAG ACTTCAAGTC     2353

CCCCCCTTAA TTTTTATATA ATGGTAGTAG TAGGTTTGTT CGTAACTTAT CGGCAATAGT    2413

AATATGTTCC CATTATCAAC A                                               2434

(2) INFORMATION FOR SEQ ID NO:16:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:16:

Met Tyr Gln Arg Pro Met Gln Val Gln Gly Gln Gln Ala Gln Ser
 1               5                  10                  15

Phe Val Gly Lys Lys Asn Thr Ile Gly Ser Val His Gly Lys Ala Pro
                20                  25                  30

Met Leu Met Ala Asn Asn Asp Val Phe Thr Ile Gly Pro Tyr Arg Ala
```

```
                    35                  40                  45
Arg Lys Asp Arg Met Arg Val Ser Val Leu Glu Lys Tyr Glu Val Ile
     50                  55                  60
Gly Tyr Ile Ala Ala Gly Thr Tyr Gly Lys Val Tyr Lys Ala Lys Arg
 65                  70                  75                  80
Gln Ile Asn Ser Gly Thr Asn Ser Ala Asn Gly Ser Ser Leu Asn Gly
                 85                  90                  95
Thr Asn Ala Lys Ile Pro Gln Phe Asp Ser Thr Gln Pro Lys Ser Ser
                100                 105                 110
Ser Ser Met Asp Met Gln Ala Asn Thr Asn Ala Leu Arg Arg Asn Leu
            115                 120                 125
Leu Lys Asp Glu Gly Val Thr Pro Gly Arg Ile Arg Thr Thr Arg Glu
    130                 135                 140
Asp Val Ser Pro His Tyr Asn Ser Gln Lys Gln Thr Leu Ile Lys Lys
145                 150                 155                 160
Pro Leu Thr Val Phe Tyr Ala Ile Lys Lys Phe Lys Thr Glu Lys Asp
                165                 170                 175
Gly Val Glu Gln Leu His Tyr Thr Gly Ile Ser Gln Ser Ala Cys Arg
            180                 185                 190
Glu Met Ala Leu Cys Arg Glu Leu His Asn Lys His Leu Thr Thr Leu
    195                 200                 205
Val Glu Ile Phe Leu Glu Arg Lys Cys Val His Met Val Tyr Glu Tyr
    210                 215                 220
Ala Glu His Asp Leu Leu Gln Ile Ile His Phe His Ser His Pro Glu
225                 230                 235                 240
Lys Arg Met Ile Pro Pro Arg Met Val Arg Ser Ile Met Trp Gln Leu
                245                 250                 255
Leu Asp Gly Val Ser Tyr Leu His Gln Asn Trp Val Leu His Arg Asp
            260                 265                 270
Leu Lys Pro Ala Asn Ile Met Val Thr Ile Asp Gly Cys Val Lys Ile
    275                 280                 285
Gly Asp Leu Gly Leu Ala Arg Lys Phe His Asn Met Leu Gln Thr Leu
    290                 295                 300
Tyr Thr Gly Asp Lys Val Val Val Thr Ile Trp Tyr Arg Ala Pro Glu
305                 310                 315                 320
Leu Leu Leu Gly Ala Arg His Tyr Thr Pro Ala Val Asp Leu Trp Ser
                325                 330                 335
Val Gly Cys Ile Phe Ala Glu Leu Ile Gly Leu Gln Pro Ile Phe Lys
            340                 345                 350
Gly Glu Glu Ala Lys Leu Asp Ser Lys Lys Thr Val Pro Phe Gln Val
    355                 360                 365
Asn Gln Leu Gln Arg Ile Leu Glu Val Leu Gly Thr Pro Asp Gln Lys
    370                 375                 380
Ile Trp Pro Tyr Leu Glu Lys Tyr Pro Glu Tyr Asp Gln Ile Thr Lys
385                 390                 395                 400
Phe Pro Lys Tyr Arg Asp Asn Leu Ala Thr Trp Tyr His Ser Ala Gly
                405                 410                 415
Gly Arg Asp Lys His Ala Leu Ser Leu Leu Tyr His Leu Leu Asn Tyr
            420                 425                 430
Asp Pro Ile Lys Arg Ile Asp Ala Phe Asn Ala Leu Glu His Lys Tyr
    435                 440                 445
Phe Thr Glu Ser Asp Ile Pro Val Ser Glu Asn Val Phe Glu Gly Leu
    450                 455                 460
```

```
Thr Tyr Lys Tyr Pro Ala Arg Arg Ile His Thr Asn Asp Asn Asp Ile
465                 470                 475                 480

Met Asn Leu Gly Ser Arg Thr Lys Asn Asn Thr Gln Ala Ser Gly Ile
                485                 490                 495

Thr Ala Gly Ala Ala Asn Ala Leu Gly Gly Leu Gly Val Asn Arg
            500                 505                 510

Arg Ile Leu Ala Ala Ala Ala Ala Ala Ala Val Ser Gly Asn
        515                 520                 525

Asn Ala Ser Asp Glu Pro Ser Arg Lys Asn Arg Arg
530                 535                 540
```

(2) INFORMATION FOR SEQ ID NO:17:

(i) SEQUENCE CHARACTERISTICS:
        (A) LENGTH: 1610 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 495..1463

(xi) SEQUENCE DESCRIPTION: SEQ ID NO:17:

```
GGTACCAGGT CAAGAAGCAG AATACCCAAG GGCATCCTCC TTAATGAGTT GATTTAAACA      60

ATTTAAAATT TTTAAATCTC ATTACGTTTT CCGCATACGA ATTGGTGGGA GACTTTCAAC     120

CCAAAGCATA TTACTGAGTA AAAAAAATTT TACTCCATTT TGTAAGCTTC GATTTGTGAC     180

GATTCTTTGG TCATGGATTG AAGAACTTTA AACGAGAAGA AATTAGAAAA CAGGTGAAGA     240

CCACTATTTA GTTCTTTACC GCAACATAGG ATAAACAAAG TTATTTTCTT ACTCCTTTAT     300

ATATTTGAAA AAATATAAAA TCCACGGAAA ACATCGAAA ATTCATTTTT CATGAAGGAA      360

AATTAGGGTT CATACAGGAG TAGAGTTCAT TGATGTGGTA GCAACCTTGT TAGCACTCAT     420

ATTGTTCGAA CAAAAAATGC CCTCTCAAAC TTTAGTTGAA GAGCGATAAG GCATCTGAAT     480

CTCAAAAGTT AGAC ATG TCG GGG AGC TTC TGG ACA TCT ACA CAA AGG CAT       530
             Met Ser Gly Ser Phe Trp Thr Ser Thr Gln Arg His
               1               5                      10

CAT TGG CAA TAT ACC AAG GCA TCA TTG GCT AAA GAG AGG CAG AAG TTA       578
His Trp Gln Tyr Thr Lys Ala Ser Leu Ala Lys Glu Arg Gln Lys Leu
         15                  20                  25

TGG CTA TTG GAG TGC CAG CTG TTT CCT CAA GGT TTG AAT ATT GTA ATG       626
Trp Leu Leu Glu Cys Gln Leu Phe Pro Gln Gly Leu Asn Ile Val Met
         30                  35                  40

GAT TCG AAG CAA AAC GGC ATC GAA CAA TCC ATC ACA AAG AAT ATA CCA       674
Asp Ser Lys Gln Asn Gly Ile Glu Gln Ser Ile Thr Lys Asn Ile Pro
 45                  50                  55                  60

ATA ACT CAC CGA GAC TTA CAC TAT GAT AAA GAT TAT AAT CTA AGG ATC       722
Ile Thr His Arg Asp Leu His Tyr Asp Lys Asp Tyr Asn Leu Arg Ile
                 65                  70                  75

TAC TGC TAT TTC CTG ATA ATG AAG CTT GGA AGG AGA CTA AAT ATA AGA       770
Tyr Cys Tyr Phe Leu Ile Met Lys Leu Gly Arg Arg Leu Asn Ile Arg
             80                  85                  90

CAG TAT GCA CTG GCT ACA GCA CAT ATT TAT CTA TCA AGG TTT TTA ATA       818
Gln Tyr Ala Leu Ala Thr Ala His Ile Tyr Leu Ser Arg Phe Leu Ile
         95                  100                 105

AAG GCT TCA GTT AGA GAA ATA AAC CTA TAT ATG CTG GTT ACT ACG TGT       866
Lys Ala Ser Val Arg Glu Ile Asn Leu Tyr Met Leu Val Thr Thr Cys
     110                 115                 120
```

```
GTA TAT TTA GCA TGC AAA GTT GAA GAA TGC CCG CAA TAT ATC AGA ACT       914
Val Tyr Leu Ala Cys Lys Val Glu Glu Cys Pro Gln Tyr Ile Arg Thr
125                 130                 135                 140

TTG GTA AGT GAA GCC CGT ACC TTA TGG CCC GAA TTT ATT CCT CCT GAC       962
Leu Val Ser Glu Ala Arg Thr Leu Trp Pro Glu Phe Ile Pro Pro Asp
            145                 150                 155

CCT ACT AAA GTT ACT GAG TTT GAG TTC TAC TTA CTA GAA GAA TTG GAA      1010
Pro Thr Lys Val Thr Glu Phe Glu Phe Tyr Leu Leu Glu Glu Leu Glu
                160                 165                 170

AGT TAC TTA ATT GTC CAC CAC CCT TAT CAA TCC TTA AAG CAA ATT GTT      1058
Ser Tyr Leu Ile Val His His Pro Tyr Gln Ser Leu Lys Gln Ile Val
            175                 180                 185

CAA GTC TTA AAG CAA CCG CCA TTT CAA ATA ACA CTA TCG TCA GAT GAT      1106
Gln Val Leu Lys Gln Pro Pro Phe Gln Ile Thr Leu Ser Ser Asp Asp
                190                 195                 200

CTA CAA AAC TGT TGG TCC TTA ATC AAC GAC AGT TAT ATA AAT GAT GTT      1154
Leu Gln Asn Cys Trp Ser Leu Ile Asn Asp Ser Tyr Ile Asn Asp Val
205                 210                 215                 220

CAT TTG CTT TAC CCT CCT CAT ATT ATC GCT GTT GCA TGT TTA TTC ATT      1202
His Leu Leu Tyr Pro Pro His Ile Ile Ala Val Ala Cys Leu Phe Ile
            225                 230                 235

ACG ATT TCC ATT CAT GGG AAA CCA ACC AAA GGA TCA TCG TTA GCA TCT      1250
Thr Ile Ser Ile His Gly Lys Pro Thr Lys Gly Ser Ser Leu Ala Ser
                240                 245                 250

GCG GCT TCT GAA GCC ATC AGA GAT CCT AAA AAT TCT AGT TCT CCT GTT      1298
Ala Ala Ser Glu Ala Ile Arg Asp Pro Lys Asn Ser Ser Ser Pro Val
            255                 260                 265

CAA ATA GCT TTT AAT CGT TTT ATG GCA GAA TCT CTT GTA GAT CTT GAG      1346
Gln Ile Ala Phe Asn Arg Phe Met Ala Glu Ser Leu Val Asp Leu Glu
270                 275                 280

GAG GTT ATG GAT ACG ATT CAA GAG CAA ATT ACA TTA TAC GAT CAT TGG      1394
Glu Val Met Asp Thr Ile Gln Glu Gln Ile Thr Leu Tyr Asp His Trp
285                 290                 295                 300

GAC AAG TAC CAC GAA CAA TGG ATA AAG TTT CTG CTA CAT ACT TTG TAT      1442
Asp Lys Tyr His Glu Gln Trp Ile Lys Phe Leu Leu His Thr Leu Tyr
                305                 310                 315

CTT AGA CCA GCA TCT GCA ATT TAATCATGCG AAGAATAAAT TTAAAAACCG        1493
Leu Arg Pro Ala Ser Ala Ile
                320

TTAAGCCTGT AAATTCAATC ATTATGGTGG TGATGATCCG TTTTGGAAAT GTTTCGTCCT   1553

TGACTACCTT TGTTTAACAT GATATTGGAA CGTCAAGACA TATTGAGAAT AGGTACC      1610

(2) INFORMATION FOR SEQ ID NO:18:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:18:

Met Ser Gly Ser Phe Trp Thr Ser Thr Gln Arg His His Trp Gln Tyr
1               5                   10                  15

Thr Lys Ala Ser Leu Ala Lys Glu Arg Gln Lys Leu Trp Leu Leu Glu
                20                  25                  30

Cys Gln Leu Phe Pro Gln Gly Leu Asn Ile Val Met Asp Ser Lys Gln
            35                  40                  45

Asn Gly Ile Glu Gln Ser Ile Thr Lys Asn Ile Pro Ile Thr His Arg
        50                  55                  60
```

Asp Leu His Tyr Asp Lys Asp Tyr Asn Leu Arg Ile Tyr Cys Tyr Phe
65                  70                  75                  80

Leu Ile Met Lys Leu Gly Arg Arg Leu Asn Ile Arg Gln Tyr Ala Leu
            85                  90                  95

Ala Thr Ala His Ile Tyr Leu Ser Arg Phe Leu Ile Lys Ala Ser Val
            100                 105                 110

Arg Glu Ile Asn Leu Tyr Met Leu Val Thr Thr Cys Val Tyr Leu Ala
            115                 120                 125

Cys Lys Val Glu Glu Cys Pro Gln Tyr Ile Arg Thr Leu Val Ser Glu
130                 135                 140

Ala Arg Thr Leu Trp Pro Glu Phe Ile Pro Pro Asp Pro Thr Lys Val
145                 150                 155                 160

Thr Glu Phe Glu Phe Tyr Leu Leu Glu Glu Leu Glu Ser Tyr Leu Ile
                165                 170                 175

Val His His Pro Tyr Gln Ser Leu Lys Gln Ile Val Gln Val Leu Lys
            180                 185                 190

Gln Pro Pro Phe Gln Ile Thr Leu Ser Ser Asp Asp Leu Gln Asn Cys
            195                 200                 205

Trp Ser Leu Ile Asn Asp Ser Tyr Ile Asn Asp Val His Leu Leu Tyr
210                 215                 220

Pro Pro His Ile Ile Ala Val Ala Cys Leu Phe Ile Thr Ile Ser Ile
225                 230                 235                 240

His Gly Lys Pro Thr Lys Gly Ser Ser Leu Ala Ser Ala Ser Glu
                245                 250                 255

Ala Ile Arg Asp Pro Lys Asn Ser Ser Ser Pro Val Gln Ile Ala Phe
            260                 265                 270

Asn Arg Phe Met Ala Glu Ser Leu Val Asp Leu Glu Glu Val Met Asp
            275                 280                 285

Thr Ile Gln Glu Gln Ile Thr Leu Tyr Asp His Trp Asp Lys Tyr His
            290                 295                 300

Glu Gln Trp Ile Lys Phe Leu Leu His Thr Leu Tyr Leu Arg Pro Ala
305                 310                 315                 320

Ser Ala Ile (2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ACTACAATCC GGGCTTATCC                                            20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCTTGGTCTC AAACTCGCCC                                            20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTTGTCCTTG ATTAGCACGG                                    20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCAAAGTGAA ATTTTACTGG                                    20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TAGACTTTCG GACGTACCGG                                    20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CGGTGAGACG TTGATCTTGG                                    20

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GAAGGAAGGG GCAGGTGGTT ACGCGGTGTA TACGTATAG                    39

(2) INFORMATION FOR SEQ ID NO:26:

(i) SEQUENCE CHARACTERISTICS:
        (A) LENGTH: 63 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AGCATTCGTA AGAACTCAAG CGTAGTCTGG GACGTCGTAT GGGTACAGCT CCAGAGCACG    60

AAC    63

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TCCACGAATA TAACAGCCTG ATTTTCCCAT G    31

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TCGGCATATG GGAAAATCAG CTGTTAT    27

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCGTGGATCC TCACAGCTCC AGAGCACGAA    30

(2) INFORMATION FOR SEQ ID NO:30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGAAGAGTAC AAGGACAAAA CGGCTTGGAT GGAAACGTAG AAGGCATTCC A    51

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGGGCTACTC TCGAAGATCC CGTCATTATG TACAGCAGGT TGAGCATGCC T         51

(2) INFORMATION FOR SEQ ID NO:32:

(i) SEQUENCE CHARACTERISTICS:
　　　　(A) LENGTH: 51 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:32:

GCCTTACCGG CACGCATCAT GATGGGGACG CCCTCCCAAC GCTCGACACT T         51

(2) INFORMATION FOR SEQ ID NO:33:

(i) SEQUENCE CHARACTERISTICS:
　　　　(A) LENGTH: 50 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:33:

GCAGTGGCTG CAGGAGCTGC AGAAGCATCG GTACTGGGGG ATGCAATCCA           50

(2) INFORMATION FOR SEQ ID NO:34:

(i) SEQUENCE CHARACTERISTICS:
　　　　(A) LENGTH: 54 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:34:

GTCGACGGGT TCAACTTCTC CCTCTTTGTA ACTTGCATCA GCAAACGGAT GACA      54

(2) INFORMATION FOR SEQ ID NO:35:

(i) SEQUENCE CHARACTERISTICS:
　　　　(A) LENGTH: 50 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:35:

GGATGTCAAC AACGGTGACA GCTTCGACAA CTTCACGCTT GTGGTGAGCT           50

What is claimed is:

1. A purified multi subunit RNA polymerase II holoenzyme derived from *Saccharomyces cerevisiae* which comprises: (a) at least eight SRB polypeptides, (b) general transcription factors b, g, and e; and (c) RNA polymerase II; wherein said holoenzyme, when supplemented with general transcription factor a and TBP, catalyzes site-specific initiation of gene transcription.

2. A purified multisubunit RNA polymerase 11 holoenzyme of claim 1 wherein the holoenzyme comprises SRB 2 (SEQ ID NO:2), SRB 4 (SEQ ID NO:4), SRB 5 (SEQ ID NO:6), SRB 6 (SEQ ID NO:8), SRB 7 (SEQ ID NO:10), SRB 8 (SEQ ID NO:12), and SRB 9 (SEQ ID NO:14) and has a molecular weight of approximately 1.2 Md.

3. A purified polypeptide having an amino acid sequence as set forth in SEQ ID NO:4.

4. Isolated DNA which encodes a polypeptide having the amino acid sequence of SEQ ID NO:4 and the complement thereof.

5. A purified polypeptide having an amino acid sequence as set forth in SEQ ID NO:6.

6. Isolated DNA which encodes a polypeptide having the amino acid sequence of SEQ ID NO:6 and the complement thereof.

7. A purified polypeptide having an amino acid sequence as set forth in SEQ ID NO:10.

8. Isolated DNA which encodes a polypeptide having the amino acid sequence of SEQ ID NO:10 and the complement thereof.

9. A purified polypeptide having an amino acid sequence as set forth in SEQ ID NO:14.

10. Isolated DNA which encodes a polypeptide having the amino acid sequence of SEQ ID NO:14 and the complement thereof.

11. A purified polypeptide having an amino acid sequence as set forth in SEQ ID NO:16.

12. Isolated DNA which encodes a polypeptide having the amino acid sequence of SEQ ID NO:16 and the complement thereof.

13. A purified polypeptide having an amino acid sequence as set forth in SEQ ID NO:18.

14. Isolated DNA which encodes a polypeptide having the amino acid sequence of SEQ ID NO:18 and the complement thereof.

15. A purified holoenzyme as defined in claim 1, wherein said holoenzyme, when supplemented with general transcription factor a, TBP, and a transcriptional activator, further catalyzes activated initiation of gene transcription.

16. A purified holoenzyme as defined in claim 2, further comprising SRB 10 (SEQ ID NO:16) and SRB 11 (SEQ ID NO:18).

17. An isolated DNA as defined in claim 4, wherein said DNA has a sequence selected from the group consisting of the sequence of SEQ ID NO:3 and the complement thereof.

18. An isolated DNA as defined in claim 6, wherein said DNA has a sequence selected from the group consisting of the sequence of SEQ ID NO:5 and the complement thereof.

19. An isolated DNA as defined in claim 8, wherein said DNA has a sequence selected from the group consisting of the sequence of SEQ ID NO:9 and the complement thereof.

20. An isolated DNA as defined in claim 10, wherein said DNA has a sequence selected from the group consisting of the sequence of SEQ ID NO:13 and the complement thereof.

21. An isolated DNA as defined in claim 12, wherein said DNA has a sequence selected from the group consisting of the sequence of SEQ ID NO:15 and the complement thereof.

22. An isolated DNA as defined in claim 14, wherein said DNA has a sequence selected from the group consisting of the sequence of SEQ ID NO:17 and the complement thereof.

* * * * *